US012778566B2

(12) United States Patent
Grant et al.

(10) Patent No.: US 12,778,566 B2
(45) Date of Patent: Nov. 3, 2026

(54) DELIVERY SYSTEM AND METHOD FOR VASCULAR CLOSURE IMPLANT

(71) Applicant: Vivasure Medical Limited, Galway (IE)

(72) Inventors: Peter Grant, Galway (IE); Mark McGoldrick, Athlone (IE); Gerard Brett, Claregalway (IE)

(73) Assignee: Vivasure Medical Limited, Galway (IE)

( * ) Notice: Subject to any disclaimer, the term of this patent is extended or adjusted under 35 U.S.C. 154(b) by 108 days.

(21) Appl. No.: 18/735,726

(22) Filed: Jun. 6, 2024

(65) Prior Publication Data

US 2024/0407774 A1 Dec. 12, 2024

Related U.S. Application Data

(60) Provisional application No. 63/599,257, filed on Nov. 15, 2023, provisional application No. 63/471,725, filed on Jun. 7, 2023.

(51) Int. Cl.

| | |
|---|---|
| ***A61B 17/00*** | (2006.01) |
| ***A61B 50/00*** | (2016.01) |
| ***A61B 50/33*** | (2016.01) |

(52) U.S. Cl.

CPC .......... *A61B 17/0057* (2013.01); *A61B 50/33* (2016.02); *A61B 2017/00367* (2013.01);

(Continued)

(58) Field of Classification Search

CPC ...... A61B 17/0057; A61B 2017/00309; A61B 2017/00367; A61B 2017/00477;

(Continued)

(56) References Cited

U.S. PATENT DOCUMENTS 4,368,736 A 1/1983 Kaster
4,610,665 A * 9/1986 Matsumoto ....... A61M 39/0606 604/167.04

(Continued)

FOREIGN PATENT DOCUMENTS

AU 2009208049 A1 8/2009
CN 101028205 A 9/2007

(Continued)

OTHER PUBLICATIONS

International Search Report for PCT/EP2019/086846, mailed Mar. 12, 2020, 5 pages.

(Continued)

*Primary Examiner* — Mohamed G Gabr
(74) *Attorney, Agent, or Firm* — Nutter McClennen & Fish LLP

(57) ABSTRACT

An implantable device for sealing an aperture in a tissue of a body vessel includes: an external fixation disposed on the outside of a vessel wall; a scaffold disposed on the inside of the vessel wall and interfacing with the external fixation, at least a portion of the scaffold disposed through an aperture in the vessel wall; and a patch disposed on the inside of the vessel wall and sandwiched between the external fixation and the scaffold, the patch substantially covering the full area of the aperture, thereby sealing the aperture. A delivery and system for delivering an implantable device includes: a delivery device to deliver the implantable device to the aperture location and to seal the implantable device over the aperture; a sheath and dilator assembly; and a packaging assembly.

16 Claims, 110 Drawing Sheets

(52) U.S. Cl.
CPC ............... *A61B 2017/00477* (2013.01); *A61B 2017/00592* (2013.01); *A61B 2017/00615* (2013.01); *A61B 2017/00654* (2013.01); *A61B 2017/00862* (2013.01); *A61B 2050/005* (2016.02)

(58) Field of Classification Search
CPC ........... A61B 2017/00592; A61B 2017/00615; A61B 2017/00623; A61B 2017/00654; A61B 2017/00659; A61B 2017/00862; A61B 2050/005; A61B 2090/062; A61B 2090/0807; A61B 50/33
See application file for complete search history.

(56) References Cited

U.S. PATENT DOCUMENTS

| | | | |
|---|---|---|---|
| 5,350,399 | A | 9/1994 | Erlebacher et al. |
| 5,759,194 | A | 6/1998 | Hammerslag |
| 6,533,749 | B1 | 3/2003 | Mitusina et al. |
| 7,407,078 | B2 | 8/2008 | Shelton, IV et al. |
| 8,361,092 | B1 | 1/2013 | Asfora |
| 11,278,269 | B2 | 3/2022 | Grant et al. |
| 12,156,643 | B2 | 12/2024 | Grant et al. |
| 12,303,118 | B2 | 5/2025 | Grant et al. |
| 2001/0041902 | A1 | 11/2001 | Lepulu et al. |
| 2003/0023267 | A1 | 1/2003 | Ginn |
| 2003/0163085 | A1 | 8/2003 | Tanner et al. |
| 2005/0070957 | A1 | 3/2005 | Das |
| 2005/0192604 | A1 | 9/2005 | Carson et al. |
| 2005/0273135 | A1 | 12/2005 | Chanduszko et al. |
| 2006/0106418 | A1 | 5/2006 | Seibold et al. |
| 2007/0123816 | A1 | 5/2007 | Zhu et al. |
| 2007/0123934 | A1 | 5/2007 | Whisenant et al. |
| 2010/0069930 | A1 | 3/2010 | Roslin et al. |
| 2010/0087811 | A1 | 4/2010 | Herrin et al. |
| 2010/0234878 | A1 | 9/2010 | Hruska et al. |
| 2011/0082495 | A1 | 4/2011 | Ruiz |
| 2011/0093007 | A1 | 4/2011 | Abbott et al. |
| 2011/0196420 | A1 | 8/2011 | Ebner |
| 2011/0237976 | A1 | 9/2011 | Weitzel et al. |
| 2012/0053574 | A1 | 3/2012 | Murray, III et al. |
| 2012/0078352 | A1 | 3/2012 | Wang et al. |
| 2012/0080334 | A1 | 4/2012 | Shelton, IV et al. |
| 2013/0274795 | A1 | 10/2013 | Grant et al. |
| 2013/0282057 | A1 | 10/2013 | Green et al. |
| 2014/0018846 | A1 | 1/2014 | Grant et al. |
| 2014/0018847 | A1 | 1/2014 | Grant et al. |
| 2014/0180314 | A1 | 6/2014 | Asfora |
| 2016/0095648 | A1 | 4/2016 | Churchill et al. |
| 2016/0143639 | A1 | 5/2016 | Asfora |
| 2016/0166241 | A1 | 6/2016 | McGoldrick et al. |
| 2016/0174953 | A1 | 6/2016 | Grant et al. |
| 2017/0100250 | A1 | 4/2017 | Marsot et al. |
| 2017/0143343 | A9 | 5/2017 | Asfora |
| 2017/0333014 | A1* | 11/2017 | Grant ................. A61B 17/0057 |
| 2018/0064429 | A1 | 3/2018 | Phillips et al. |
| 2019/0021710 | A1* | 1/2019 | McGoldrick ...... A61B 17/0057 |
| 2022/0031294 | A1 | 2/2022 | Grant et al. |
| 2022/0110617 | A1* | 4/2022 | Reynolds ................ A61L 31/06 |
| 2022/0160341 | A1 | 5/2022 | Grant et al. |

FOREIGN PATENT DOCUMENTS

| | | | |
|---|---|---|---|
| CN | 101389276 | A | 3/2009 |
| CN | 102711631 | A | 10/2012 |
| CN | 102802538 | A | 11/2012 |
| CN | 103391750 | A | 11/2013 |
| CN | 104254301 | A | 12/2014 |
| CN | 104540472 | A | 4/2015 |
| CN | 104739461 | A | 7/2015 |
| CN | 105286928 | A | 2/2016 |
| CN | 105431097 | A | 3/2016 |
| EP | 2548518 | A1 | 1/2013 |
| EP | 2697721 | B1 | 9/2019 |
| WO | WO-2001/17440 | A1 | 3/2001 |
| WO | WO-2007/078812 | A2 | 7/2007 |
| WO | WO-2010/118312 | A2 | 10/2010 |
| WO | WO-2010/151510 | A1 | 12/2010 |
| WO | WO-2011/027003 | A1 | 3/2011 |
| WO | WO-2011/057282 | A2 | 5/2011 |
| WO | WO-2012/065189 | A1 | 5/2012 |
| WO | WO-2013/128292 | A2 | 9/2013 |
| WO | WO-2013/158919 | A1 | 10/2013 |
| WO | WO-2013/162689 | A1 | 10/2013 |
| WO | WO-2015/017551 | A2 | 2/2015 |
| WO | WO-2017/102941 | A1 | 6/2017 |
| WO | WO-2020/141122 | A1 | 7/2020 |
| WO | WO-2023/073137 | A1 | 5/2023 |
| WO | WO-2024/251919 | A1 | 12/2024 |

OTHER PUBLICATIONS

International Search Report, PCT/EP2017/062035 (Vascular Closure Device filed May 18, 2017), ISA/EPO, 5 pages, Oct. 19, 2017.
Written Opinion for PCT/EP2019/086846, mailed Mar. 12, 2020, 8 pages.
Written Opinion, PCT/EP2017/062035 (Vascular Closure Device filed May 18, 2017), ISA/EPO, 8 pages, Oct. 19, 2017.
Invitation to Pay Additional Fees for PCT/EP2024/065679, 8 pages (mailed Aug. 2, 2024).
Provisional Opinion for PCT/EP2024/065679, 9 pages (mailed Aug. 2, 2024).
International Search Report for PCT/EP2024/065679, 7 pages (mailed Jul. 25, 2024).
Written Opinion for PCT/EP2024/065679, 15 pages (mailed Jul. 25, 2024).

* cited by examiner

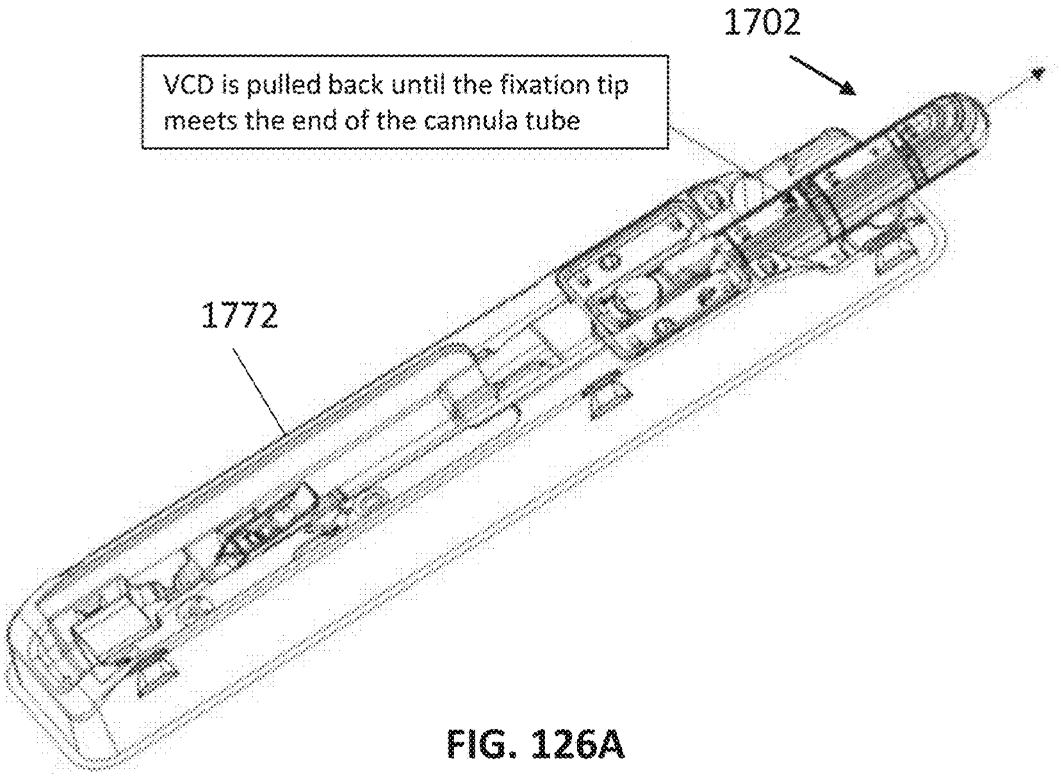
FIG. 126A
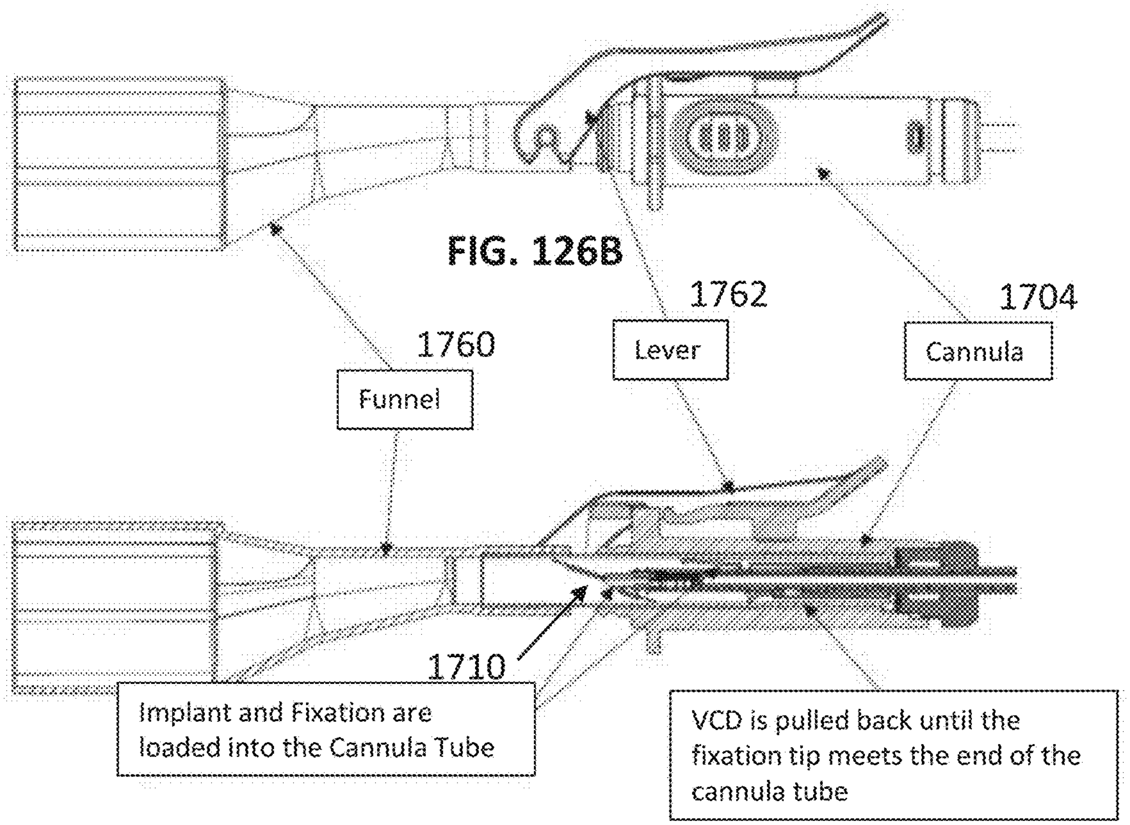
FIG. 126B
FIG. 126C

Rotating the Release Cams causes the Push Hub to move forward in the handle and releases the Scaffold from the Bayonet feature of the delivery shaft

DELIVERY SYSTEM AND METHOD FOR VASCULAR CLOSURE IMPLANT

CROSS-REFERENCE TO RELATED APPLICATIONS

This application claims priority to and the benefit of U.S. Provisional Application No. 63/471,725, filed Jun. 7, 2023, and U.S. Provisional Application No. 63/599,257, filed Nov. 15, 2023, the title of each of which is "Delivery System and Method for Vascular Closure Implant", the disclosures of which are incorporated by reference herein in their entireties.

BACKGROUND

During a surgical or endoscopic operation or surgery on a body vessel of a patient, e.g., a blood vessel, an aperture or opening or wound may be formed (e.g., from an arteriotomy or a venotomy) in the tissue of the vessel. Following the procedure, the aperture needs to be closed in order for the vessel to heal. One relatively new type of closure apparatus has a flexible disc that is delivered into the body vessel to seal the aperture. The disc retains the tissue in apposition until the aperture in the vessel is healed, allowing the wound to heal from the inside of the vessel.

In certain patients, the area surrounding the tissue within the body vessel may be diseased and/or may have accumulations (e.g., plaque or calcified lesions on the tissue wall). Due to the irregular surface topology of such areas, the effectiveness of the seal made by certain closure apparatuses is reduced, as channels are formed between the disc and the tissue surface.

There are benefits in improving the seal formed by a closure apparatus when closing an aperture formed in the tissue of the body vessel.

SUMMARY

The provided technologies provide an implant closure device having a mesh layer formed on a flexible substrate, collectively forming a sealable member or patch, which improves a seal of an aperture in the body vessel. During closure of the aperture, the patch is held against the inner-luminal tissue of the vessel wall such that the textured surface of the mesh layer is oriented against the tissue. The meshing facilitates a faster and more secure adherence of the patch to the surrounding edges at the puncture site. Furthermore, the provided technologies promote platelet-capture and encourage platelet aggregation on the mesh layer. The platelet impregnated mesh layer facilitates cellular adhesion, enabling the patch to act, in essence, as a "biological glue." Thus, faster time to hemostasis, improved security of the sealing, and improved apposition of the implant to the vessel wall can be obtained.

In some embodiments, the patch is sized such that the patch forms a tamponade of the aperture when the patch is positioned against an interior luminal surface of the tissue adjacent the aperture. The patch may be held in place at the aperture by an internal scaffold and by an external fixation, with the internal scaffold and external fixation mechanically held together with the patch and the tissue of the vessel sandwiched between them so that the patch covers the aperture. The combination of the patch, the scaffold, the external fixation, and other components may be collectively termed a vascular closure device or an implant or an implantable device. In some embodiments, a delivery device may be used to position the components of the vascular closure device at the aperture. The combination of the vascular closure device and the delivery device may be collectively termed a vascular closure system.

Further features and aspects of example embodiments of the present invention are described in more detail below.

In one aspect, the present embodiments are directed to avascular closure system for sealing an aperture in a wall of a body vessel (e.g., an artery or vein), including: an implantable closure device; a delivery device for delivery of the implantable closure device; and an introducer assembly comprising a sheath assembly, a dilator assembly disposed coaxially inside the sheath assembly, and a guidewire.

In some embodiments, the implantable closure device of the vascular closure system includes: an external fixation disposed on the outside of the vessel wall; a scaffold disposed on the inside of the vessel wall and interfacing with the external fixation, with at least a portion of the scaffold disposed through an aperture in the vessel wall; and a patch disposed on the inside of the vessel wall and sandwiched between the external fixation and the scaffold, the patch substantially covering the full area of the aperture, thereby sealing the aperture.

In some embodiments, the delivery device of the vascular closure system includes: a first shaft, a second shaft, and a third shaft, wherein each shaft is releasably coupled to a component of the implantable closure device for moving the implantable closure device into position at the aperture; a handle, including: three cams disposed in linear arrangement with the first cam disposed adjacent to the distal end of the handle, the second cam disposed proximally from the first cam, and the third cam disposed proximally from the second cam, the three cams at least partially forming the outer structure of the handle, wherein each of the three cams interacts with a corresponding first hub, second hub, and third hub disposed radially inward of each cam, wherein at least one shaft of the first, second, and third shafts is disposed concentrically within at least one other shaft of the first, second, and third shafts; and a cannula assembly for holding the implantable closure device prior to positioning the implantable closure device at the aperture.

In some embodiments, each of the first cam, second cam, and third cam includes a hollow cylinder comprising ridges parallel to the axis of the cylinder on the outer surface of the cylinder.

In some embodiments, each of the first cam, second cam, and third cam includes a helical track on the inner surface of each cylinder, and each of the first hub, second hub, and third hub comprises two cam follower protrusions to interface with the helical tracks of each of the first cam, second cam, and third cam to convert rotational movement of the cams into linear movement of the hubs. In some embodiments, the rotational movement of the cams is converted into rotational movement of the hubs.

In some embodiments, the handle of the vascular closure system includes at least one cam lock for releasably stopping movement of at least one cam, wherein the cam lock includes a depressible button.

In some embodiments, the closure system further includes a packaging tray and lid assembly containing the delivery device and implantable closure device, the packaging tray and lid assembly including: a packaging tray for holding the delivery device and a packaging funnel; and a packaging lid releasably coupled to the packaging tray to retain the delivery device, wherein the packaging funnel contains the implantable closure device, and wherein the packaging funnel is positioned at the distal end of the delivery device.

In some embodiments, the packaging tray includes a rectangular exterior and an interior shaped to match the external shape of the delivery device and the packaging funnel.

In some embodiments, the packaging lid includes a plurality of protrusions that are releasably pressed into a plurality of indentations on the outer rim of the upper surface of the packaging tray.

In some embodiments, the packaging funnel includes a mouth, a tapered stem, a spout, and a lever connected to the spout via a hinge for releasably coupling the packaging funnel to a portion of the delivery device.

In some embodiments, the sheath assembly includes: a sheath shaft including a hollow cylinder and evenly spaced distance markings on the exterior surface of the hollow cylinder; a sheath hub including a proximal mouth opening, a distal primary opening connected to the proximal end of the sheath shaft, and a flush tube opening disposed at an angle from the distal primary opening; a flush tube connected to the flush tube opening; a three-way stopcock valve connected to the distal end of the flush tube; and a sheath seal disposed within the proximal mouth opening of the sheath hub, the sheath seal including a flexible polymeric disc with a linear slit disposed in the center of the flexible polymeric disc.

In some embodiments, the dilator assembly includes: a dilator shaft including a hollow cylinder with a tapered distal end; a dilator hub including a proximal mouth opening, two spring clips that can be releasably coupled with the sheath hub; and a dilator insert including a cylindrical body and a narrowed interior lumen.

In some embodiments, the cannula assembly includes: a cannula body including a hollow cylindrical body, a flange at the distal end of the cannula body, and a protrusion on the distal surface of the flange; a cannula tube including a hollow cylinder disposed within the interior lumen of the cannula body; and a cannula cap disposed at the proximal end of the cannula body.

In another aspect, the present embodiments are directed to a vascular closure system for sealing an aperture in a wall of a body vessel, including: an implantable closure device; a delivery device for delivery of the implantable closure device, including: a first shaft, a second shaft, and a third shaft, wherein each shaft is releasably coupled to a component of the implantable closure device for moving the implantable closure device into position at the aperture; and an introducer assembly including a sheath assembly, a dilator assembly disposed coaxially inside the sheath assembly, and a guidewire.

In some embodiments, the implantable closure device includes: an external fixation disposed on the outside of the vessel wall; a scaffold disposed on the inside of the vessel wall and interfacing with the external fixation, with at least a portion of the scaffold disposed through an aperture in the vessel wall; and a patch disposed on the inside of the vessel wall and sandwiched between the external fixation and the scaffold, the patch substantially covering the full area of the aperture, thereby sealing the aperture.

In some embodiments, the delivery device further includes: a handle, including: three cams disposed in linear arrangement with the first cam disposed adjacent to the distal end of the handle, the second cam disposed proximally from the first cam, and the third cam disposed proximally from the second cam, the three cams at least partially forming the outer structure of the handle, wherein each of the three cams interacts with a corresponding first hub, second hub, and third hub disposed radially inward of each cam, wherein at least one shaft of the first, second, and third shafts is disposed concentrically within at least one other shaft of the first, second, and third shafts; and a cannula assembly for holding the implantable closure device prior to positioning the implantable closure device at the aperture.

In some embodiments, each of the first cam, second cam, and third cam includes a hollow cylinder comprising ridges parallel to the axis of the cylinder on the outer surface of the cylinder, wherein each of the first cam, second cam, and third cam includes a helical track on the inner surface of each cylinder, wherein each of the first hub, second hub, and third hub includes two cam follower protrusions to interface with the helical tracks of each of the first cam, second cam, and third cam to convert rotational movement of the cams into linear movement of the hubs, and wherein the rotational movement of the cams is converted into rotational movement of the hubs, and wherein the handle includes at least one cam lock for releasably stopping movement of at least one cam, wherein the cam lock includes a depressible button.

In some embodiments, the sheath assembly includes: a sheath shaft including a hollow cylinder and evenly spaced distance markings on the exterior surface of the hollow cylinder; a sheath hub including a proximal mouth opening, a distal primary opening connected to the proximal end of the sheath shaft, and a flush tube opening disposed at an angle from the distal primary opening; a flush tube connected to the flush tube opening; a three-way stopcock valve connected to the distal end of the flush tube; and a sheath seal disposed within the proximal mouth opening of the sheath hub, the sheath seal including a flexible polymeric disc with a linear slit disposed in the center of the flexible polymeric disc, wherein the dilator assembly includes: a dilator shaft including a hollow cylinder with a tapered distal end; a dilator hub including a proximal mouth opening, two spring clips that can be releasably coupled with the sheath hub; and a dilator insert including a cylindrical body and a narrowed interior lumen, and wherein the cannula assembly includes: a cannula body including a hollow cylindrical body, a flange at the distal end of the cannula body, and a protrusion on the distal surface of the flange; a cannula tube including a hollow cylinder disposed within the interior lumen of the cannula body; and a cannula cap disposed at the proximal end of the cannula body.

In another aspect, the present embodiments are directed to a method of sealing an aperture in a wall of a body vessel using a vascular closure device and a delivery device to deliver the vascular closure device, including: providing a patient with a guidewire and a sheath assembly disposed in the aperture of the body vessel; providing the vascular closure device and the delivery device; loading an implant for vascular closure into a cannula of the delivery device, and removing the delivery device from a packaging tray in which the delivery device and the implant were provided; engaging the cannula of the delivery device with a sheath hub of the sheath assembly disposed in the body vessel; pushing the delivery device distally until the implant reaches the end of the sheath shaft; rotating a sheath cam on a handle of the delivery device by 360° to retract the cannula proximally and to push the implant distally out of the end of the sheath shaft; pulling the delivery device assembly distally so that the implant reaches the inner wall of the body vessel at the location of the aperture to be closed; depressing a fixation cam lock on the handle of the delivery device to enable rotation of a fixation cam on the handle of the delivery device; and rotating the fixation cam on the handle of the delivery device by 360° to push an external fixation out of the cannula and onto a scaffold of the implant.

In some embodiments, the method further includes, after rotating the fixation cam on the handle of the delivery device by 360°: pulling the guidewire proximally out of the delivery device and away from the patient; rotating a release cam on the handle of the delivery device by 180° to push a guidewire closure pin into a guidewire lumen in the scaffold of the implant and to unhook the scaffold from a bayonet shaft of the delivery device; and pulling the delivery device proximally away from the patient.

In another aspect, the present embodiments include an implantable device for sealing an aperture in a tissue of a body vessel, the implantable device comprising: an external fixation disposed on the outside of a vessel wall; a scaffold disposed on the inside of the vessel wall and interfacing with the external fixation, at least a portion of the scaffold disposed through an aperture in the vessel wall; and a patch disposed on the inside of the vessel wall and sandwiched between the external fixation and the scaffold, the patch substantially covering the full area of the aperture, thereby sealing the aperture.

In another aspect, the present disclosure provides a system for sealing an aperture in a tissue of a body vessel of a subject, which comprises (1) an implantable device comprising a flexible (e.g., rollable) patch that (a) is positionable against an internal surface of the tissue adjacent the aperture in the tissue when the implantable device is in a sealing position, (b) comprises a flexible substrate and a mesh layer disposed on (e.g., in contact with) the flexible substrate, and (c) has an elongated shape so that a longitudinal dimension of the flexible patch is greater than a lateral dimension of the flexible patch (e.g., wherein the flexible patch is oval in shape) (e.g., wherein the longitudinal dimension is at least 10, 20, 30, 40 or 50% greater than the lateral dimension); and (ii) a delivery device for delivering the implantable device into the subject for positioning of the flexible patch against the internal surface of the tissue adjacent the aperture.

In some embodiments, an average thickness of the flexible patch is greater than 100 μm (e.g., within a range of 100 μm to 500 μm, 200 μm to 400 μm, 200 μm to 300 μm, 200 μm to 280 μm or 200 μm to 250 μm).

In some embodiments, the aperture is located in a blood vessel, and a longitudinal axis of the flexible patch is aligned with (e.g., parallel to) a longitudinal axis of the blood vessel.

In some embodiments, the longitudinal dimension of the flexible patch is within a range of about 6 mm to about 10 mm and the lateral dimension of the flexible patch is within a range of about 4 mm to about 8 mm (e.g., wherein an outer diameter of the aperture is about 10 F, or French (i.e., French scale for catheter size, where 1 F=⅓ mm)).

In some embodiments, the longitudinal dimension of the flexible patch is within a range of about 10 mm to about 14 mm and the lateral dimension of the flexible patch is within a range of about 7 mm to about 11 mm (e.g., wherein an outer diameter of the aperture is about 15 F).

In some embodiments, the longitudinal dimension of the flexible patch is within a range of about 13 mm to about 17 mm and the lateral dimension of the flexible patch is within a range of about 10 mm to about 14 mm (e.g., wherein an outer diameter of the aperture is about 20 F).

In some embodiments, the longitudinal dimension of the flexible patch is within a range of about 18 mm to about 22 mm and the lateral dimension of the flexible patch is within a range of about 13 mm to about 17 mm (e.g., wherein an outer diameter of the aperture is about 26 F).

In some embodiments, the longitudinal dimension of the flexible patch is within a range of about 21 mm to about 25 mm and the lateral dimension of the flexible patch is within a range of about 15 mm to about 19 mm (e.g., wherein an outer diameter of the aperture is about 30 F).

In some embodiments, the longitudinal dimension of the flexible patch is within a range of about 25 mm to about 29 mm and the lateral dimension of the flexible patch is within a range of about 18 mm to about 22 mm (e.g., wherein an outer diameter of the aperture is about 35 F).

In some embodiments, an average thickness of the flexible substrate is within a range of 100 μm to 500 μm, 150 μm to 300 μm, 150 μm to 250 μm, or 190 μm to 220 μm.

In some embodiments, an average thickness of the mesh layer is within a range of 5 μm to 200 μm, 20 μm to 100 μm, or 20 μm to 80 μm.

In some embodiments, the mesh layer is in contact with the aperture when in the sealing position.

In some embodiments, the implantable device further comprises a support member or scaffold.

In some embodiments, the support member or scaffold comprises a base plate and a column or neck, the neck is disposed in and through the aperture, and the base is disposed in the body vessel to retain the patch against the interior surface of the tissue of the body vessel when the device is in the sealing position.

In some embodiments, the delivery system contains the implantable device, and the flexible patch is in a rolled conformation therein.

In some embodiments, the mesh layer comprises a plurality of electrospun fibers (e.g., facilitates tissue adhesion to the flexible patch by promoting platelet aggregation, or blood clotting with fibrin reinforcement of a platelet plug, etc., in the sealing position).

In some embodiments, the mesh layer comprises a synthetic agent and/or a biological agent.

In some embodiments, the implantable device comprises at least one material selected from the group consisting of polydioxanone, poly-L-lactide, poly-D-lactide, poly-DL-lactide, polyglycolide, ε-caprolactone, polyethylene glycol, and copolymers thereof.

In some embodiments, the implantable device comprises an external fixation positionable near an exterior surface of the tissue adjacent to the aperture when the device is in the sealing position. In some embodiments, the external fixation is moveable to be positioned near the exterior surface of the tissue adjacent to the aperture such that a portion of the tissue is disposed between the external fixation and the patch when the device is in the sealing position (e.g., wherein the neck comprises an engagement portion to secure the external fixation to the scaffold).

In some embodiments, the mesh layer comprises a plurality of fibers each having a diameter in a range from 0.3 μm to 8 μm.

In some embodiments, the plurality of fibers makes up from 1 volume % to 35 volume % or 5 volume % to 25 volume % of the mesh layer.

In some embodiments, the system includes a closure pin disposed within the scaffold neck for sealing the guidewire lumen after the guidewire is removed from the guidewire lumen. The closure pin may include an angled tip, a substantially circular pin head, a pair of first and second distally extending arms, a rupture portion, an offset bore, an angled pin, a slidable rod, and/or an L-shaped closure pin. Distally pushing the closure pin into the scaffold neck causes the closure pin to seal the guidewire lumen.

In some embodiments, the scaffold neck includes an internal taper, a gradual tapered portion, a ramp portion, a sleeve portion, an angled surface, and/or a partial bore.

In some embodiments, the scaffold neck extends externally at an angle from the base plate, the neck including at least one lumen disposed therethrough.

In some embodiments, the scaffold neck includes at least two retaining tabs, wherein the retaining tabs are disposed circumferentially around the exterior of the scaffold neck and extend radially away from the scaffold neck, and wherein the retaining tabs interface with a collar of the external fixation, thereby causing the external fixation to be coupled to the scaffold, with the patch sandwiched between the base plate of the scaffold and the external fixation.

In some embodiments, the external fixation includes: a collar; a base ring; an anterior rib connecting the collar and the base ring; and a posterior post connecting the collar and the base ring. In some embodiments, the external fixation further includes a tab disposed at an angle from the collar, the tab including a protrusion.

In some embodiments, the scaffold comprises a threaded portion at the base of the neck, the threads of the threaded portion interacting with the opening of the patch to hold the patch against the upper surface of the base plate of the scaffold.

In some embodiments, the closure pin includes: a cylindrical body; a tip disposed at the distal end of the cylindrical body that comprises at least one of an angled tip and a stepped tapered tip; and a substantially cylindrical head disposed at the proximal end of the cylindrical body.

In some embodiments, the pin head comprises a rectangular cutout, the rectangular cutout interfacing with the protrusion on the external fixation.

In some embodiments, the scaffold neck comprises at least one of an internal taper, a gradual tapered portion, and a ramp portion.

In some embodiments, each retaining tab of the scaffold neck includes: a first protrusion; a notch; a flat portion; and a second protrusion, wherein the first protrusion, the notch, the flat portion, and the second protrusion are arranged longitudinally within the retaining tab along an axial direction of the scaffold neck, wherein the first protrusion and the second protrusion extend out radially from the surface of the scaffold neck, wherein the first protrusion extends further radially outwardly than the second protrusion, and wherein the notch is disposed at a smaller radius that the second protrusion.

In some embodiments, a longitudinal dimension of the patch is within a range of about 6 to about 29 mm and a lateral dimension of the patch is within a range of about 4 mm to about 22 mm.

In some embodiments, the patch includes: a base layer having a thickness within a range of 190-220 μm; and an electrospun layer having a thickness within a range of 20-80 μm, wherein a total thickness of the patch is within a range of 210-300 μm.

In some embodiments, the patch comprises an opening disposed at the center of the patch, the scaffold neck passing through the opening in the patch.

In another aspect, the present embodiments are directed to a vascular closure system for sealing an aperture in a tissue of a body vessel, the system including: the implantable device; and a device delivery system, wherein the implantable device is stowed within the delivery system with the patch in a rolled configuration prior to delivery of the implantable device to the aperture in the tissue of the body vessel.

In some embodiments, the delivery system includes: an introducer sheath; a guidewire; a pusher shaft (or push tube); a delivery shaft; a loading cannula; a receiving funnel; an outer shaft (or fixation shaft); and a handle.

In some embodiments, the patch includes: a base layer comprising a thickness within a range of 190-220 μm; and an electrospun layer comprising a thickness within a range of 20-80 μm, wherein the total thickness of the patch is within a range of 210-300 μm.

In some embodiments, the handle comprises a handle body, a rotatable sheath cam, a cam lock, a rotatable fixation cam, and a rotatable release cam. In some embodiments, rotating the rotatable sheath cam causes the sheath to retract proximally, thereby allowing the scaffold and patch to exit from the introducer sheath and expand within the vessel. In some embodiments, rotating the rotatable fixation cam causes the external fixation to advance distally toward the scaffold and patch, thereby allowing the neck of the scaffold to engage with the collar of the external fixation.

In some embodiments, rotating the release cam causes the closure pin to be pushed into the neck of the scaffold, and causes the implantable device to be released.

In another aspect, the present embodiments are directed to a method of sealing an aperture in a body vessel using an implantable closure device and a closure system, including the following steps: inserting an introducer sheath of the closure system into a surgical opening and into the aperture; loading the implantable closure device into a loading cannula of the closure system; connecting the loading cannula to a receiving funnel of the closure system; pushing a handle of the closure system proximally to engage with the loading cannula; rotating a sheath cam on the handle by 360°; pulling the closure system proximally to retract the delivery system until the closure device is at the position of the aperture in the vessel to be closed; depressing a cam lock button on the handle; rotating a fixation cam on the handle by 360°; pulling a guidewire of the closure system proximally to remove it from the delivery system; rotating a release cam on the handle by 180°; and pulling the closure system proximally until the delivery system is completely removed from the surgical opening.

In another aspect, the present embodiments are directed to a vascular closure system for sealing an aperture in a wall of a body vessel, the system comprising: a vascular closure device assembly (72) comprising a closure pin (70), a flexible patch (22), a scaffold comprising a scaffold base (20) and scaffold neck (30), and an external fixation component (18 or 1706), wherein the scaffold neck comprises multiple retaining tabs (24) extending out of the scaffold neck (30); and a delivery device for delivery of the vascular closure device assembly.

In certain embodiments, the delivery device for delivery of the vascular closure device comprises one or more rotatable fixation cams (1718, 1738, 1714, 1740, 1720, 1734).

In certain embodiments, the one or more rotatable fixation cams are rotatable to perform one, two, or all three of (i), (ii), and (iii) as follows: (i) retract an introducer sheath (e.g., in order to expose the vascular closure device assembly in the vessel), (ii) push the external fixation component (18 or 1706) toward the scaffold and snap onto the scaffold, and (iii) deploy a guidewire hole blocking pin and release the vascular closure device.

In certain embodiments, the one or more rotatable fixation cams comprises one or more cams rotatable to push a guidewire pin into the scaffold and simultaneously detach the scaffold from a bayonet (1731) of a delivery shaft of the delivery device.

In certain embodiments, the external fixation component (18 or 1706) has a cage-like (e.g., three-dimensional) structure.

In certain embodiments, the delivery device for delivery of the vascular closure device assembly comprises: one or more shafts (e.g., three shafts) each releasably coupled to a component of the vascular closure device assembly for moving the implantable vascular closure device assembly into position (e.g., at the aperture); and an introducer assembly comprising a sheath assembly, a dilator assembly disposed coaxially inside the sheath assembly, and a guidewire.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable and/or bioabsorbable.

As used herein, a "cam" is a rotating or sliding part of a device that operates as a portion in a mechanical linkage to transform rotary motion into linear motion.

As used herein, a "carriage" is a movable part of a device that supports or enables the movement of another movable part.

As used herein, a "fixation" or "external fixation" is a mechanical part or apparatus that immobilizes and aligns some portion(s) of a patient's anatomy with, optionally, another apparatus or part in order to promote healing in the patient of some injury. In some embodiments, an external fixation is a part of an implantable vascular closure device that holds other components of the closure device against a vessel opening or arteriotomy so that the opening may heal. As used herein, a fixation or an external fixation does not refer to an apparatus attached to the exterior of a limb to facilitate healing of broken bones.

As used herein, "bioabsorbable" materials are those that, when introduced into cells, are broken down by cellular machinery (e.g., enzymatic degradation) or by hydrolysis into components that cells can either reuse, reabsorb, or dispose of without significant toxic effects on the cells. In certain embodiments, components generated by breakdown of a bioabsorbable material do not induce inflammation and/or other adverse effects in vivo. In some embodiments, bioabsorbable materials are enzymatically broken down. Alternatively or additionally, in some embodiments, bioabsorbable materials are broken down by hydrolysis. In some embodiments, bioabsorbable polymeric materials break down into their component polymers and/or monomers. In some embodiments, breakdown of bioabsorbable materials (including, for example, bioabsorbable polymeric materials) includes hydrolysis of ester bonds. In some embodiments, breakdown of materials (including, for example, bioabsorbable polymeric materials) includes cleavage of urethane linkages.

As used herein, "implant" is an object that is placed within a subject during a medical operation. The object may be biodegradable and/or bioabsorbable.

As used herein, "mesh" materials are those that, when introduced into a blood vessel, promote platelet capture (e.g., whereby the captured platelets encourages localized platelet activation, e.g., due to the contact with the collagen from the exposed wound, at the wound surface).

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

As used herein, the term "substantially", and grammatical equivalents, refer to the qualitative condition of exhibiting at least a majority and total or near-total extent or degree of a characteristic or property of interest. One of ordinary skill in the art will understand that material and chemical phenomena rarely, if ever, go to completion and/or proceed to completeness or achieve or avoid an absolute result.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Figures are presented herein for illustration purposes only, not for limitation.

BRIEF DESCRIPTION OF THE DRAWINGS

The Drawings, which are comprised of at least the following Figures, is for illustration purposes only, not for limitation.

FIG. 115 is another cut-away perspective view of the interior of a delivery system handle, according to aspects of the present embodiments.

FIG. 116 is a flow chart diagram of a method of sealing an aperture, according to aspects of the present embodiments.

FIG. 117 is a perspective view of a delivery system assembly, according to aspects of the present embodiments.

FIG. 118 is a side view (left) and a front view (right) of a delivery system assembly, according to aspects of the present embodiments.

FIG. 119 is an image of exploded parts of a vascular closure device (VCD) assembly that is part of a delivery system assembly, according to aspects of the present embodiments.

FIGS. 120A and 120B are images of parts of a VCD assembly (sheath cam top and sheath cam bottom pieces), according to aspects of the present embodiments.

FIGS. 121A and 121B are parts of a VCD assembly (fixation cam top and fixation cam bottom pieces), according to aspects of the present embodiments.

FIGS. 122A and 122B are images of parts of a VCD assembly (release cam top, and release cam bottom pieces), according to aspects of the present embodiments.

FIGS. 123A and 123B are images of a cannula assembly that is part of a delivery system assembly, according to aspects of the present embodiments.

FIG. 124A is an image of a funnel, cannula assembly and VCD assembly, according to aspects of the present embodiments.

FIG. 124B is an image of a funnel and canula assembly, including a lever and canula body, according to aspects of the present embodiments.

FIG. 124C is a cross-sectional view of a funnel and cannula assembly, according to aspects of the present embodiments.

Figure 125A:
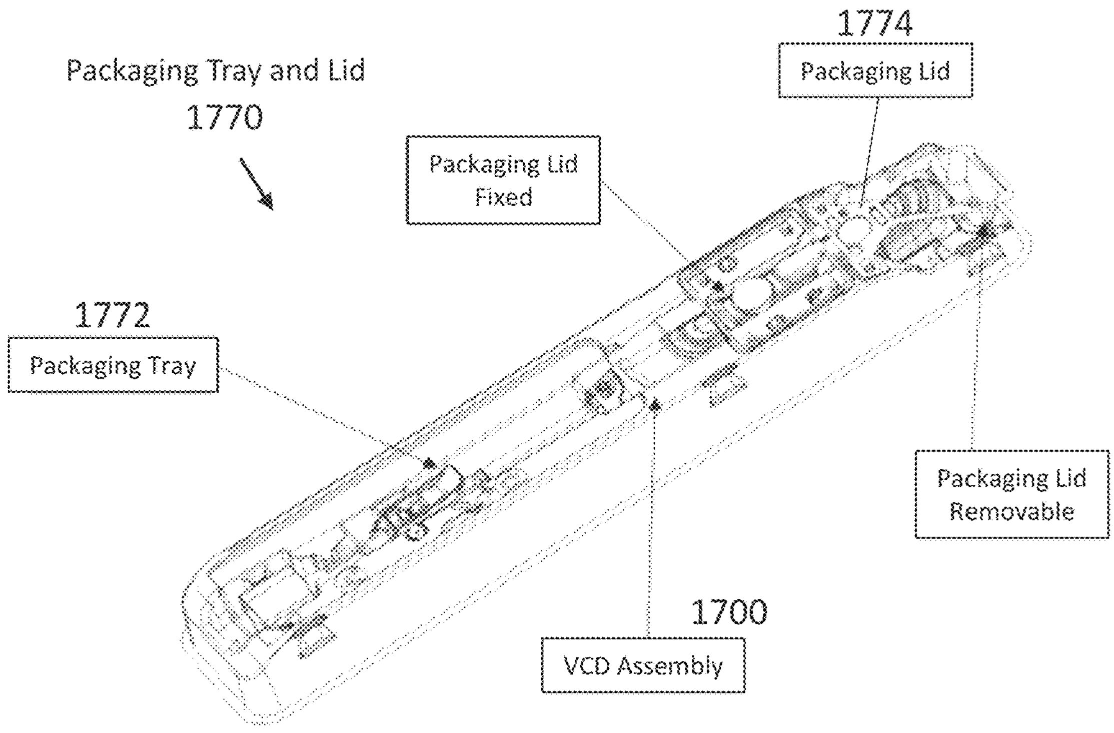

FIG. 125A is an image of a delivery system assembly held in a packaging tray and lid assembly with packaging lid fixed, according to aspects of the present embodiments.

Figure 125B:
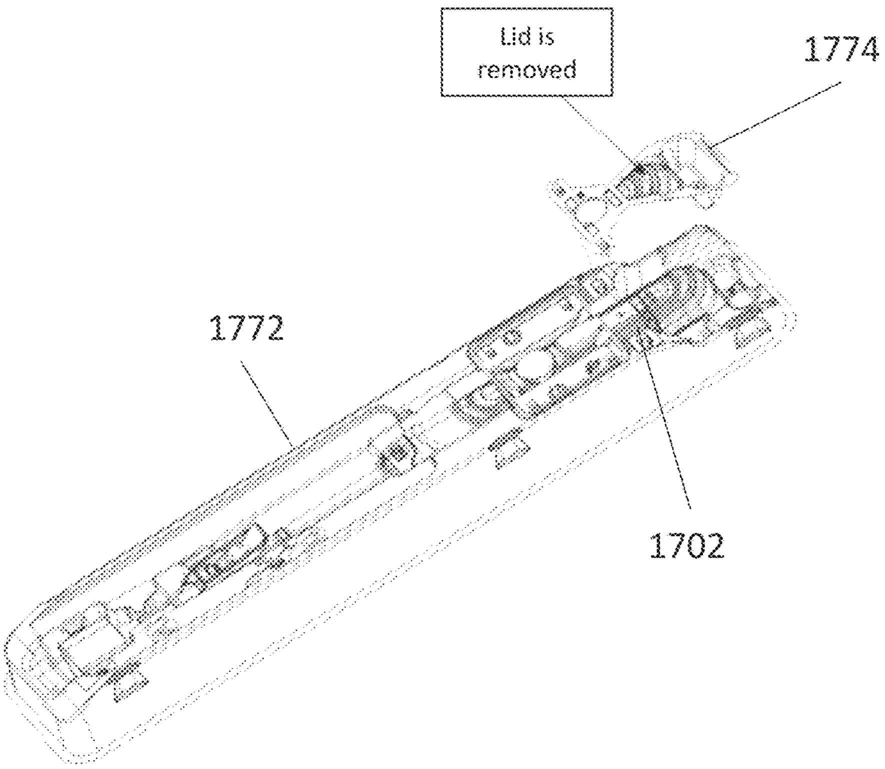

FIG. 125B is an image of a delivery system assembly held in a packaging tray and lid assembly with packaging lid removed, according to aspects of the present embodiments.

FIG. 126A is an image of a delivery system assembly held in a packaging tray with the VCD pulled back until the fixation tip meets the end of the cannula tube, according to aspects of the present embodiments.

FIG. 126B is an image of a funnel and cannula assembly, according to aspects of the present embodiments.

FIG. 126C is a cross-sectional view of a funnel and cannula assembly, where the VCD is pulled back until the fixation tip meets the end of the cannula tube, according to aspects of the present embodiments.

Figure 127A:
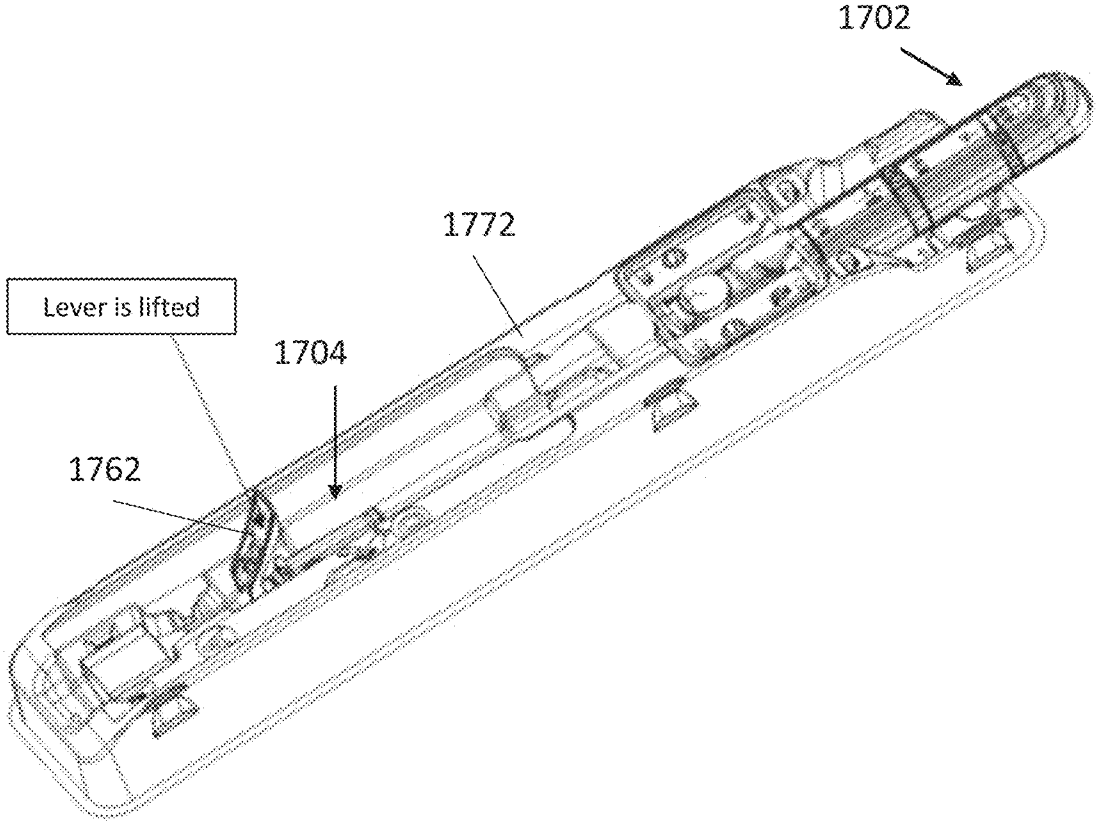

FIG. 127A is an image of a delivery system assembly held in a packaging tray when lever is lifted, according to aspects of the present embodiments.

Figure 127B:
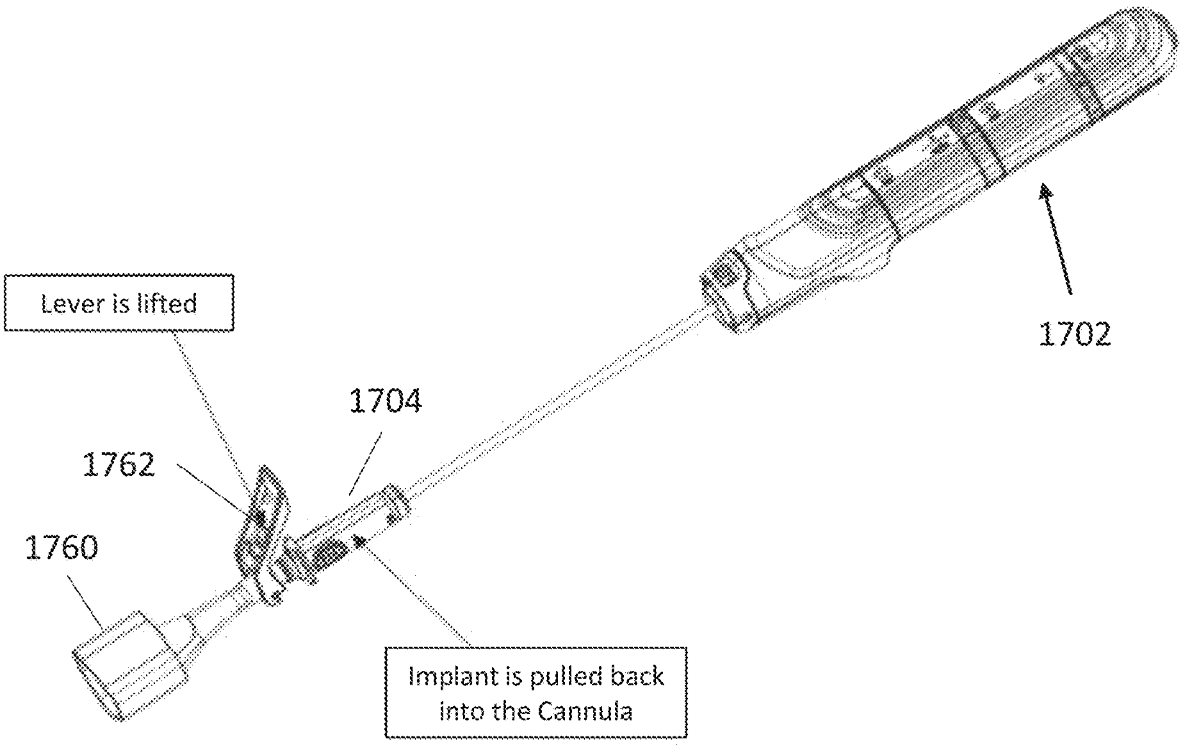

FIG. 127B is an image of a delivery system assembly when the lever is lifted, and the implant is pulled back into the cannula, according to aspects of the present embodiments.

Figure 128A:
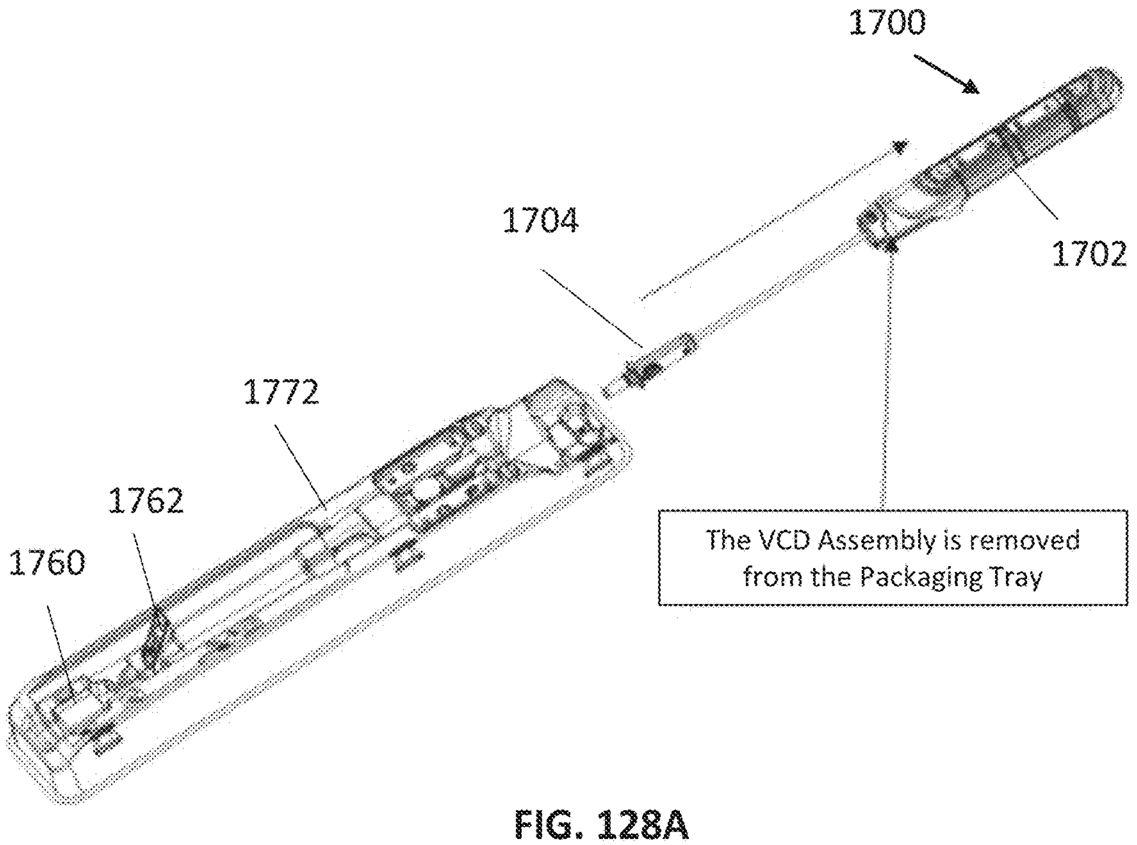

FIG. 128A is an image of a delivery system assembly being removed from the packaging tray, according to aspects of the present embodiments.

Figure 128B:
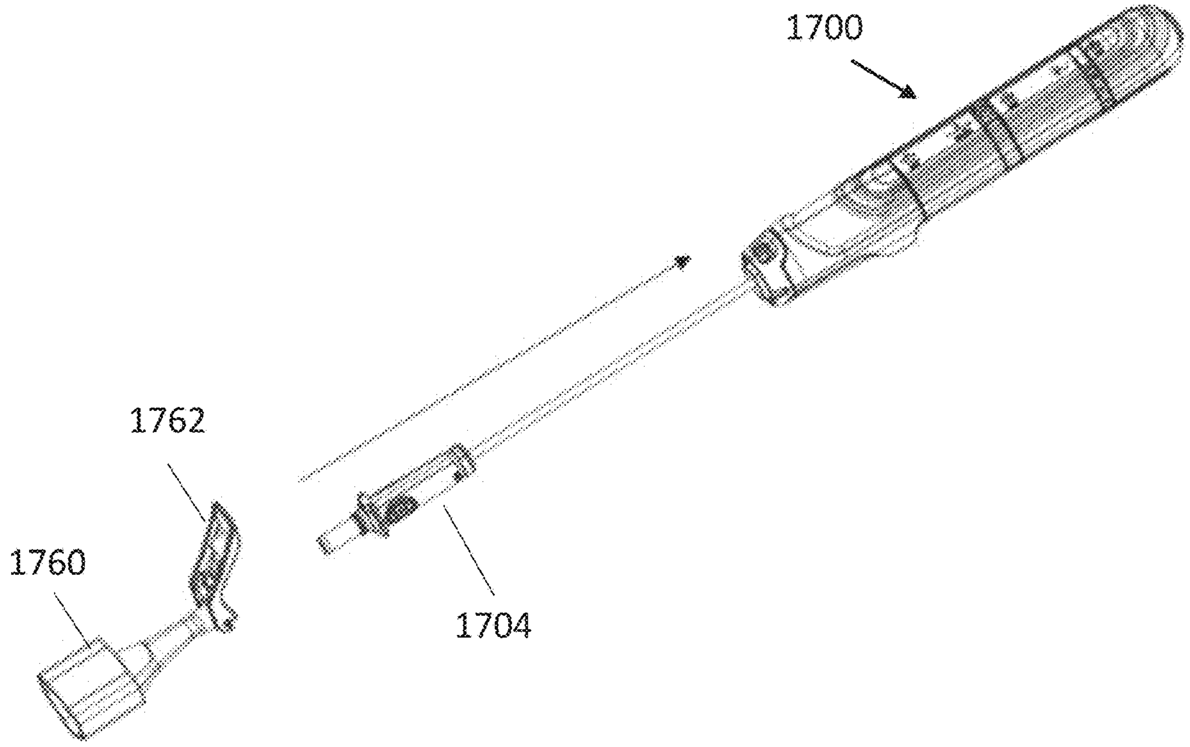

FIG. 128B is an image of the VCD assembly being pulled back from the funnel and lever, according to aspects of the present embodiments.

Figure 129A:
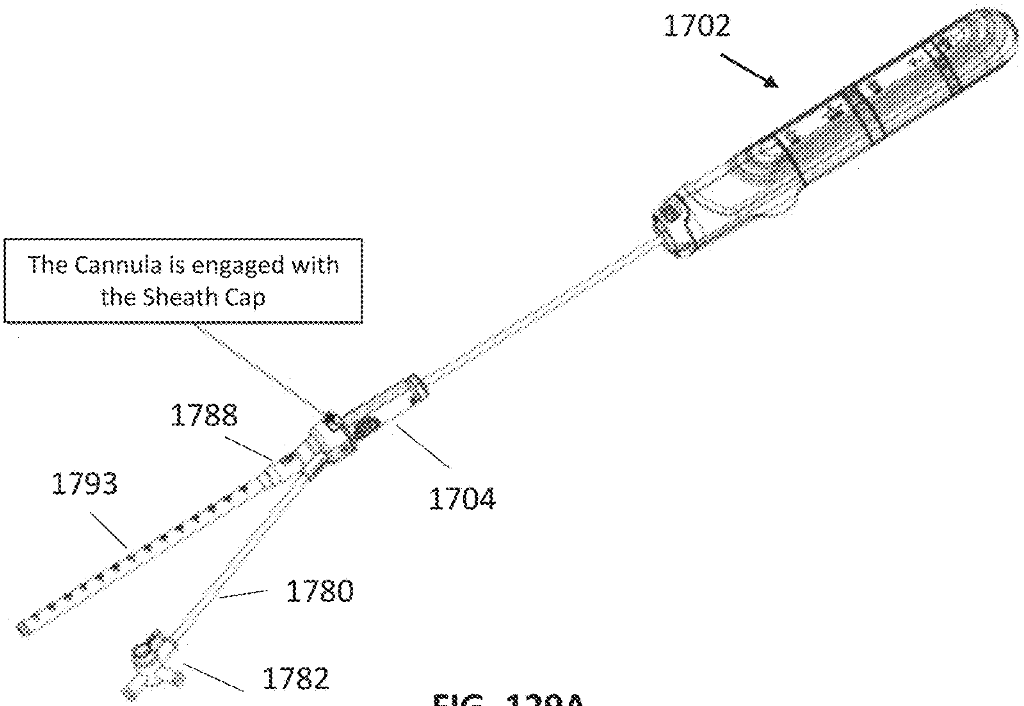

FIG. 129A is a perspective view of the VCD assembly and cannula engaged with the sheath cap of the sheath assembly, according to aspects of the present embodiments.

Figure 129B:
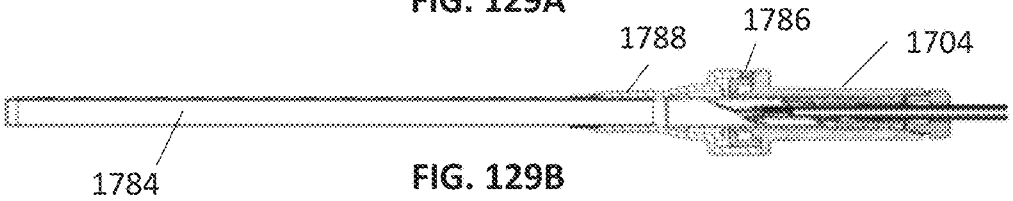

FIG. 129B is a cross-sectional view of the cannula engaged with the sheath cap of the sheath assembly, according to aspects of the present embodiments.

Figure 129C:
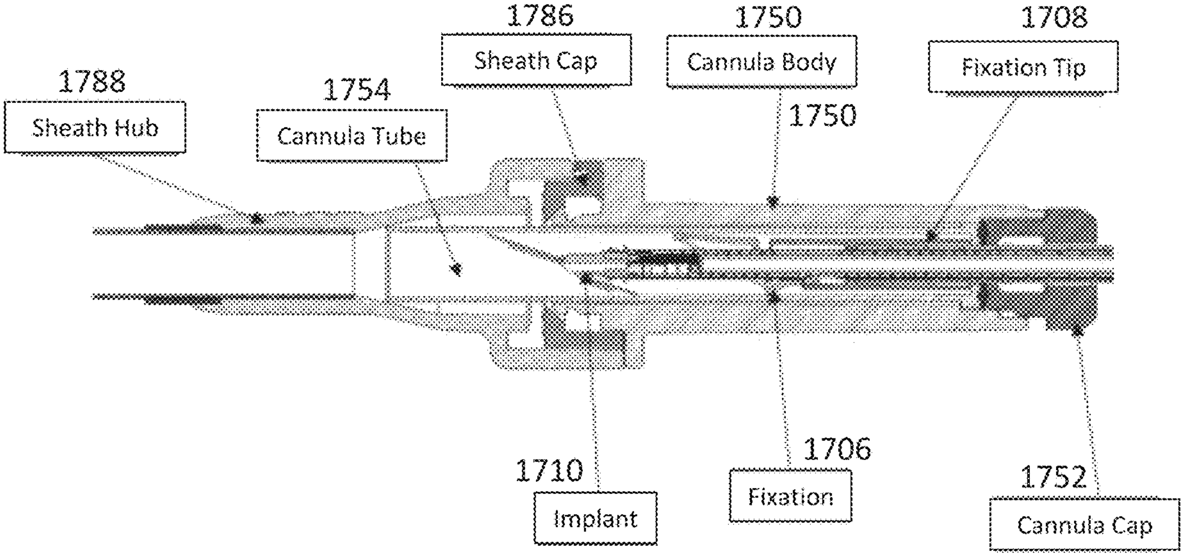

FIG. 129C is an enlarged cross-sectional view of the cannula engaged with the sheath cap of the sheath assembly, according to aspects of the present embodiments.

Figure 130A:
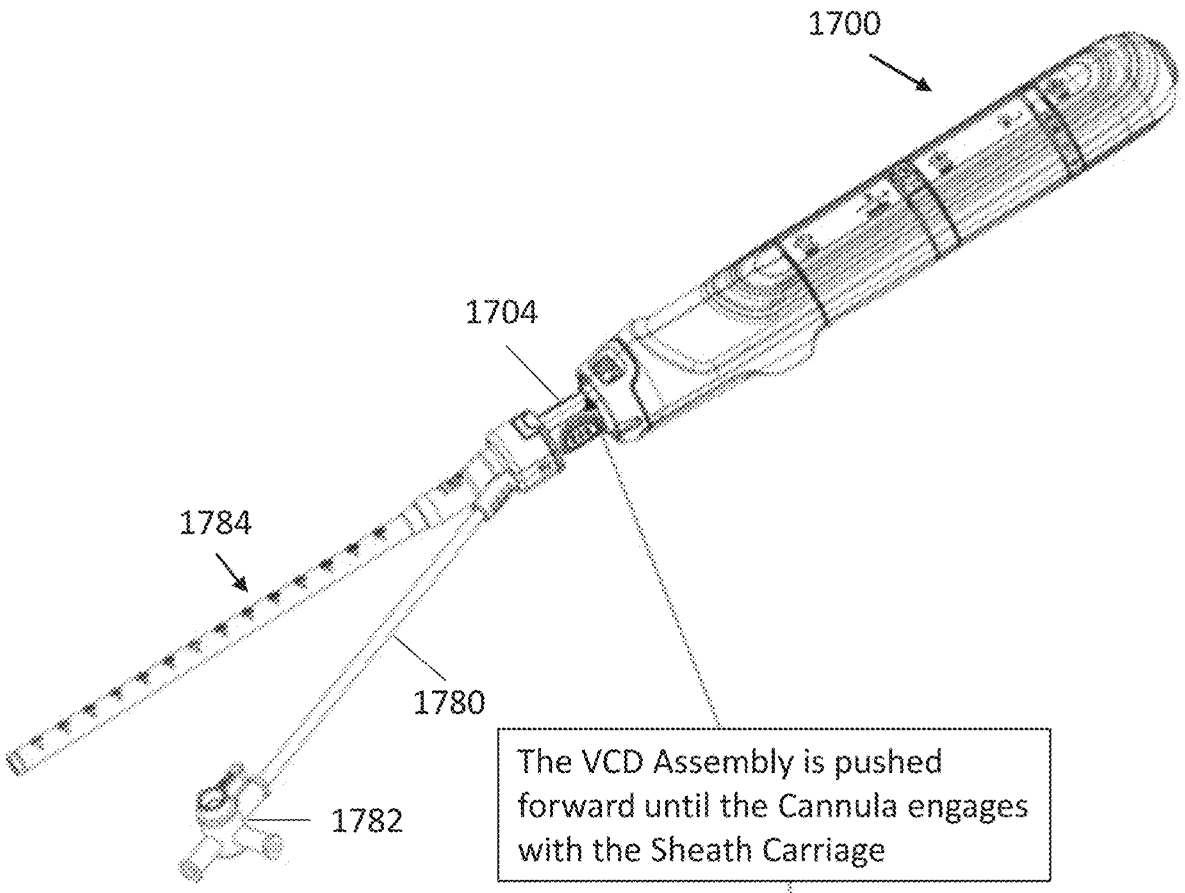

FIG. 130A is an image of a delivery system assembly, where the VCD assembly is pushed forward until the cannula engages with the sheath carriage in the VCD assembly, according to aspects of the present embodiments.

Figure 130B:
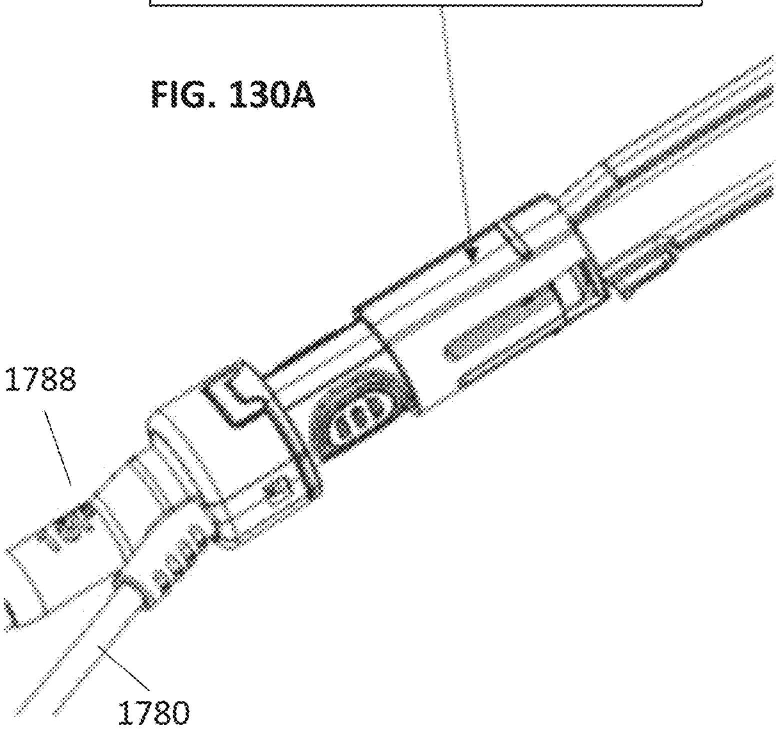

FIG. 130B is an enlarged view of the sheath cap and cannula engaged with the sheath carriage, according to aspects of the present embodiments.

Figure 131A:
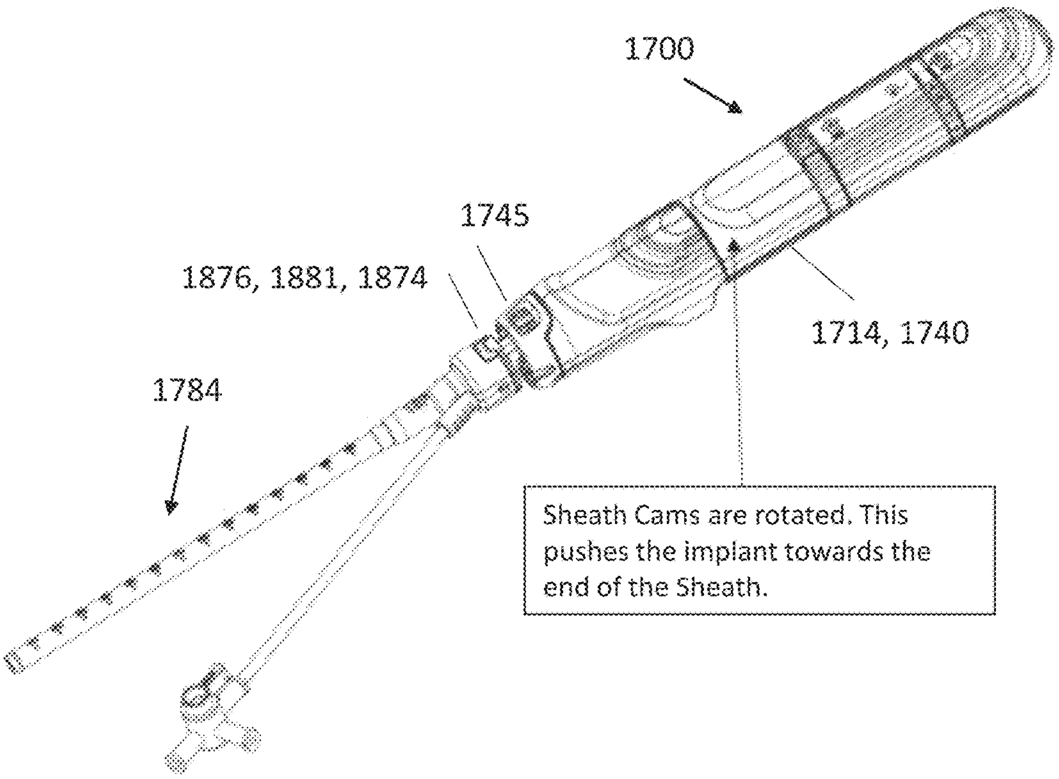

FIG. 131A is an image of a delivery system assembly with VCD assembly engaged with sheath assembly and with sheath cams on the VCD assembly rotated to push the implant towards the end of the sheath, according to aspects of the present embodiments.

Figure 131B:
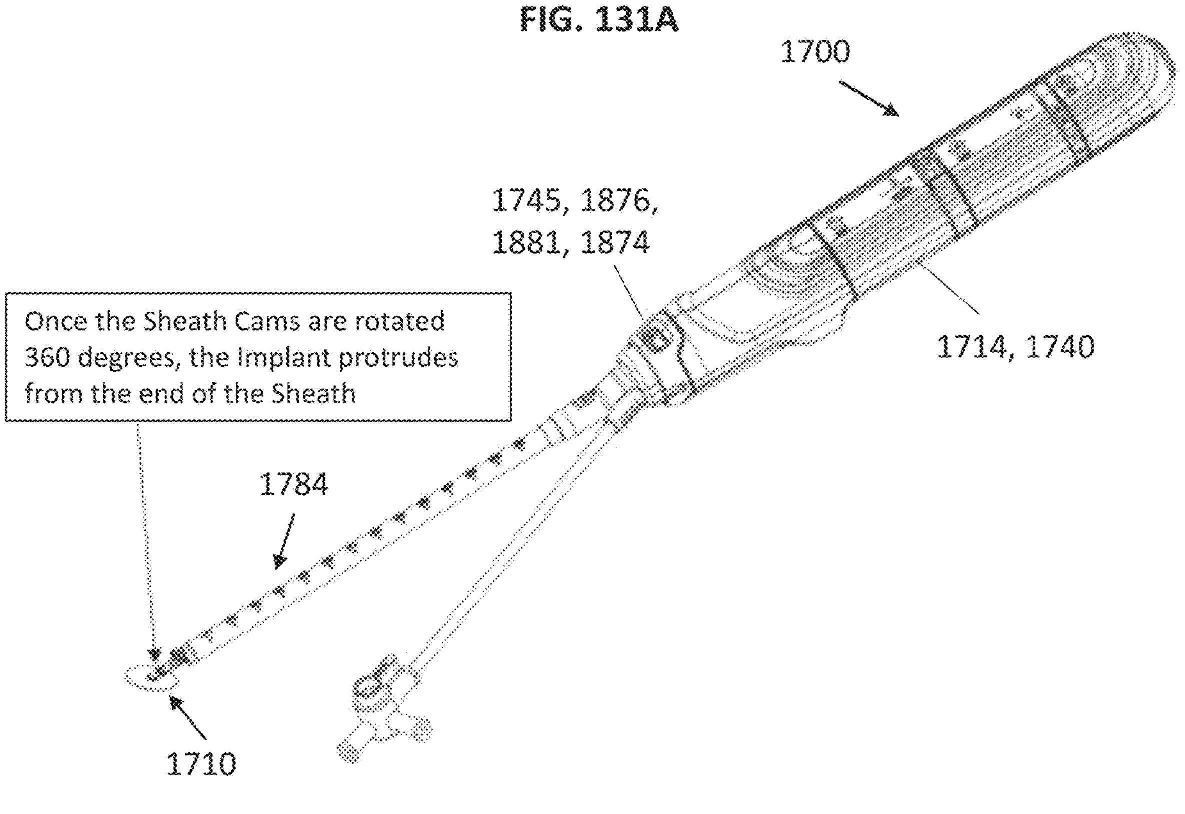

FIG. 131B is an image of a delivery system assembly with VCD assembly engaged with sheath assembly and with implant protruding from the end of the sheath once the sheath cams are rotated 360 degrees, according to aspects of the present embodiments.

Figure 132:
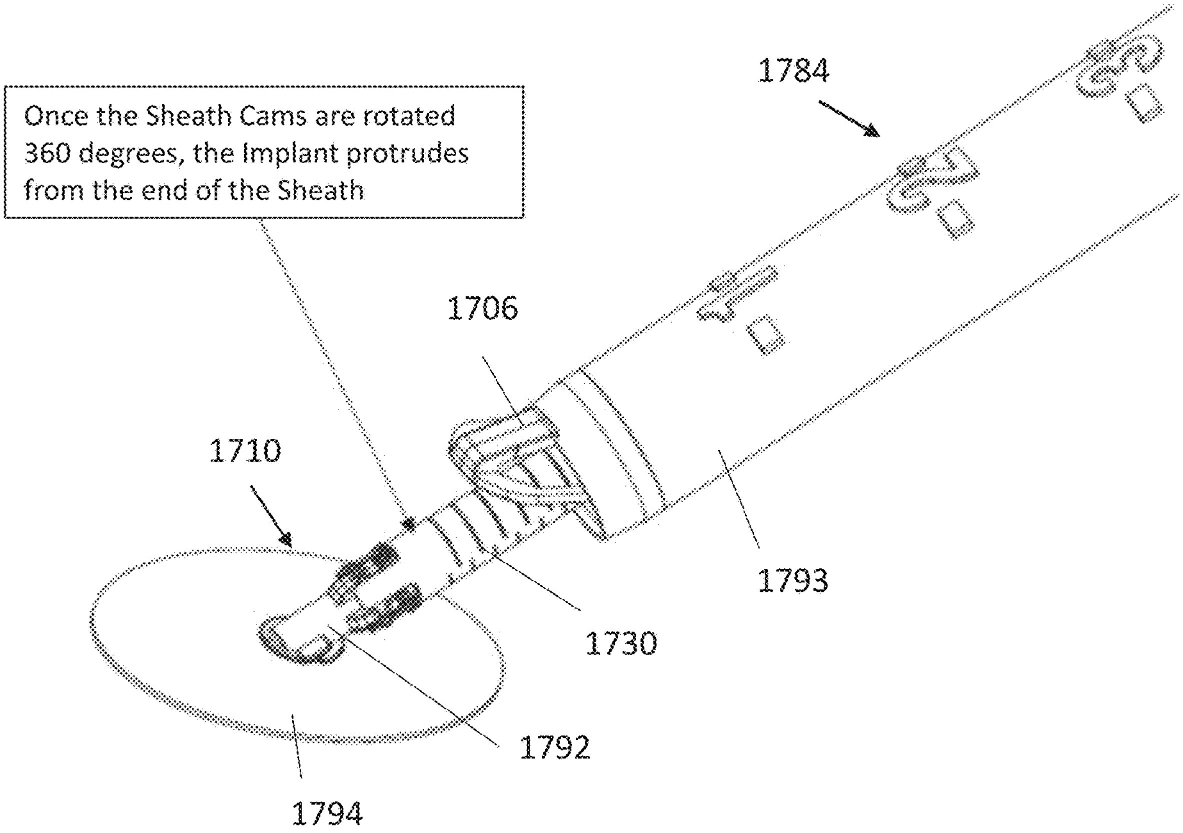

FIG. 132 is an enlarged view of the implant protruding from the end of the sheath after the sheath cams are rotated 360 degrees, according to aspects of the present embodiments.

Figure 133A:
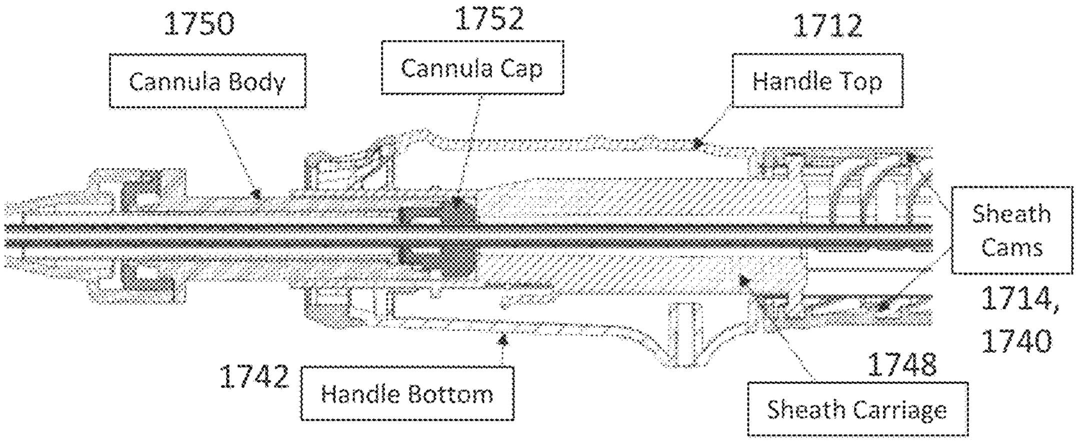

FIG. 133A is a cross-sectional view of the cannula body engaged with the sheath carriage, according to aspects of the present embodiments.

Figure 133B:
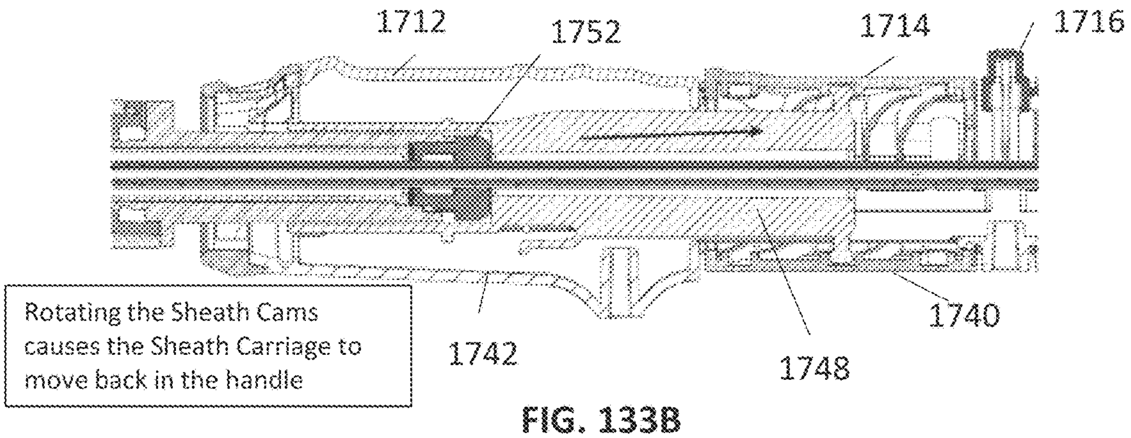

FIG. 133B is a cross-sectional view of the cannula body engaged with the sheath carriage, with the sheath carriage moving back in the handle when the sheath cams are rotated, according to aspects of the present embodiments.

Figure 133C:
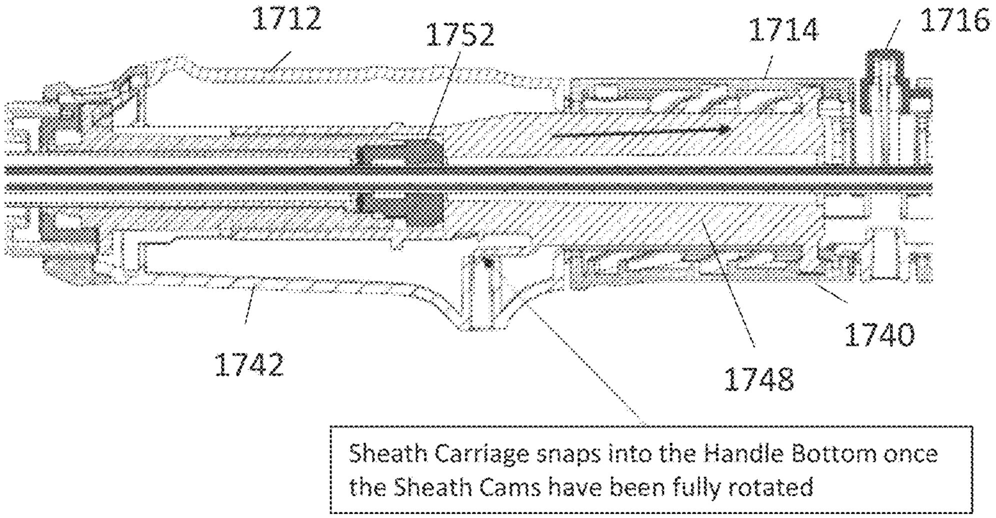

FIG. 133C is a cross-sectional view of the sheath carriage moving into the handle and snapping into the handle bottom once the sheath cams have been fully rotated, according to aspects of the present embodiments.

Figure 134A:
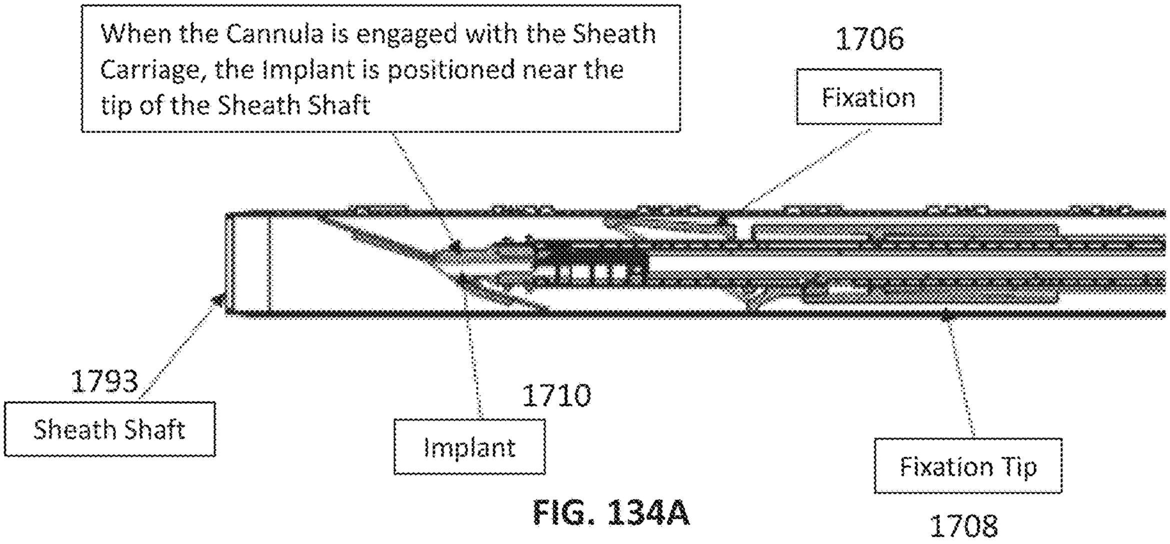

FIG. 134A is a cross-sectional view of the implant positioned near the tip of the sheath shaft while the cannula is engaged with the sheath carriage, according to aspects of the present embodiments.

Figure 134B:
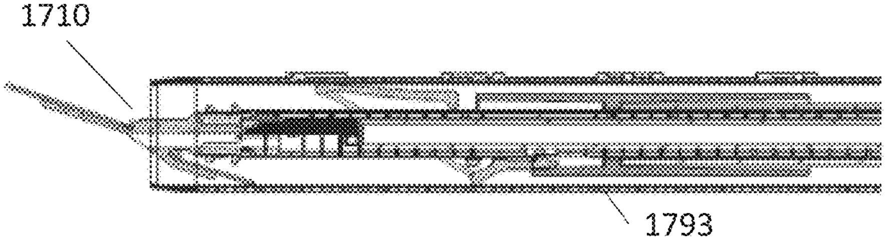

FIG. 134B is a cross-sectional view of the implant partially protruding from the tip of the sheath shaft, according to aspects of the present embodiments.

Figure 134C:
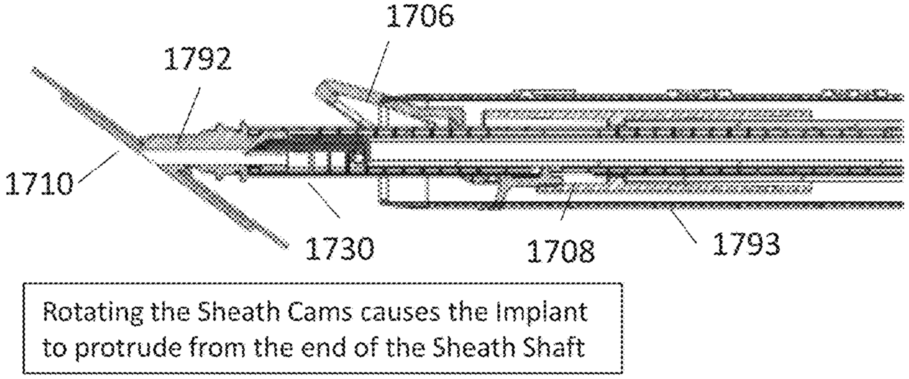

FIG. 134C is a cross-sectional view of the implant fully protruding from the tip of the sheath shaft, according to aspects of the present embodiments.

Figure 135A:
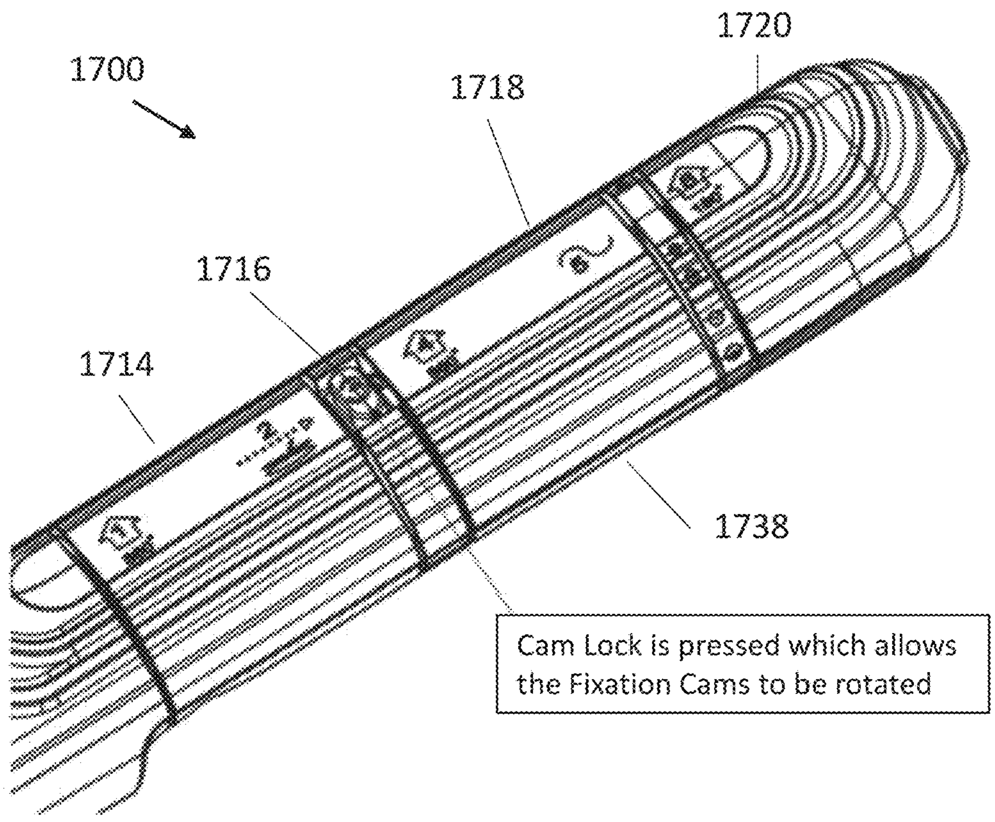

FIG. 135A is an image of a handle of a VCD assembly, with cam lock pressed to allow fixation cams to be rotated, according to aspects of the present embodiments.

Figure 135B:
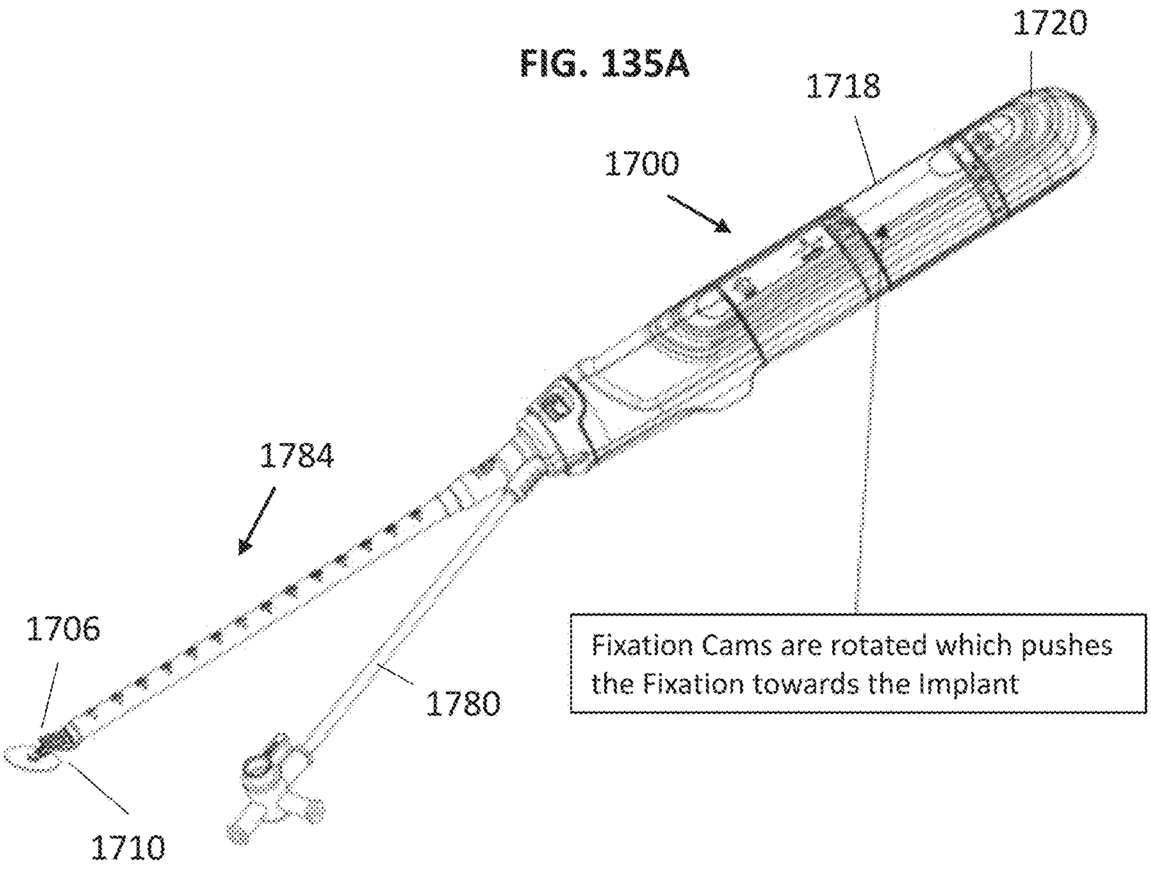

FIG. 135B is an image of a VCD assembly and sheath assembly, with an implant protruding from the sheath and an external fixation advancing toward the implant after the fixation cams are rotated to push the fixation towards the implant, according to aspects of the present embodiments.

Figure 136A:
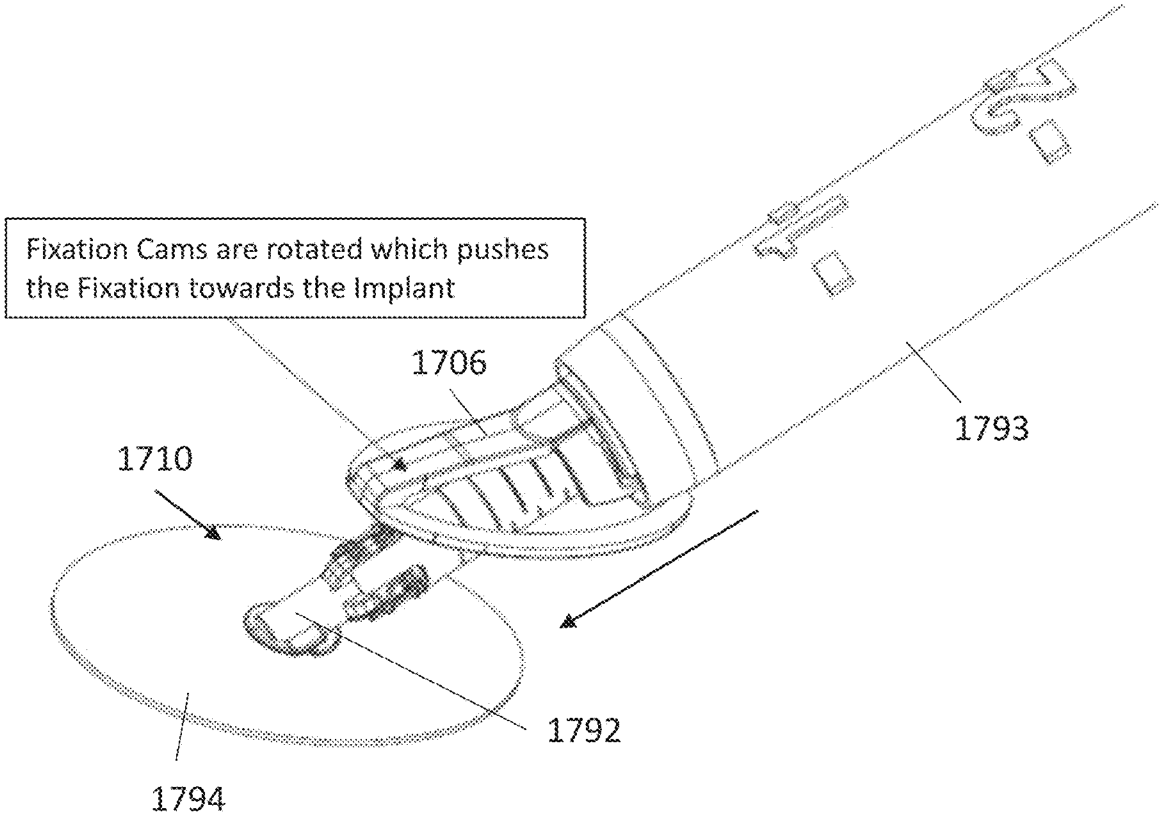

FIG. 136A is an enlarged view of the fixation moving toward the implant upon rotation of the fixation cams, according to aspects of the present embodiments.

Figure 136B:
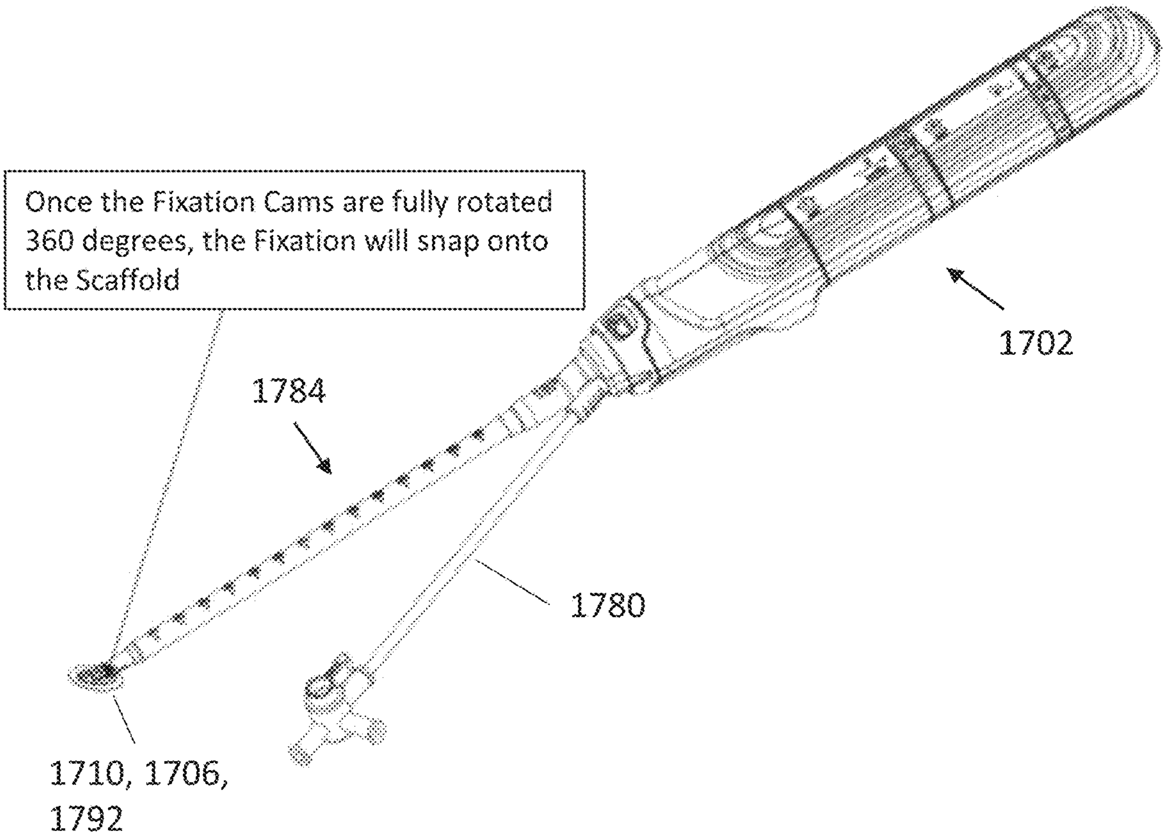

FIG. 136B is an image of a VCD assembly engaged with a sheath assembly with the external fixation snapped onto the scaffold protruding from the tip of the sheath shaft once the fixation cams are fully rotated 360 degrees, according to aspects of the present embodiments.

Figure 137A:
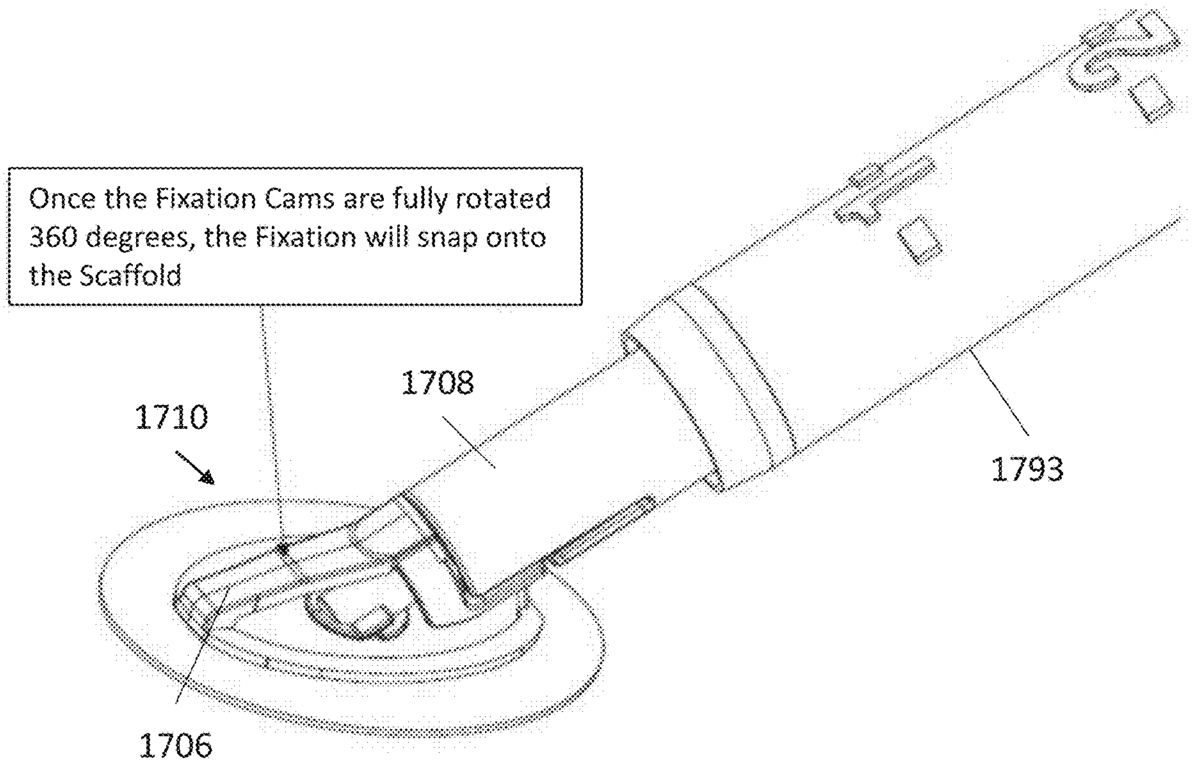

FIG. 137A is an enlarged view of the external fixation snapped onto the scaffold of the implant, according to aspects of the present embodiments.

Figure 137B:
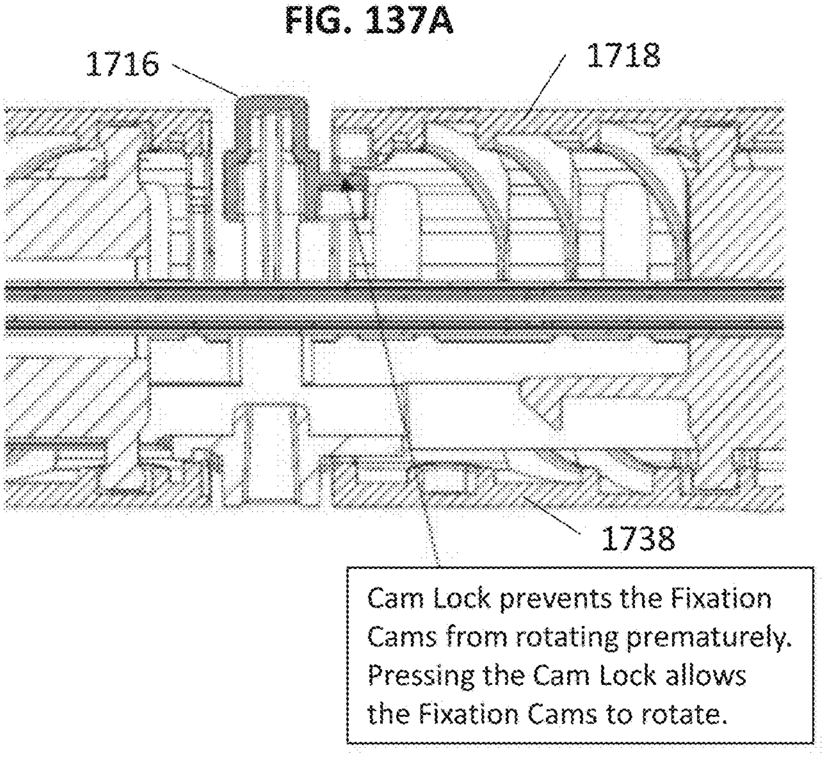

FIG. 137B is a cross-sectional view of a VCD assembly handle showing a cam lock preventing the fixation cams from rotating prematurely, and pressing the cam lock allows the fixation cams to rotate, according to aspects of the present embodiments.

Figure 138A:
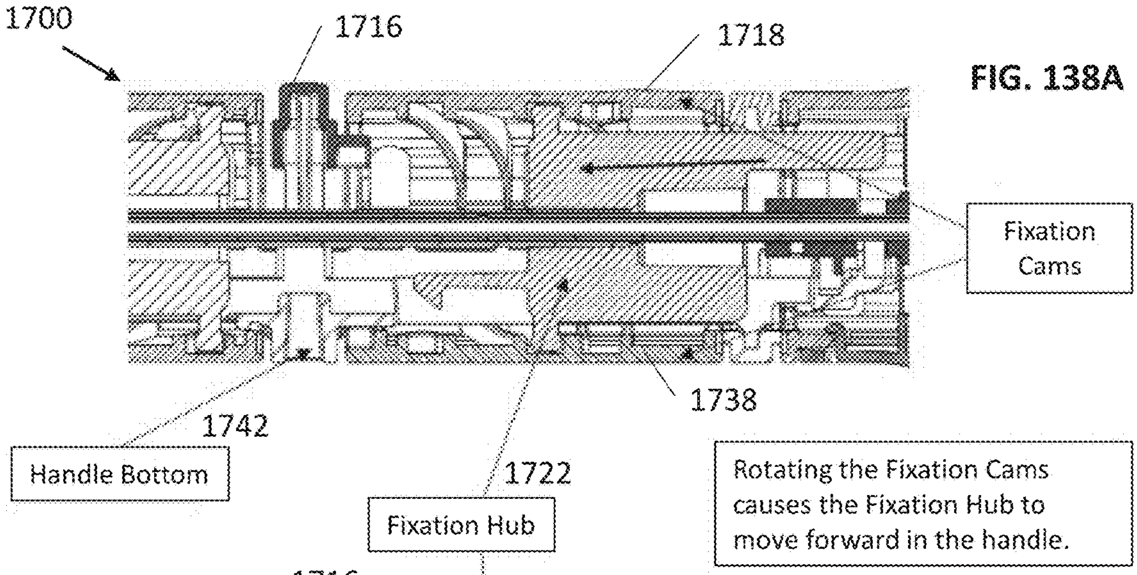

FIG. 138A is a cross-sectional view of the VCD assembly handle and shows the fixation hub moving forward in the handle when the fixation cams are rotated, according to aspects of the present embodiments.

Figure 138B:
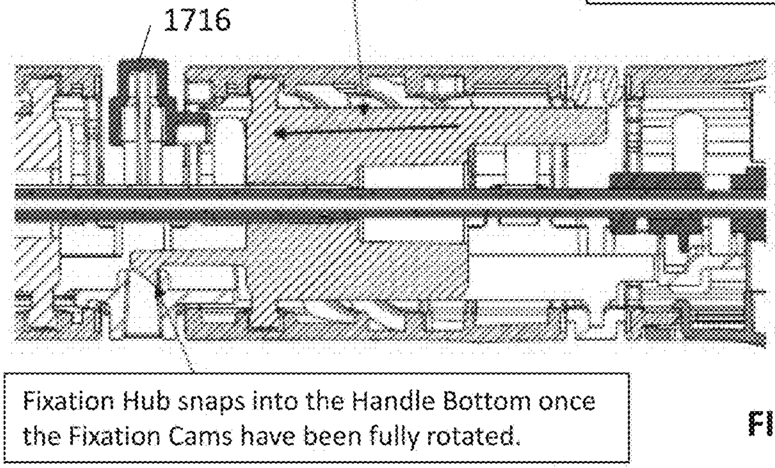

FIG. 138B is a cross-sectional view of the VCD assembly handle and shows the fixation hub snapping into the handle bottom once the fixation cams have been fully rotated, according to aspects of the present embodiments.

Figure 138C:
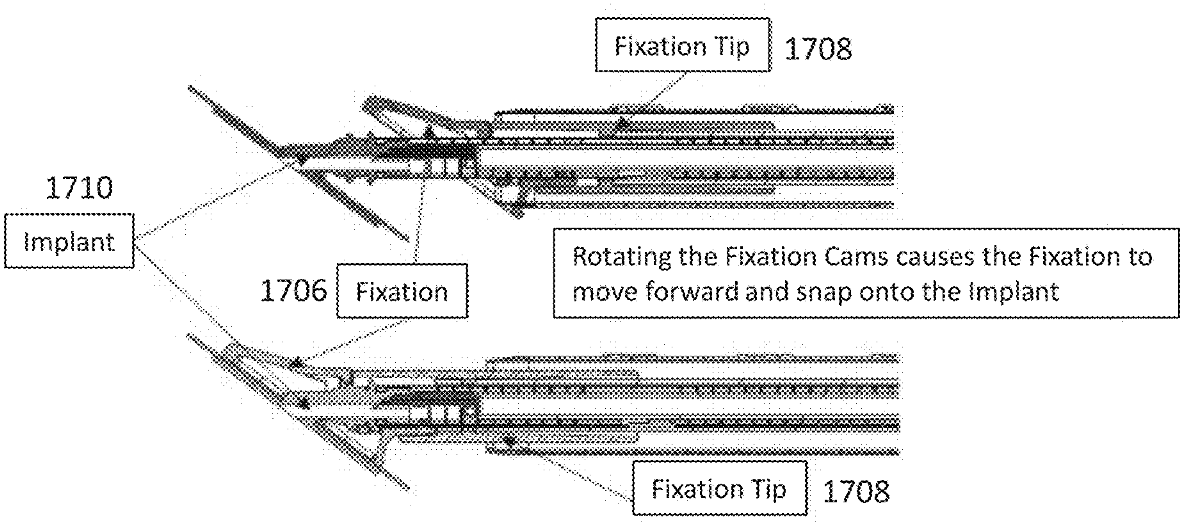

FIG. 138C is two cross-sectional views of the implant protruding from the sheath shaft, the upper view showing the fixation and implant separated; after rotating the fixation causes the fixation to move forward, the fixation snaps onto the implant as shown in the lower view, according to aspects of the present embodiments.

Figure 139A:
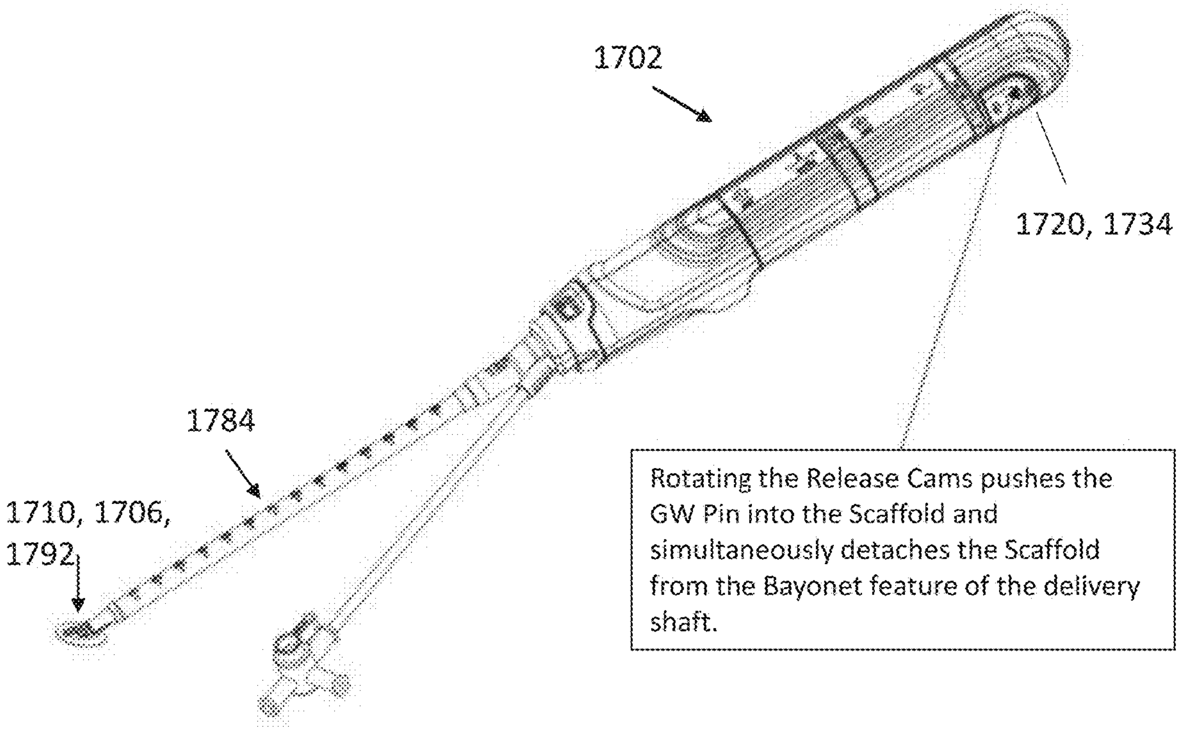

FIG. 139A is an image of a VCD assembly with release cams partially rotated, which pushes the guidewire pin into the scaffold and simultaneously detaches the scaffold from the bayonet, according to aspects of the present embodiments.

Figure 139B:
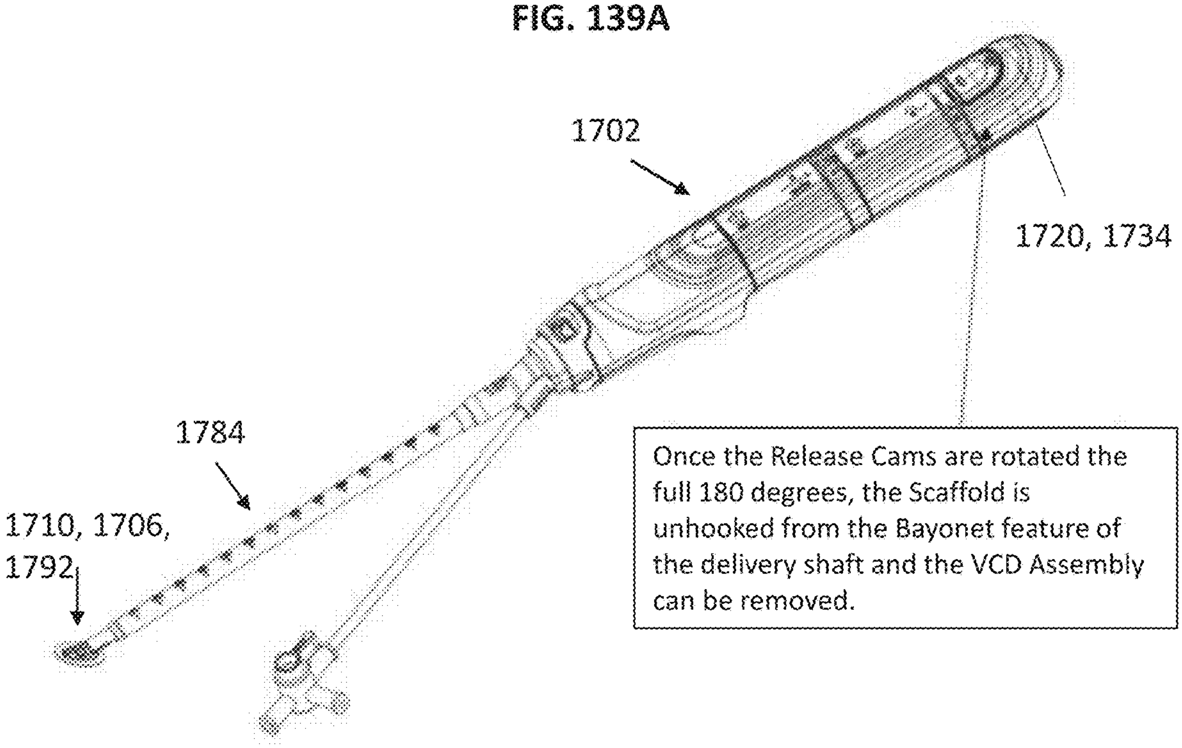

FIG. 139B is an image of a VCD assembly with release cams rotated the full 180 degrees, which causes the scaffold to be unhooked from the bayonet, so that the VCD assembly can be removed from the implant, according to aspects of the present embodiments.

Figure 140A:
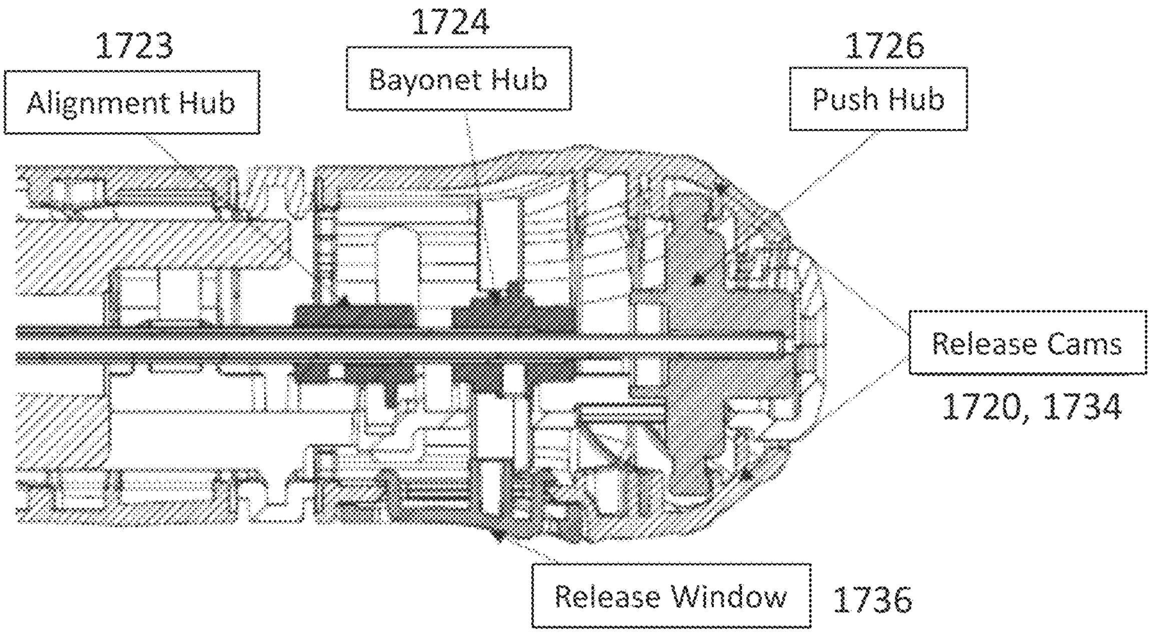

FIG. 140A is a cross-sectional view of a VCD assembly handle, showing a bayonet hub and release cams, according to aspects of the present embodiments.

Figure 140B:
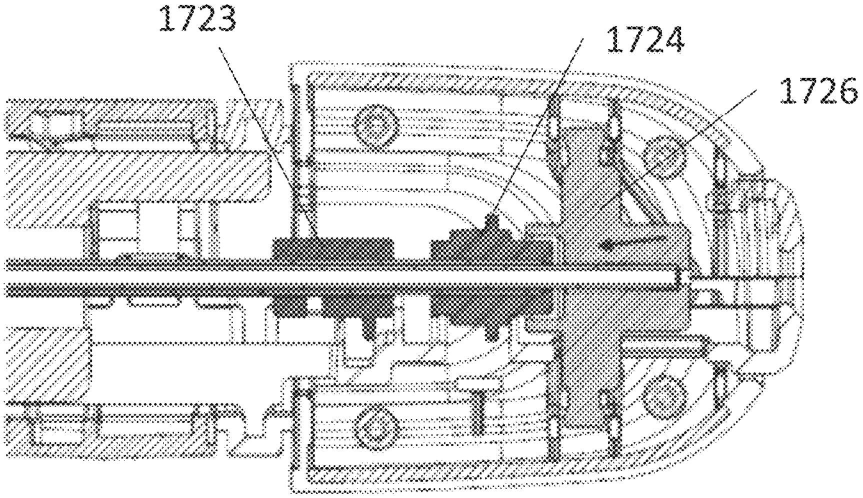

FIG. 140B is a cross-sectional view of a VCD assembly handle, showing the push hub moving forward in the handle and releasing the scaffold from the bayonet when the release cams are rotated, according to aspects of the present embodiments.

Figure 141A:
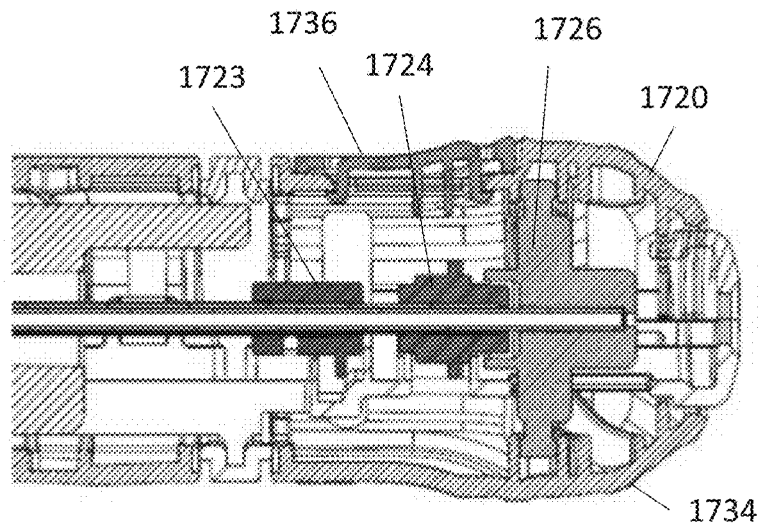

FIG. 141A is a cross-sectional view of a VCD assembly handle, showing the push hub has moved forward in the handle, according to aspects of the present embodiments.

Figure 141B:
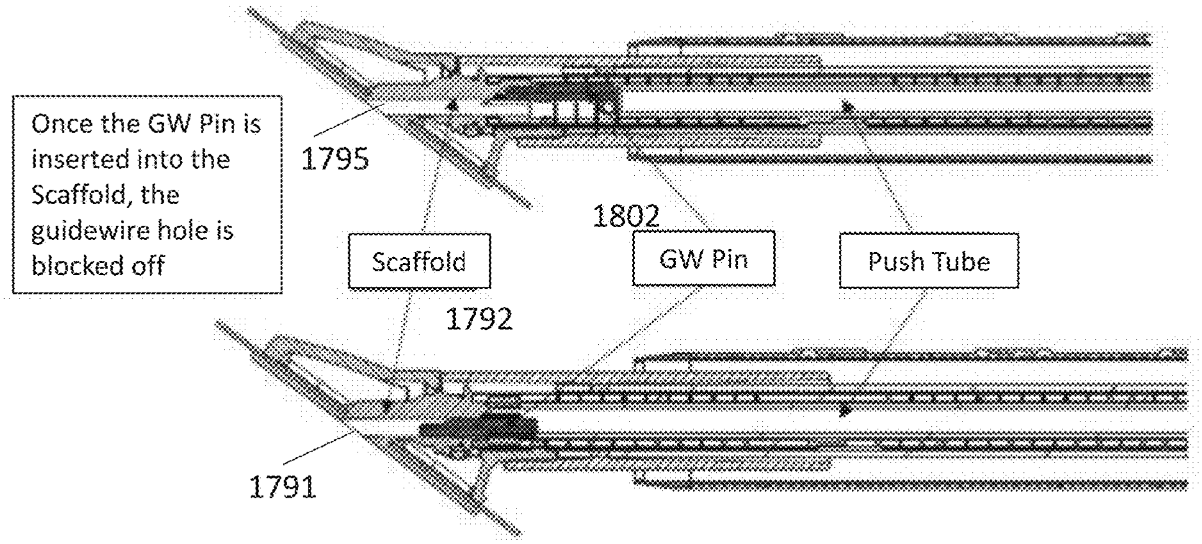

FIG. 141B is two cross-sectional views of a sheath shaft with fixation and implant pushed together and protruding from the sheath shaft end; in the upper view the guidewire pin is not yet inserted; in the lower view the guidewire pin is inserted into the scaffold, blocking off the guidewire hole, according to aspects of the present embodiments.

Figure 142A:
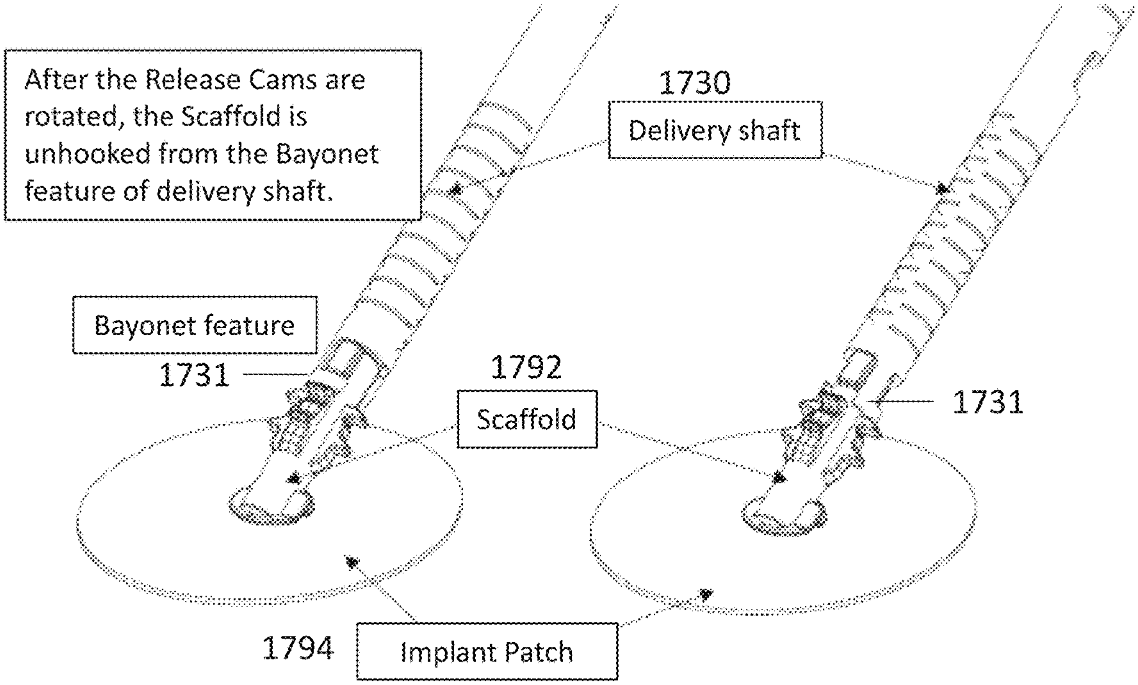

FIG. 142A is two views of an implant and scaffold in relation to the bayonet; in the left view, the scaffold is hooked on the end of the bayonet; in the right view, the scaffold is unhooked from the bayonet after the release cams are rotated, according to aspects of the present embodiments.

Figure 142B:
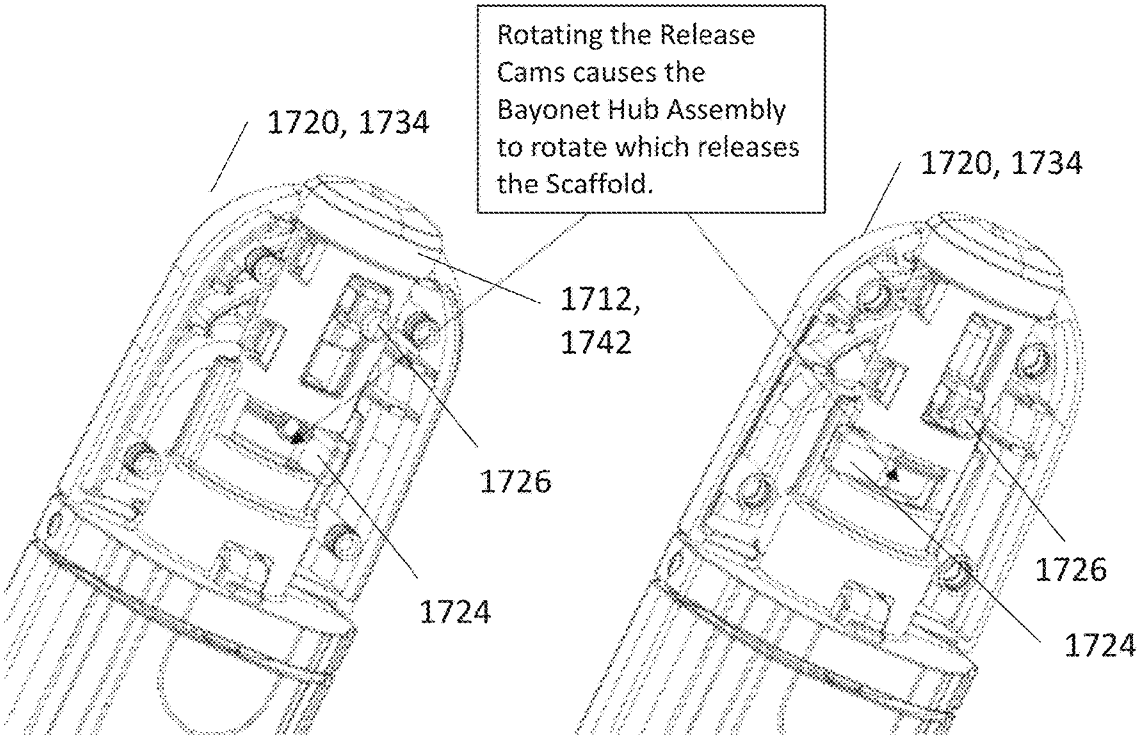

FIG. 142B is two cut-away views of a VCD handle showing release cams; upon rotation of the release cams the bayonet hub assembly rotates to release the scaffold, according to aspects of the present embodiments.

Figure 143A:
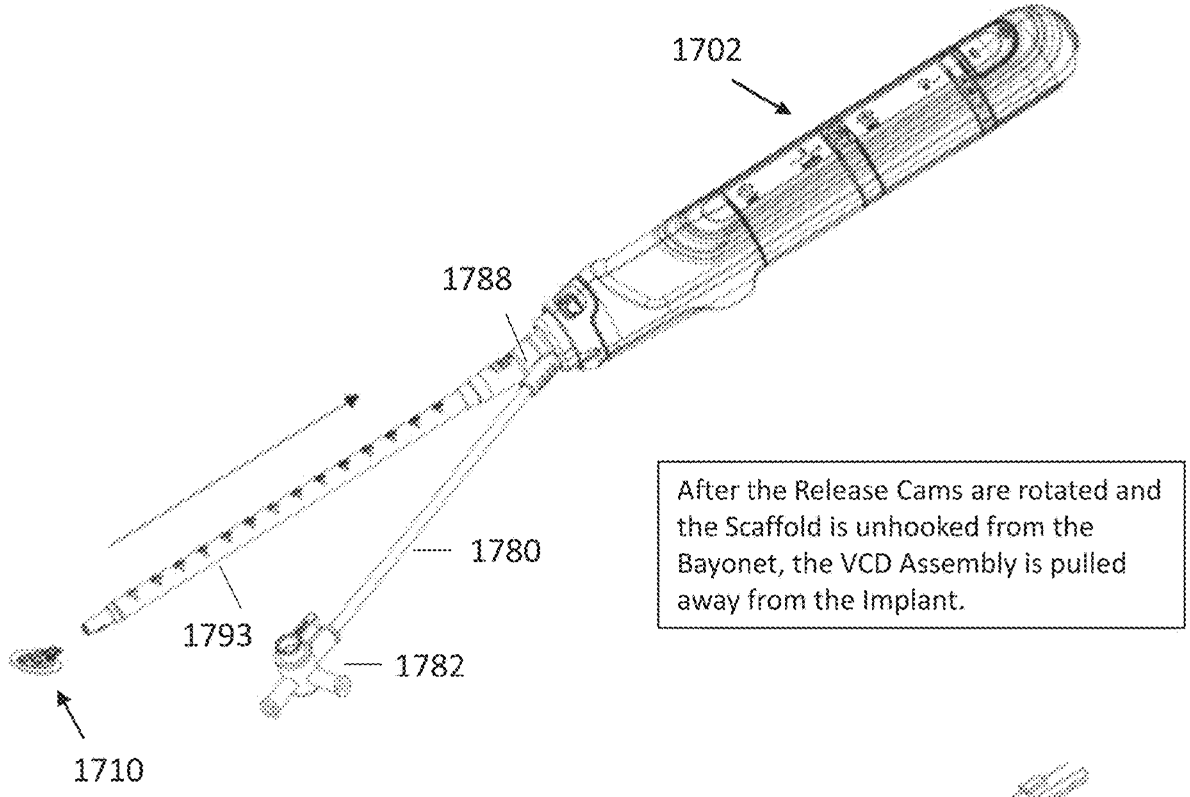

FIG. 143A is an image of a delivery system assembly moving away from a released implant, after the release cams are rotated so that the scaffold is unhooked from the bayonet, according to aspects of the present embodiments.

Figure 143B:
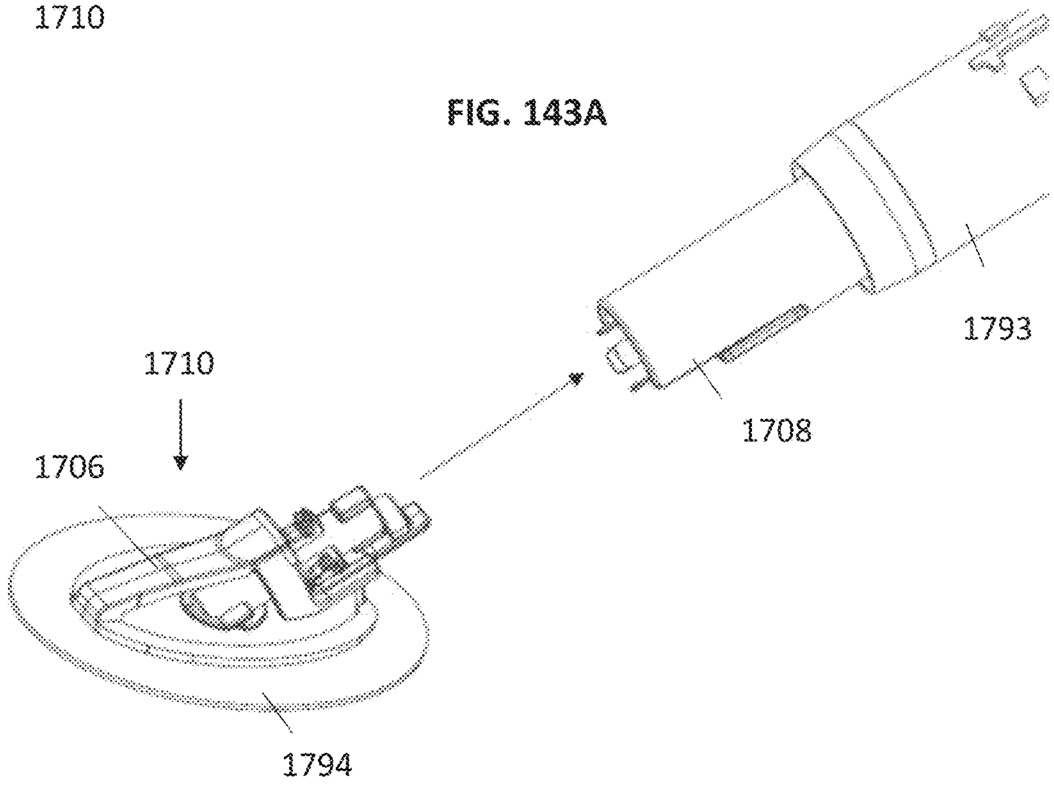

FIG. 143B is an enlarged view of a fixation tip and sheath shaft tip moving away from an implant after the bayonet is unhooked from the scaffold of the implant, according to aspects of the present embodiments.

Figure 144A:
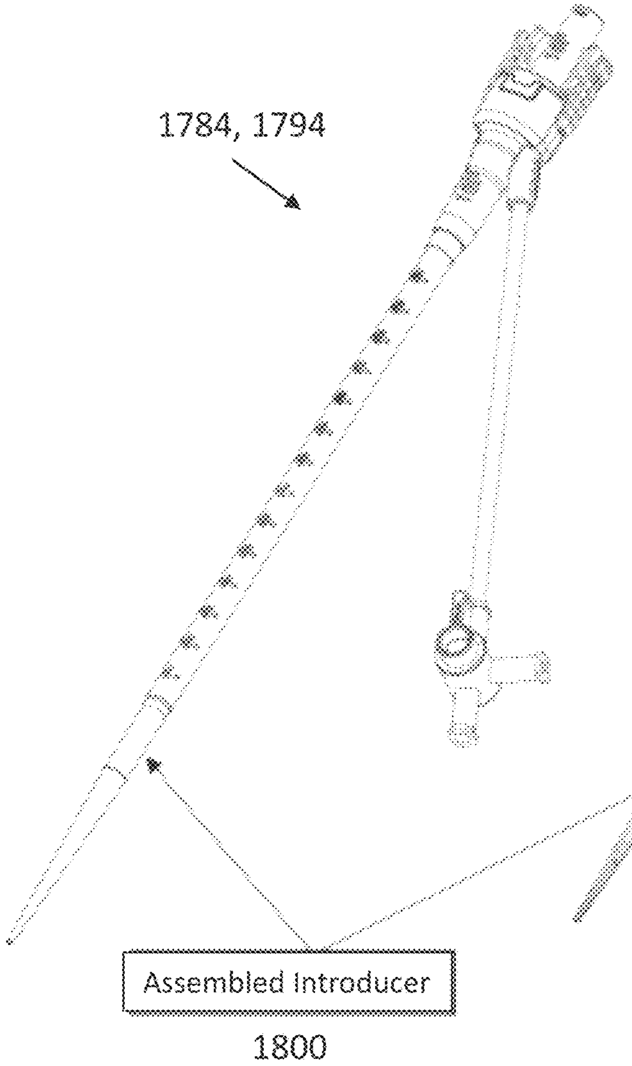

FIG. 144A is an image of an assembled introducer, which includes a sheath assembly and a dilator assembly, according to aspects of the present embodiments.

Figure 144B:
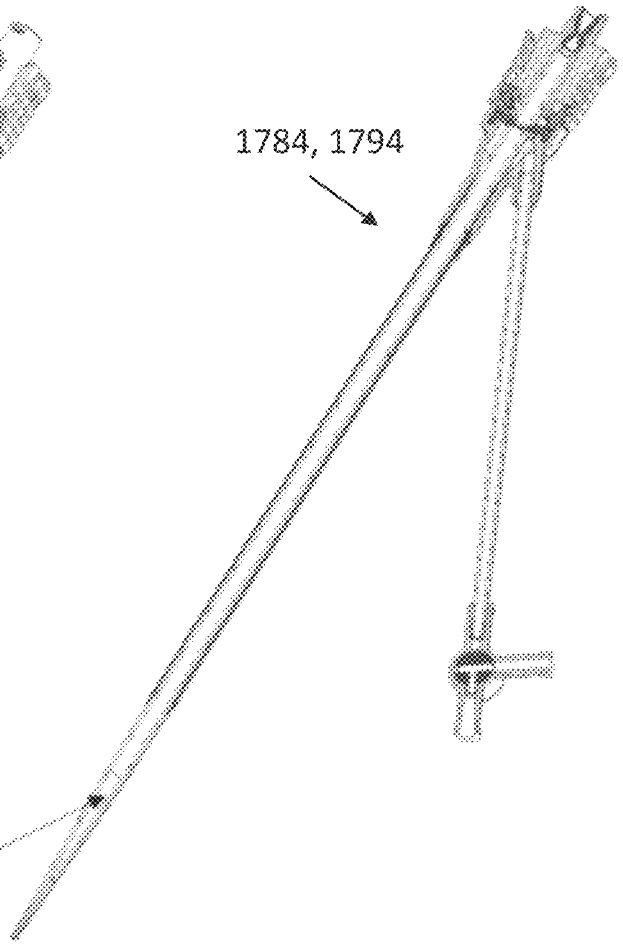

FIG. 144B is a cross-sectional view of an assembled introducer, which includes a sheath assembly and a dilator assembly, according to aspects of the present embodiments.

Figure 145:
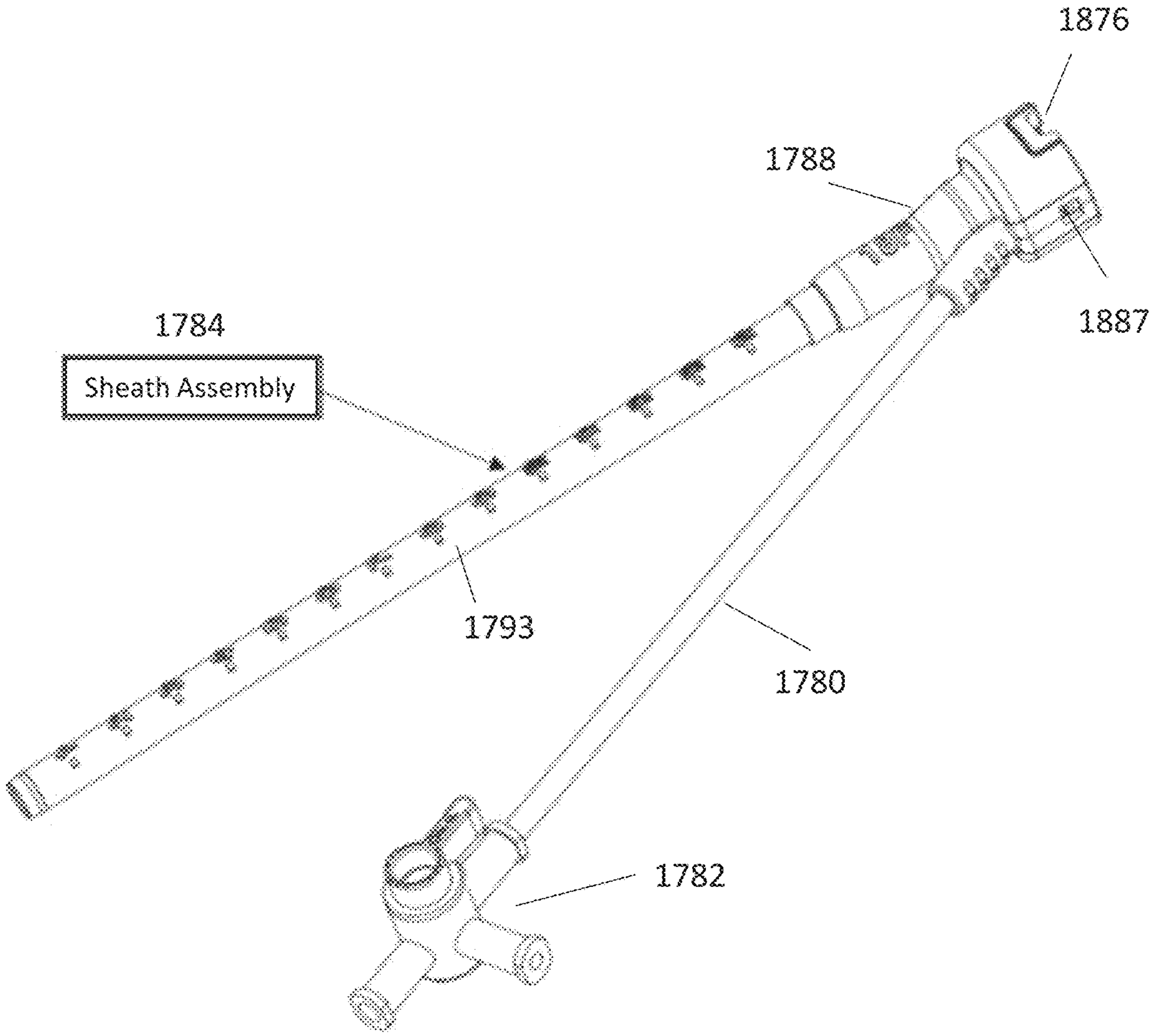

FIG. 145 is an image of a sheath assembly, according to aspects of the present embodiments.

Figure 146A:
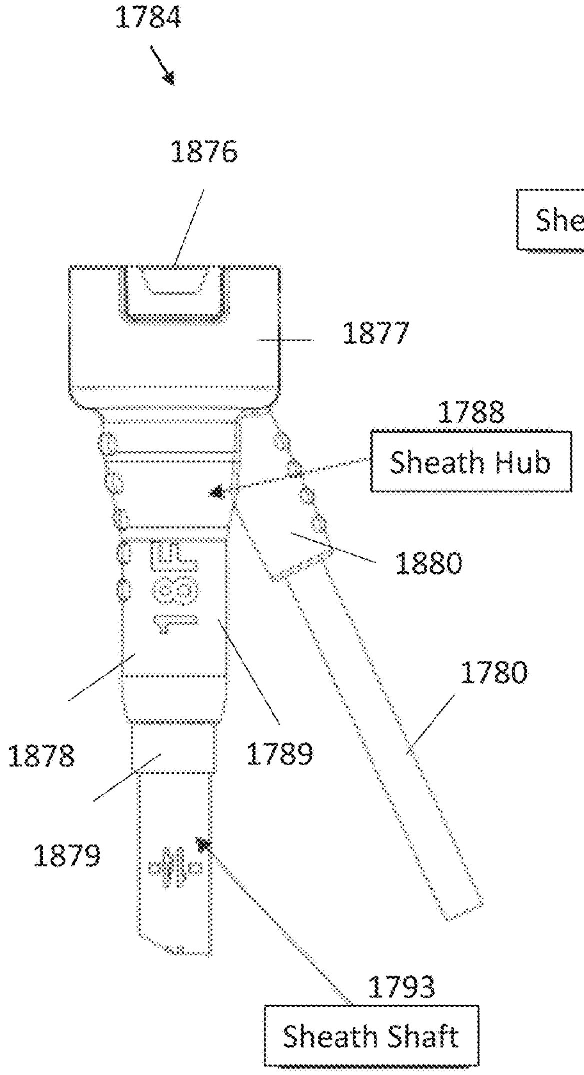

FIG. 146A is an image of a sheath hub portion of a sheath assembly, according to aspects of the present embodiments.

Figure 146B:
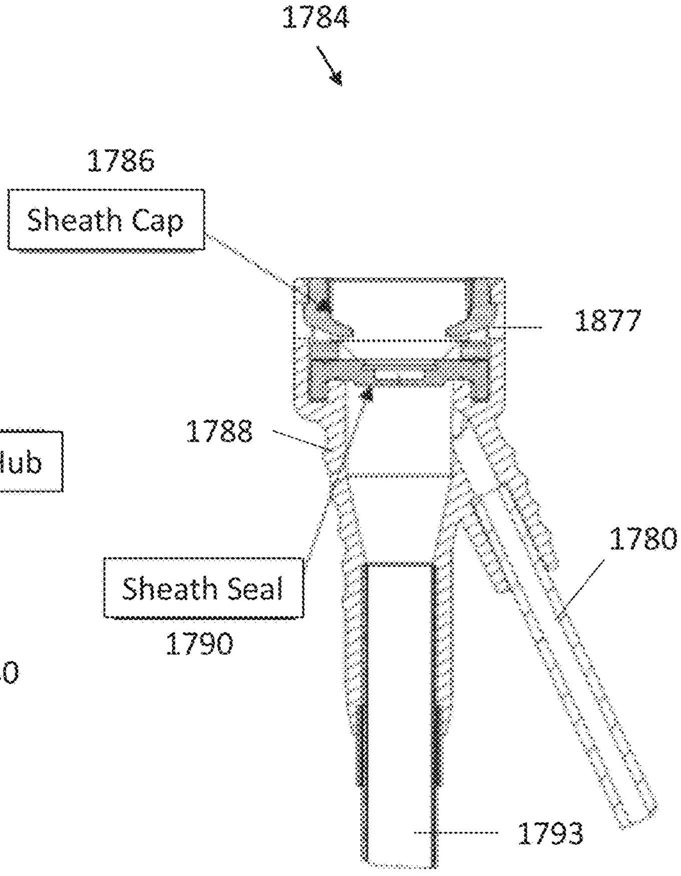

FIG. 146B is a cross-sectional view of a sheath hub portion of a sheath assembly, according to aspects of the present embodiments.

Figure 147:
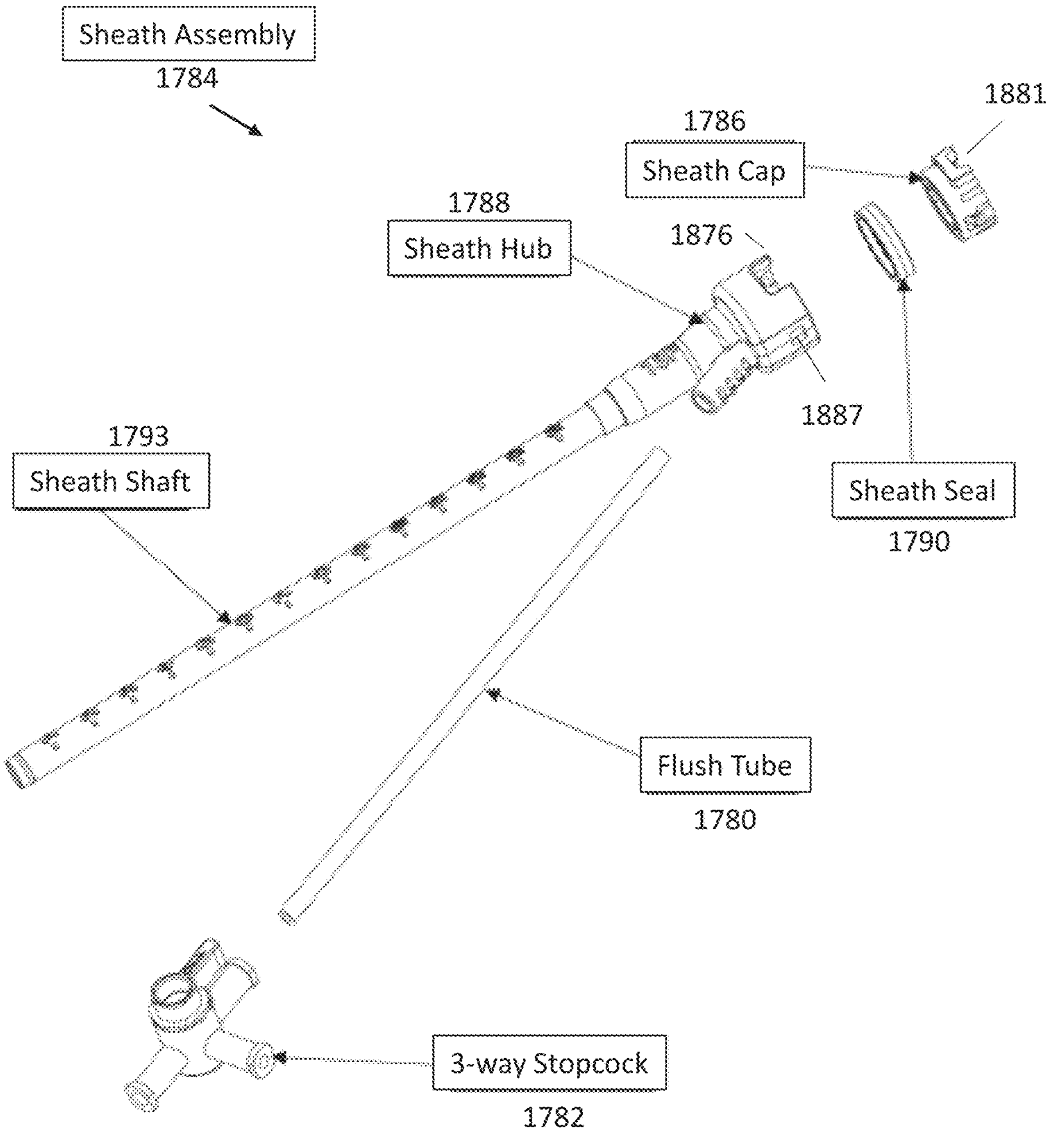

FIG. 147 is an exploded view of the component parts of a sheath assembly, according to aspects of the present embodiments.

Figure 148A:
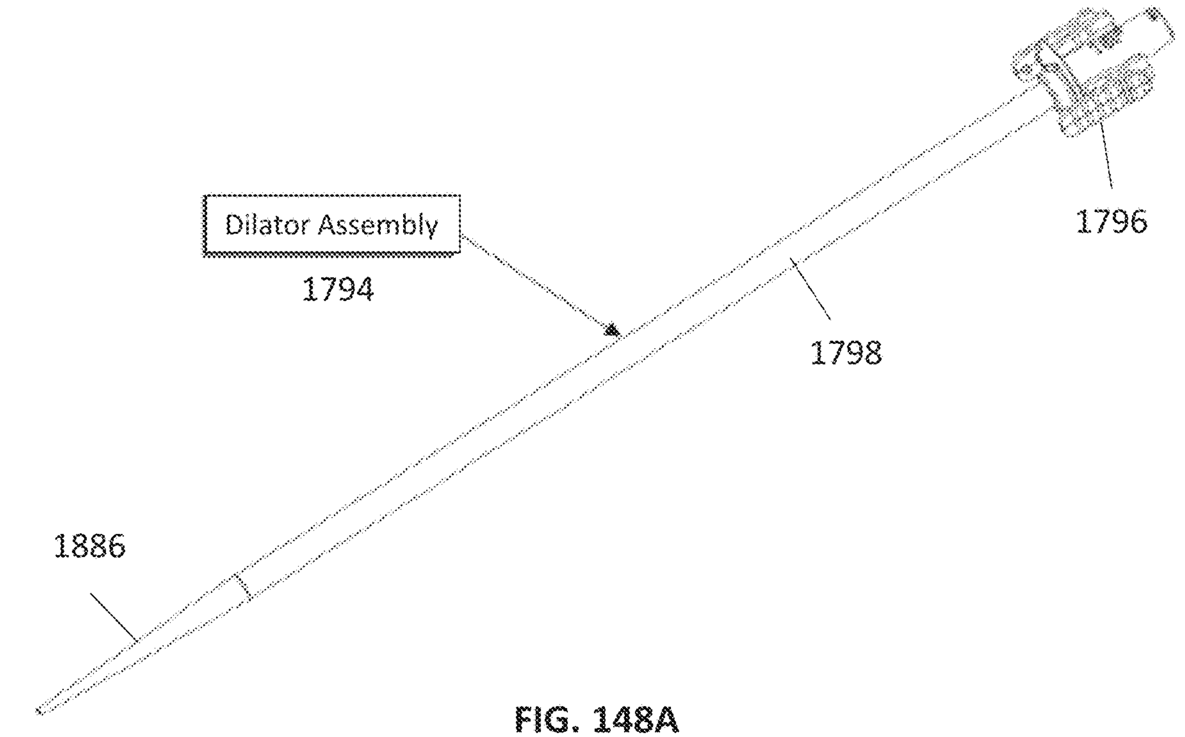

FIG. 148A is an image of a dilator assembly, according to aspects of the present embodiments.

Figure 148B:
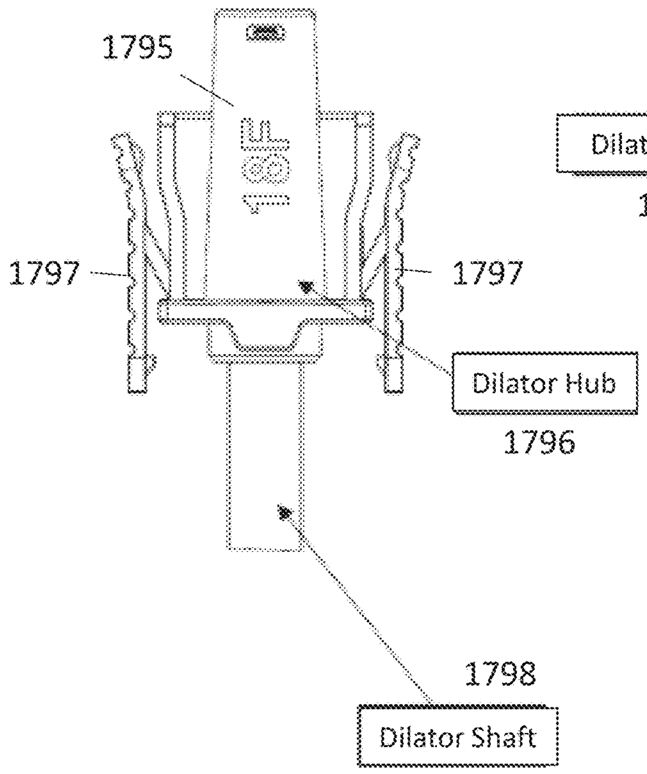

FIG. 148B is an image of a dilator hub portion of a dilator assembly, according to aspects of the present embodiments.

Figure 148C:
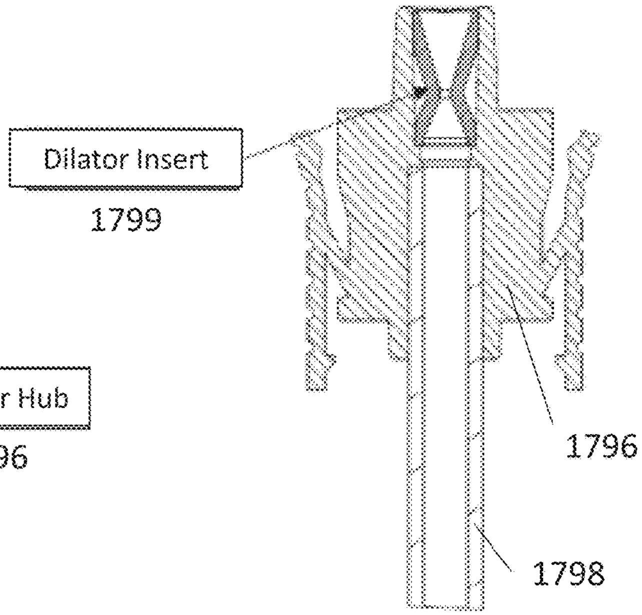

FIG. 148C is a cross-sectional view of dilator hub portion of a dilator assembly, according to aspects of the present embodiments.

Figure 149:
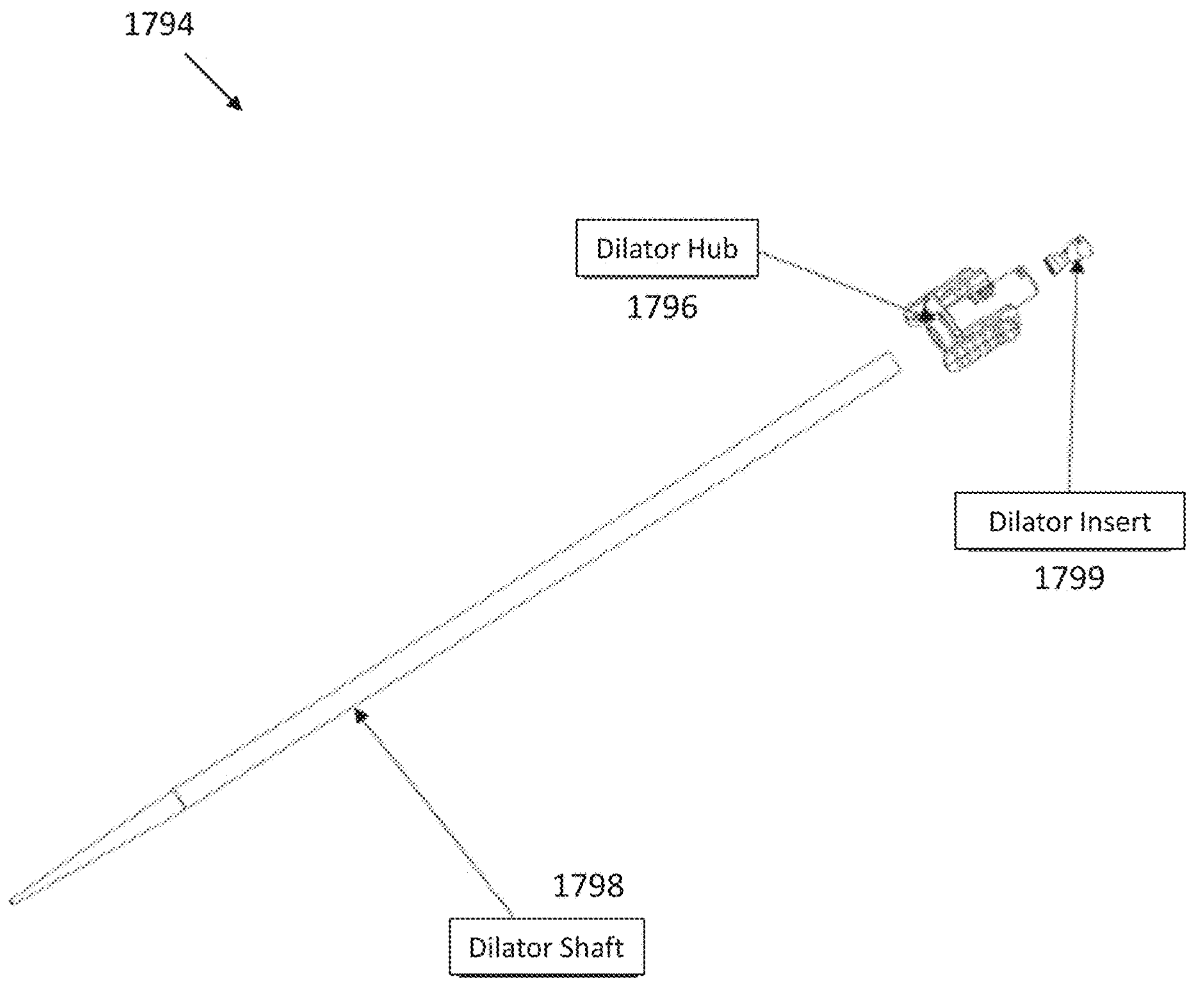

FIG. 149 is an exploded view of the component parts of a dilator assembly, according to aspects of the present embodiments.

Figure 150:
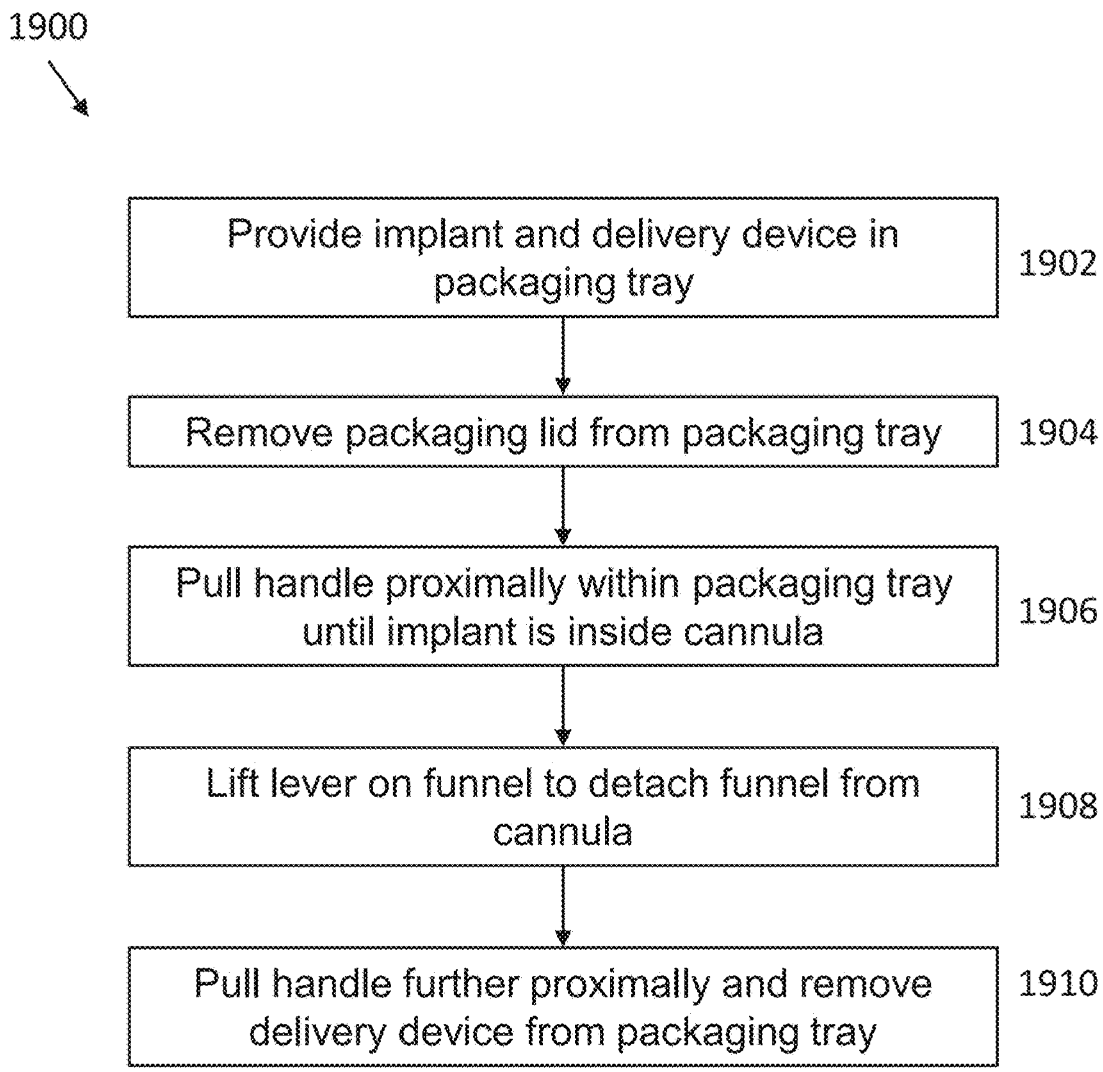

FIG. 150 is a flow chart diagram of a method of loading an implant into a VCD assembly, according to aspects of the present embodiments.

Figure 151:
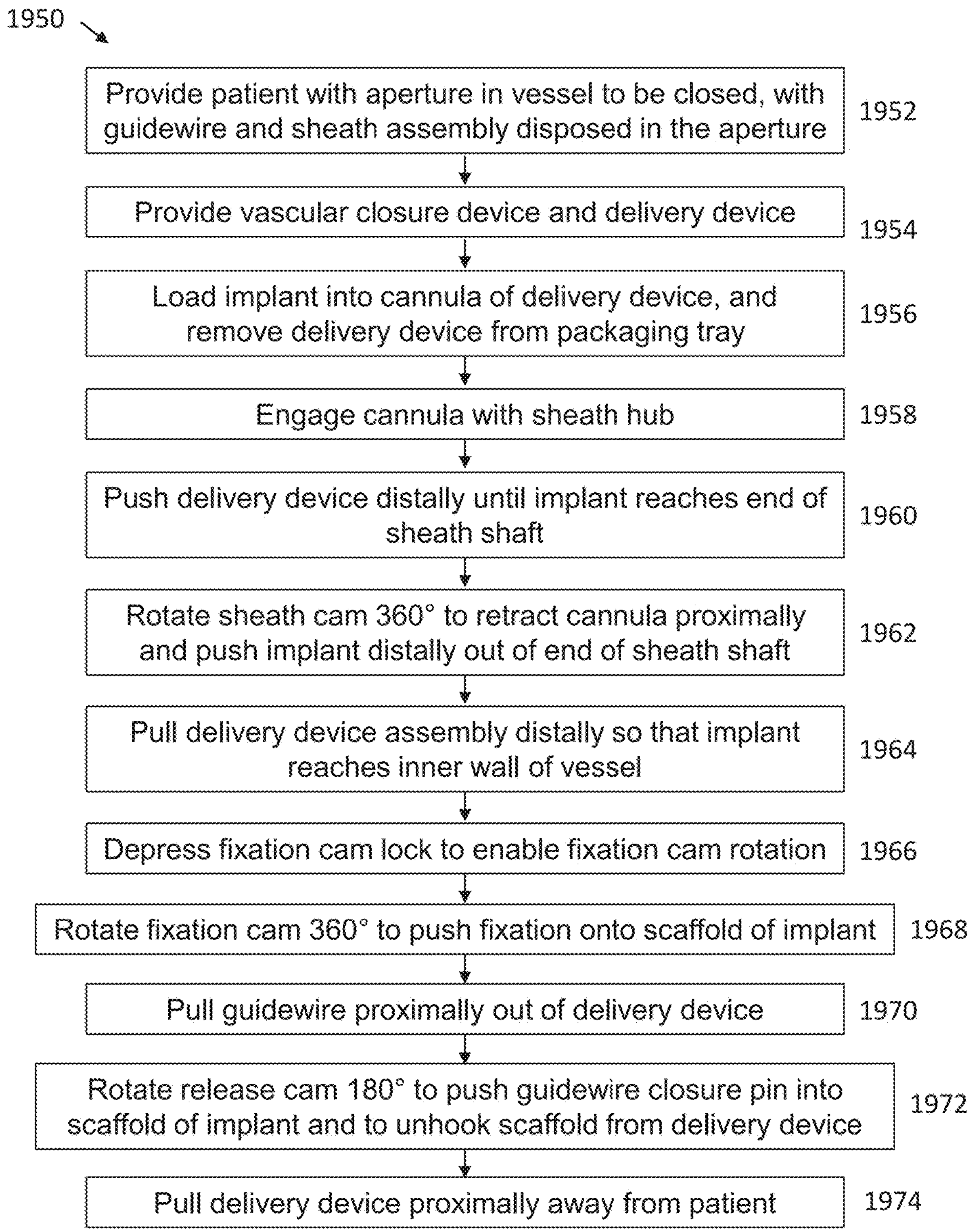

FIG. 151 is a flow chart diagram of a method of sealing an aperture using a VCD assembly and implant, according to aspects of the present embodiments.

DETAILED DESCRIPTION

Overview

As described herein, illustrative embodiments provide a vascular closure implantable device for sealing an aperture in a tissue of a body vessel. Examples of a body vessel include a blood vessel, which may be a vein or an artery. Examples of the blood vessel include, but are not limited to, the femoral artery, subclavian artery, ascending and descending aorta, auxiliary and brachial arteries, femoral vein, iliac vein, subclavian vein, and vena cava. In some embodiments, the systems, devices, and methods are used to close a surgical perforation in a body cavity, such as the gastrointestinal tract, heart, peritoneal cavity, esophagus, vagina, rectum, trachea, bronchi, and blood vessel.

First Embodiment of Closure Device

Figure 1:
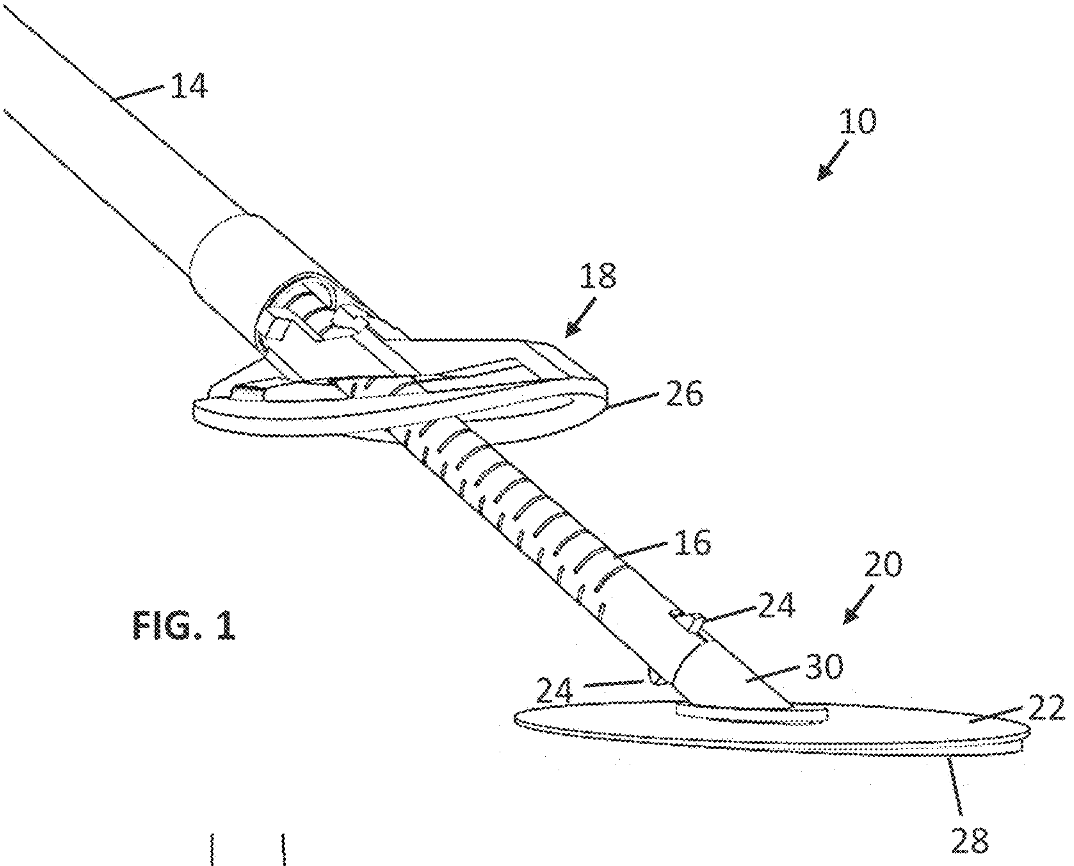
FIG. 1 is a perspective view of a vascular closure device and system, according to the present embodiments.

FIG. 1 is a perspective view of a vascular closure device 12 and system 10, according to the present embodiments. The system 10 includes an outer shaft 14, a distal scaffold retention shaft 16, and external fixation 18, a scaffold 20, and a patch 22. The outer shaft 14 and the distal scaffold retention shaft 16 may collectively form and/or be components of a delivery system. The external fixation 18, the scaffold 20, and the patch 22 collectively form the vascular closure device 10. A scaffold base 28 is visible under the patch 22. The scaffold 20 includes a scaffold neck 30 (or protrusion), protruding upwardly and at an angle from the scaffold base 28. In operation, the outer shaft 14 and the distal scaffold retention shaft 16 may be used to deliver the device 12 to an aperture or vascular opening such that the external fixation 18 may be coupled to the scaffold 20 via one or more retaining tabs 24 disposed in the scaffold neck 30 (for example, on either side, spaced out by about 180 degrees). The external fixation 18 includes an upper lip 26 which, in a final deployment position, is position outside a blood vessel, artery, etc. for helping to form a seal externally. The patch 22 and scaffold 20 (including the scaffold base 28) are disposed within the blood vessel, artery, vein, etc. to internally push against the vessel walls, opposite the upper lip 26.

Examples of the patch 22 (also referred to as a "flexible wing" or sealable member or patch) are described in U.S. Patent Application Publication No. 2014/0018847, titled "Percutaneous Perforation Closure Systems, Devices, and Methods," patented as U.S. Pat. No. 9,662,099, the content of which is incorporated by reference herein in its entirety. Among other things, this disclosure provides details of a variant of the patch 22 design, as well as the vascular closure device 12.

Figure 2:
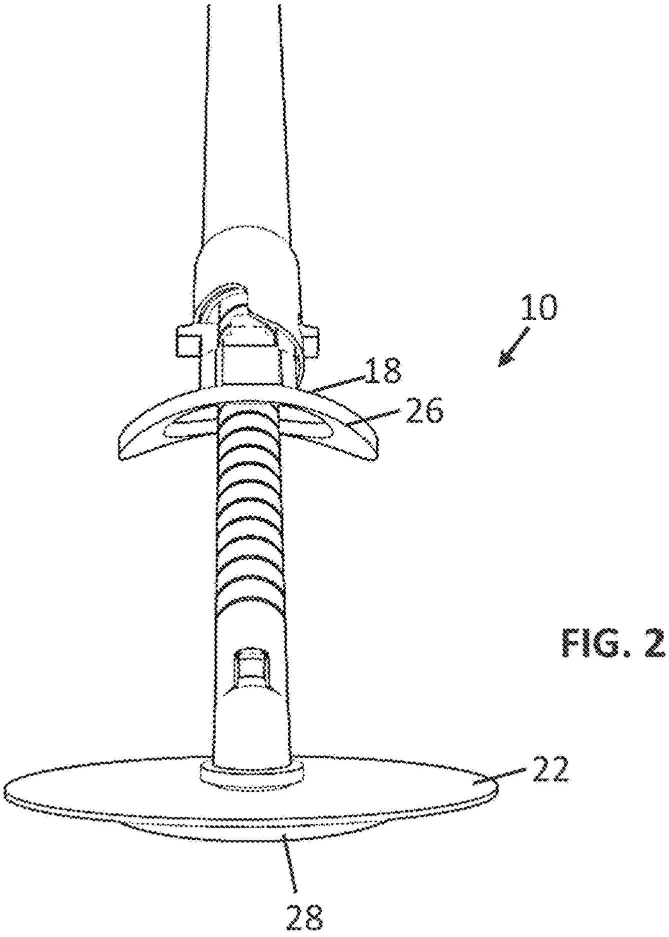
FIG. 2 is a front view of a vascular closure device and system, according to the present embodiments.

FIG. 2 is a front view of a vascular closure device 12 and system 10, according to the present embodiments. In the view of FIG. 2, the curvature of the upper lip 26 (part of the external fixation) is illustrated. The upper lip 26 is concave from the perspective of the patch 22 such that it is contoured to match the external contouring of the blood vessel, vein, artery, and/or other organ on which the device 12 is being deployed. The scaffold base 28 is also visible in FIG. 2.

Figure 3:
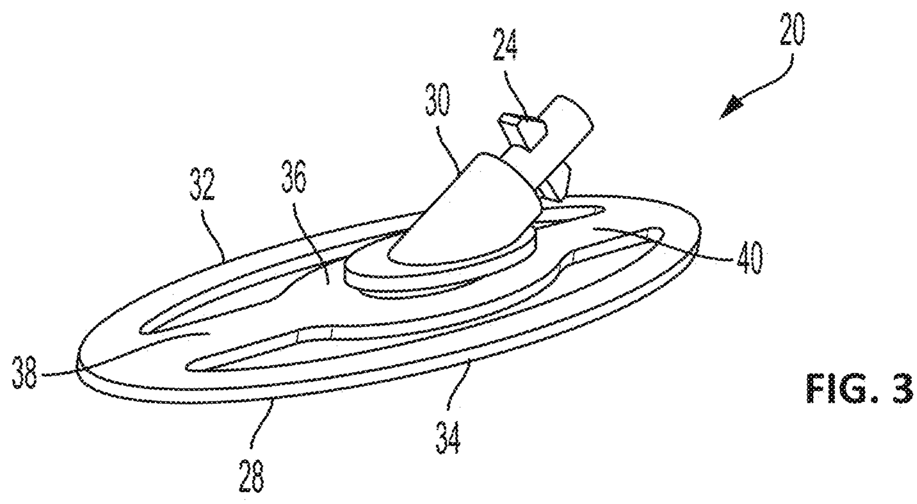
FIG. 3 is a perspective view of a scaffold, according to the present embodiments.
Figure 4:
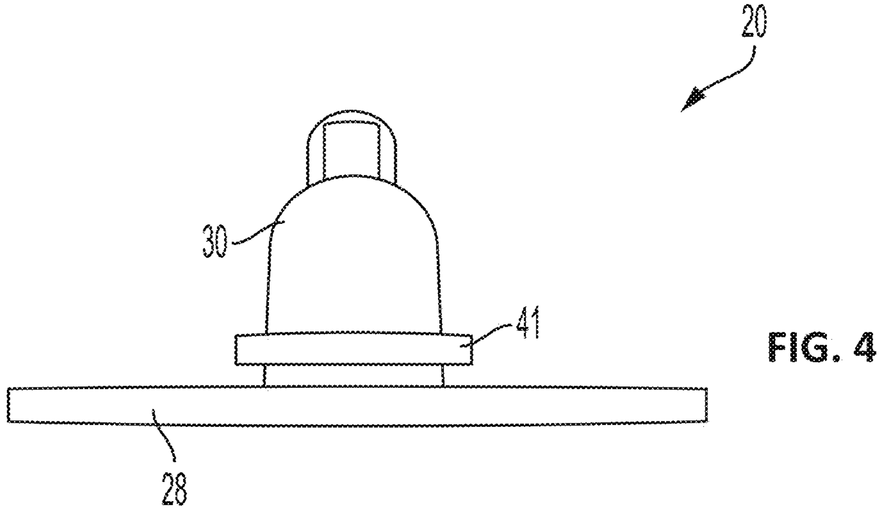
FIG. 4 is a front view of a scaffold, according to the present embodiments.

FIG. 3 is a perspective view of a scaffold 20, according to the present embodiments. The scaffold 20 may include the scaffold neck 30, the scaffold base 28, and one or more retaining tabs 24. The scaffold base 28 may include one or more curved members (for example, a first curved member 32 on a first side of the scaffold base 28 and a second curved member 34 on a second side of the scaffold base 28, opposite of the first curved member 32. Each of the first and second curved members 32, 34 may be separated from a central oval portion 36 via first and second gaps 42, 44 shown in FIG. 5. The scaffold neck 30 may protrude upwardly from the central oval portion 36, which may be oval-shaped and may be coupled to the proximal and distal portions of the scaffold base via proximal and distal straight members 40, 38. As illustrated in FIG. 4, the scaffold 20 may include a scaffold lip 41 disposed on a bottom portion of the scaffold neck 30 such that the patch 22 (shown in FIGS. 9-11) may be disposed onto the scaffold 20, and may stay in place when positioned thereon. Stated otherwise, the scaffold neck 30 is disposed through the patch 22, which rests above the scaffold base 28, but below the scaffold lip 41.

Figure 5:
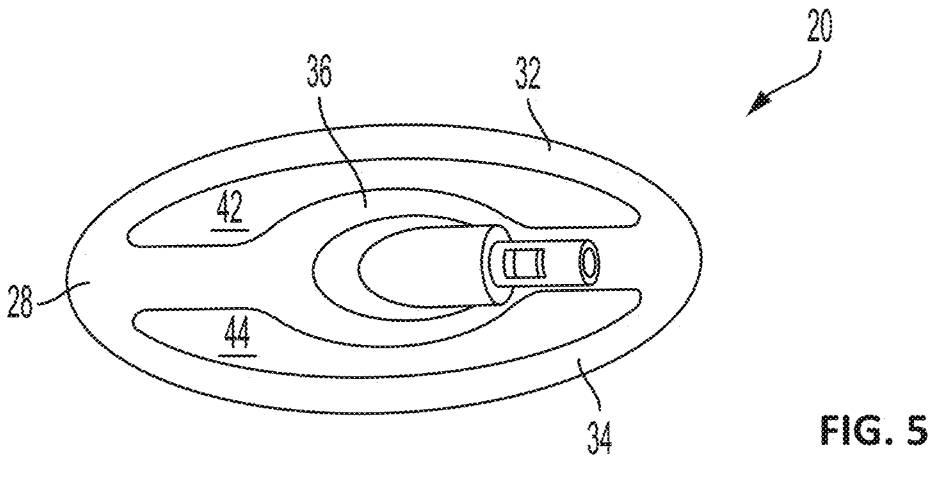
FIG. 5 is a top view of a scaffold, according to the present embodiments.

Referring to FIGS. 3-5, the scaffold may be generally oval-shaped and may include a length that is at least 2 times greater that the width (or in some embodiments, from about 1.75 to 2.25 times width, or from about 1.5 to about 2.5 times the width). The first and second curved members 32, 34, as well as the first and second gaps 42, 44 may be dimensioned such that the flexibility of the scaffold 20 may be "tuned" to allow sufficient flexibility for the scaffold 20 to be bendable (for example to fit within a loading cannula when being deployed within a blood vessel, in some embodiments), while also being rigid enough to provide structure and rigidity to the patch 22 during sealing. The oval shape of the scaffold 20 also helps to minimize the lateral dimension of the scaffold 20 during deployment through a vessel aperture, while simultaneously allowing for a larger interfacing surface area with the patch 22 while sealing.

Figure 6:
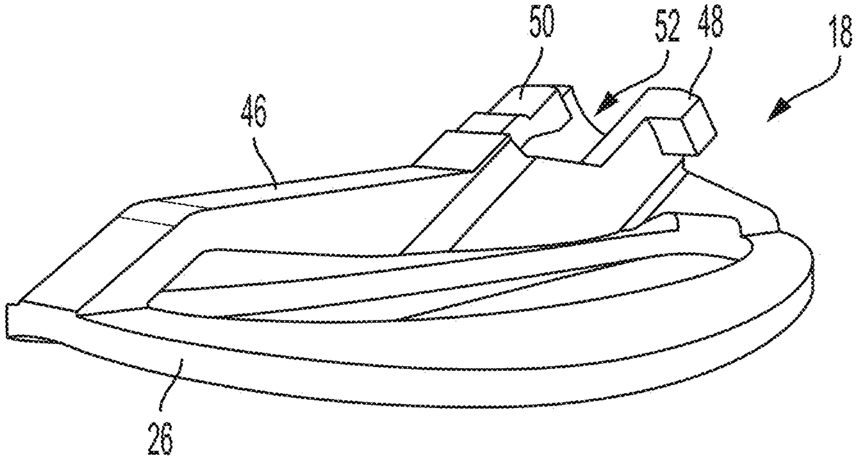
FIG. 6 is a perspective view of an external fixation, according to the present embodiments.
Figure 7:
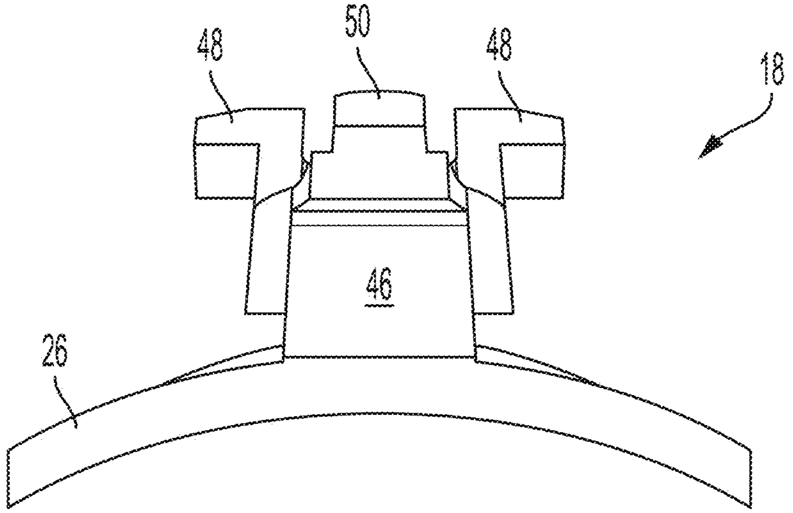
FIG. 7 is a front view of an external fixation, according to the present embodiments.
Figure 8:
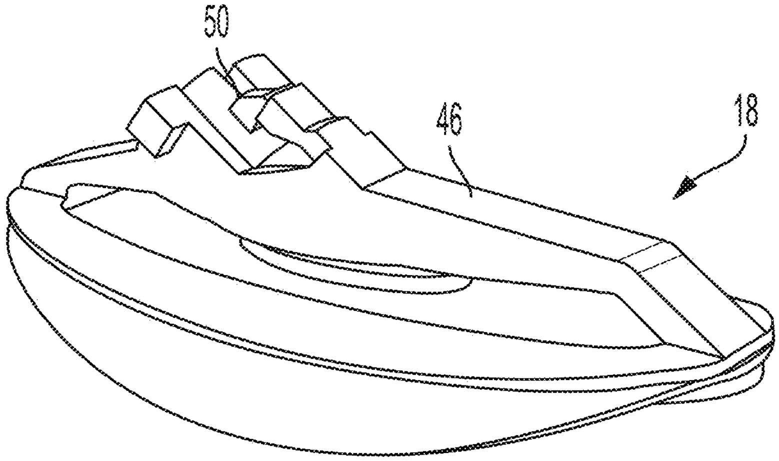
FIG. 8 is a perspective view of vascular closure device, according to the present embodiments.

FIGS. 6-8 show perspective and front views of the external fixation 18, according to the present embodiments. The external fixation 18 includes a rib 46 coupled to one or more lateral tabs 48, as well as at least one catch 50, and the upper lip 26. As the device is being deployed in its final position (i.e., in the sealing position) the scaffold neck 30 may be disposed within a space 52 within the external fixation 52 such that the one or more retaining tabs 24 of the scaffold 20 interface and catch on the one or more catches 50 of the external fixation 18, thereby fastening the two pieces together (with the patch 22, and walls of the blood vessel sandwiched between the upper lip 26 and the scaffold base 28). The one or more lateral tabs 48, when laterally squeezed together, may be used to subsequently release the external fixation 18 from the scaffold 20, should the need arise.

Figure 9:
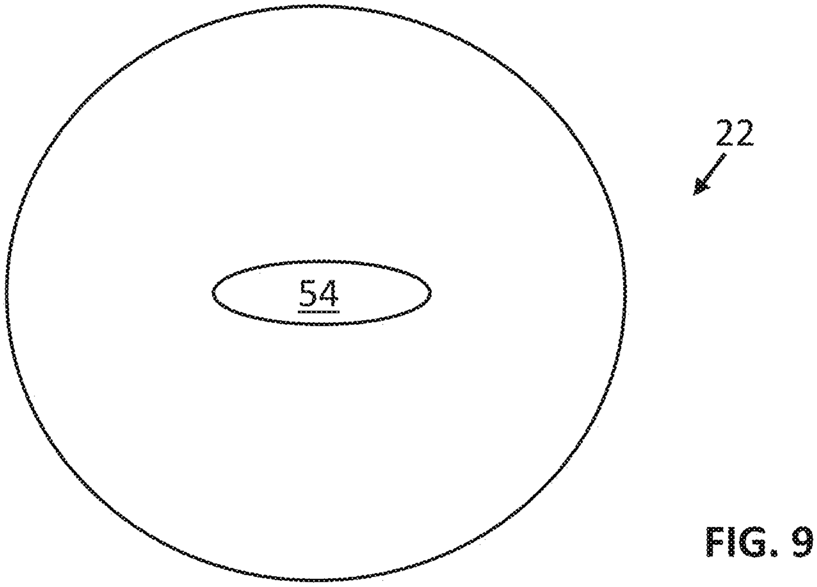
FIG. 9 is a top view of a patch, according to the present embodiments.

FIG. 9 illustrates a top view of the patch 22, according to the present embodiments. The patch 22 may include a hole 54 (for example, an oval-shaped hole 54) through which the scaffold neck 30 may be disposed while in operation.

Figure 10:
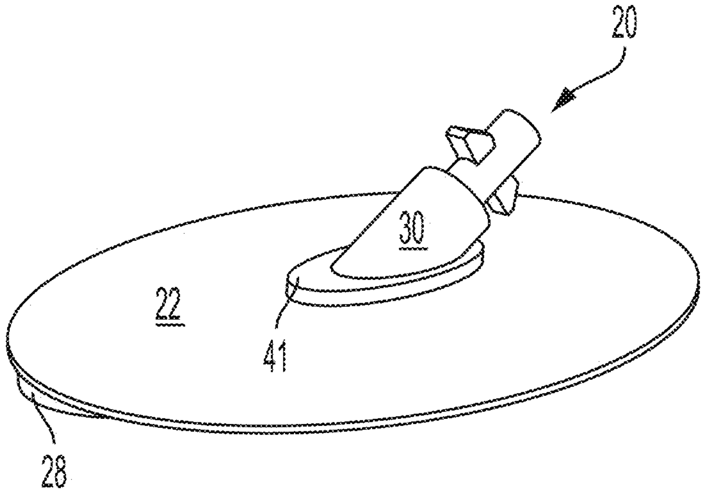
FIG. 10 is a perspective view of a scaffold with a patch disposed thereon, according to the present embodiments.

FIG. 10 is a perspective view of a scaffold 20 with a patch 22 disposed thereon, according to the present embodiments. The scaffold neck 30 may be disposed through the hole 54 in the patch 22 while the patch 22 may be layered between the scaffold base 28 and the scaffold lip 41.

Figure 11:
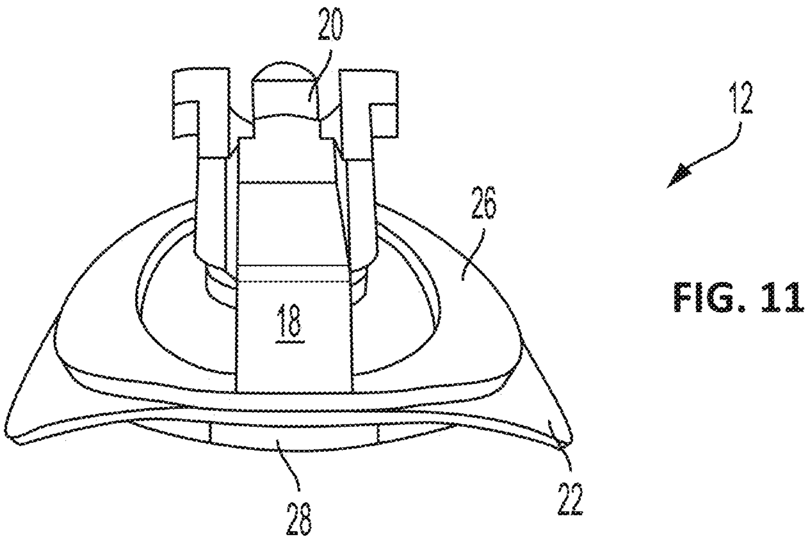
FIG. 11 is a front view of vascular closure device, according to the present embodiments.

FIG. 11 is a front view of vascular closure device 12, according to the present embodiments. The vascular closure device 12 includes the patch 22, scaffold 20, and external fixation 18 all assembled together with the patch 22 being disposed between the upper lip 26 and the scaffold base 28 (each of the patch 22 and the scaffold base 28 bending and/or flexing to match the contouring of the upper lip 26).

Figure 12:
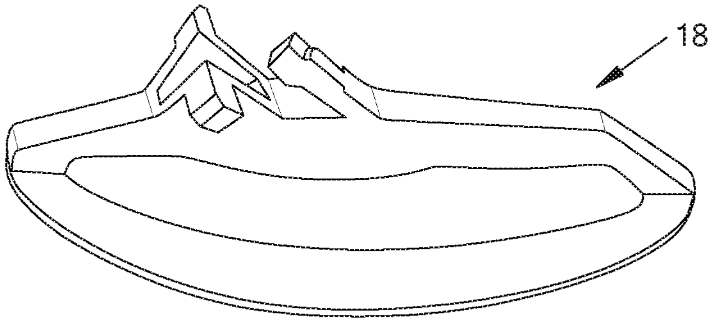
FIG. 12 is a perspective view photograph of an external fixation, according to the present embodiments.

FIG. 12 is a perspective view photograph of an external fixation 18, according to the present embodiments.

Figure 13:
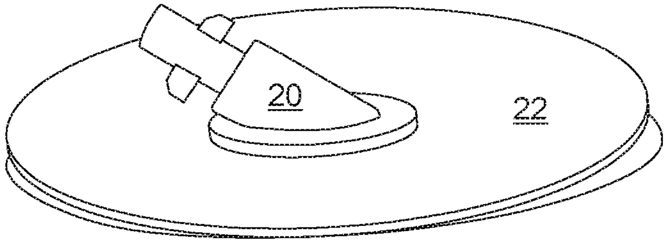
FIG. 13 is a perspective view photograph of a scaffold with a patch disposed thereon, according to the present embodiments.

FIG. 13 is a perspective view photograph of a scaffold 20 with a patch 22 disposed thereon, according to the present embodiments.

Figure 14:
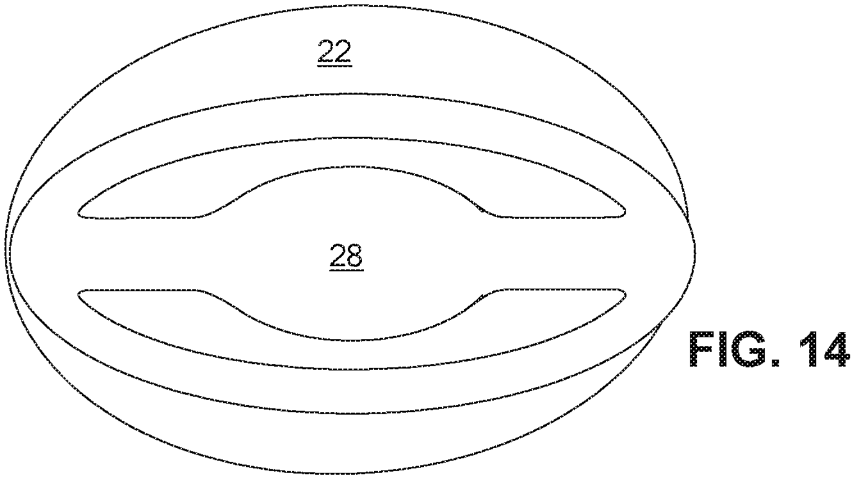
FIG. 14 is a top view photograph of a scaffold base with a patch disposed thereon, according to the present embodiments.

FIG. 14 is a top view photograph of a scaffold base 28 with a patch 22 disposed thereon, according to the present embodiments.

Figure 15:
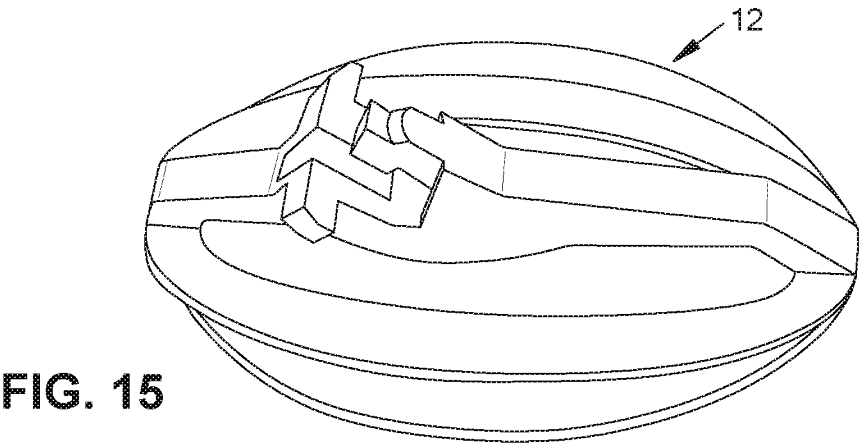
FIG. 15 is a perspective view photograph of an assembled vascular closure device, according to the present embodiments.

FIG. 15 is a perspective view photograph of an assembled vascular closure device 12, according to the present embodiments.

Figure 16:
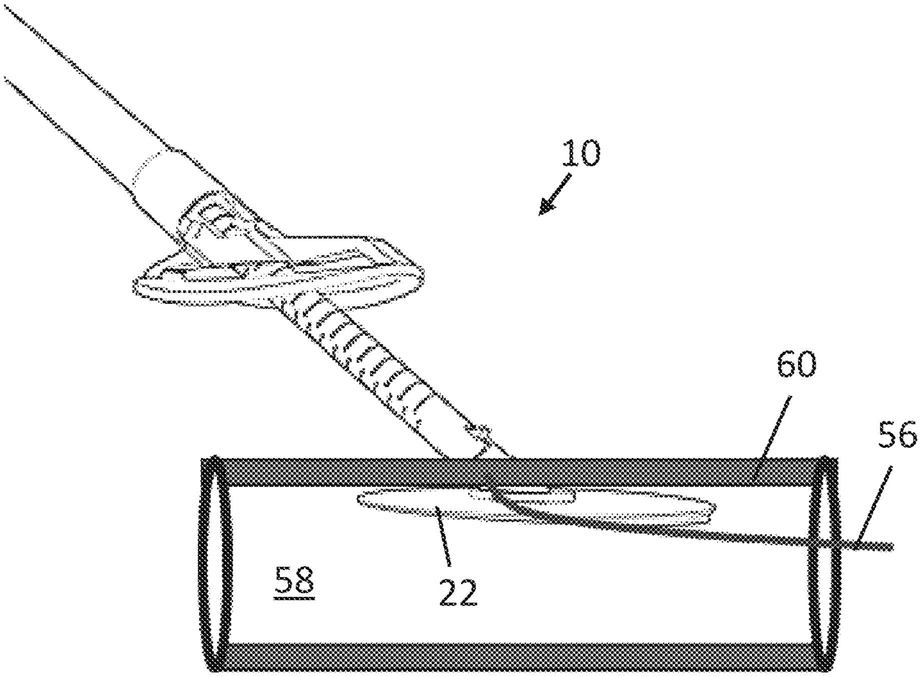
FIG. 16 is a side view of a vascular closure device and system, according to the present embodiments.

FIG. 16 is a side view of a vascular closure device and system 10, according to the present embodiments. The system 10 may include a guidewire 56 for helping to deploy the patch 22 and scaffold 20 within a blood vessel and/or other organ 58. The guidewire 56 may be deployed through each of the patch 22, scaffold (i.e., through the scaffold neck 30) the outer shaft 14, the distal scaffold retention shaft 16, and the external fixation 18). The guidewire 56 may be retracted one the placement of the device 12 has been finalized. As illustrated, each of the patch 22 and scaffold 20 internal to a vessel wall 60, while the external fixation 18 remains external to the vessel wall 60. The scaffold 20 (i.e., the scaffold base 28) is visible beneath the patch 22 near the guidewire 56 and is unlabeled for clarity purposes.

Figure 17:
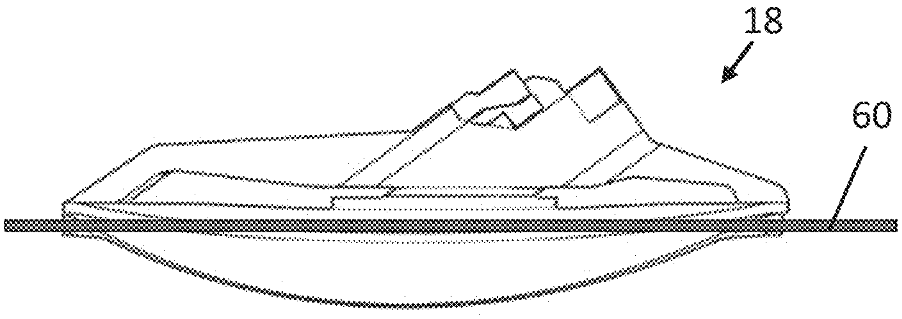
FIG. 17 is a side view of a vascular closure device, according to the present embodiments.

FIG. 17 is a side view of the external fixation 18 when deployed adjacent the vessel wall 60, according to the present embodiments.

Figure 18:
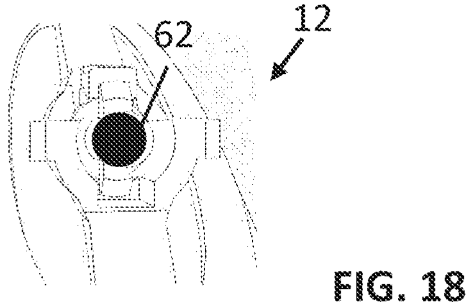
FIG. 18 is a top view of a vascular closure device, according to the present embodiments.

FIG. 18 is a top view of a vascular closure device 12 with a closure pin 62 disposed in the guidewire hole after the guidewire 56 has been retracted, according to the present embodiments. In some embodiments, a guidewire may not be used at all, in which case the closure pin 62 may be disposed within the device 12 throughout deployment.

Figure 19:
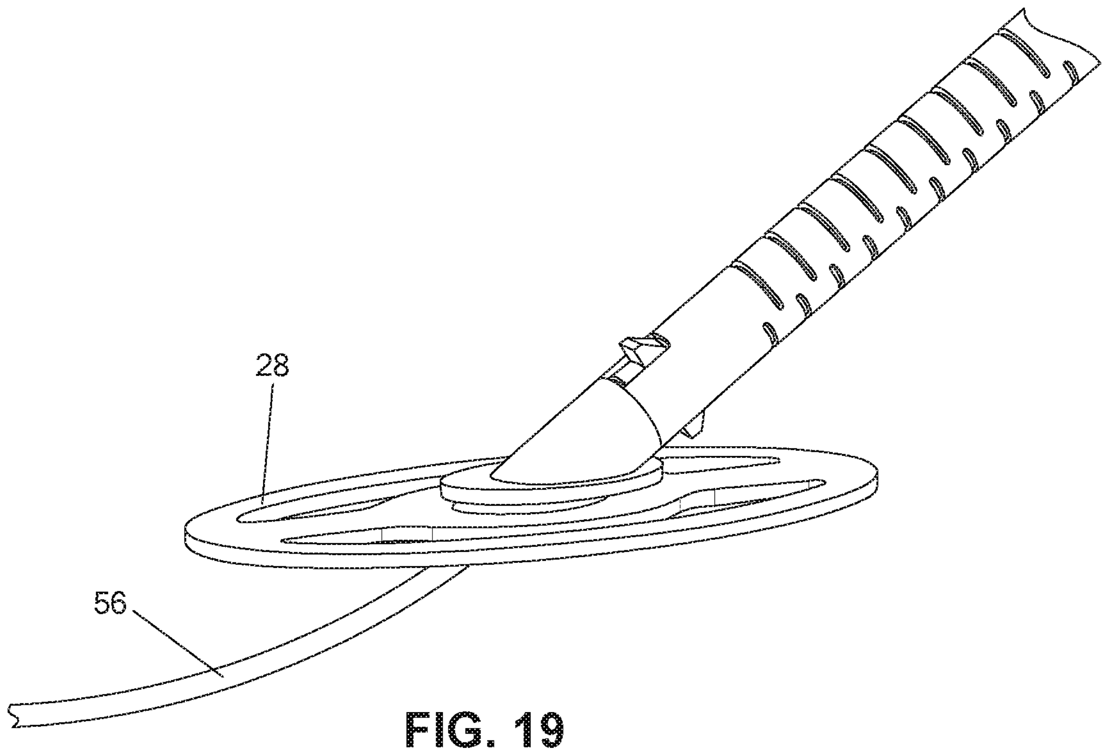
FIG. 19 is a perspective view of a vascular closure device and system, according to the present embodiments.

FIG. 19 is a perspective view of a vascular closure device and system including the scaffold 20 (for example, the scaffold base 28) and guidewire 56, according to the present embodiments. Other components have been omitted for clarity.

Figure 20:
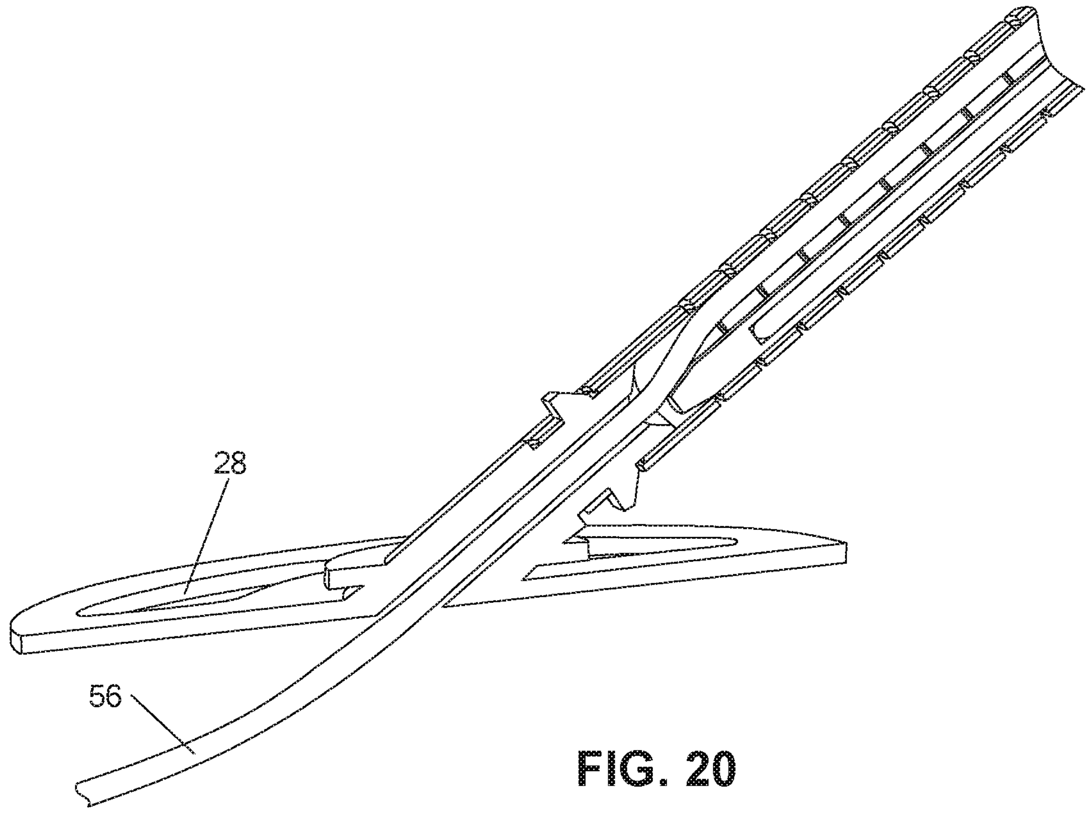
FIG. 20 is a side, cross-sectional view of a vascular closure device and system, according to the present embodiments.
Figure 21:
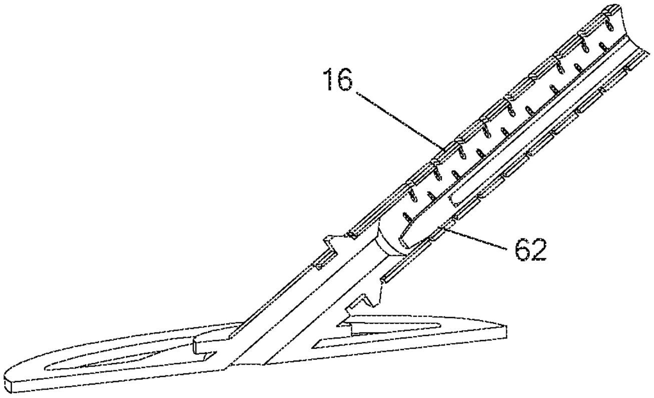
FIG. 21 is a side, cross-sectional view of a vascular closure device and system, according to the present embodiments.

FIG. 20 is a side, cross-sectional view of a vascular closure device and system including the scaffold 20 and guidewire 56, according to the present embodiments. Other components have been omitted for clarity.

Figure 22:
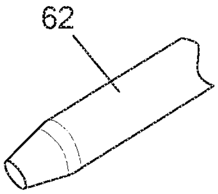
FIG. 22 shows a perspective view of a closure pin, according to the present embodiments.
Figure 23:
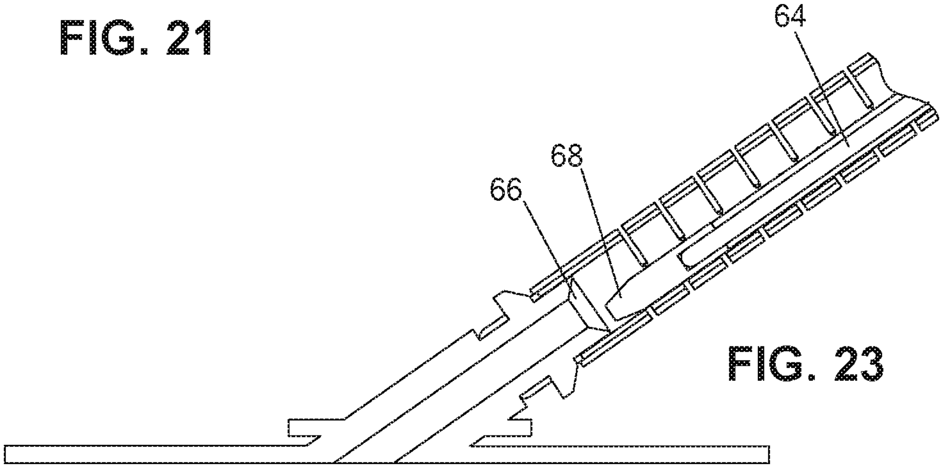
FIG. 23 is a side, cross-sectional view of a vascular closure device and system, according to the present embodiments.
Figure 24:
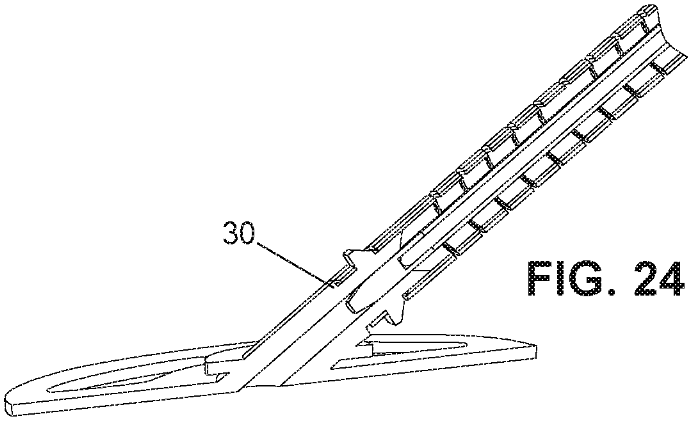
FIG. 24 is a side, cross-sectional view of a vascular closure device and system, according to the present embodiments.
Figure 25:
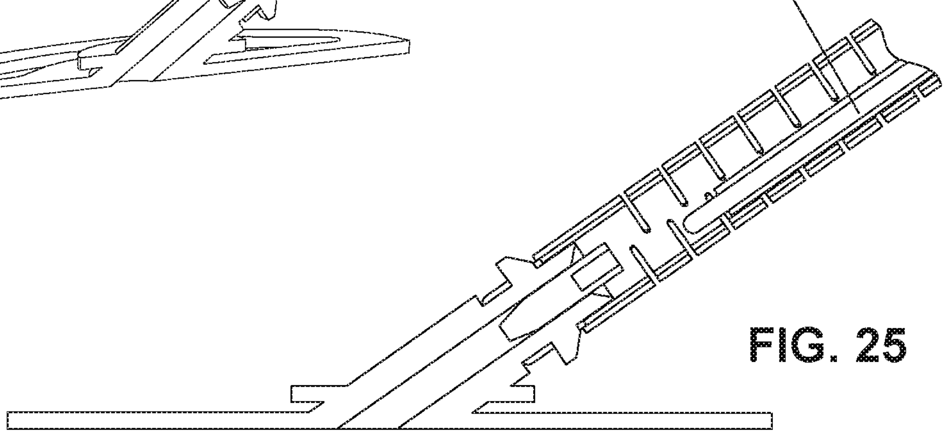
FIG. 25 is a side, cross-sectional view of a vascular closure device and system, according to the present embodiments.

FIGS. 21 and 23-25 illustrate a side, cross-sectional view of a vascular closure device and system, according to the present embodiments. In FIGS. 21 and 23-25, a closure pin 62 (FIG. 22) is shown being pushed into the center of the scaffold neck 30 by a pusher rod 64, after the guidewire 56 is retracted. The pusher rod 64 may subsequently be retracted, as shown in FIG. 25. While not deployed, each of the pusher rod 64 and closure pin 62 may be stored within the distal scaffold retention shaft 16. The scaffold neck 30 may include an angled inner surface 66 that may interface with an angled closure pin tip 68 to encourage the closure pin to move toward the center of the scaffold neck 30 when being pushed distally by the pusher rod 64 (since, in a stored position, the closure pin 62 and pusher rod 64 are offset from a central axis of the distal scaffold retention shaft 16 to allow space for the guidewire 56). The angle of the angled inner surface 66 may be larger relative to a longitudinal (or central) axis of the distal scaffold retention shaft 16 than the angle of the angled closure pin tip 68 relative to the same.

In operation, each of the patch 22 and scaffold 20 may be folded or wrapped within the outer shaft 14 and the distal scaffold retention shaft 16 such that they may be deployed through the aperture in the vessel wall 60 and within the blood vessel, artery, etc. Once inside the vessel, each of the patch 22 and scaffold 20 may expand. The distal scaffold retention shaft 16 may be pulled proximally to bring the patch 22 and scaffold 20 toward the aperture, thereby sealing the aperture. The outer shaft 14 may be pushed distally such that the external fixation 18 locks with the scaffold 20, thereby forming a solid anchor to which the scaffold and patch may attach on the outside of the vessel wall 60. Each of the outer shaft 14 and the distal scaffold retention shaft 16 may be decoupled from the respective components of the device 12 by a 90-degree clockwise rotation, when looking in the distal direction.

The patch 22 (and optionally the scaffold 20 and/or external fixation) forms, in some embodiments, a flexible bilayer bioabsorbable polymer film which, in some embodiments is electrospun onto a substrate material.

Electrospinning employs, in some embodiments, electrical force to draw very fine fibers (e.g., micro- or nano-scale) of polymers, ceramics, metals, carbon and/or composite materials from a liquid and/or a solution/melt. Electrospinning typically generates a jet in a high-voltage field to produce elongated fibers. A high-voltage electrical field is applied between a capillary where a suitable solution or melt is stored and a collection screen on which an electrically charged jet solidifies. For example, one electrode from a high-voltage source may be contacted with the solution/melt (e.g., needle, capillary) and the other attached to the collection screen. When a voltage is applied to a droplet of the solution/melt, the droplet is stretched into a jet due to electrostatic repulsion and surface tension. The jet is whipped by electrostatic repulsion until it is deposited on the collection screen. Electrospinning can be adjusted to produce continuous liquid jets by controlling parameters (e.g., molecular weight, viscosity, conductivity, surface tension, and electric potential, flow rate, concentration, distance between capillary and collection screen, temperature, needle gauge, etc.). The method beneficially ensures, among other benefits as described herein (e.g., combined with secondary processing (e.g., reduced pressure processing), that no solvent made from the manufacturing process is carried over into the final product. Of course, other methods of generating very fine fibers may be employed.

The mesh layer 102 and/or the substrate 104 comprise, in some embodiments, at least one material selected from the group consisting of Polydioxanone, Poly-L-lactide, Poly-D-lactide, Poly-DL-lactide, Polyglycolide, F-Caprolactone, Polyethylene glycol, and a copolymer thereof. In some embodiments, the material of the mesh layer 102 and/or substrate layer 104 is a copolymer of, for example, but not limited to, Polydioxanone, Poly-L-lactide, Poly-D-lactide, Poly-DL-lactide, Polyglycolide, F-Caprolactone, and Polyethylene glycol. In some embodiments, the copolymer includes (a) monomers of Polydioxanone, Poly-L-lactide, Poly-D-lactide, Poly-DL-lactide, Polyglycolide, F-Caprolactone, or Polyethylene glycol, and (b) one or more additional monomers. In some embodiments, the (a) and (b) monomers form a polymer that is bioabsorbable. One of ordinary skill in the art will appreciate that other bioabsorbable and/or biodegradable material may be employed.

A bioabsorbable polymer can have crystalline and amorphous regions and are therefore, in general, semi-crystalline in nature. Degradation of a bioabsorbable polymer, in certain embodiments, initiates in the amorphous regions, with the crystalline regions degrading at a slower rate relative to the amorphous regions. Without wishing to be tied to a particular theory, and for illustrative purposes only, degradation of a polymer such as polydioxanone (PDO) occurs along the polymer back bone by hydrolysis of the ester bonds. This non-specific ester bond scission may occur randomly along the polymer chain with water penetration initially breaking the chemical bonds and converting the long polymer chains into natural monomeric acids found in the body, such as lactic acid. Such monomeric acids are then phagocytized by the enzymatic action of special types of mononuclear and multinuclear white blood cells. The polymer is, thus, degraded into non-toxic, low molecular weight residues that are capable of being eliminated from the body by normal metabolic pathways, e.g., via exhalation and/or excretion. Such a pathway thereby enables reference to the breakdown of such polymers in vivo through terminology such as absorbable, bioabsorbable, degradation, biodegradation, resorption, and bioresorption, among others. For example, in certain embodiments, the implanted device (e.g., the patch, the external fixation outside the vessel wall, and the scaffold inside the vessel wall) is made of PDO, and the entire implanted device bioabsorbs within 180 days.

In certain embodiments, the patch 22 preferably has a range between about 60 μm and about 120 μm in thickness. The range of thicknesses may be between 50 μm and 500 μm, or between 75 μm and 250 μm, or between 100 μm and 200 μm. In certain embodiments, the electrospun layer 102 substantially consists of fibers in the range from 0.3 μm to 8 μm diameter, with a layer thickness preferably in the range from 10 μm to 60 μm. The fibers may be arranged in a random or patterned orientation.

Figure 26:
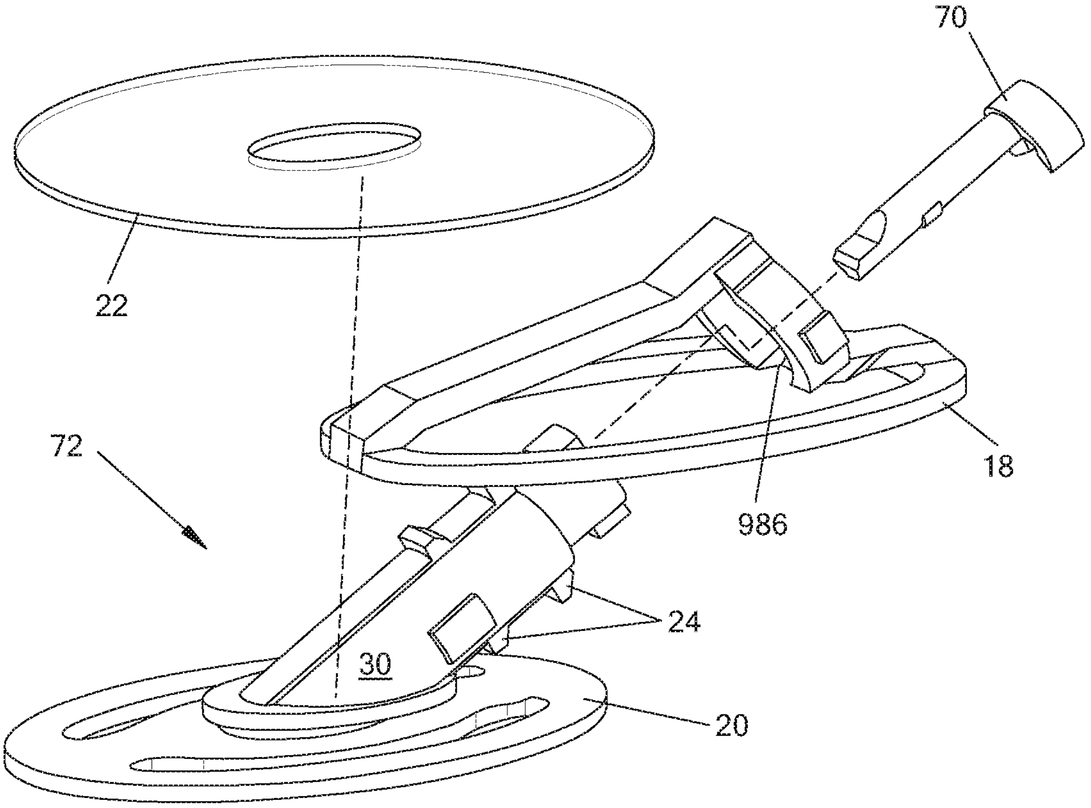
FIG. 26 is a view of a vascular closure device assembly, with the component parts separated, according to the present embodiments.

FIG. 26 is a view of a vascular closure device assembly 72, according to the present embodiments. The vascular closure device assembly 72 includes a closure pin 70, a flexible patch 22, the scaffold (including the scaffold base 20 and scaffold neck 30), and an external fixation 18. In the embodiment of FIG. 26, the device assembly 72 includes two retaining tabs 24 extending out of the scaffold neck 30 on each of the underside and topside of the scaffold neck. The multiple sets of retaining tabs 24 interface with the external fixation 18 such that the external fixation 18 may be fixed around the scaffold neck 30, and on the top of the flexible patch 22, to keep the assembly 72 sandwiched together for sealing a vascular aperture or opening. The multiple sets of retaining tabs 24 allow the assembly 72 to accommodate multiple vessel wall thicknesses and varying anatomies.

Figure 27:
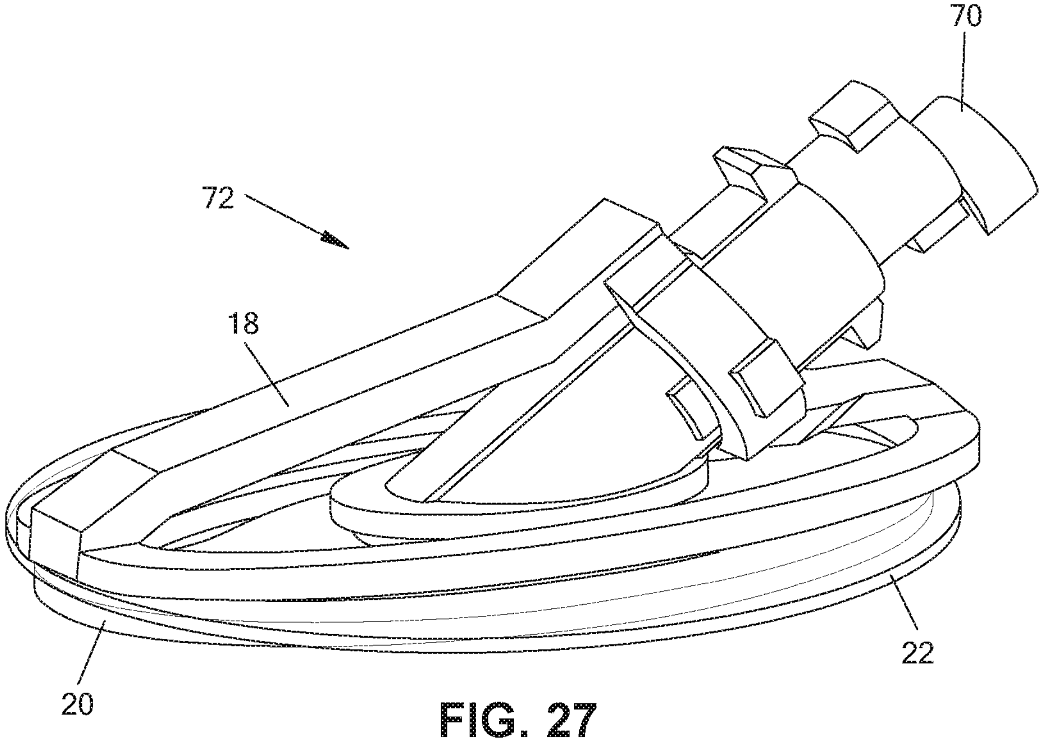
FIG. 27 is a view of a vascular closure device assembly, with the component parts assembled, according to the present embodiments.

FIG. 27 is a view of a vascular closure device assembly 72, according to the present embodiments. The scaffold neck 30 has two retaining tabs 24 for adjusting the distance between the distal edge of the external fixation 18 and the top surface of the scaffold base 20/patch 22. In the embodiment of FIG. 27, the vascular closure device assembly 72 is fully assembled with the external fixation 18 positioned in the tighter configuration, so as to accommodate a thinner tissue thickness. FIGS. 89-92 show additional embodiments and configurations that include a device with four different sets of teeth protruding from the scaffold neck 30, 122, thereby allowing the device to accommodate 4 different vessel wall thicknesses and different tissue tract anatomies. As shown in FIGS. 26 and 27, and as described in greater detail below in connection with FIGS. 46-77, the closure pin 70 may be used to close (that is, seal) a guidewire lumen after the guidewire is withdrawn from the scaffold.

Figure 28:
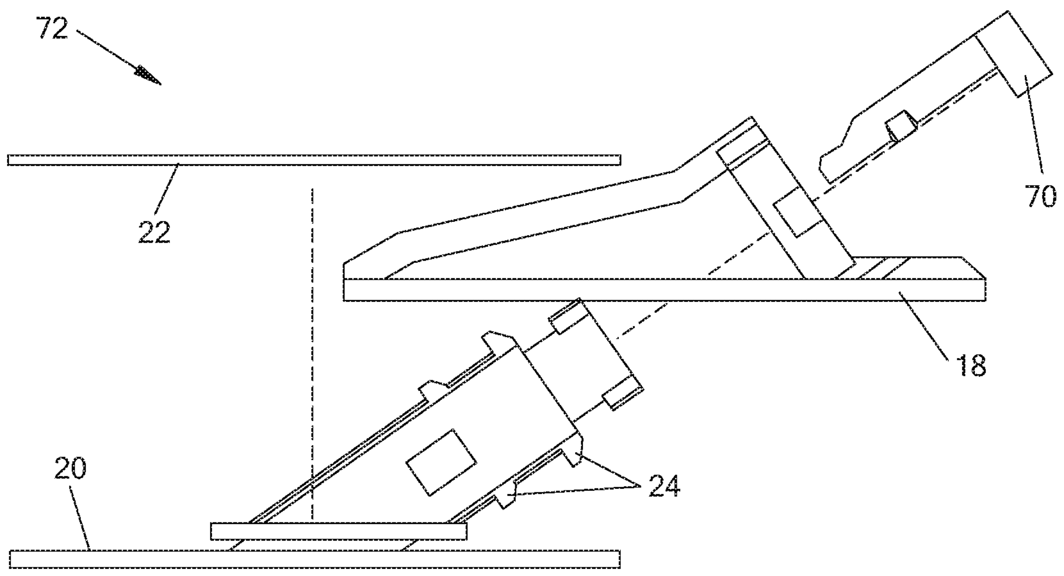
FIG. 28 is a side view of a vascular closure device assembly, with the component parts separated, according to the present embodiments.
Figure 29:
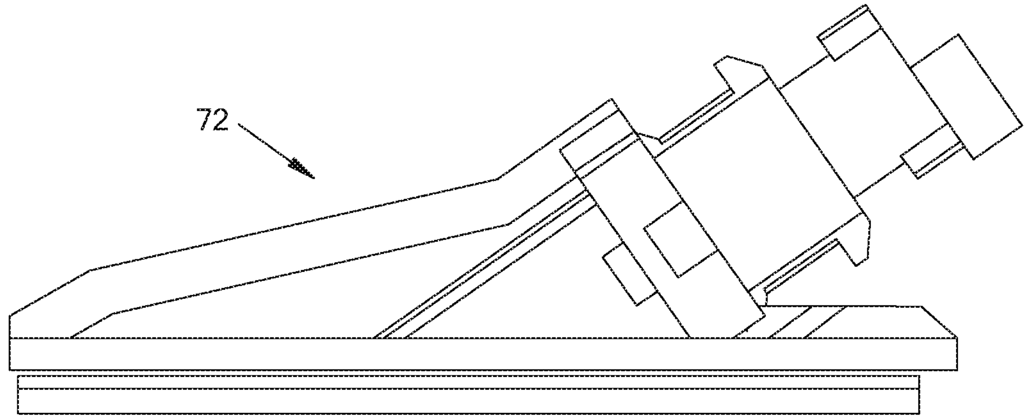
FIG. 29 is a side view of a vascular closure device assembly, with the component parts assembled, according to the present embodiments.

FIGS. 28 and 29 show alternate side views of the unassembled and fully assembled vascular closure device assembly 72, according to the present embodiments. The device assembly configuration of FIGS. 28 and 29 is the same as that of FIGS. 26 and 27.

Figure 30:
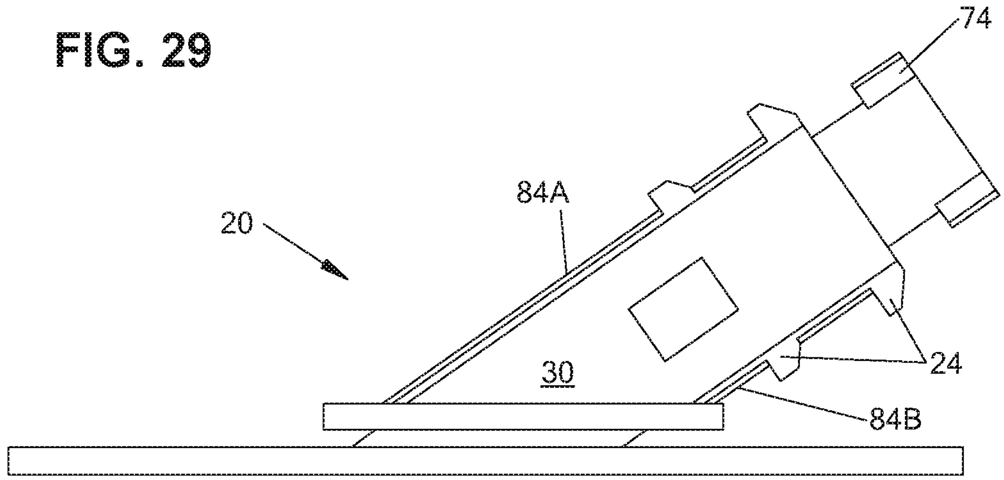
FIG. 30 is a side view of a vascular closure device scaffold, according to the present embodiments.
Figure 31:
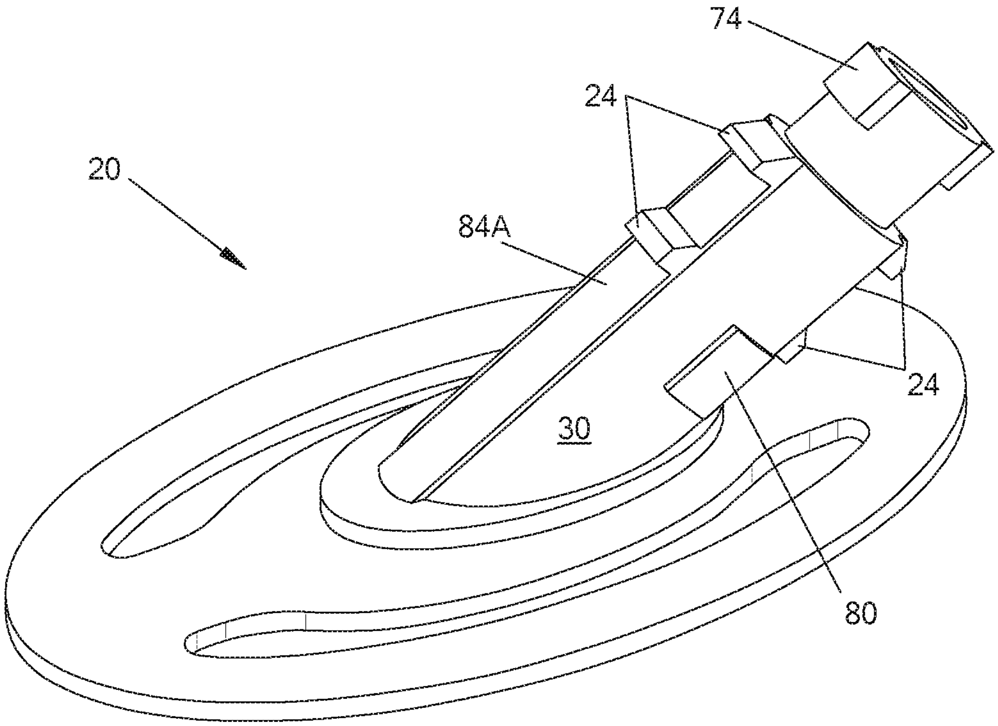
FIG. 31 is a perspective view of a vascular closure device scaffold, according to the present embodiments.
Figure 32:
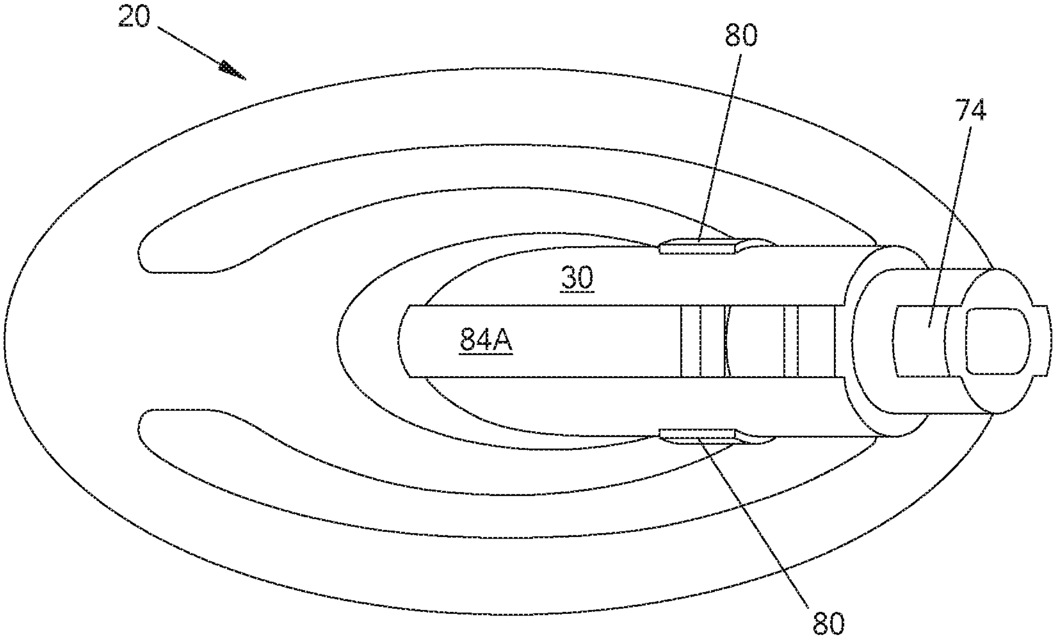
FIG. 32 is a top view of a vascular closure device scaffold, according to the present embodiments.
Figure 33:
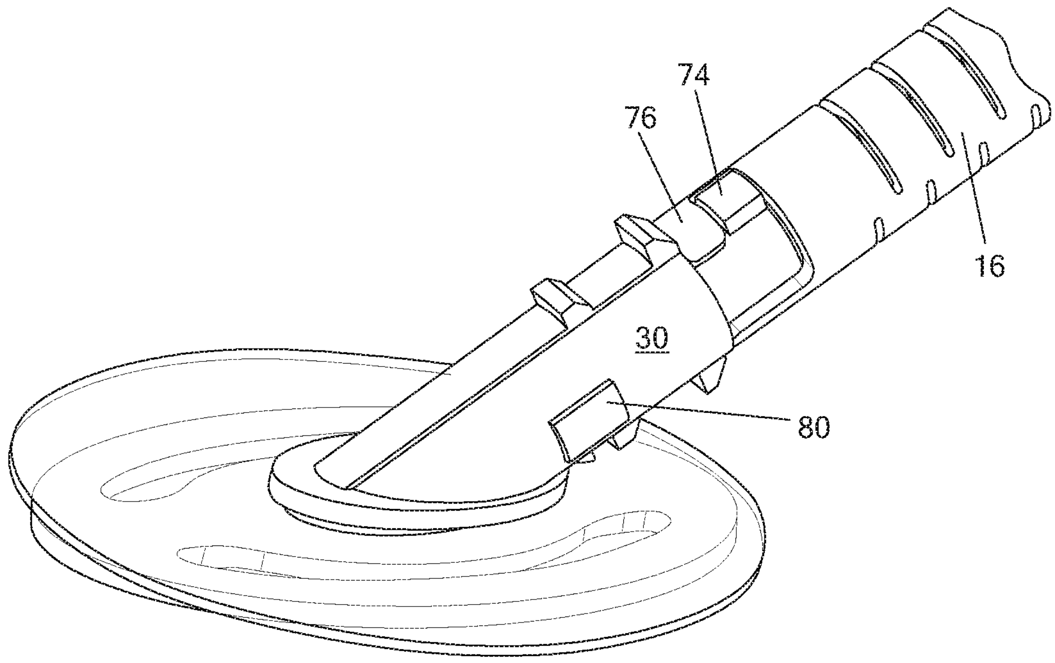
FIG. 33 is a view of a vascular closure device and delivery shaft, according to the present embodiments.
Figure 34:
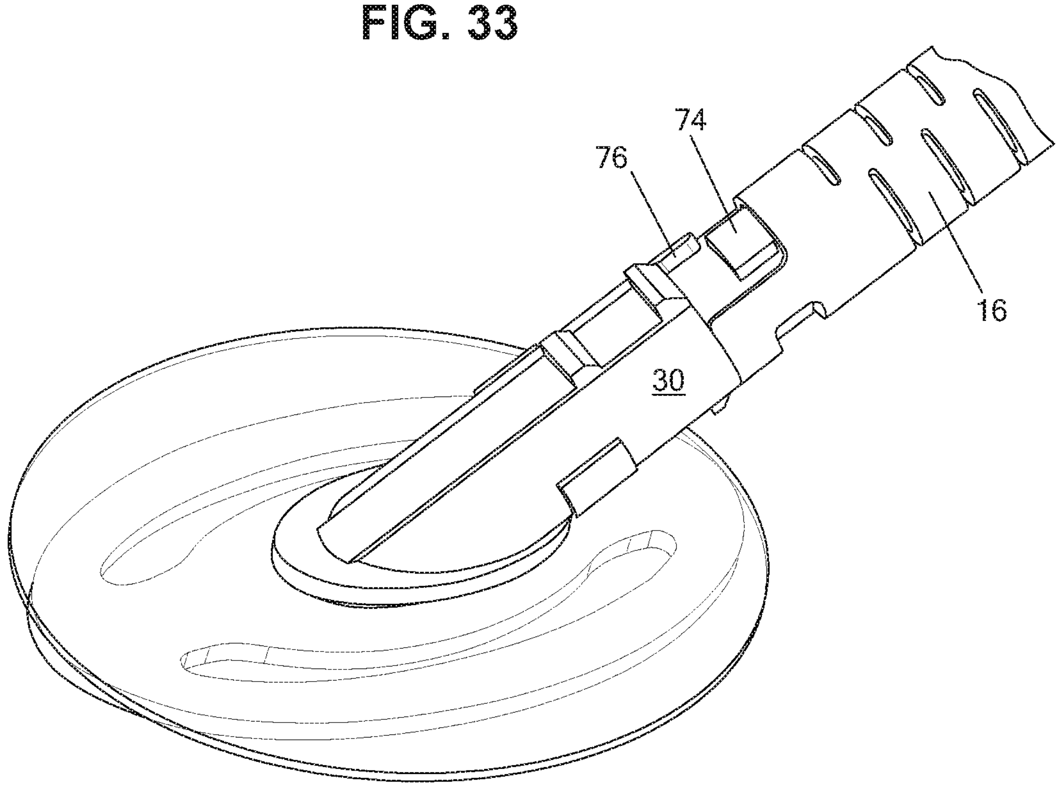
FIG. 34 is a view of a vascular closure device and delivery shaft, according to the present embodiments.

FIGS. 30-32 illustrate side, perspective, and top views of a vascular closure device scaffold 20, according to the present embodiments. The embodiment of FIG. 30 includes two sets of retaining tabs 24. In addition, the scaffold 20 includes a first linear ridge 84A on the top side of the scaffold neck and a second linear ridge 84B on the bottom side of the scaffold neck 30. The first and second linear ridges 84A, 84B interface with corresponding grooves 986 (shown in FIGS. 26, 39, and 87) in the external fixation 18 such that the external fixation 18 remains properly aligned (i.e., with the scaffold base 20 and flexible patch 22) as it slides distally down the scaffold neck 30. The grooves 986 are disposed within an internal surface of the collar 984 on opposing sides. The scaffold 20 may also include a set of raised tabs 74 disposed on opposite sides of the proximal end of the scaffold neck 30. In some embodiments, the raised tabs 74 may be substantially square-shaped. The raised tabs 74 interface with L-shaped slots 76 in the scaffold retention shaft 16, thereby forming a bayonet mount, as shown in FIGS. 33 and 34, which illustrate views of a vascular closure device and delivery shaft (scaffold retention shaft 16). In the configuration of FIG. 33, the L-shaped slot 76 is positioned distally from the raised tab 74 when the scaffold 20 is in delivery position, thereby preventing distal or proximal movement of the scaffold 20 relative to the scaffold retention shaft 16. In the configuration of FIG. 34, the L-shaped slot 76 has been rotated (that is, the entire scaffold retention shaft 16 has been rotated) relative to the scaffold 20, such that the L-shaped slot 76 is no longer positioned distal of the raised tab 74. In the position shown in FIG. 34, the scaffold retention shaft 16 may disengage with the scaffold 20 and may be withdrawn in a proximal direction, once the scaffold has been positioned about the wound, aperture, and/or vessel opening.

Figure 35:
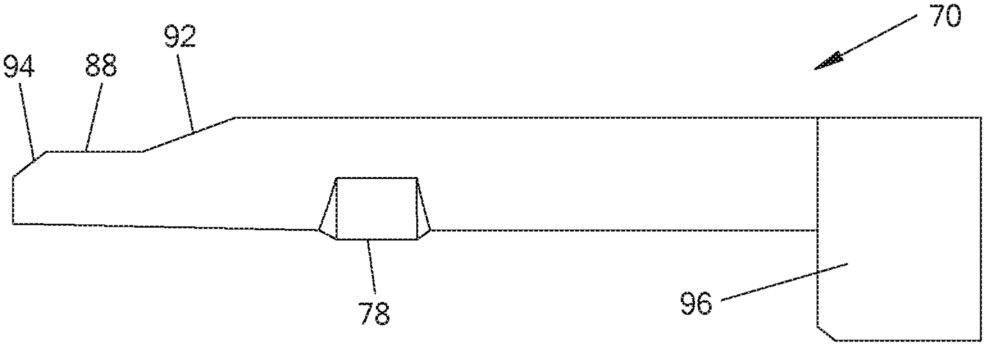
FIG. 35 is a side view of a vascular closure device pin, according to the present embodiments.
Figure 36:
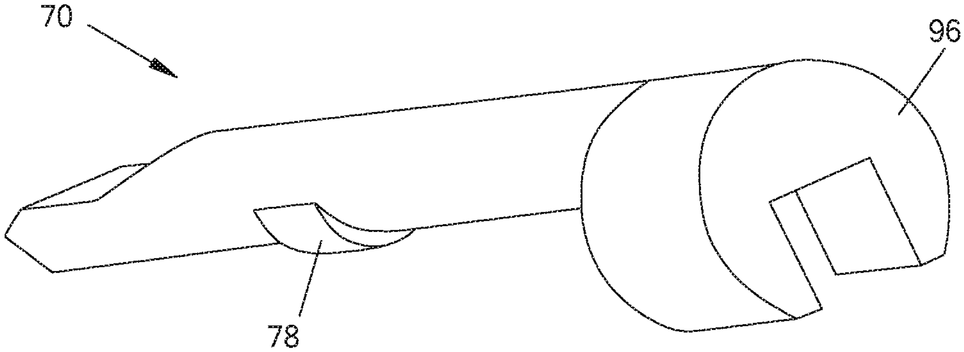
FIG. 36 is a perspective view of a vascular closure device pin, according to the present embodiments.
Figure 37:
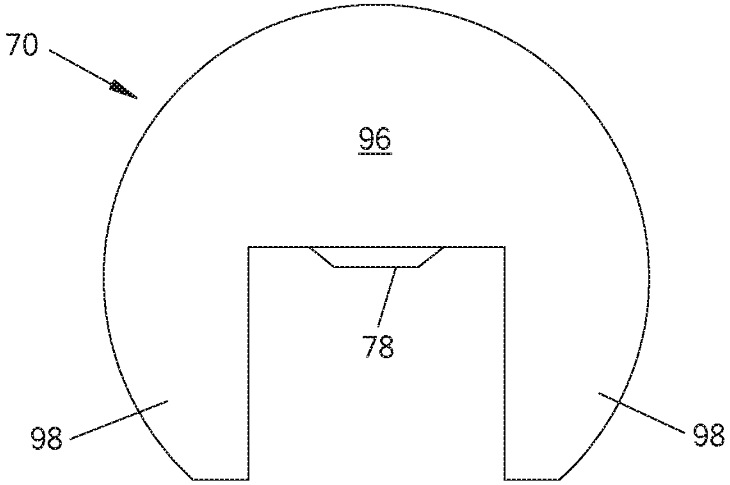
FIG. 37 is a back view of a vascular closure device pin, according to the present embodiments.

FIGS. 35-37 illustrate side, perspective, and front views of a vascular closure device closure pin 70, according to the present embodiments. The closure pin 70 may include an outer diameter of from about 0.03 inches to about 0.035 inches (for example, in a range from 0.031 inches to 0.034 inches, or 0.032 inches to 0.033 inches) such that it may be used to seal or close a guidewire lumen with an inner diameter of about 0.035 inches. The closure pin 70 may include a stepped tapered shape at the distal end with a stepped portion 88 located distally of a tapered portion 92. The closure pin 70 may also include a chamfer 94 located distally of the stepped portion 88. The stepped tapered shape allows the closure pin 70 to interface with internal tapers and/or features of the scaffold neck 30 to encourage the closure pin 70 to slide into the guidewire lumen when pushed distally, as illustrated in further detail in FIGS. 52 and 53.

Referring still to FIGS. 35-37, the closure pin 70 may also include at least one bump feature 78 which provides a wedging effect when the closure pin 70 is driven distally into the guidewire lumen (or hole) in the scaffold neck 30. The bump feature 78 provides additional friction and interference between the closure pin 70 and the internal surface of the guidewire lumen, thereby creating a compression fit therebetween when the closure pin 70 is pushed distally. The closure pin 70 also includes a head section 96 with a larger cross-sectional area than the rest of the closure pin 70, thereby helping to facilitate the closure pin 70 to be driven into the guidewire lumen via a push tube (not shown). The closure pin may also include two curved arms 98 that are part of the pin head section 96 and wrap around the guidewire 56 (and allow the guidewire 56 (shown in FIG. 16) to be withdrawn therethrough).

Figure 38:
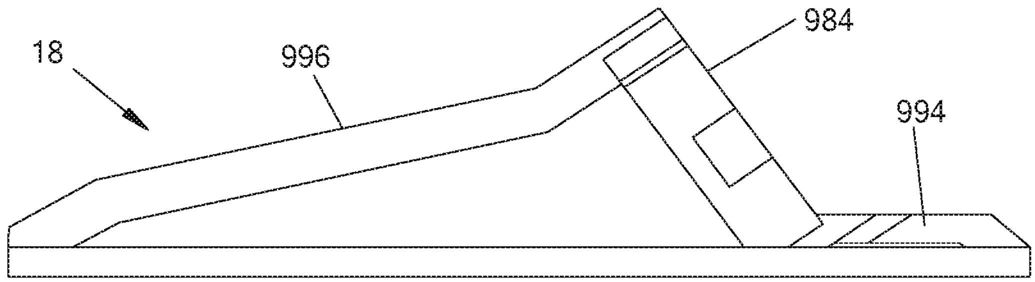
FIG. 38 is a side view of a vascular closure device external fixation, according to the present embodiments.
Figure 39:
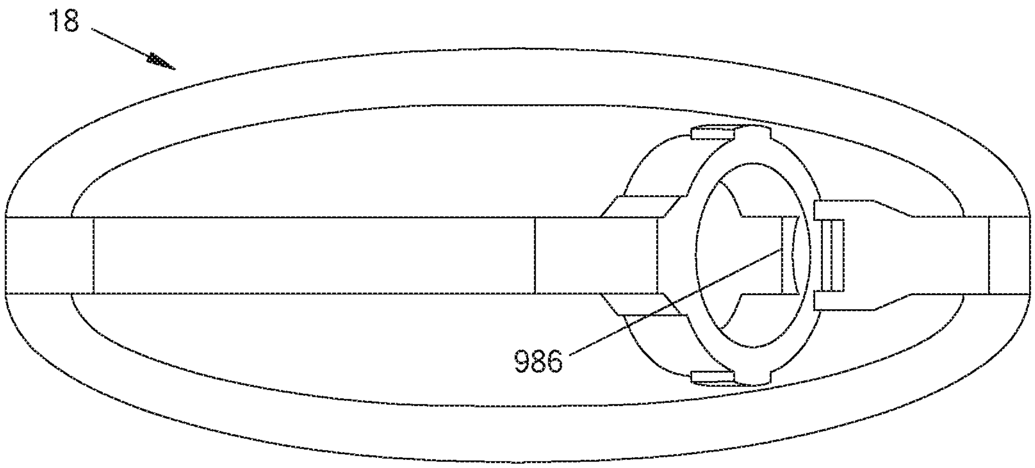
FIG. 39 is a top view of a vascular closure device external fixation, according to the present embodiments.
Figure 40:
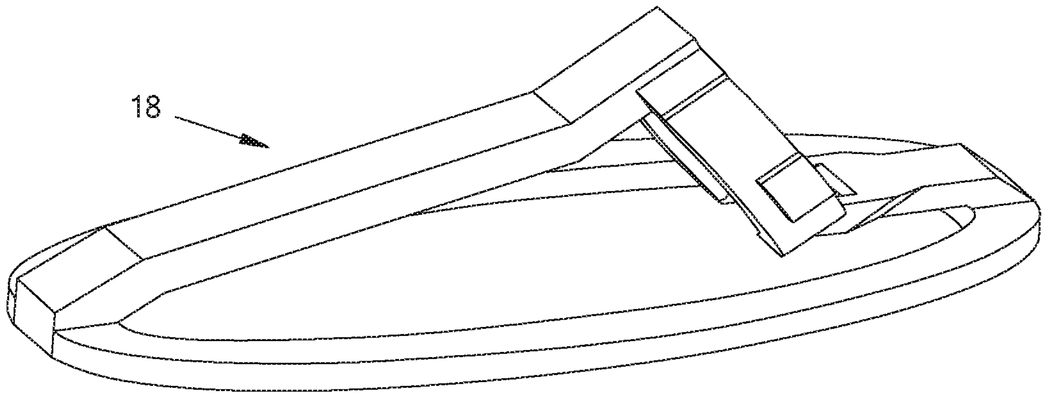
FIG. 40 is a perspective view of a vascular closure device external fixation, according to the present embodiments.
Figure 87:
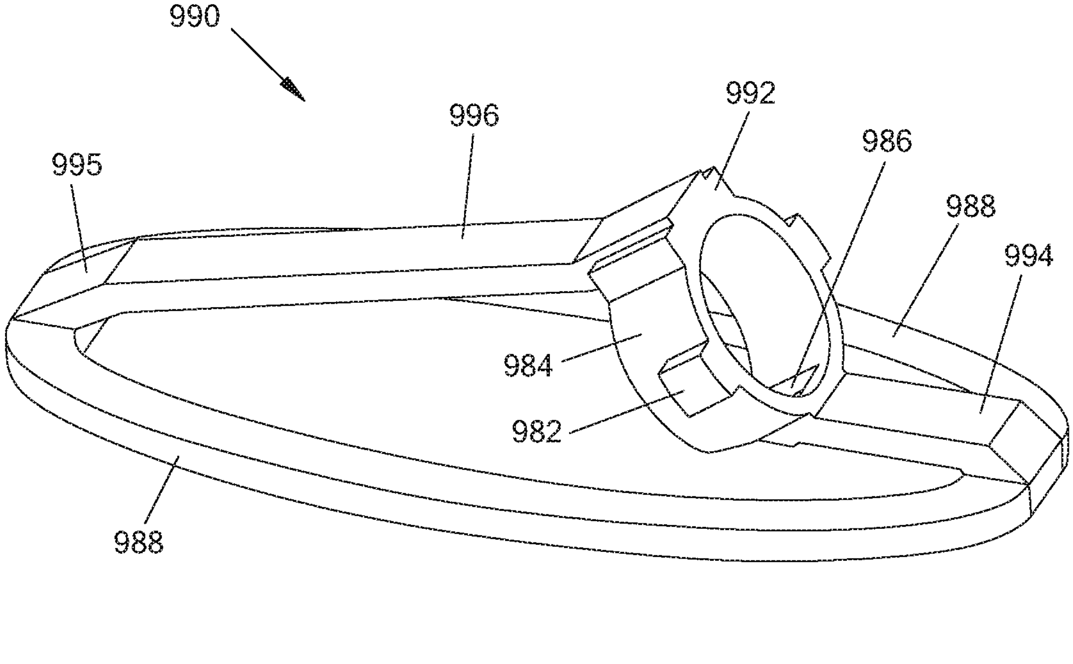
FIG. 87 is an image of an external fixation used for a closure device, according to aspects of the present embodiments.

FIGS. 38-40 illustrate side, top, and perspective views of a vascular closure device external lock 18 (or external fixation 18), according to the present embodiments. The external fixation 18 may include anterior and posterior members 996, 994 or ribs connecting to the collar 984 to provide both support and flexibility such that the ribs 996, 994 may adapt and conform to the various vessel wall morphologies and tissue tract anatomies that are experienced in clinical use. The external fixation 18 is also shown in FIG. 87 and described in further detail below.

Figure 41:
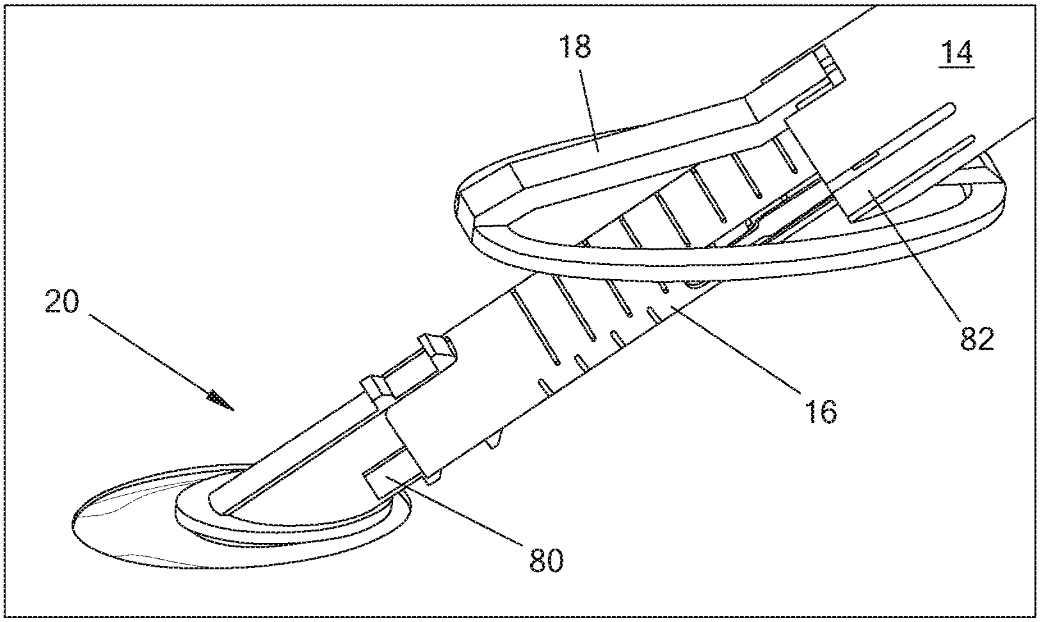
FIG. 41 is a view of a vascular closure device and delivery system, according to the present embodiments.
Figure 42:
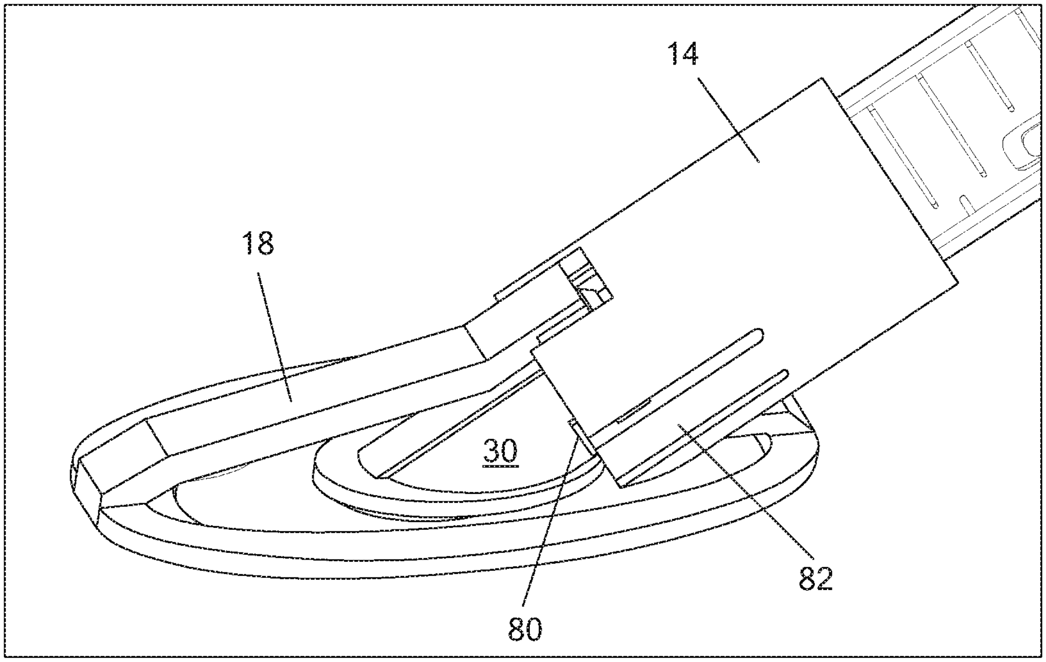
FIG. 42 is a view of a vascular closure device and delivery system, according to the present embodiments.
Figure 43:
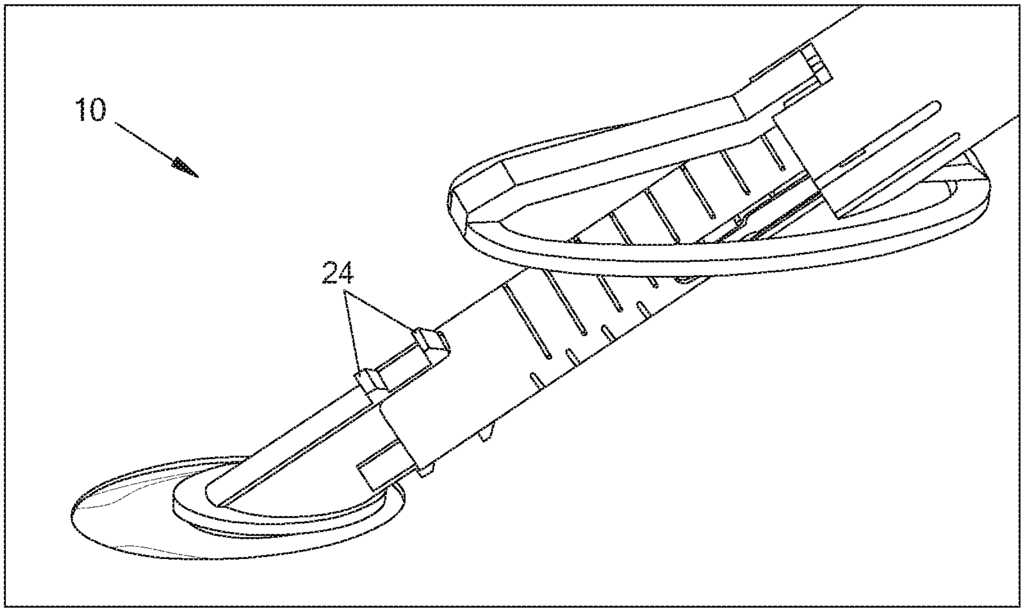
FIG. 43 is a view of a vascular closure device delivery system and device, according to the present embodiments.

FIGS. 41-43 illustrate views of a vascular closure device and delivery system, according to the present embodiments. In the embodiments of FIGS. 41 and 42, the external fixation 18 is being delivered to the scaffold 20 via an outer shaft that is concentrically disposed around the scaffold retention shaft 16, and coupled to the external fixation 18. In FIG. 41, the external fixation 18 is coupled to the outer shaft 14 via a pair of retention clips 82 on opposing lateral sides of the outer shaft 14 such that the external fixation 18 may be pushed distally toward the scaffold 20. The retention clips 82 are monolithic with the outer shaft 14 and extend axially toward the distal end of the outer shaft 14 such that the distal ends of the retention clips 82 are free to bend and flex, with inherent stiffness and elasticity. Internal, radially-inwardly-extending lips (not shown) at the distal ends of the retention clips 82 interface with the underside (or distal surface of) the collar 984, thereby holding the external fixation 18 in place. As illustrated in FIG. 42, once the external fixation 18 is brought around the scaffold neck 30, the retention clips 82 of the outer shaft 14 interface with a corresponding pair of raised tabs 80 on the scaffold neck 30 that push the retention clips 82 radially outward, thereby causing them to release the external fixation 18 (and allowing the outer shaft 14 to decouple from the external fixation 18 and be proximally withdrawn). By this point, the collar 984 has been pushed around and past at least one set retaining tabs 24 (depending on the vessel wall thickness), such that the external fixation 18 will remain sandwiched against the patch 22 and scaffold base 20. In FIG. 42, a portion of the outer shaft 14 appears as translucent such that the scaffold retention shaft 16 therewithin is visible.

Figure 44:
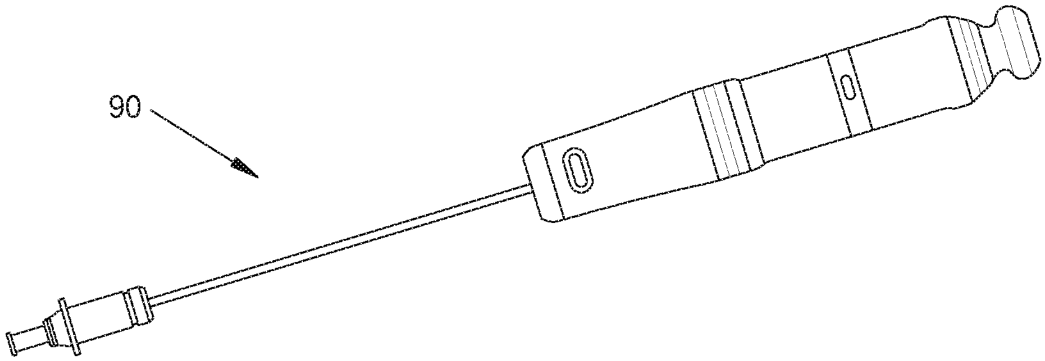
FIG. 44 is a view of a vascular closure device delivery system and handle, according to the present embodiments.
Figure 45:
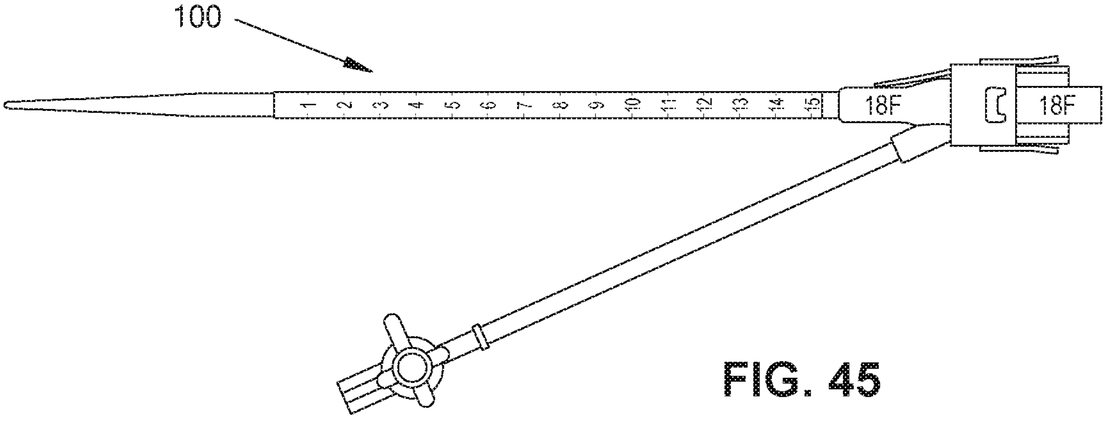
FIG. 45 is a view of a vascular closure device introducer, according to the present embodiments.

FIG. 44 is a view of a vascular closure device introducer 90, according to the present embodiments. FIG. 45 is a view of a vascular closure device and system 100, according to the present embodiments.

Guidewire Lumen Closure

First Embodiment of Closure Pin

Figure 46:
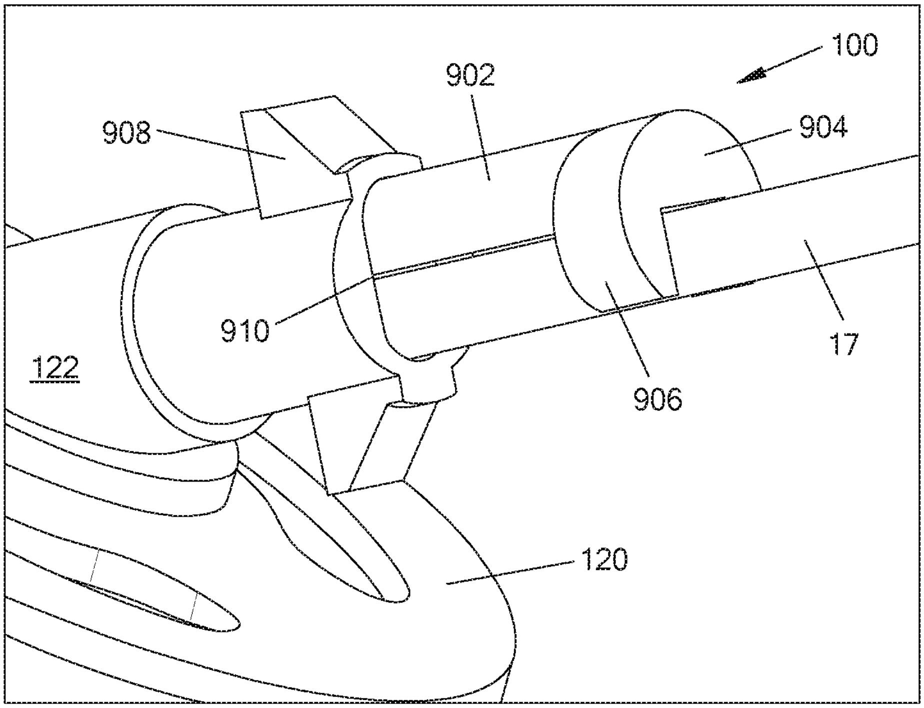
FIG. 46 is an image of a closure device with a guidewire lumen closure pin, according to aspects of the present embodiments.
Figure 47:
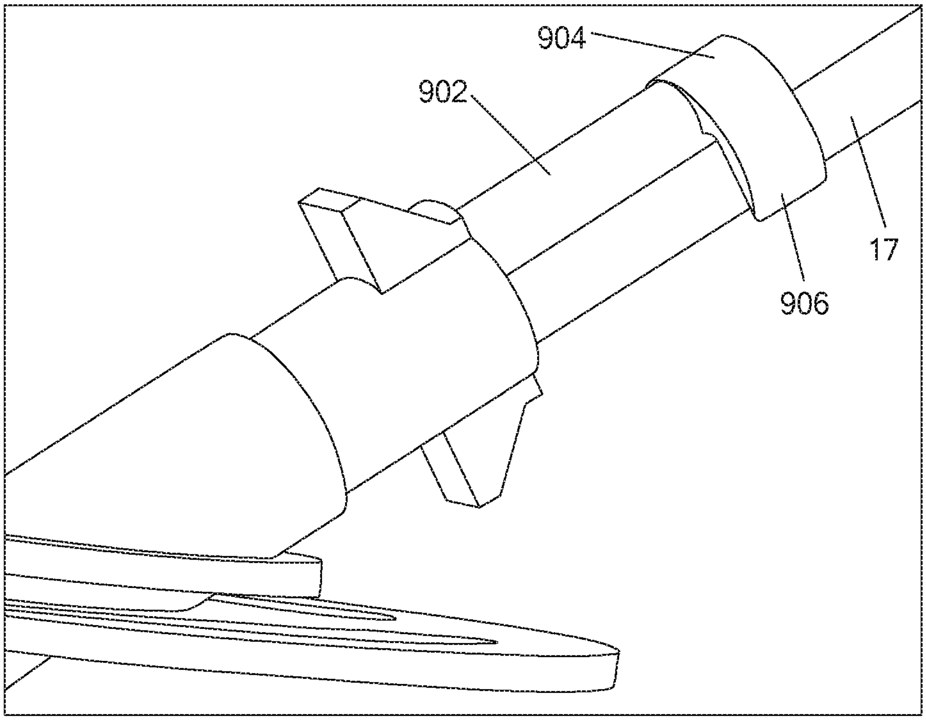
FIG. 47 is an image of a closure device with a guidewire lumen closure pin, according to aspects of the present embodiments.
Figure 48:
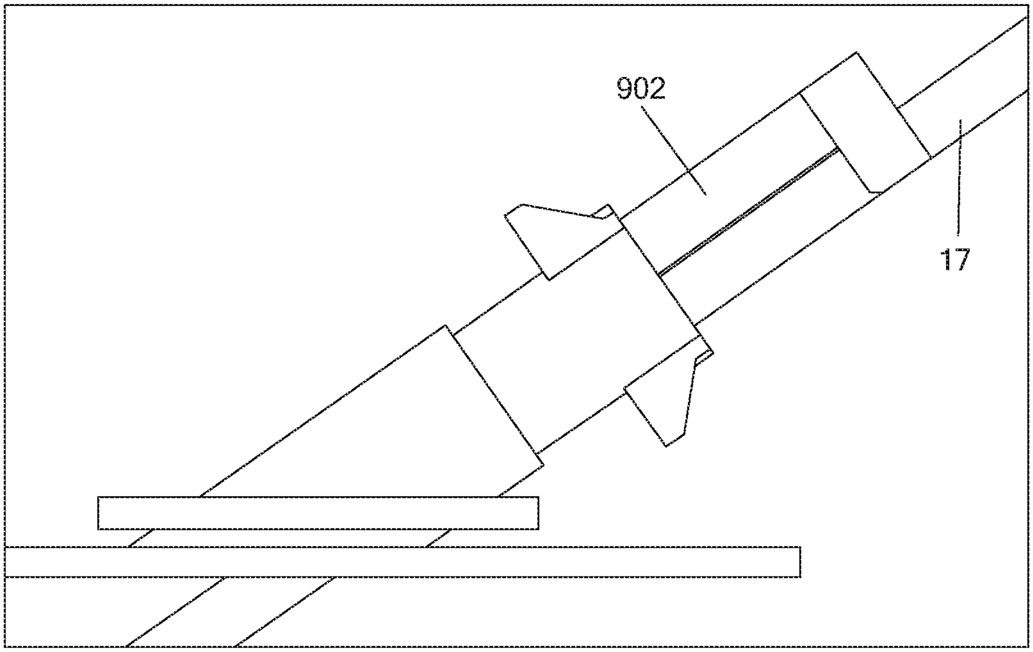
FIG. 48 is an image of a closure device with a guidewire lumen closure pin, according to aspects of the present embodiments.
Figure 49:
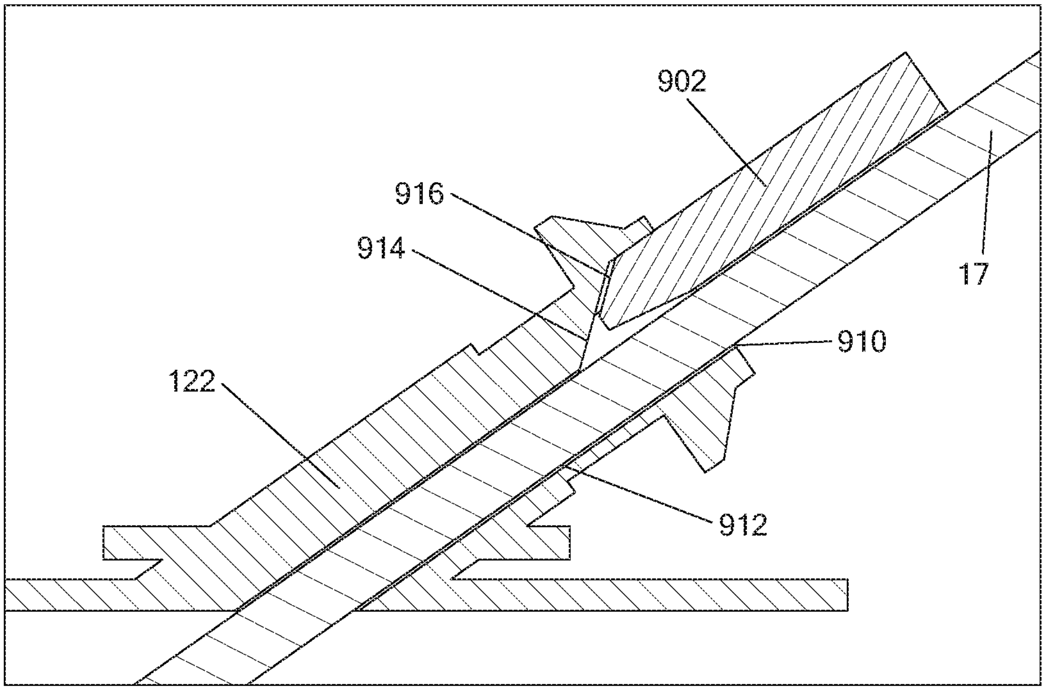
FIG. 49 is an image of a closure device with a guidewire lumen closure pin, according to aspects of the present embodiments.
Figure 50:
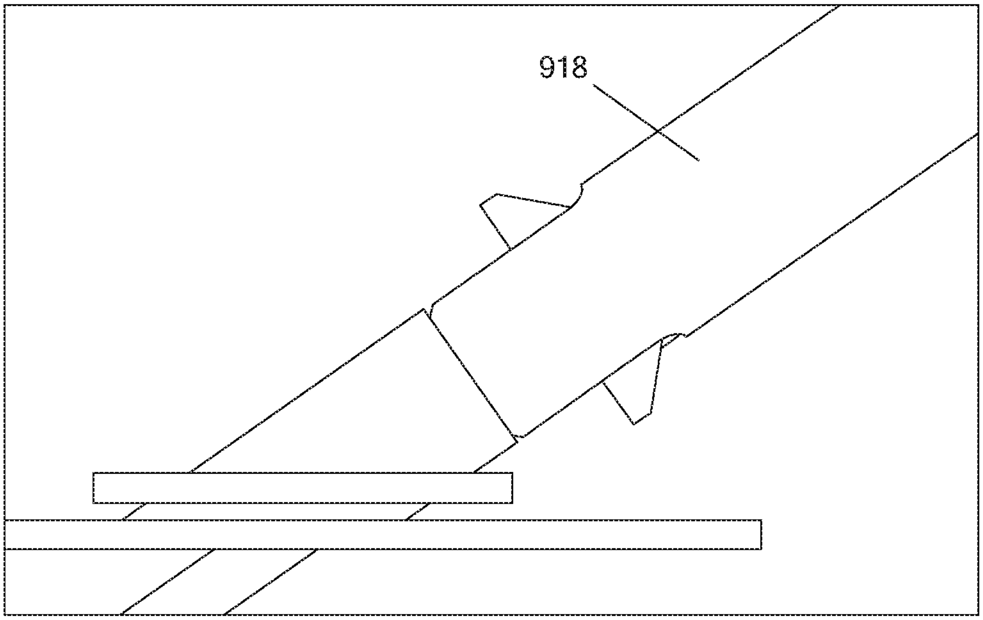
FIG. 50 is an image of a closure device with a guidewire lumen closure pin, according to aspects of the present embodiments.
Figure 51:
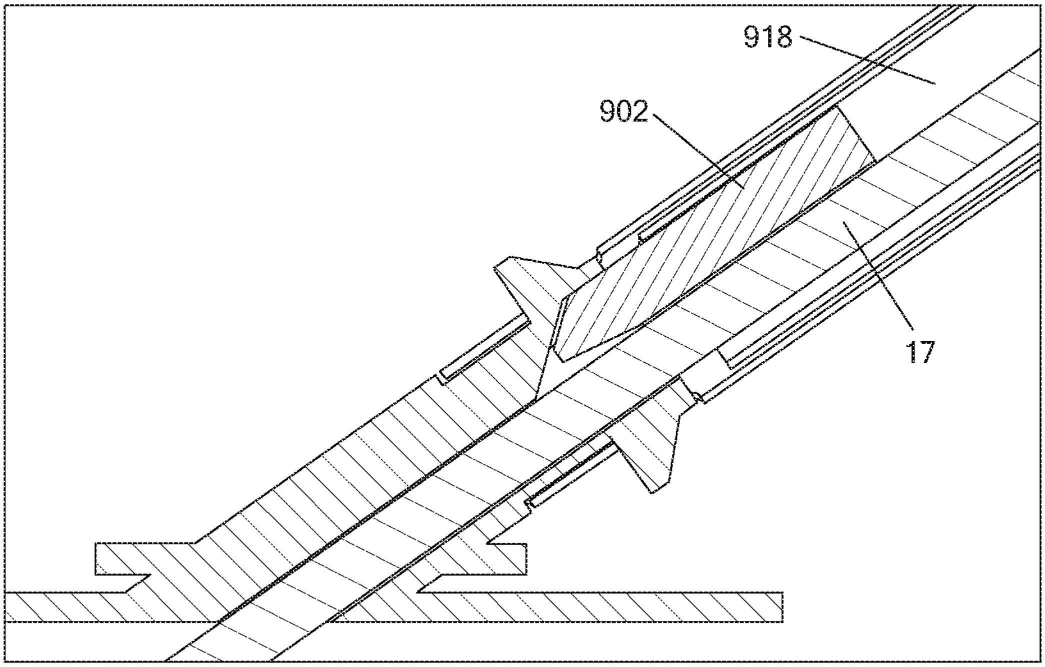
FIG. 51 is an image of a closure device with a guidewire lumen closure pin, according to aspects of the present embodiments.

FIGS. 46-57 illustrate images of a first embodiment of a closure device 100 with a first embodiment of a guidewire lumen closure pin 902, according to aspects of the present embodiments. As shown in FIG. 46, the device 100 includes a closure pin 902 disposed adjacent to, and in contact with, the guidewire 17. The closure pin 902 may include a generally circular or cylindrical pin head 904, as well as two curved arms 906 that are part of the pin head 904 and wrap around the guidewire 17. In use, the closure pin 902 and/or the guidewire 17 may be slidably disposed within a mouth 910 disposed within the scaffold neck 122, which extends at an angle from the base 120 (i.e., the scaffold base). The scaffold neck 122 may include two retaining tabs 908 disposed on opposite sides of the scaffold neck 122, approximately 180 degrees apart. FIGS. 47 and 48 illustrate other views of the device 100 including the closure pin 902 and guidewire 17. FIG. 49 illustrates a cross section of the guidewire 17 and closure pin 902 inserted into the mouth 910, with the guidewire 17 also disposed within a guidewire lumen 912, the guidewire lumen 912 being disposed all the way through the scaffold neck 122. At a transition between the guidewire lumen 912 and the mouth 910, the scaffold neck 122 may include an internal taper 914 that angles radially inward and interfaces with a corresponding angled tip 916 of the closure pin 902, such that the internal taper 914 pushes the closure pin 902 toward (and into) the guidewire lumen 912 when the closure pin 902 is pushed distally into the mouth 910 (i.e., after the guidewire 17 is removed from the guidewire lumen 912). In some embodiments, the angle of the internal taper 914 and the angled tip 916 may be complementary (for example 30 degrees and 60 degrees, 45 degrees and 45 degrees, or 60 degrees and 30 degrees, respectively, relative to a longitudinal axis of the scaffold neck 122 and/or guidewire lumen 912).

Figure 52:
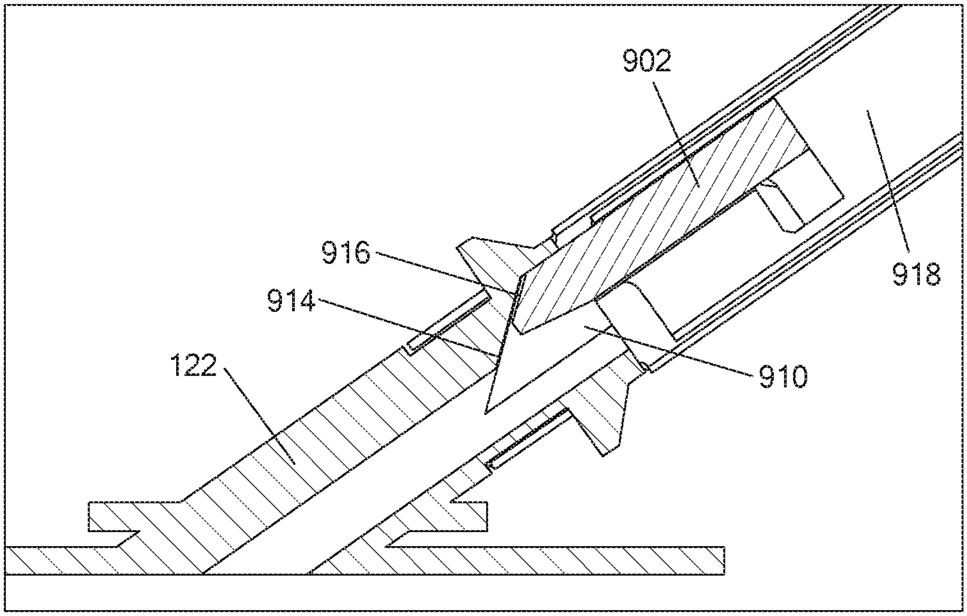
FIG. 52 is an image of a closure device with a guidewire lumen closure pin, according to aspects of the present embodiments.
Figure 53:
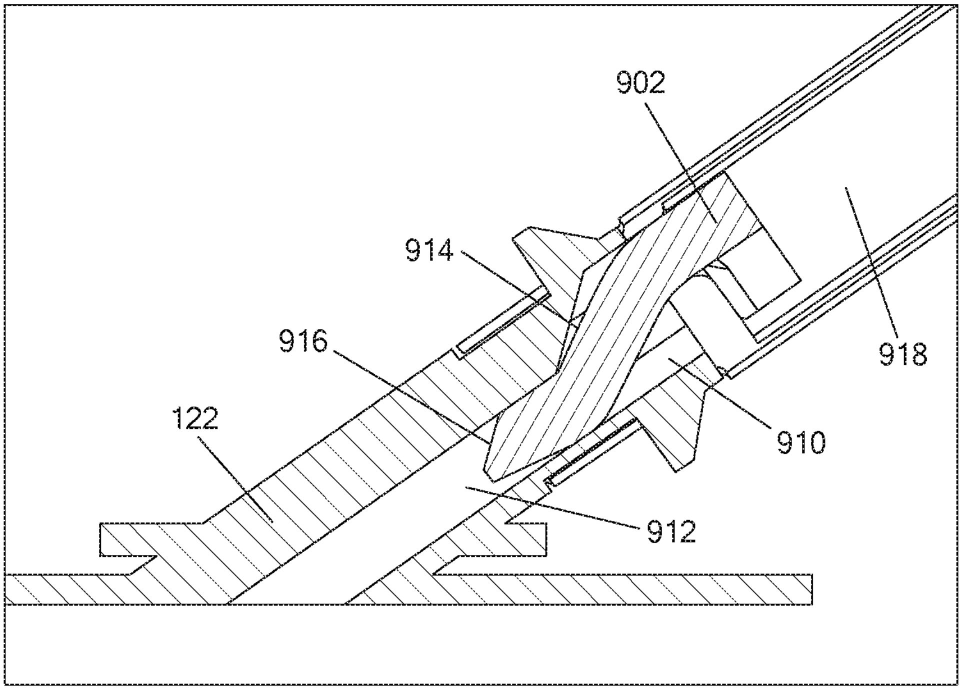
FIG. 53 is an image of a closure device with a guidewire lumen closure pin, according to aspects of the present embodiments.

FIGS. 50-54 illustrate images of the first embodiment of a closure device 100 with a guidewire lumen closure pin 902 including external and/or cross-sectional views of the delivery shaft 918, according to aspects of the present embodiments. FIG. 52 illustrates the closure pin 902 with the angled tip 918 disposed within the mouth 910 after the guidewire 17 has been removed from the scaffold neck 122. As the closure pin 902 is pushed farther into the scaffold neck 122, the internal taper 914 pushes the angled tip 916 of the closure pin 902 into the guidewire lumen 912, as shown in FIG. 53, thereby closing the guidewire lumen 912 and sealing the closure site. The closure pin 902 and guidewire 17 may be approximately the same diameter (for example 0.035 inches (35 mils) (or from about 0.025 inches to about 0.04 inches, or from about 0.015 inches to about 0.05 inches) such that each may move within the guidewire lumen 912 with a slight clearance that does not allow blood to flow past (i.e., in the very small annulus between the outer surface of the closure pin 902 and/or guidewire 17 and the inner surface of the guidewire lumen 912).

Figure 54:
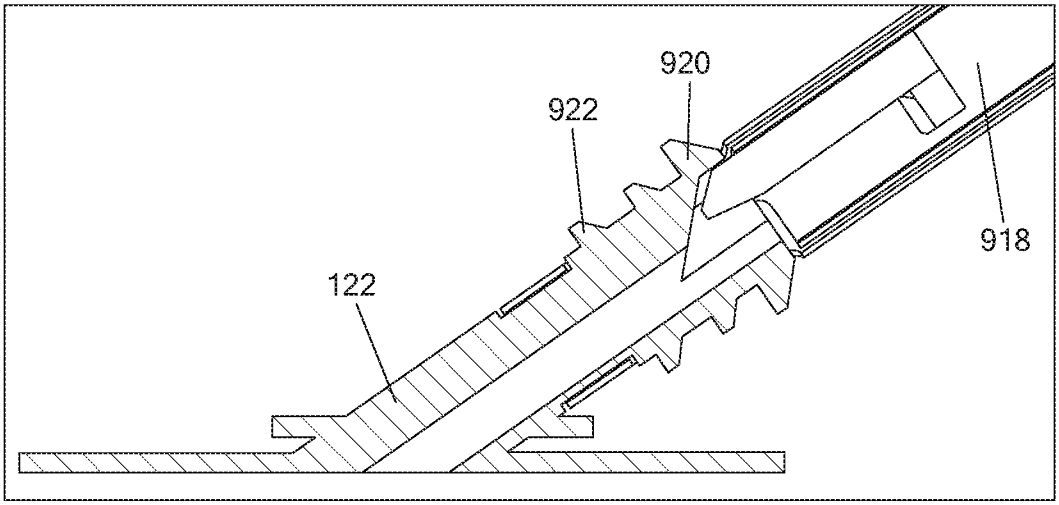
FIG. 54 is an image of a closure device with a guidewire lumen closure pin, according to aspects of the present embodiments.
Figure 55:
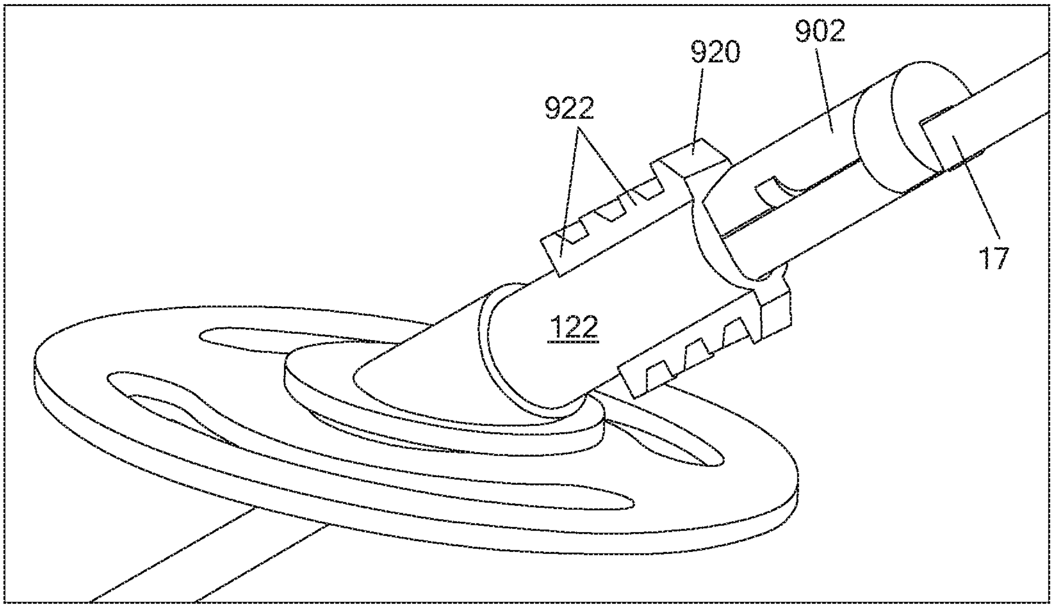
FIG. 55 is an image of a closure device with a guidewire lumen closure pin, according to aspects of the present embodiments.
Figure 56:
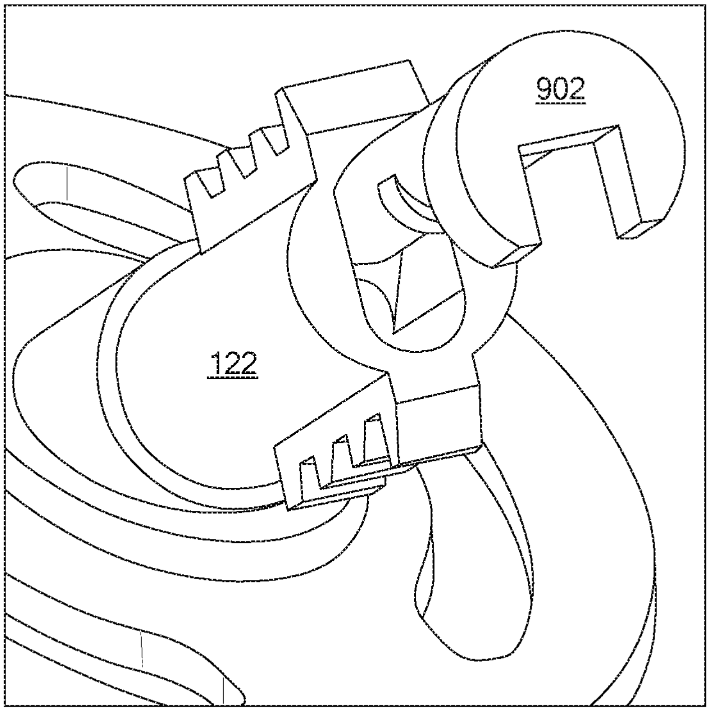
FIG. 56 is an image of a closure device with a guidewire lumen closure pin, according to aspects of the present embodiments.
Figure 57:
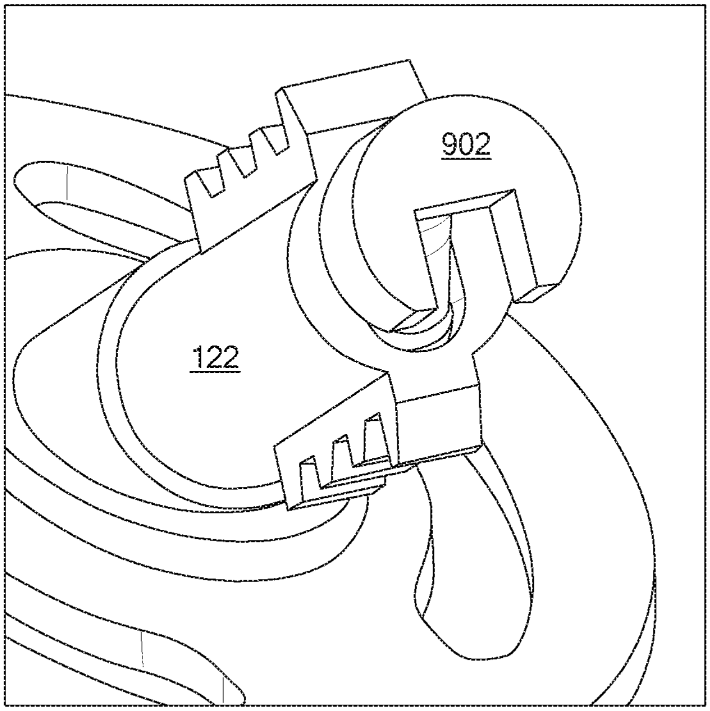
FIG. 57 is an image of a closure device with a guidewire lumen closure pin, according to aspects of the present embodiments.
Figure 58:
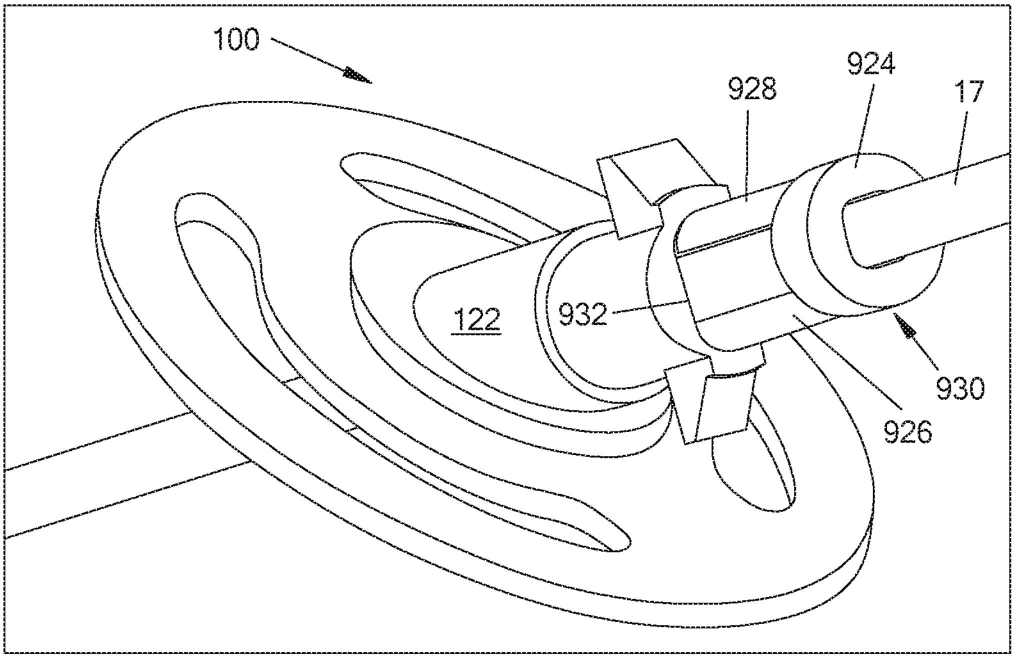
FIG. 58 is an image of a closure device with a guidewire lumen closure pin, according to aspects of the present embodiments.

FIGS. 54 and 55 illustrate images of the closure device 100 with the first embodiment of the guidewire lumen closure pin 902, according to aspects of the present embodiments. In the embodiments illustrated in FIGS. 54 and 55, the device 100 includes 3 sets and 4 sets of retaining tabs 920, 922, respectively. In FIG. 54, the device includes a first set of retaining tabs 920 located at a proximal-most end of the scaffold neck 122, as well as two additional sets (i.e., pairs) of retaining tabs 922 located distally from the first pair of retaining tabs 920. In some embodiments, the first pair of retaining tabs 920 may be larger than each of the second, third, and fourth pairs (in the embodiment of FIG. 55) of retaining tabs 922. Each pair or set of retaining tabs 920, 922 may include two retaining tabs protruding from opposite sides of the scaffold neck 122, spaced approximately 180 degrees apart. The additional locking tabs allow for more closure positions to help accommodate various tissue thicknesses (for example, as illustrated in connection with the different closure positions shown in FIGS. 89-92). FIGS. 56 and 57 illustrate the closure pin 902 in open and closed positions, respectively, within the scaffold neck 122.

Second Embodiment of Closure Pin

Figure 59:
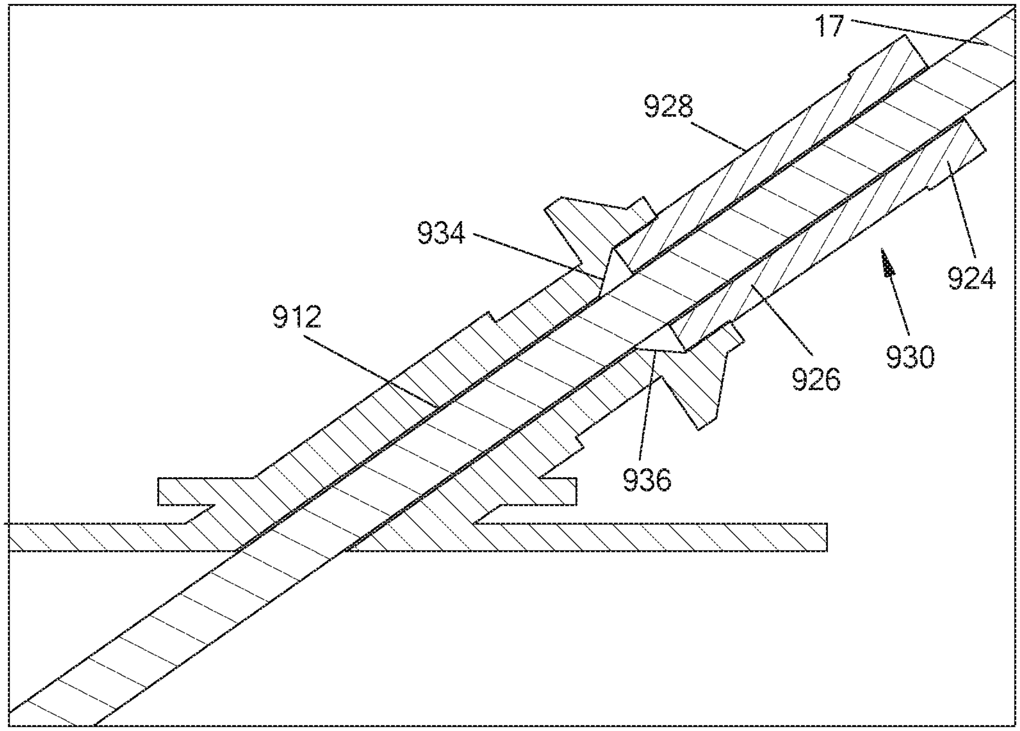
FIG. 59 is an image of a closure device with a guidewire lumen closure pin, according to aspects of the present embodiments.
Figure 60:
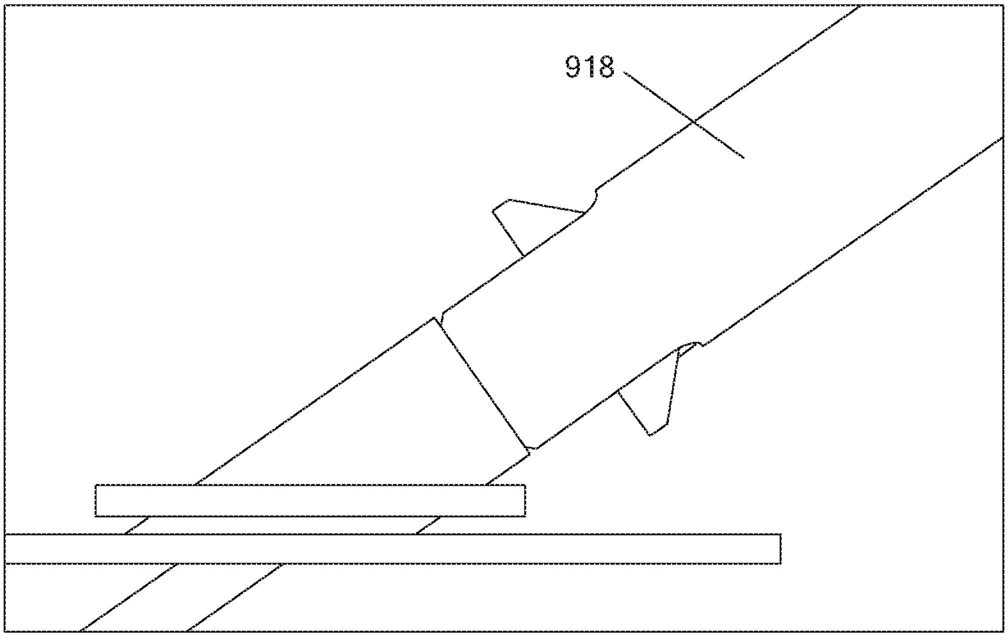
FIG. 60 is an image of a closure device with a guidewire lumen closure pin, according to aspects of the present embodiments.
Figure 61:
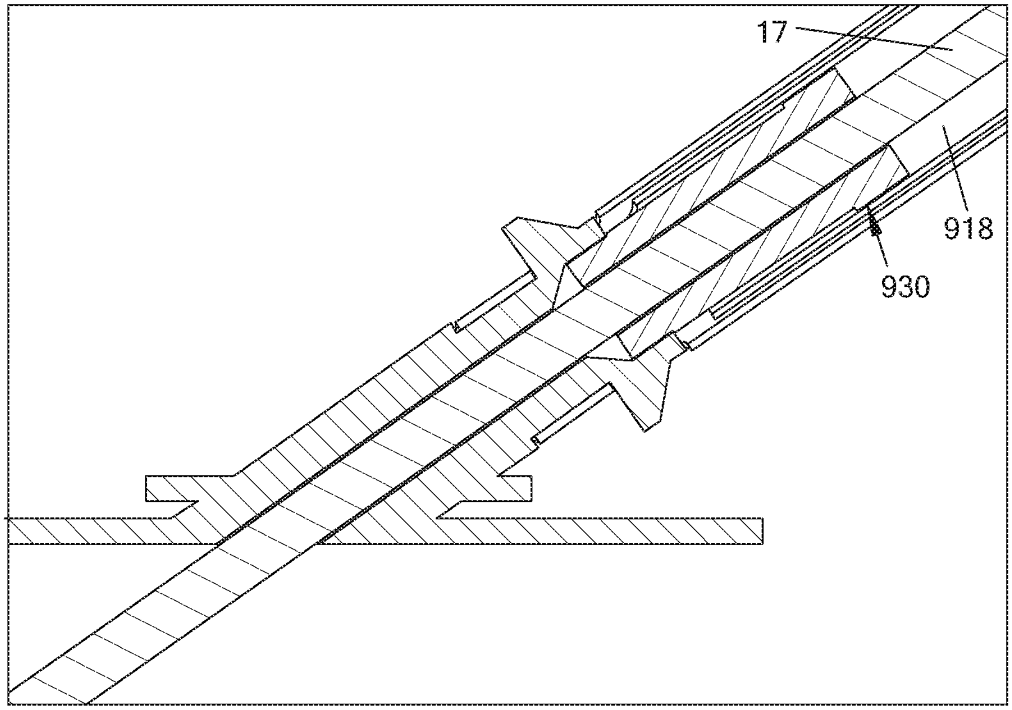
FIG. 61 is an image of a closure device with a guidewire lumen closure pin, according to aspects of the present embodiments.
Figure 62:
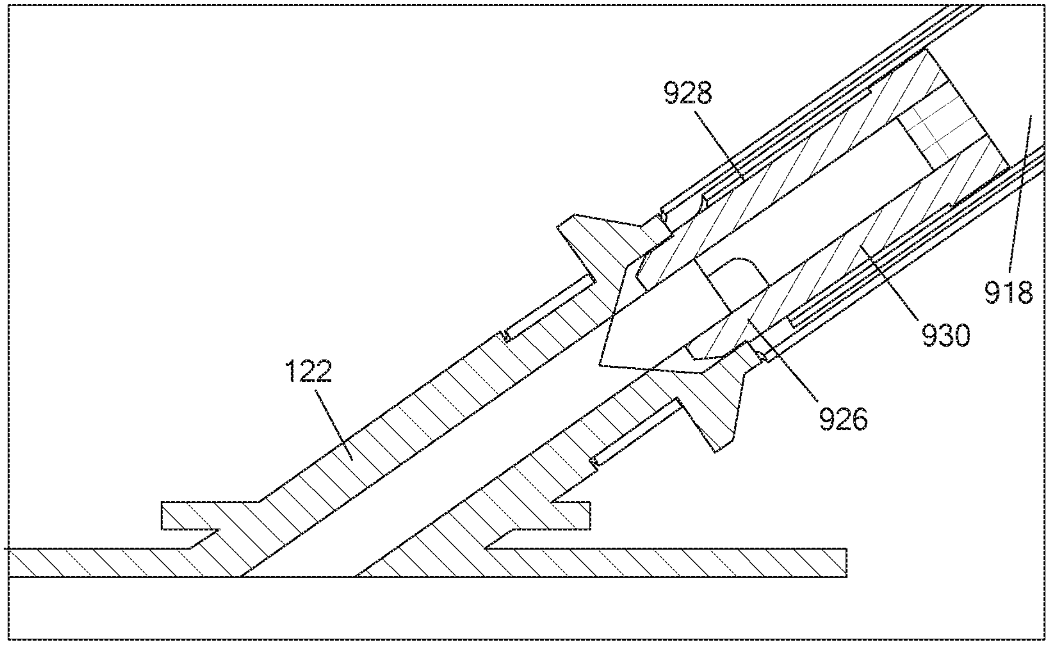
FIG. 62 is an image of a closure device with a guidewire lumen closure pin, according to aspects of the present embodiments.
Figure 63:
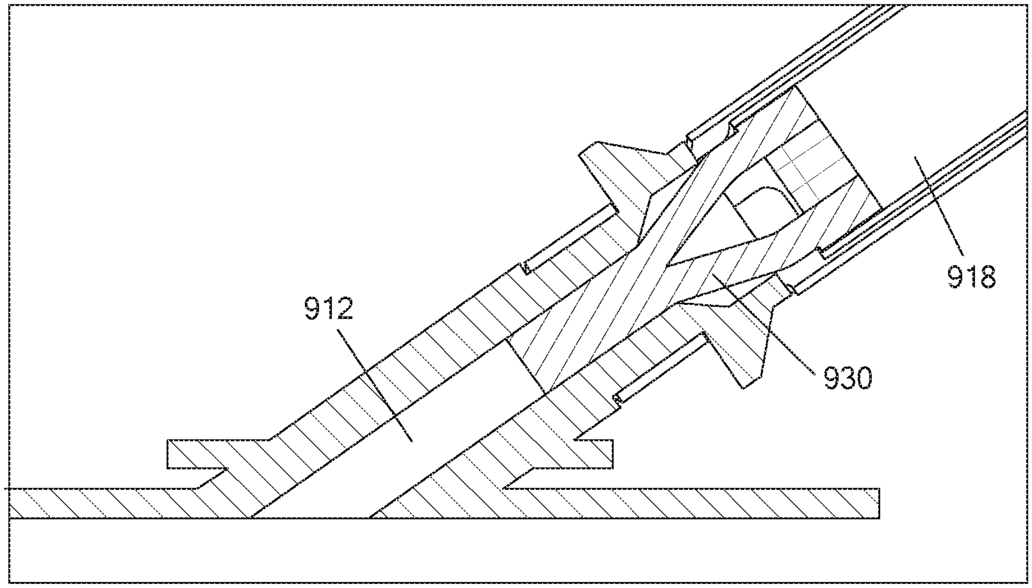
FIG. 63 is an image of a closure device with a guidewire lumen closure pin, according to aspects of the present embodiments.

FIGS. 58-63 illustrate images of the closure device 100 with a second embodiment of the guidewire lumen closure pin 930, according to aspects of the present embodiments. The second embodiment of the closure pin 930 may include a circular or cylindrical pin head 924 configured to be concentrically disposed about the guidewire 17 when the guidewire is within the column 122 (or scaffold neck). The closure pin 930 may include first and second arms 926 and 928 configured to be disposed on opposite sides of the guidewire 17, and slidable within an elongated mouth 932 disposed within the column 122. The column 122 may include first and second internal tapers 934, 936, as shown in FIG. 59, to push the first and second arms 926, 928 into the guidewire lumen 912 as the closure pin 930 is pushed into the column 122 after the guidewire 17 is removed. FIGS. 60-63 illustrate the delivery shaft 918 (in addition to the closure device 100) with the second embodiment of the closure pin 930. FIGS. 62 and 63 illustrate the closure pin 930 after the guidewire 17 has been removed. FIG. 62 illustrates the position and shape of the closure pin 930 prior to being pushed further into the column 122, while FIG. 63 shows the closure pin 930 after being pushed into the guidewire lumen 912, thereby sealing the guidewire lumen 912. Because the first and second arms 926, 928 together fill the guidewire lumen 912 when in the sealed position of FIG. 63, each of the first and second arms 926, 928 may include a cross-sectional area that is roughly half of the cross-sectional area of the guidewire lumen 912.

Third Embodiment of Closure Pin

Figure 64:
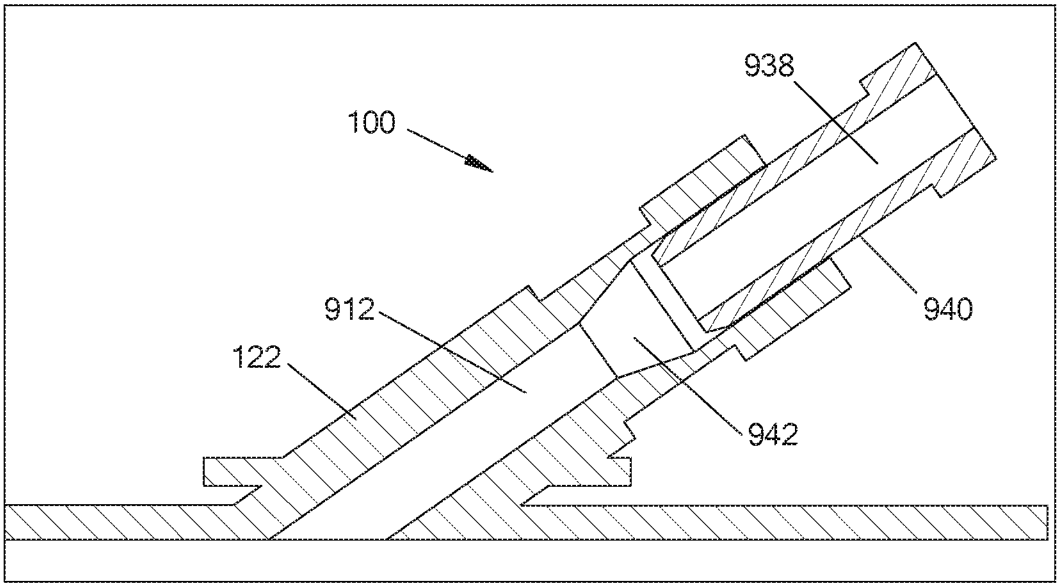
FIG. 64 is an image of a closure device with a guidewire lumen closure pin, according to aspects of the present embodiments.
Figure 65:
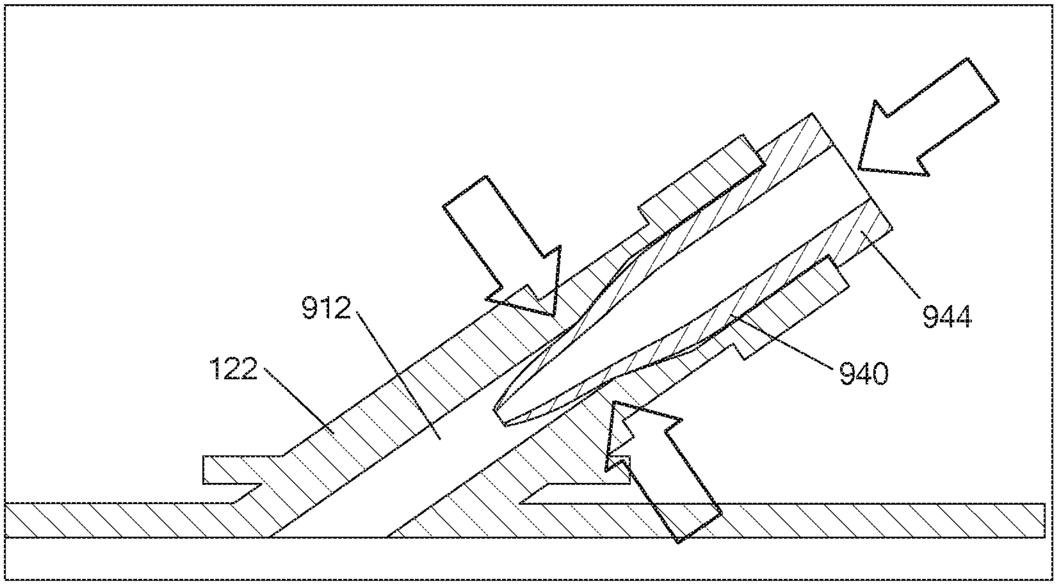
FIG. 65 is an image of a closure device with a guidewire lumen closure pin, according to aspects of the present embodiments.

FIGS. 64 and 65 illustrate images of the closure device 100 with a third embodiment of the guidewire lumen closure pin 940, according to aspects of the present embodiments. The third embodiment of the closure pin 940 may include a circular or cylindrical pin head 944 configured to be concentrically disposed about the guidewire 17 when the guidewire is within the column 122 (and closure pin 940). The closure pin 940 may also include a through bore 938 running through the entire length of the closure pin 940, within which the guidewire 17 is disposed when it is within the column 122 (or scaffold neck). The device 100 shown in FIGS. 64 and 65 (specifically the column 122) includes a gradual tapered portion 942 with a cone-shaped interior for making the transition from a larger diameter of the closure pin 940 in the open position of FIG. 64 to the smaller diameter of the guidewire lumen 912. As a distal force is applied to the pin head 944 (see arrow pointing at the back of the pin in FIG. 65), the inner walls of the column 122 (or scaffold neck) at the gradual tapered portion 942 exert radially inward pressure on the closure pin 940 causing the closure pin 940 to be pinched or crimped inwardly (see arrows pointing inward at the tip of the pin in FIG. 65), thereby filling the entire space of the smaller diameter guidewire lumen 912 and sealing the guidewire lumen 912 in the process.

Fourth Embodiment of Closure Pin

Figure 66:
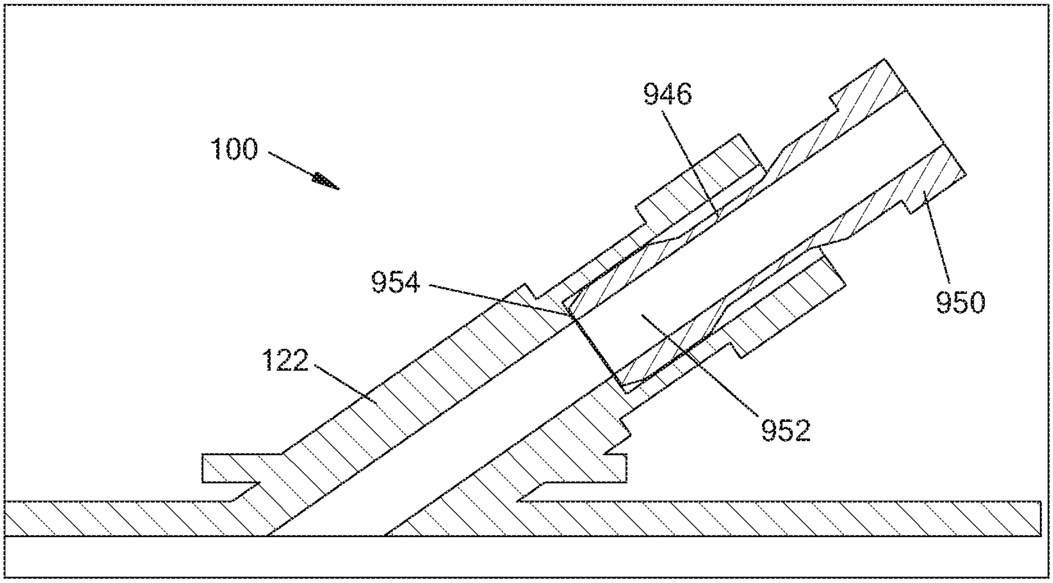
FIG. 66 is an image of a closure device with a guidewire lumen closure pin, according to aspects of the present embodiments.
Figure 67:
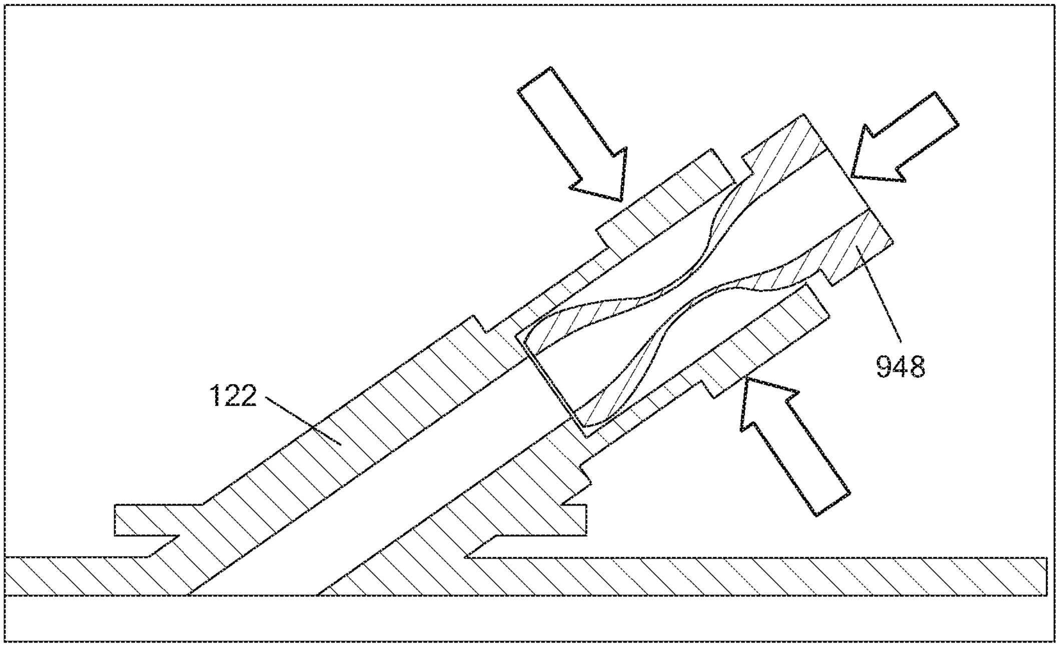
FIG. 67 is an image of a closure device with a guidewire lumen closure pin, according to aspects of the present embodiments.
Figure 68:
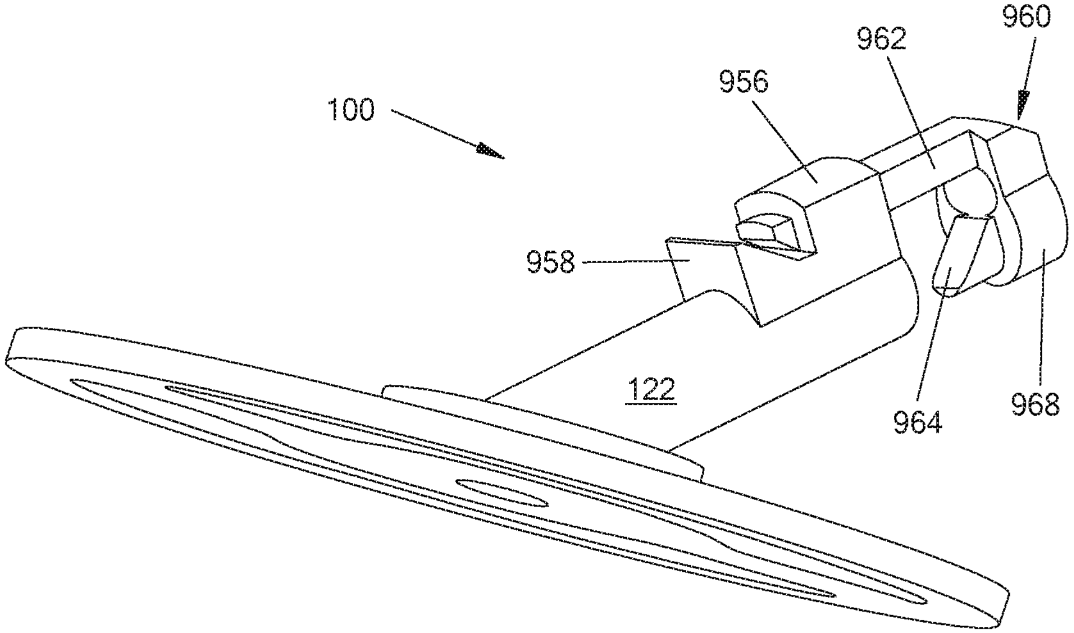
FIG. 68 is an image of a closure device with a guidewire lumen closure pin, according to aspects of the present embodiments.
Figure 69:
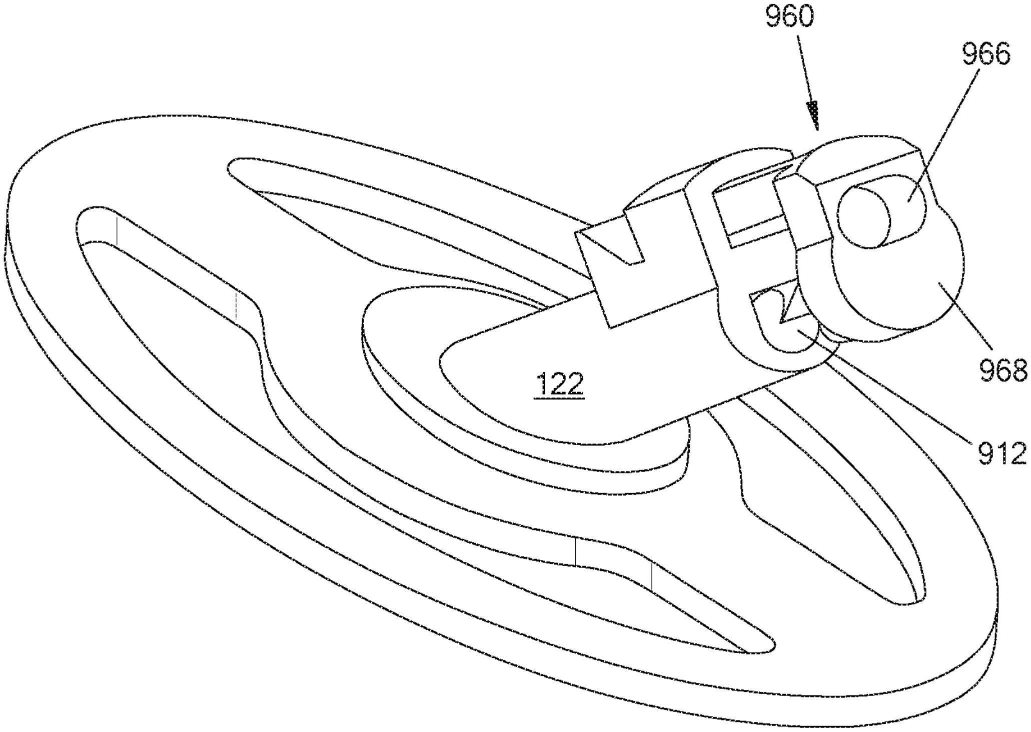
FIG. 69 is an image of a closure device with a guidewire lumen closure pin, according to aspects of the present embodiments.
Figure 70:
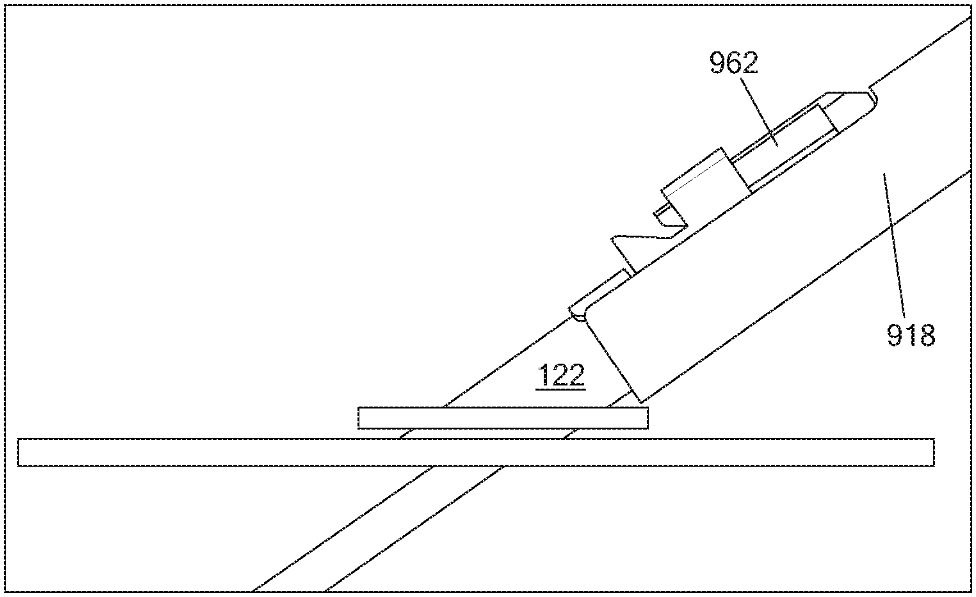
FIG. 70 is an image of a closure device with a guidewire lumen closure pin, according to aspects of the present embodiments.

FIGS. 66 and 67 illustrate images of the closure device 100 with a fourth embodiment of the guidewire lumen closure pin 950, according to aspects of the present embodiments. The fourth embodiment of the closure pin 950 may include a circular or cylindrical pin head 948 configured to be concentrically disposed around the guidewire 17 when the guidewire is within the column 122 (and closure pin 950). The closure pin 950 may also include a throughbore 952 running through the entire length of the closure pin 950, within which the guidewire 17 is disposed when it is within the scaffold neck 122. The closure pin 950 shown in FIGS. 66 and 67 includes a rupture portion 952 with thin walls disposed within a longitudinal mid-section of the closure pin 950. The scaffold neck 122 of FIGS. 66 and 67 may include an internal orthogonal stop 954. In FIG. 67, as a distal force is applied to the pin head 948 (along white arrow), the distal end of the closure pin 950 contacts the internal orthogonal stop 954 causing the rupture portion 952 to rupture or crimp inwardly (due to the thinner walls of the rupture portion 946 (along the dark grey arrows), thereby filling the entire space of the guidewire lumen 912 and sealing the guidewire lumen 912 in the process.

Fifth Embodiment of Closure Pin

Figure 71:
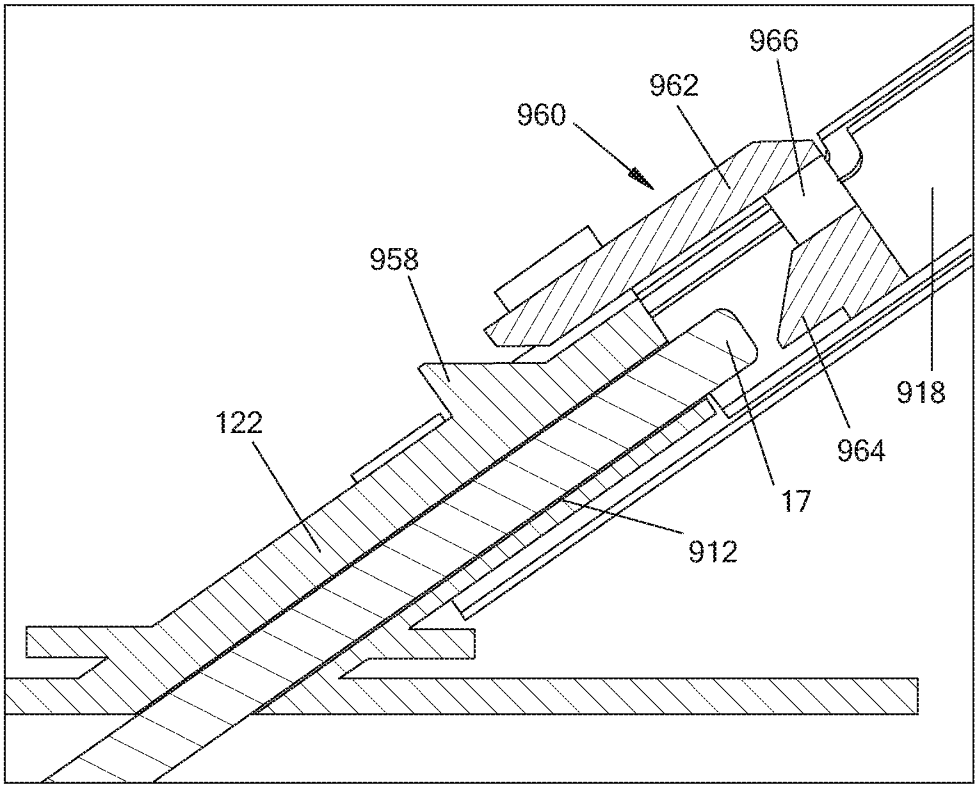
FIG. 71 is an image of a closure device with a guidewire lumen closure pin, according to aspects of the present embodiments.
Figure 72:
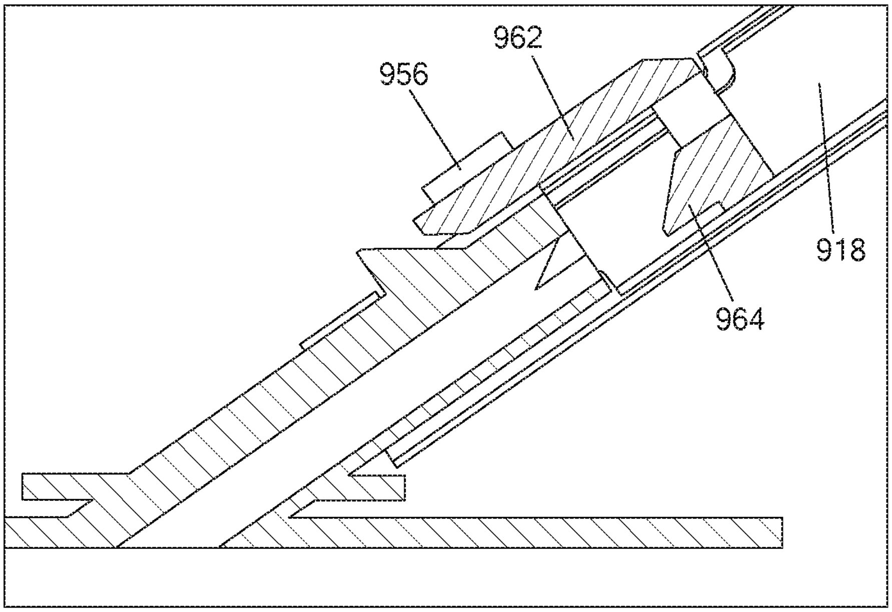
FIG. 72 is an image of a closure device with a guidewire lumen closure pin, according to aspects of the present embodiments.
Figure 73:
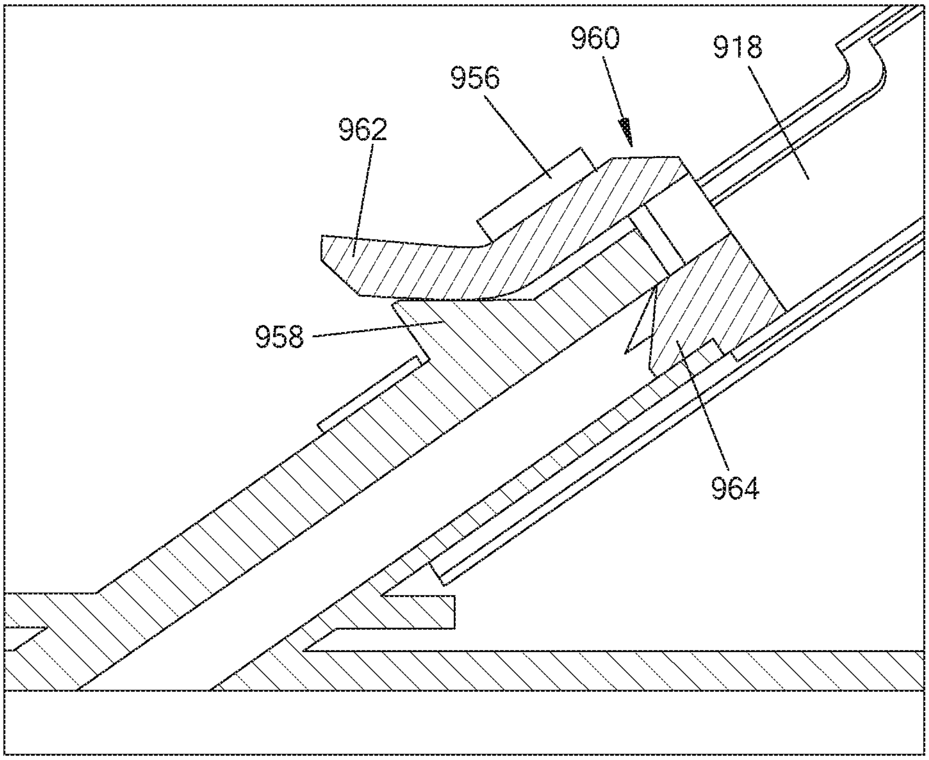
FIG. 73 is an image of a closure device with a guidewire lumen closure pin, according to aspects of the present embodiments.
Figure 74:
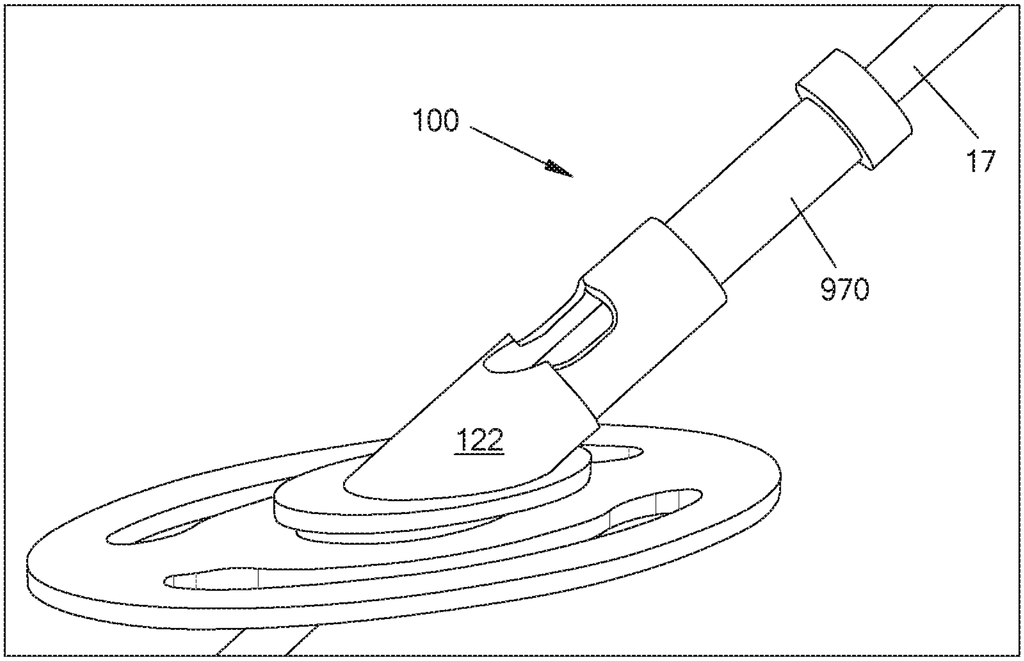
FIG. 74 is an image of a closure device with a guidewire lumen closure pin, according to aspects of the present embodiments.
Figure 75:
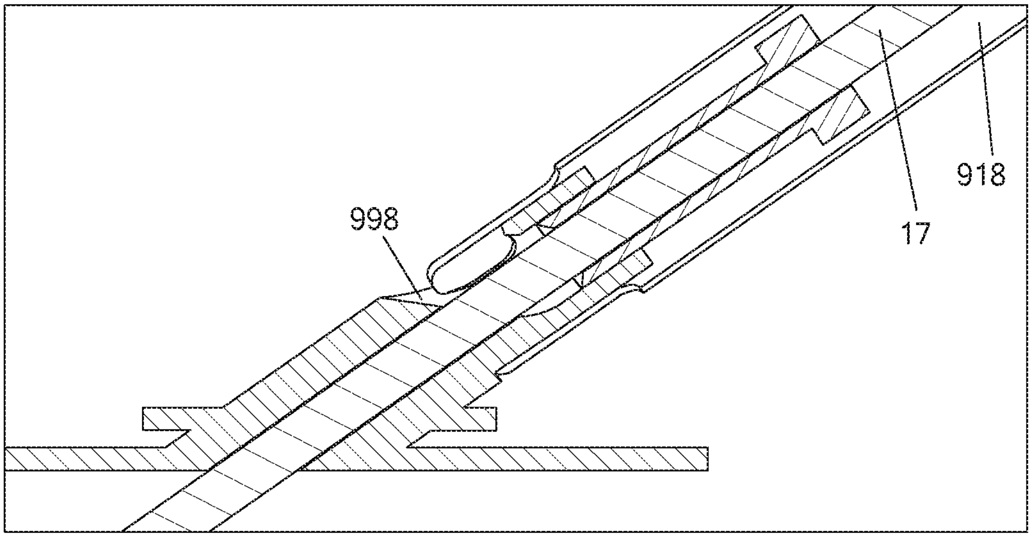
FIG. 75 is an image of a closure device with a guidewire lumen closure pin, according to aspects of the present embodiments.
Figure 76:
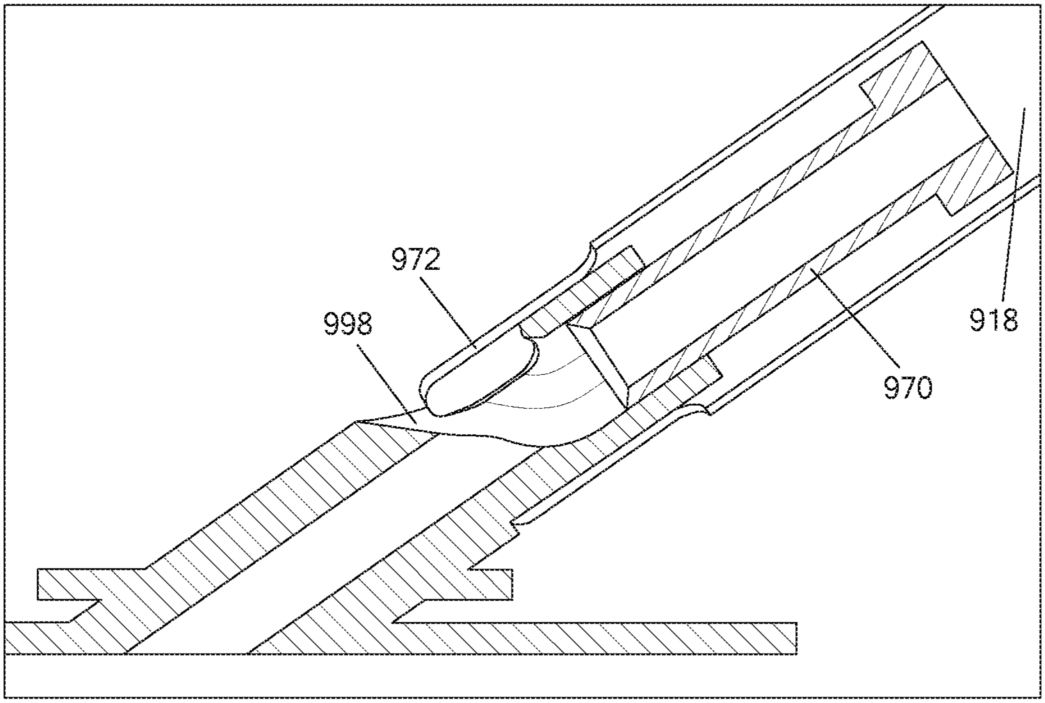
FIG. 76 is an image of a closure device with a guidewire lumen closure pin, according to aspects of the present embodiments.
Figure 77:
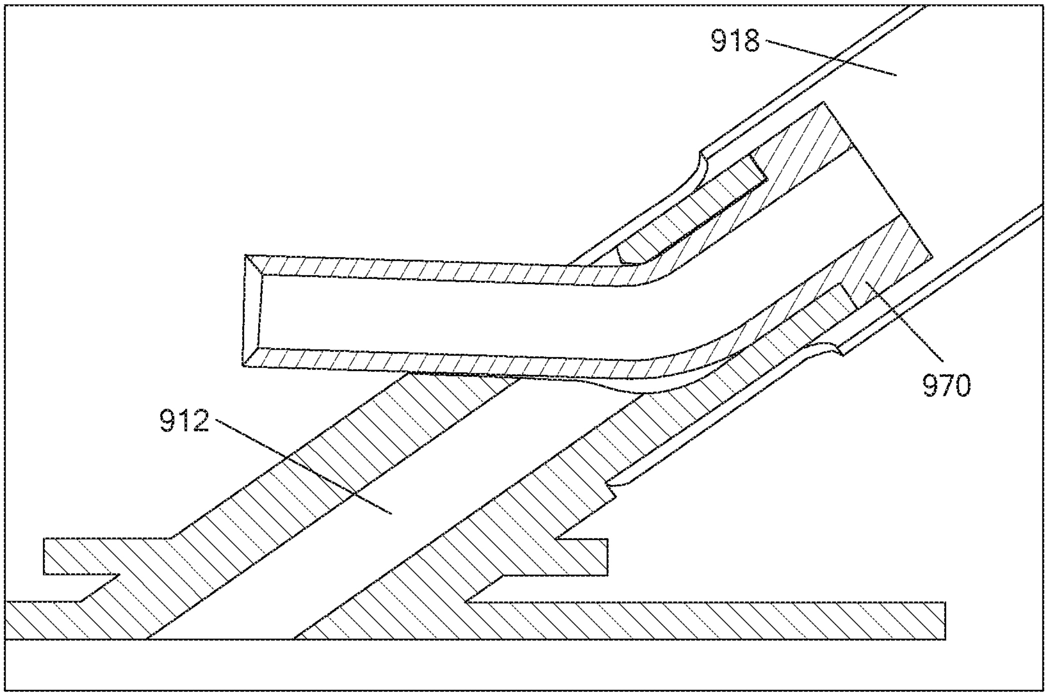
FIG. 77 is an image of a closure device with a guidewire lumen closure pin, according to aspects of the present embodiments.
Figure 78:
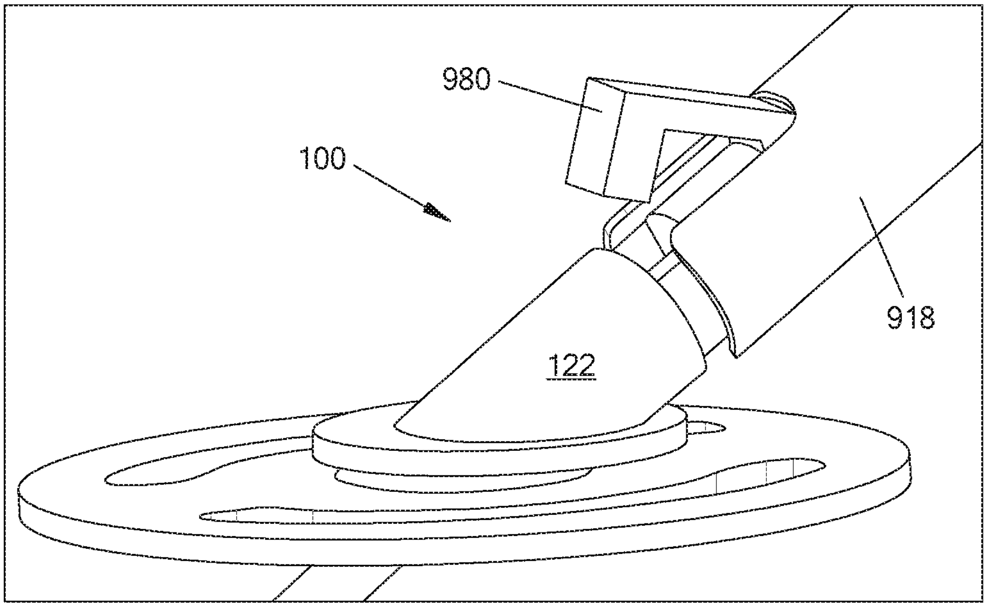
FIG. 78 is an image of a closure device with a guidewire lumen closure pin, according to aspects of the present embodiments.
Figure 79:
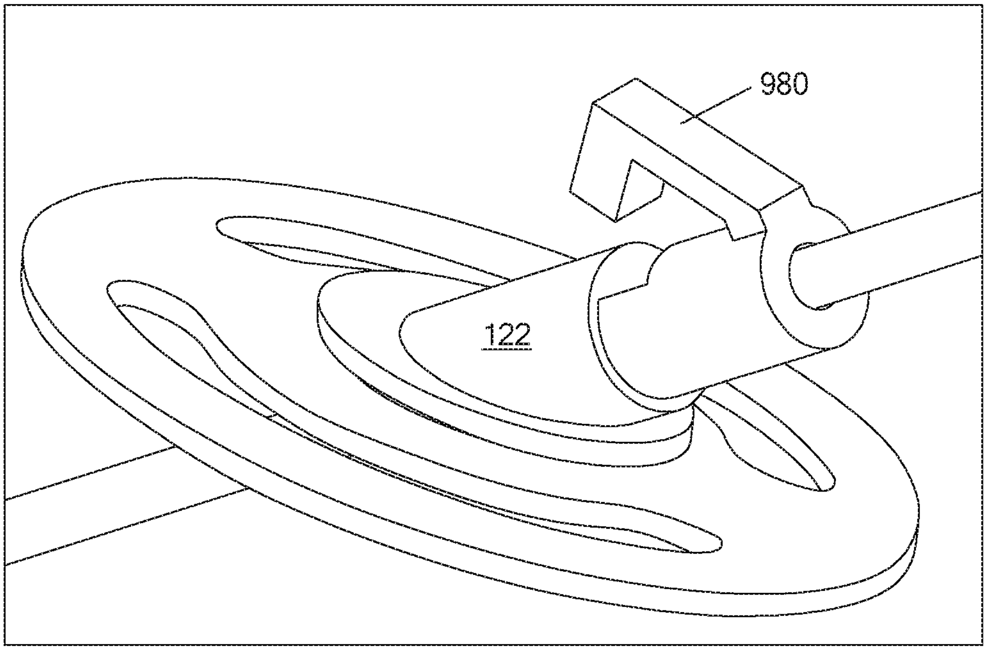
FIG. 79 is an image of a closure device with a guidewire lumen closure pin, according to aspects of the present embodiments.
Figure 80:
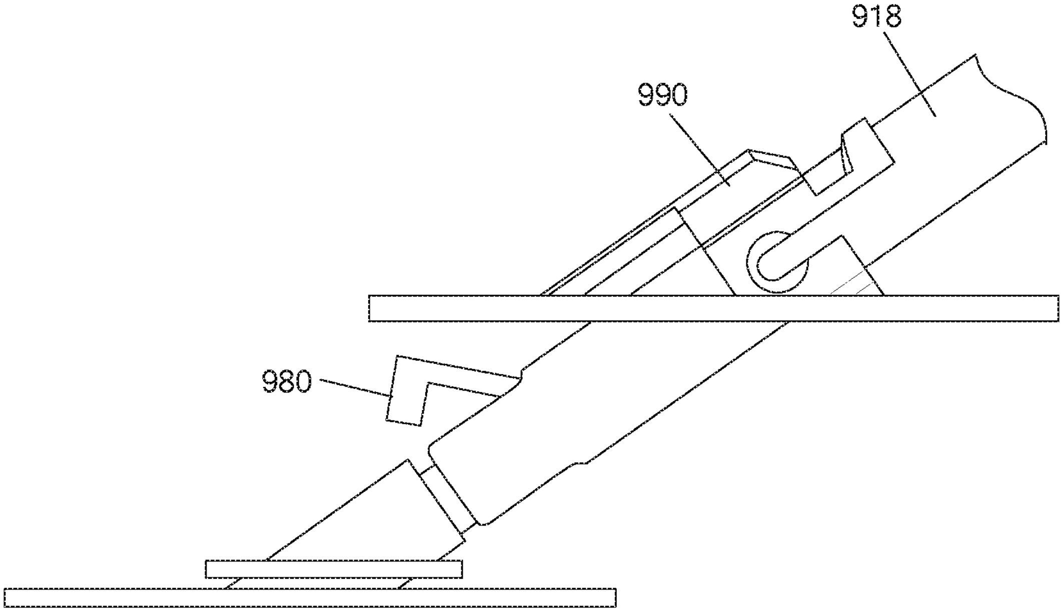
FIG. 80 is an image of a closure device with a guidewire lumen closure pin, according to aspects of the present embodiments.
Figure 81:
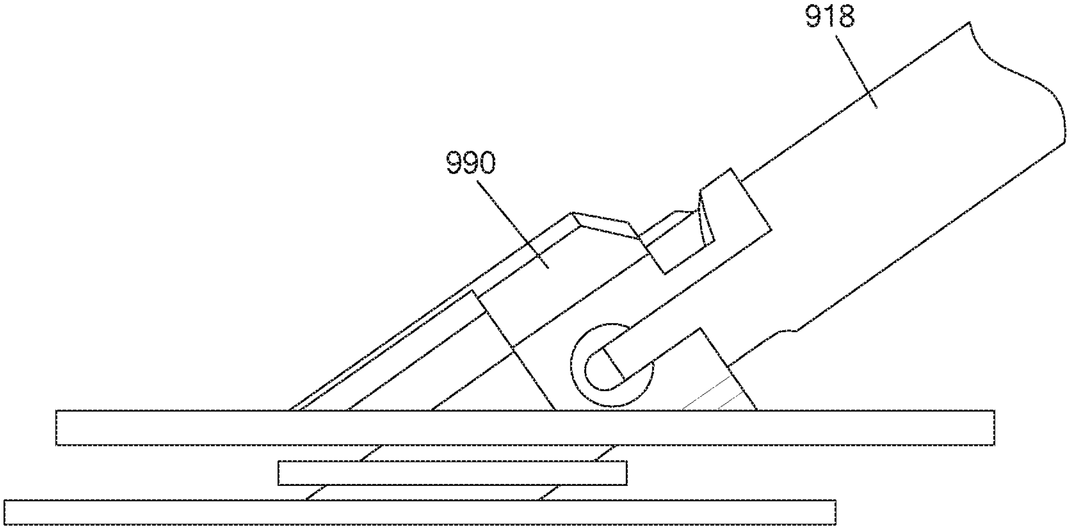
FIG. 81 is an image of a closure device with a guidewire lumen closure pin, according to aspects of the present embodiments.
Figure 82:
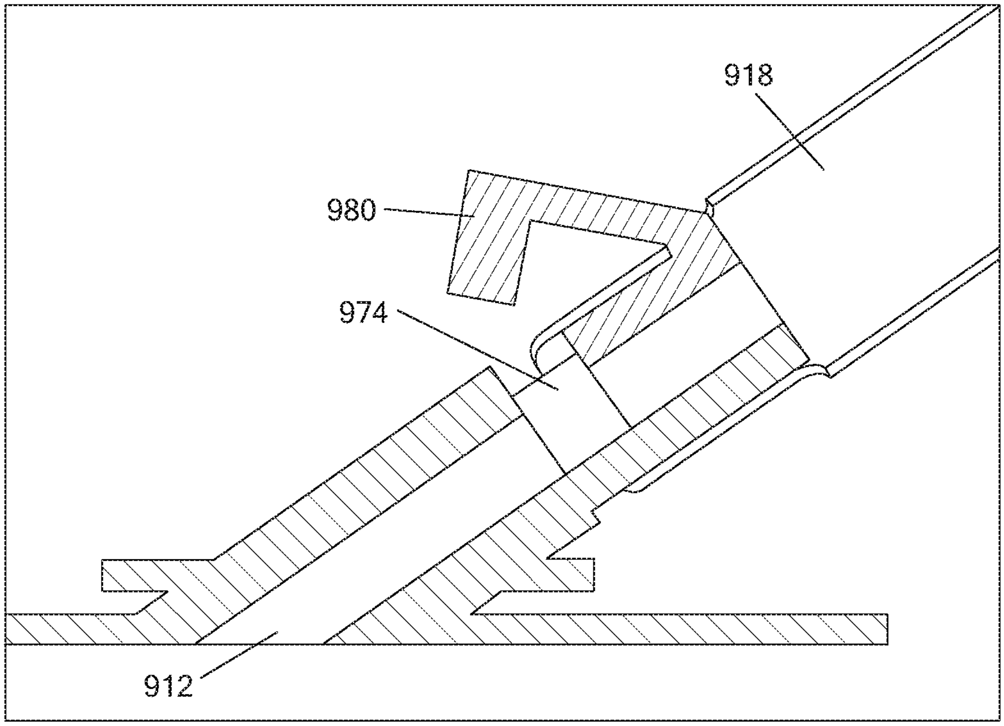
FIG. 82 is an image of a closure device with a guidewire lumen closure pin, according to aspects of the present embodiments.

FIGS. 68-73 illustrate images of the closure device 100 with a fifth embodiment of the guidewire lumen closure pin 960, according to aspects of the present embodiments. The fifth embodiment of the closure pin 960 may include a slidable rod 962, an offset bore 966, an angled pin portion 964, and pin head 968. In some embodiments, both the angled pin portion 964 and the slidable rod 962 protrude distally form the pin head 968 while the offset bore 966 includes a hole disposed through the pin head 968 that is offset from the guidewire lumen 912. Stated otherwise, a centerline of the offset bore 966 is not collinear with a centerline of the guidewire lumen 912. The slidable rod 962 is configured to slide within a sleeve 956 disposed in column 122. At a distal end of the sleeve 956, the scaffold neck 122 may include a ramp portion 958 for deflecting the slidable rod at an angle as it protrudes through the sleeve 956, as show in FIGS. 71-73. FIGS. 70-73 illustrate the delivery shaft 918. As illustrated in FIG. 71, the guidewire 17 and guidewire lumen 912 are linearly offset form the offset bore 966, through which the guidewire is installed when it is in the scaffold neck 122. Accordingly, the guidewire 17 must bend in order to go through both the offset bore 966 and the guidewire lumen 912, which are not collinear with each other. Once the guidewire 17 is removed and the closure pin 960 is pushed distally toward the scaffold neck 122, the angled pin portion 964 (which is collinear with the guidewire lumen 912) is pushed into the guidewire lumen 912, thereby closing the guidewire lumen 912, as shown in FIG. 73. The slidable rod 962 bends at it deflects off the ramp portion 958. The inherent stiffness and partial elasticity of the slidable rod 963, in connection with the sheath 956, helps to hold the closure pin 960 into place once it is in the closed position.

Sixth Embodiment of Closure Pin

FIGS. 74-77 illustrate images of the closure device 100 with a sixth embodiment of the guidewire lumen closure pin 970, according to aspects of the present embodiments. The sixth embodiment of the closure pin 970 is concentrically disposed 360 degrees around the guidewire 17 and deflects off an angled surface 998 and through an aperture 972 in the scaffold neck 122 (or scaffold neck) and/or delivery shaft 918 such that a distal end of the closure pin 970 protrudes across the guidewire lumen 912 and out of the aperture 972, thereby sealing the guidewire lumen 912, as show in FIG. 77.

Seventh Embodiment of Closure Pin

Figure 83:
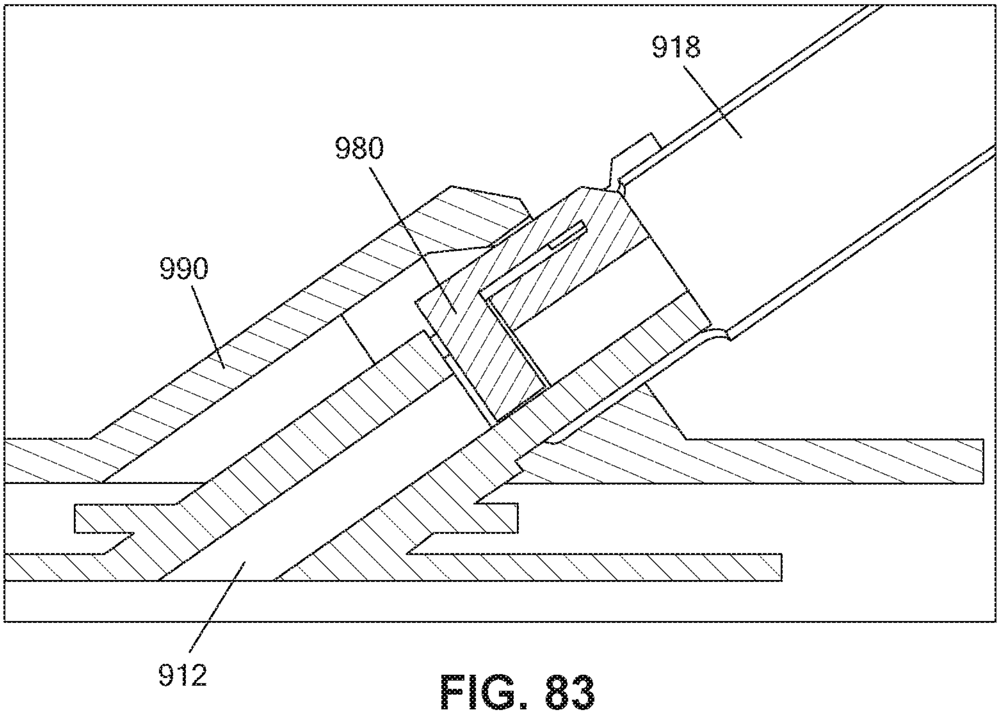
FIG. 83 is an image of a closure device with a guidewire lumen closure pin, according to aspects of the present embodiments.

FIGS. 78-83 illustrate images of the closure device 100 with a seventh embodiment of the guidewire lumen closure pin 980, according to aspects of the present embodiments. The seventh embodiment of the closure pin 980 includes an L-shaped closure pin 980 that is integrated into (and monolithic with) the scaffold neck 122. As an external fixation 990 slides down the delivery shaft and over the L-shaped closure pin 980 (FIGS. 80 and 81), the external fixation 990 forces the orthogonal tip of the L-shaped closure pin 980 into a partial bore 974 in only one sidewall of the column 122 (i.e., rather than all the way through both side walls; shown in FIG. 82). The orthogonal tip of the L-shaped closure pin 980 traverses the guidewire lumen 912, thereby sealing the guidewire lumen 912, as shown in FIG. 83. In the embodiments of each of FIGS. 46-77, the closure device may include a push tube disposed concentrically within the delivery shaft 918, the push tube being used for distally pushing the closure pins 902, 930, 940, 950, 960, and 970 into the column 122 and/or guidewire lumen 912 after the guidewire 17 has been withdrawn from the guidewire lumen 912. In each of the second, third, fourth, sixth, and seventh embodiments of the closure pin 930, 940, 950, 970, 980, the scaffold neck 122 is configured such that the guidewire 17 and guidewire lumen 912 are centered (i.e., concentric) within the scaffold neck 122. In each of the first and fifth embodiments of the closure pin 902, 960, the scaffold neck 122 is configured such that the guidewire 17 and guidewire lumen 912 are offset (i.e., eccentric) within the scaffold neck 122.

External Fixation Design

Figure 84:
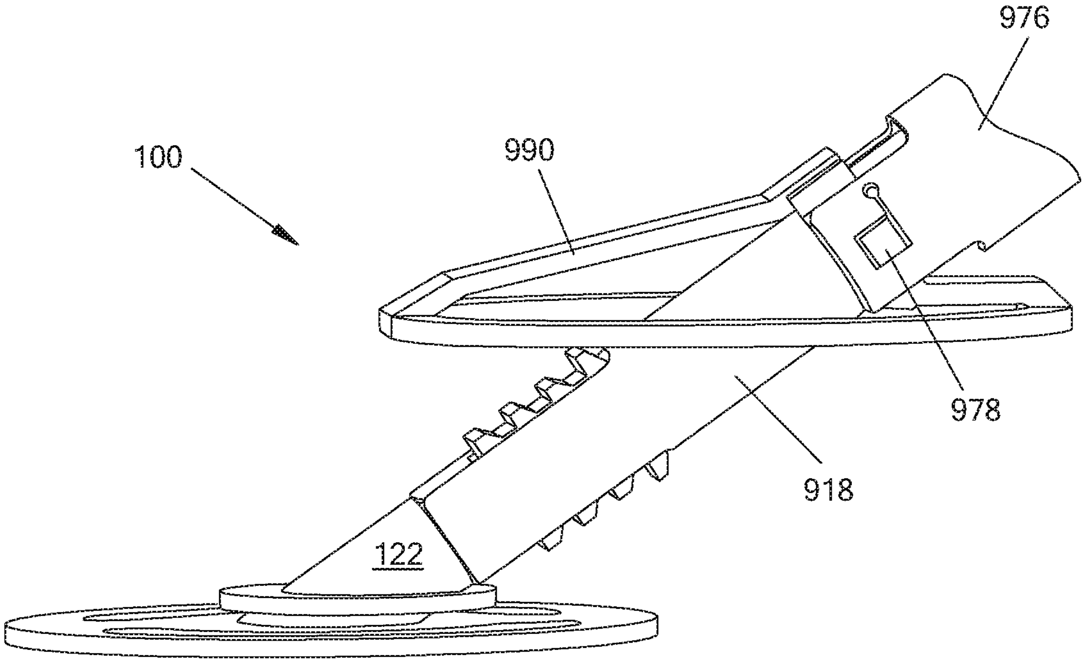
FIG. 84 is an image of a closure device, according to aspects of the present embodiments.
Figure 85:
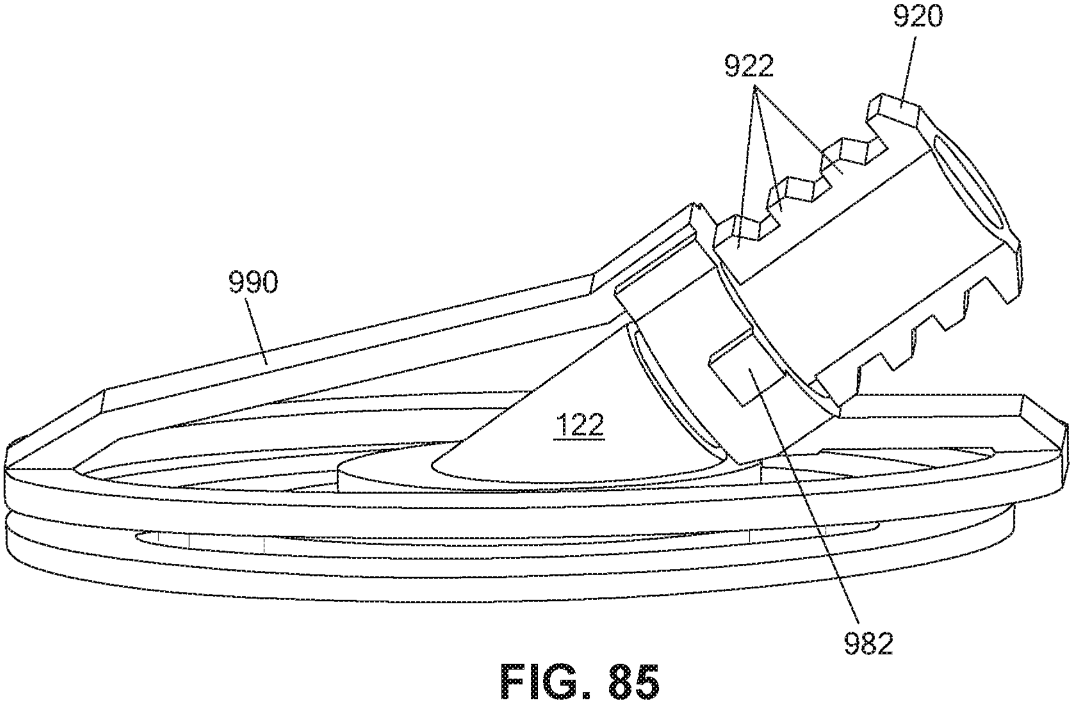
FIG. 85 is an image of a closure device, according to aspects of the present embodiments.
Figure 86:
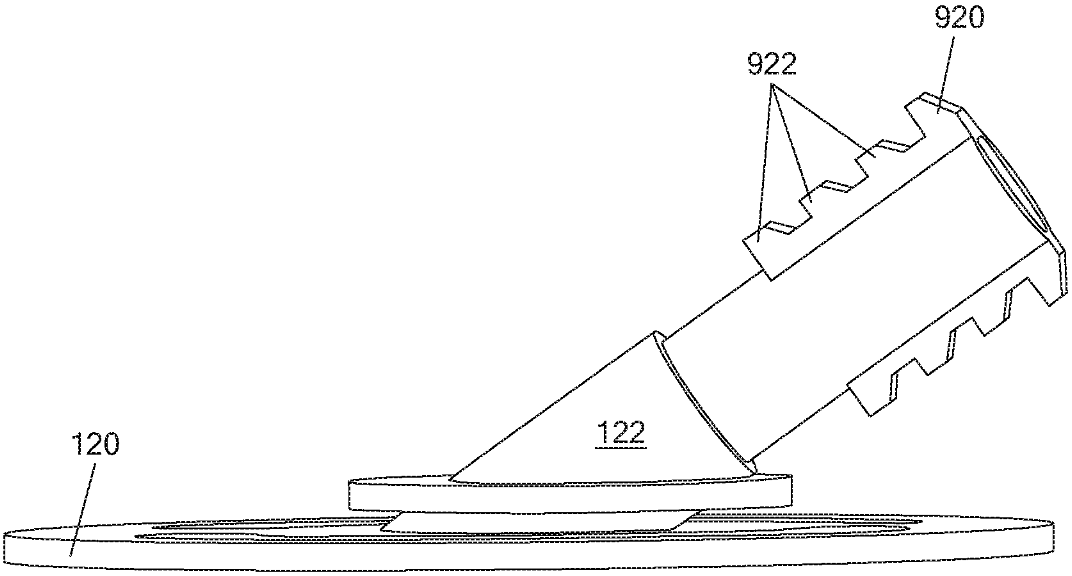
FIG. 86 is an image of a scaffold used for a closure device, according to aspects of the present embodiments.
Figure 88:
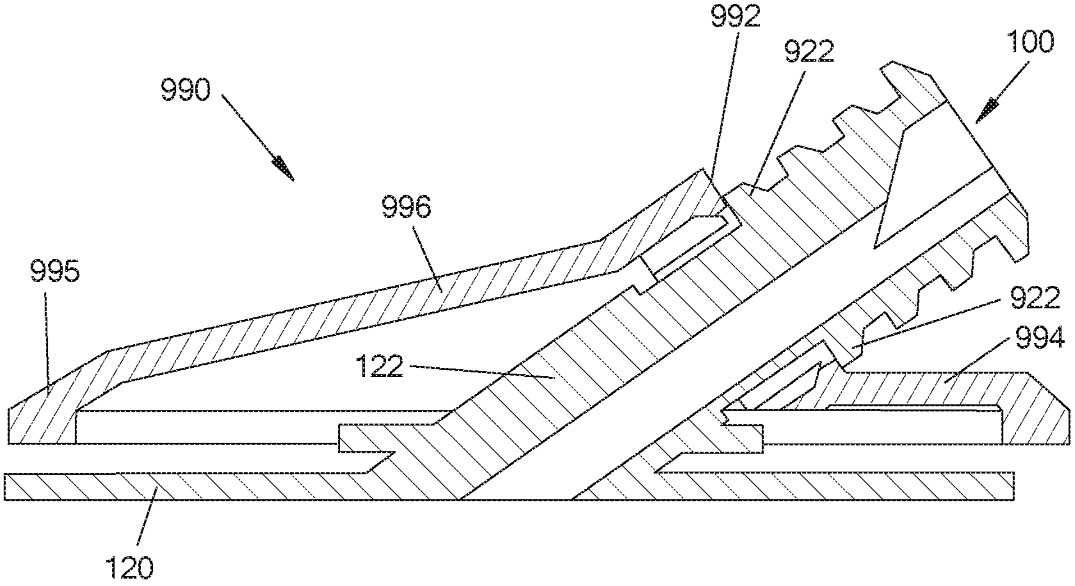
FIG. 88 is an image of a closure device, according to aspects of the present embodiments.

FIGS. 84-88 illustrate images of the closure device 100 including the external fixation 990 and base 120 with scaffold neck 122 protruding therefrom, according to aspects of the present embodiments. As shown in FIG. 84, the delivery tube 976 concentrically slides around the delivery shaft 918 to deliver the external fixation 990 to the closure site. The delivery tube 976 may include square-shaped recesses 978 on opposing sides for interfacing with square-shaped lateral protrusions 982 on the external fixation 990 during delivery of the external fixation 990 to the closure site. The scaffold neck 122 may include four pairs of locking tabs, with a proximal pair of retaining tabs 920 being larger than each of the second, third, and fourth pairs of retaining tabs 922, similar to the embodiments of FIGS. 55-57. The locking tabs interface with a top surface 992 of a collar 984 of the external fixation 990, as shown in FIGS. 85, 87, and 88. The collar 984 becomes disposed around the scaffold neck 122 as the external fixation 990 moves distally toward the closure site. Referring to FIG. 87, the external fixation 990 may include an anterior member 996 and a posterior member 994, both coupled to opposing sides of the collar 984. In some embodiments, the anterior and posterior members 996, 994 are each coupled to lateral members 988 on opposing lateral sides of the external fixation 990, a configuration which provides enhanced flexibility of the external fixation. The collar 984 may also include an internal recess 986 that interfaces with the retaining tabs 920, 922 allowing and/or encouraging movement of the external fixation 990 in a distal direction around the scaffold neck 122. The collar 984 may include a larger diameter compared to previous designs to accommodate a larger-diameter scaffold neck 122, which in turn may be larger to accommodate a thicker (for example, 0.035 inch) guidewire 17. The 0.035 inch guidewire 17 (or, for example 0.02 to 0.05 inch guidewire 17) allows procedures to be performed without the need to do a wire exchange during the closure process, thereby saving time and eliminating steps. The top surface 992 of the collar 984 prevents movement in the proximal direction of the external fixation along the delivery shaft 918 after the collar 984 has engaged the retaining tabs 920, 922.

FIG. 88 shows the external fixation 990 engaged with the base 120 and scaffold neck 122, according to aspects of the present embodiments. In the configuration of FIG. 88, the fourth pair of retaining tabs 922 (that is, on opposing sides of the scaffold neck 122) interface with corresponding portions of the top surface 992 of the collar 984 to prevent proximal movement of the external fixation 990 relative to the base 120. For clarity purposes, the flexible patch is omitted from FIGS. 83, 84, and 88-92, but would be present in operation. Referring to FIGS. 87 and 88, the external fixation 990 may include an anterior member that includes two segments: a short steep first segment 995, and a longer less steep second segment 996, with the short steep first segment 995 being located distal of, and connecting to, the longer less steep second segment 996. The short steep first segment 995 may be oriented at an angle of about 30 degrees (or from about 28 degrees to about 32 degrees, or from about 25 degrees to about 35 degrees) from the horizontal plane (i.e., the plane of base 120). The longer less steep second segment 996 may be oriented at an angle of about 13 degrees (or from about 11 degrees to about 15 degrees, or from about 8 degrees to about 18 degrees) from the horizontal plane (i.e., the plane of base 120). The posterior member 994 may be oriented such that it is substantially parallel to (for example, angled within about 1 degree and/or within about 2 degrees of) the horizontal plane (i.e., the plane of base 120). In some embodiments, the posterior member 994 may be less than half the length of the longer less steep second segment of the anterior member 996. The centerline of scaffold neck 122 (for example, the centerline of guidewire lumen 912) may be oriented at an angle of about 35 degrees (or from about 33 degrees to about 37 degrees, or from about 30 degrees to about 40 degrees) from the horizontal plane (i.e., the plane of base 120). In some embodiments, each of the anterior member 996, the posterior member 994, and the lateral members 998 may include a cross section with a width that is greater than the height while the collar 984 may include a cross section in which the height is greater than the width. The configuration and design of external fixation 990 (for example, the orientations and relative dimension of each of the anterior member 996, the posterior member 994, the lateral members 998, the collar 984, and other features of the external fixation 990) allow the external fixation 990 to accommodate the various loads (distal, proximal, lateral loads, etc.) experienced when in use, while simultaneously allowing the necessary flexibility required for closure of the target site. As a result, the present embodiments allow closure device 100 to accommodate the variety of tissue types and anatomy/disease states of patient's tissue tracts.

Figure 89:
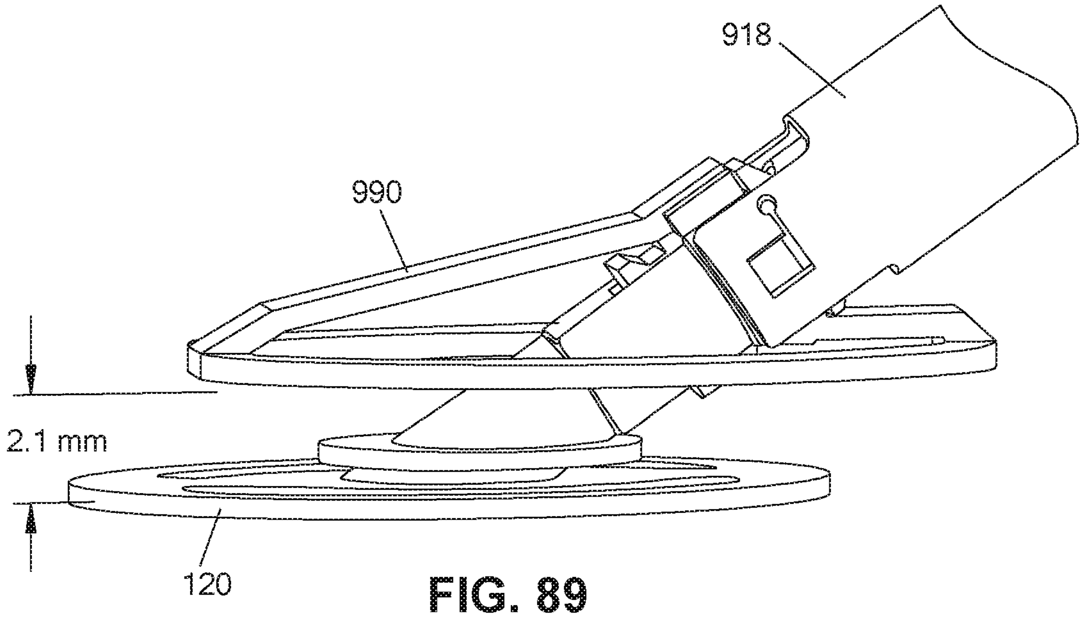
FIG. 89 is an image of a closure device, according to aspects of the present embodiments.
Figure 90:
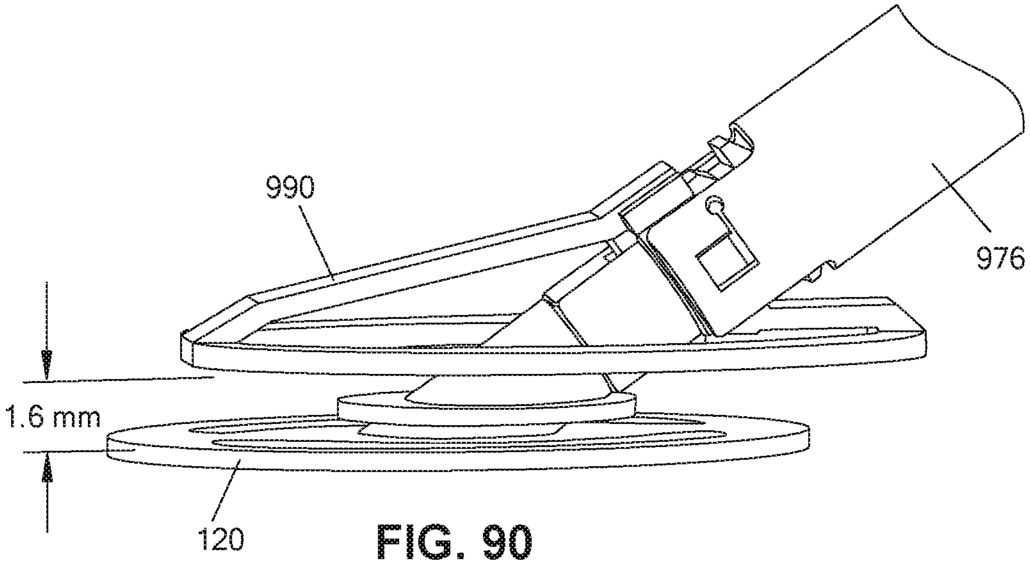
FIG. 90 is an image of a closure device, according to aspects of the present embodiments.
Figure 91:
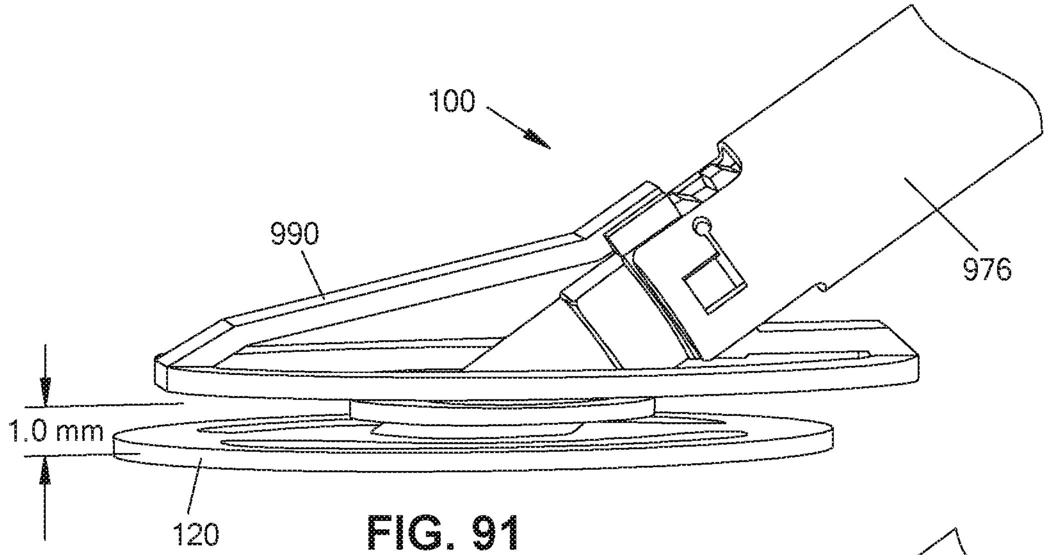
FIG. 91 is an image of a closure device, according to aspects of the present embodiments.
Figure 92:
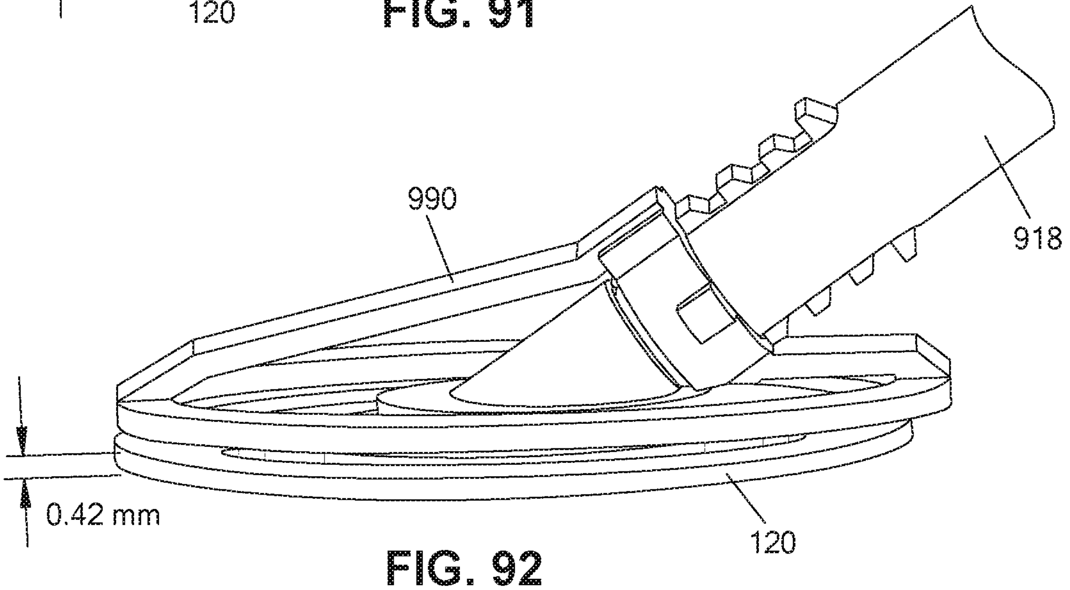
FIG. 92 is an image of a closure device, according to aspects of the present embodiments.

FIGS. 89-92 illustrate four different closure positions of the closure device 100 corresponding to each of the four sets of retaining tabs 920, 922. The various closure positions allow the closure device 100 to accommodate a range of anatomies of patients who require endovascular treatments which may require closures of arteriotomies and/or venotomies. In FIG. 89, which corresponds to the external fixation 990 being engaged with the first set of retaining tabs 920, the device is configured such that there is a 2.1 mm gap between the external fixation 990 and the base 120. In FIG. 90, which corresponds to the external fixation 990 being engaged with the second set of retaining tabs 922, the device is configured such that there is a 1.6 mm gap between the external fixation 990 and the base 120. In FIG. 91, which corresponds to the external fixation being engaged with the third set of retaining tabs 922, the device is configured such that there is a 1.0 mm gap between the external fixation 990 and the base 120. In FIG. 92, which corresponds to the external fixation being engaged with the fourth set of retaining tabs 922, the device is configured such that there is a 0.42 mm gap between the external fixation 990 and the base 120.

Other examples and methods of the delivery device are described in U.S. Patent Application Publication Nos. 2013/0274795, 2017/0333014, and 2019/0021710, which are patented as U.S. Pat. Nos. 9,572,558, 11,278,269, and 11,311,280, respectively, the contents of which are incorporated by reference herein in their entirety.

Second Embodiment of Closure Device

FIGS. 93-101 illustrate a second embodiment of the vascular closure device 1000 and system that feature various modifications to their designs that may improve performance and/or ease of use. In some embodiments, these modifications may include: increased thickness of some portions of some components to increase stiffness; decreased thickness of some portions of some components to decrease stiffness and use less material during manufacture; and curved and/or smoothed edges rather than sharp edges on various components to improve movement of components through a delivery device and through a the lumen of a body vessel and/or openings or wounds. The vascular closure device 1000 may be used to close openings in either veins or arteries.

Figure 93:
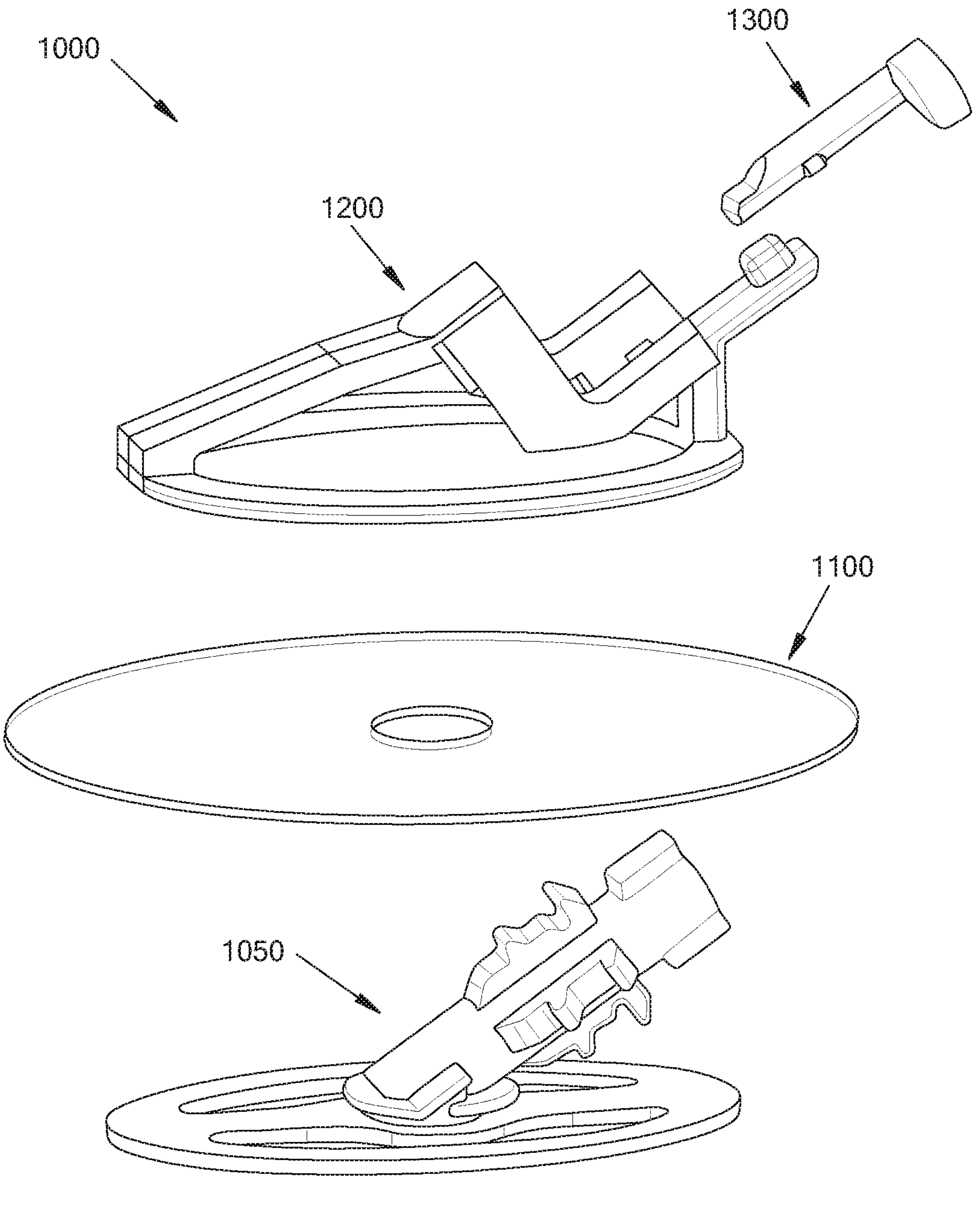
FIG. 93 is a perspective view of further embodiments of components of a closure device assembly, including a scaffold, a patch, an external fixation, and a closure pin, according to aspects of the present embodiments.

FIG. 93 illustrates a perspective view of further embodiments of components of a closure device assembly 1000, including a scaffold 1050, a patch 1100, an external fixation 1200, and a closure pin 1300, according to aspects of the present embodiments. As with the previous embodiments, the closure device assembly 1000 is used to close an aperture or vascular opening, which may be openings in arteries and/or veins in a subject.

Figure 94A:
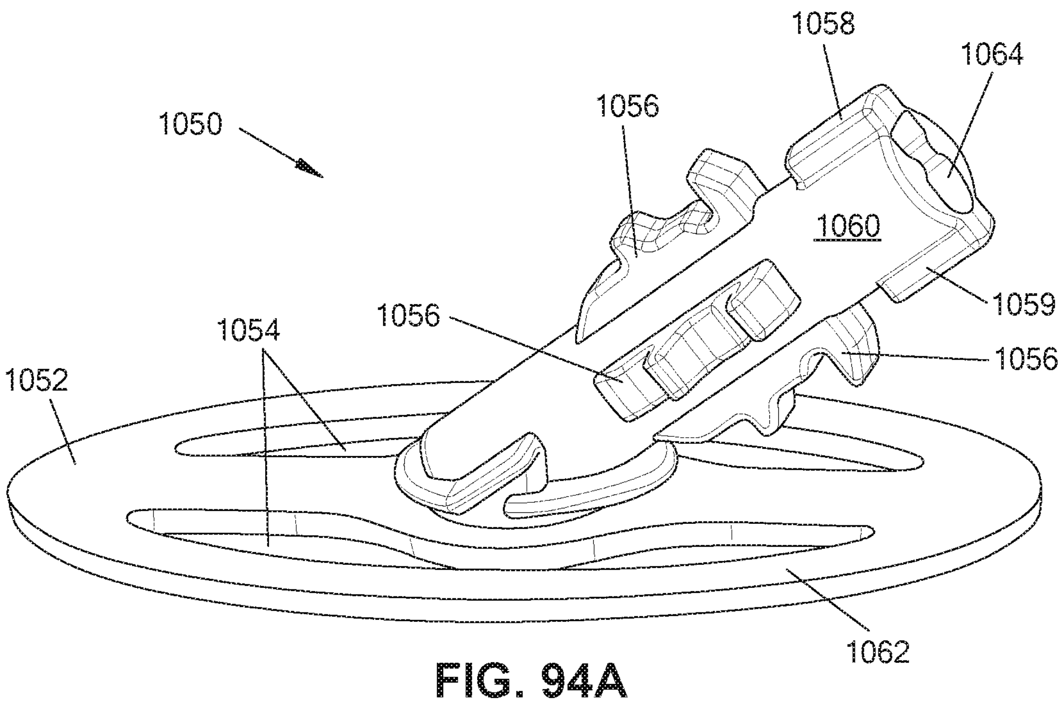
FIG. 94A is a perspective view of a scaffold, according to aspects of the present embodiments.

FIG. 94A illustrates a perspective view of a scaffold 1050, according to aspects of the present embodiments. The scaffold 1050 may include a base plate 1052 and a neck 1060. In some embodiments, the shape of the base plate 1052 may be a disc with a circular, oval, or rectangular shape, and the base plate 1052 may include one or more openings 1054. The overall shapes of the base plate 1052 and openings 1054 may allow the base plate 1052 to bend to better fit within the lumen of an artery or vein or other space. The neck 1060 may have a generally cylindrical shape.

Referring still to FIG. 94A, the scaffold neck 1060 further includes four retaining tabs 1056 that are disposed circumferentially around the outer surface of the neck 1060. The retaining tabs 1056 may include at least two curved protrusions that extend radially and may interface with an external fixation 1200. The neck 1060 may include at least two pads (i.e., retaining pads) 1058 and 1059 that may interact with the external fixation 1200 (for example, with the collar 1206 of the external fixation 1200). The scaffold neck 1060 may include an interior lumen 1064 for the passage of a guidewire 1001. The interior lumen 1064 may also be termed a guidewire lumen 1064, similar to the guidewire lumen 912 of earlier embodiments.

Figure 94B:
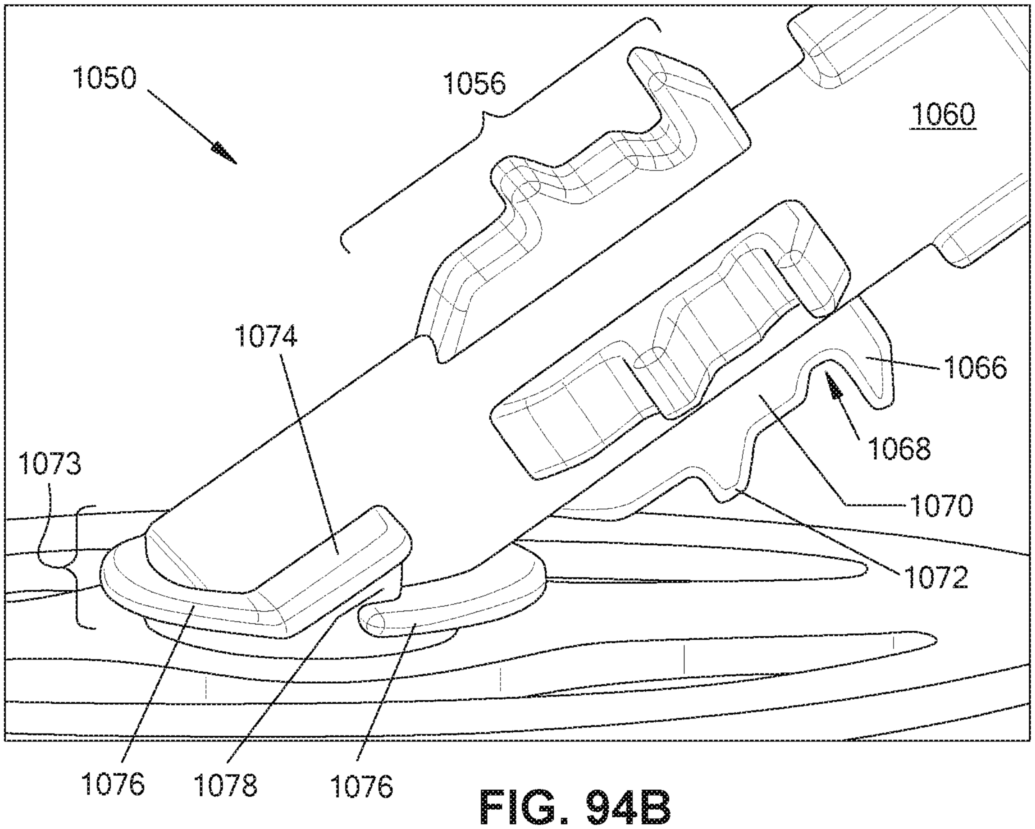
FIG. 94B is an enlarged view of a scaffold neck and base plate, according to aspects of the present embodiments.

FIG. 94B illustrates an enlarged view of a neck 1060 and base plate 1052 of a scaffold 1050, according to aspects of the present embodiments. Each retaining tab 1056 may include a first protrusion 1066, a notch 1068, a flat portion 1070, and a second protrusion 1072, which may all be aligned longitudinally along the axis of the scaffold neck 1060.

Referring still to FIG. 94B, some embodiments may include a threaded portion 1073 located at the base of the scaffold neck 1060. The threaded portion 1073 may comprise a thread 1076 disposed circumferentially around the base of the neck 1060, and terminate in a lifted portion 1074 that leaves a gap 1078 so that an interior opening 1102 in a patch 1100 may be inserted and secured by the thread 1076 to hold the patch 1100 against the upper surface of the base plate 1052 of the scaffold 1050.

Figure 95:
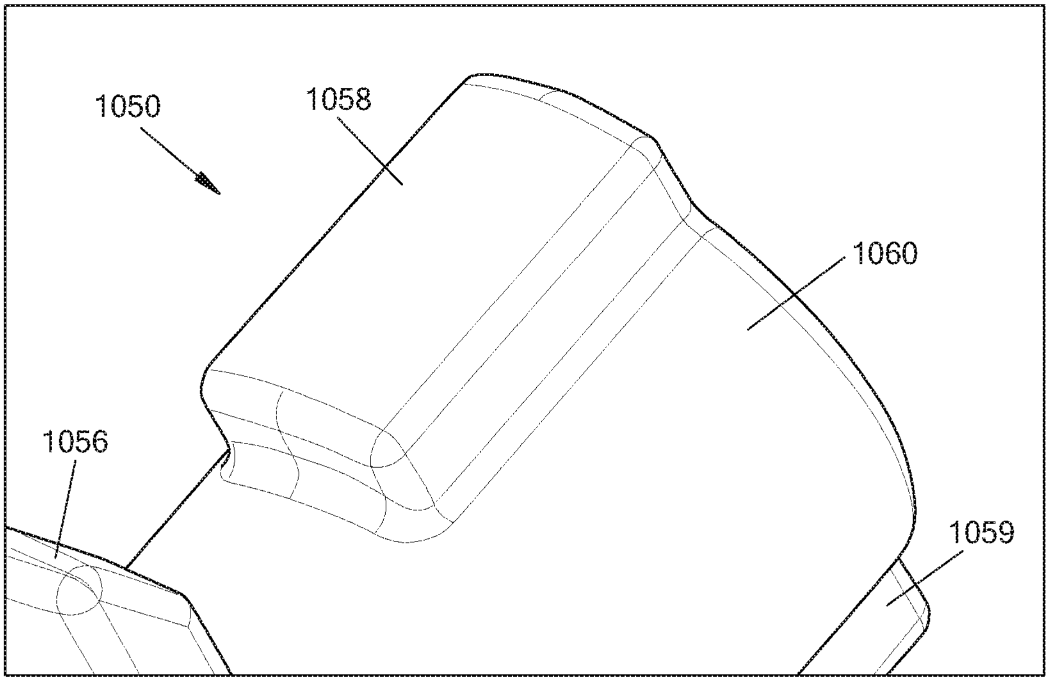
FIG. 95 is an enlarged view of the upper portion of the scaffold neck, according to aspects of the present embodiments.

FIG. 95 illustrates an enlarged view of the neck 1060 on a scaffold 1050, according to aspects of the present embodiments. One retaining pad 1058 is visible in FIG. 95. The retaining pad 1058 has a rectangular prism shape with curved edges, and is disposed on the upper portion of the neck 1060, while another retaining pad 1059 that is partially visible is disposed on the lower portion of the neck 1060. A portion of a retaining tab 1056 is also visible.

Figure 96:
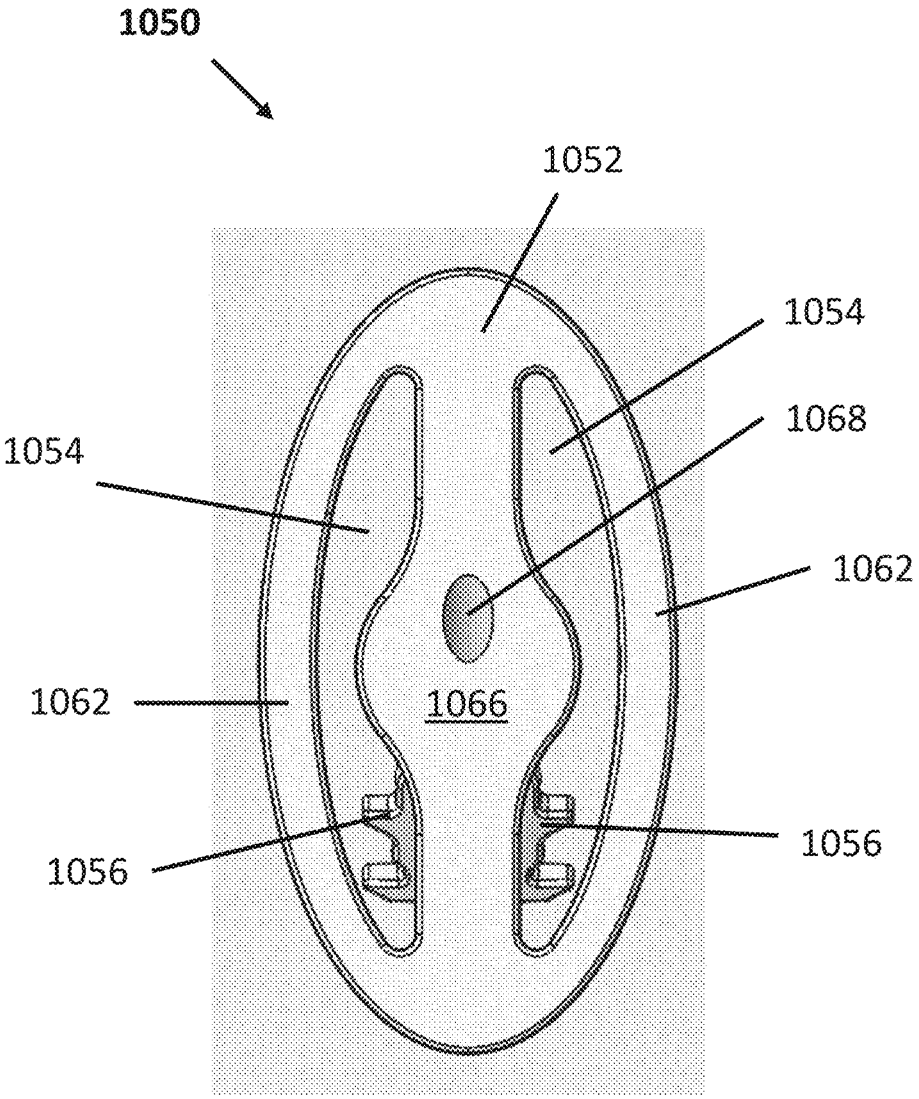
FIG. 96 is a bottom view of a scaffold, according to aspects of the present embodiments.

FIG. 96 illustrates a bottom view of a scaffold 1050, according to aspects of the present embodiments. The base plate 1052 may have curved side portions 1062 and openings 1054, and a central portion 1066. A central opening 1068 into the lumen of the neck 1060 is visible. Two of the retaining tabs 1056 are visible through the openings 1054. In this design, the figuration of the base plate 1052 uses less material than earlier embodiments such as the ones featured in FIGS. 3-5 and 31-32, and may provide certain benefits for manufacturing and/or mechanical flexibility.

Figure 97A:
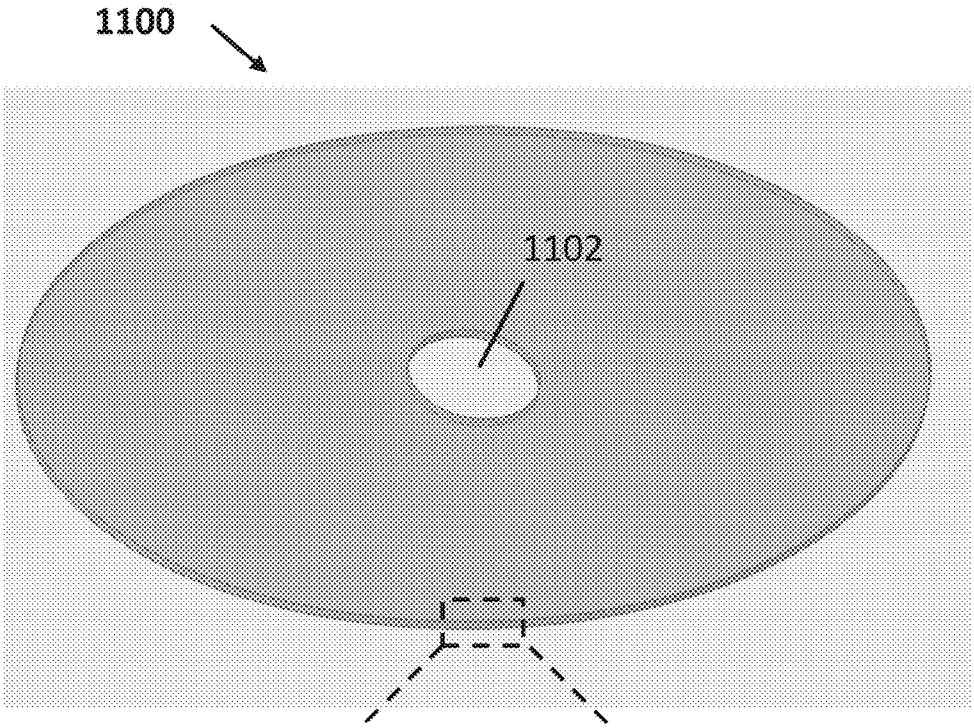
FIG. 97A is a perspective view of a patch, according to aspects of the present embodiments.

FIG. 97A illustrates a perspective view of a patch 1100 according to aspects of the present embodiments. The patch 1100 includes an opening 1102 disposed in the center of the patch 1100. The shape of the patch 1100 may be an oval or an ellipse. In some embodiments, the shape of the patch 1100 may preferentially be an oval. The opening 1102 may be an oval, an ellipse, or a circle. The patch 1100 includes at least a flexible, bioabsorbable polymer material.

Figure 97B:
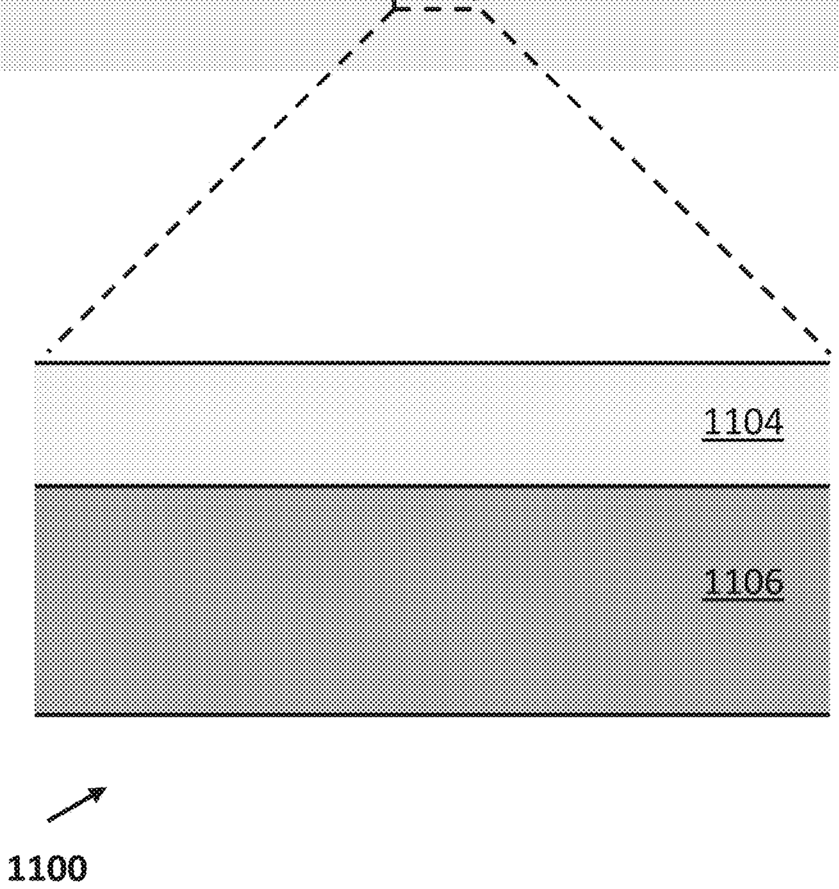
FIG. 97B is a cross-sectional view of a patch, according to aspects of the present embodiments.

FIG. 97B illustrates a cross-sectional view of a patch 1100, according to aspects of the present embodiments. In some embodiments, the patch 1100 may include a base layer 1106 that may have a thickness within a range of 190-220 μm, and an electrospun layer 1104 that may have a thickness within a range of 20-80 μm. The total thickness of the patch may be within a range of 210-300 μm.

Figure 98:
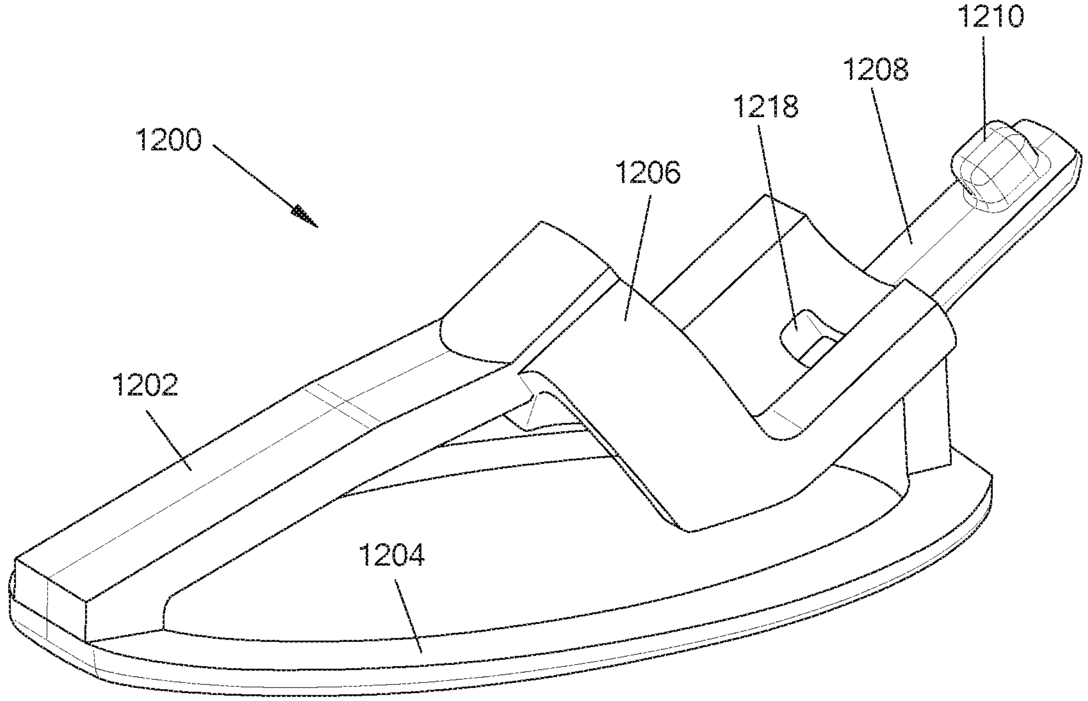
FIG. 98 is a perspective view of an external fixation, according to aspects of the present embodiments.

FIG. 98 illustrates a perspective view of an external fixation 1200, according to aspects of the present embodiments. The external fixation 1200 may include an anterior member or rib 1202 that connects to a base ring portion 1204 and a collar 1206 to provide both support and flexibility such that the overall external fixation 1200 may adapt and conform to various vessel wall morphologies and tissue tract anatomies that are experienced in clinical use. The collar 1206 is shown in more detail in FIG. 99 below.

Figure 99:
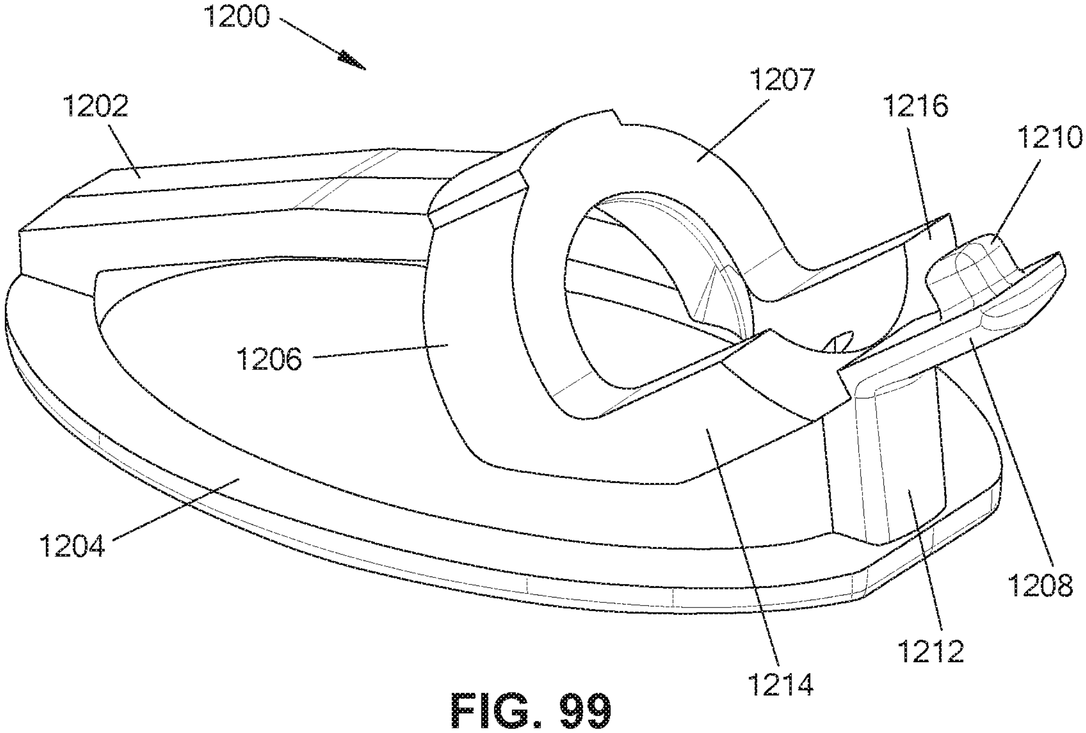
FIG. 99 is a perspective view of an external fixation, emphasizing the collar portion of the external fixation, according to aspects of the present embodiments.

FIG. 99 illustrates a perspective view of an external fixation 1200, emphasizing the collar 1206 portion of the external fixation 1200, according to aspects of the present embodiments. The collar 1206 has a semicircular portion 1206 with a flat side 1207 that extends into a diagonal portion 1214. From the side view, the collar 1206 connects to the diagonal portion 1214 in an L-like shape. The diagonal portions 1214 on either side of the scaffold 1200 connect together at another flat portion 1216 with has an opening 1218 (see FIG. 98). Overall, the general shape of the collar 1206 resembles a sectioned cylinder. The base ring portion 1204 may form a shape that is an oval, an ellipse, a square, a rectangle, or a diamond, in certain embodiments.

Referring still to FIG. 99 and FIG. 98, a posterior post 1212 rises vertically from the base ring portion 1204, connects to the second flat portion 1216 of the collar 1206, and then turns into a tab 1208 that extends diagonally away from the posterior post 1212. The tab has a protrusion 1210 in the shape of a rectangular prism with rounded edges and corners at the end of the tab 1208. The tab 1208 and protrusion 1210 interact with a delivery shaft 1408 during the delivery of the closure device.

Figure 100:
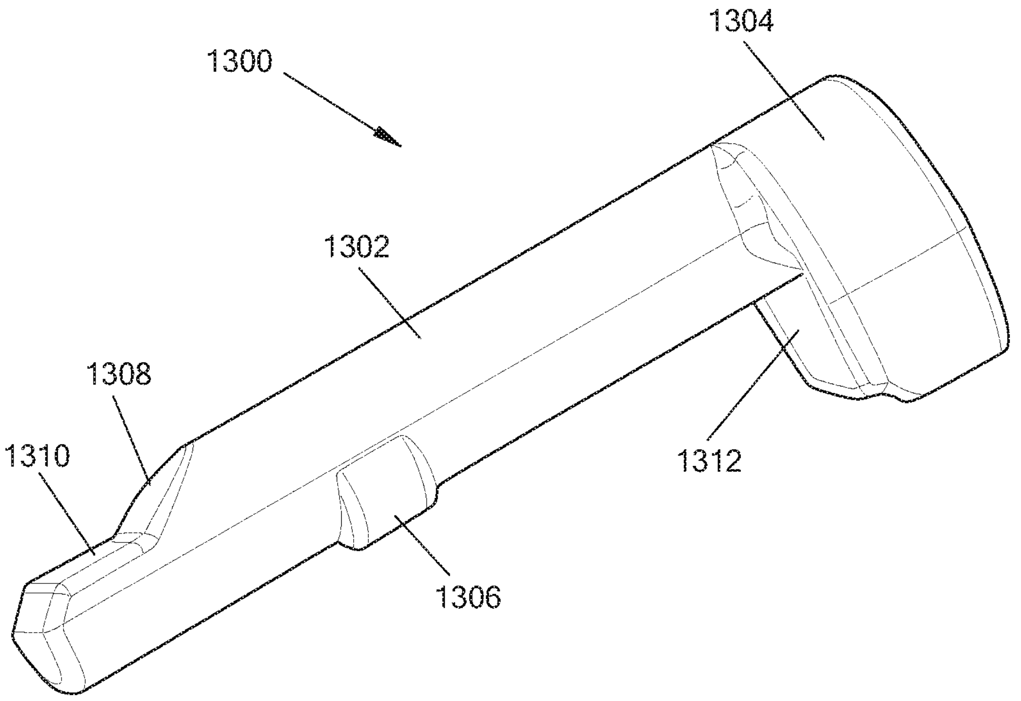
FIG. 100 is a perspective view of a closure pin, according to aspects of the present embodiments.

FIG. 100 illustrates a perspective view of a closure pin 1300, according to aspects of the present embodiments. The closure pin, when used within the closure device, is disposed within the scaffold neck for sealing the lumen of the scaffold. This closure step may occur after a guidewire is removed from the scaffold. The closure pin may include a cylindrical pin body 1302 and a cylindrical or circular pin head 1304 that has a diameter that is larger than the diameter of the cylindrical body 1302 and is connected to the proximal end of the pin body 1302 in an eccentric position. The pin head 1304 includes a rectangular cutout 1312 for interfacing with the protrusion 1210 on the external fixation 1200. The pin 1300 also includes a protrusion 1306 on the pin body 1302 for interfacing with the opening 1218 in the external fixation 1200. At the distal end of the pin 1300, there is an angled portion 1308 and a flat portion 1310 with a reduced diameter.

Figure 101:
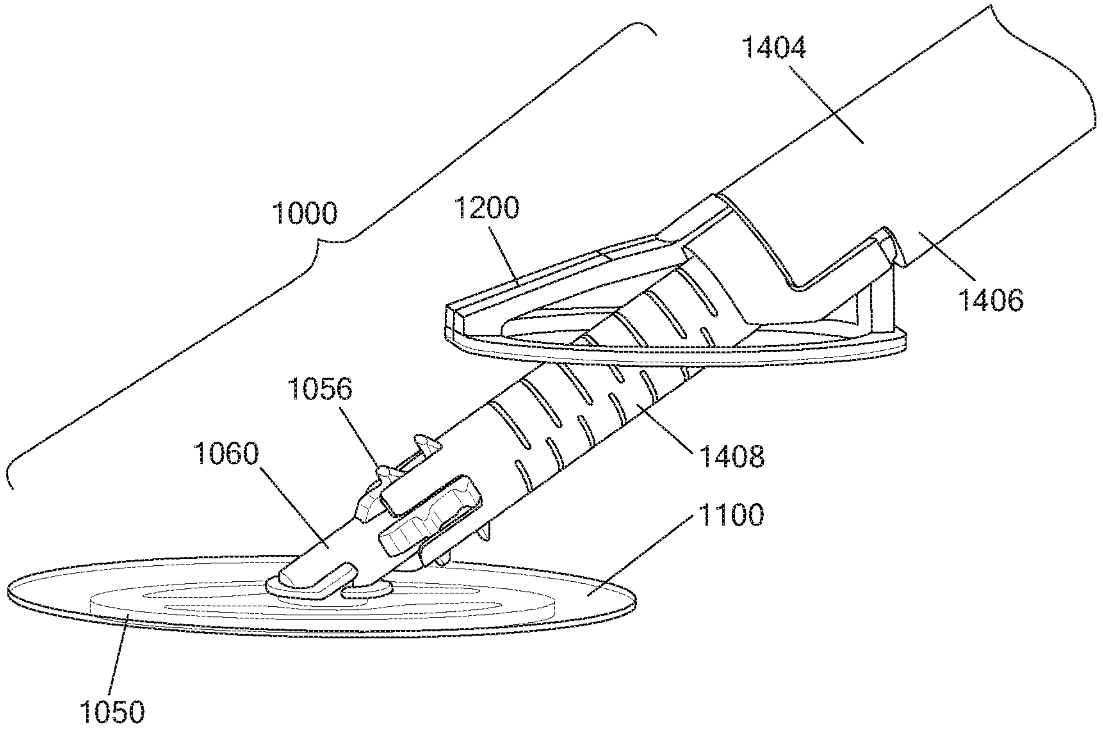
FIG. 101 is a perspective view of a vascular closure device and system with outer shaft engaged with an external fixation, according to aspects of the present embodiments.

FIG. 101 illustrates a perspective view of a vascular closure device 1000 and system with fixation shaft 1404 engaged with an external fixation 1200, according to aspects of the present embodiments. This arrangement shows an example of how the components of the closure device 1000 are assembled during delivery of the closure device 1000. The scaffold 1050 is engaged via the retaining tabs 1056 to the delivery shaft 1408. The patch 1100 is positioned directly above the scaffold 1050 and is engaged at the threaded portion 1073 of the scaffold 1050. The external fixation 1200 is engaged to the fixation shaft 1404 via the L-shaped cylinder-like scaffold neck. The distal end 1406 of the fixation shaft 1404 is shaped to accommodate the L-shaped cylinder-like scaffold neck.

Figure 102:
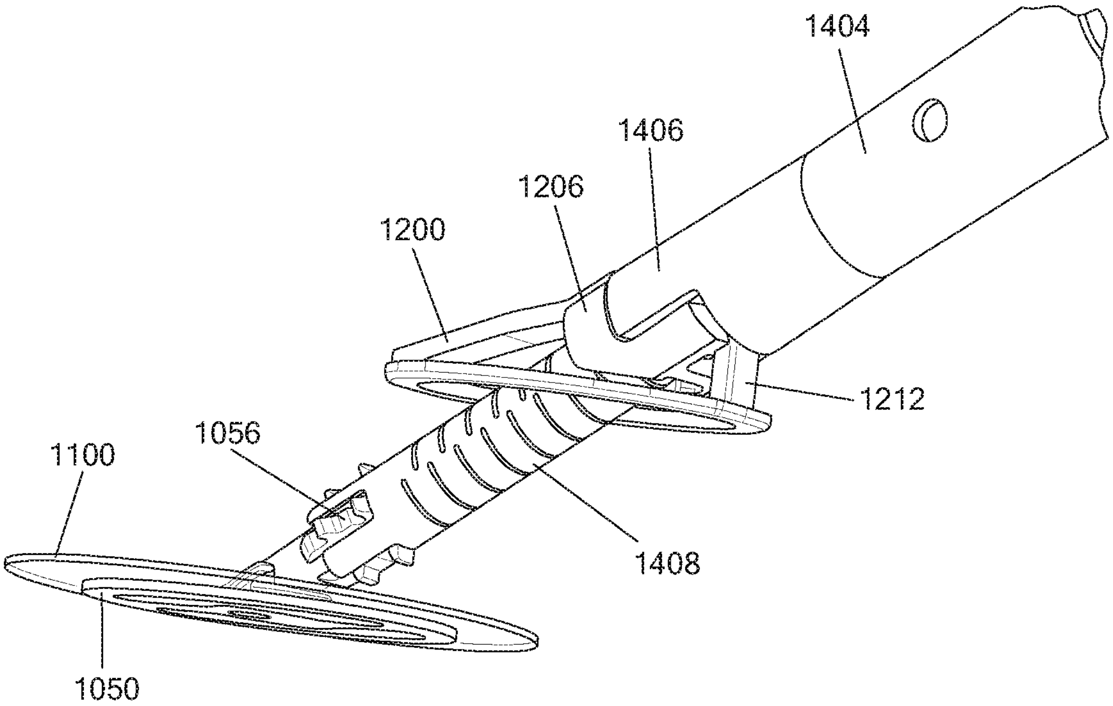
FIG. 102 is a posterior perspective view of a vascular closure device and system with outer shaft engaged with an external fixation, according to aspects of the present embodiments.

FIG. 102 illustrates a posterior perspective view of a vascular closure device 1000 and system with fixation shaft 1404 engaged with an external fixation 1200, according to aspects of the present embodiments. The vertical post 1212 is visible, but the tab 1208 and protrusion 1210 are inside the fixation shaft 1404.

Figure 103:
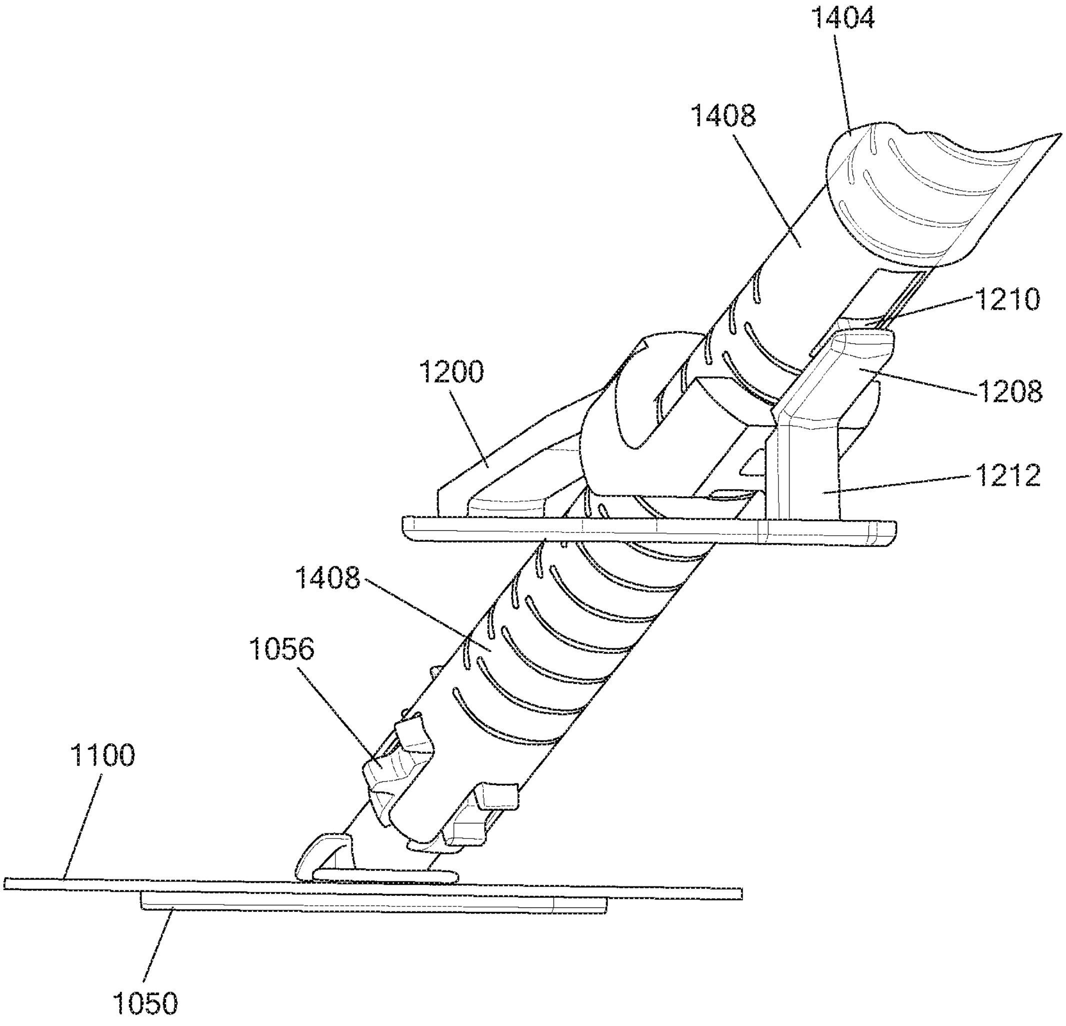
FIG. 103 is a perspective view of a vascular closure device and system with delivery shaft, according to aspects of the present embodiments.

FIG. 103 illustrates a perspective view of a vascular closure device 1000 and system with delivery shaft 1408, according to aspects of the present embodiments. With the fixation shaft 1404 partially retracted, the tab 1208 on the external fixation 1200 is visible. The protrusion 1210 on the external fixation 1200 is engaged with the notch or opening in the delivery shaft 1408.

Figure 104:
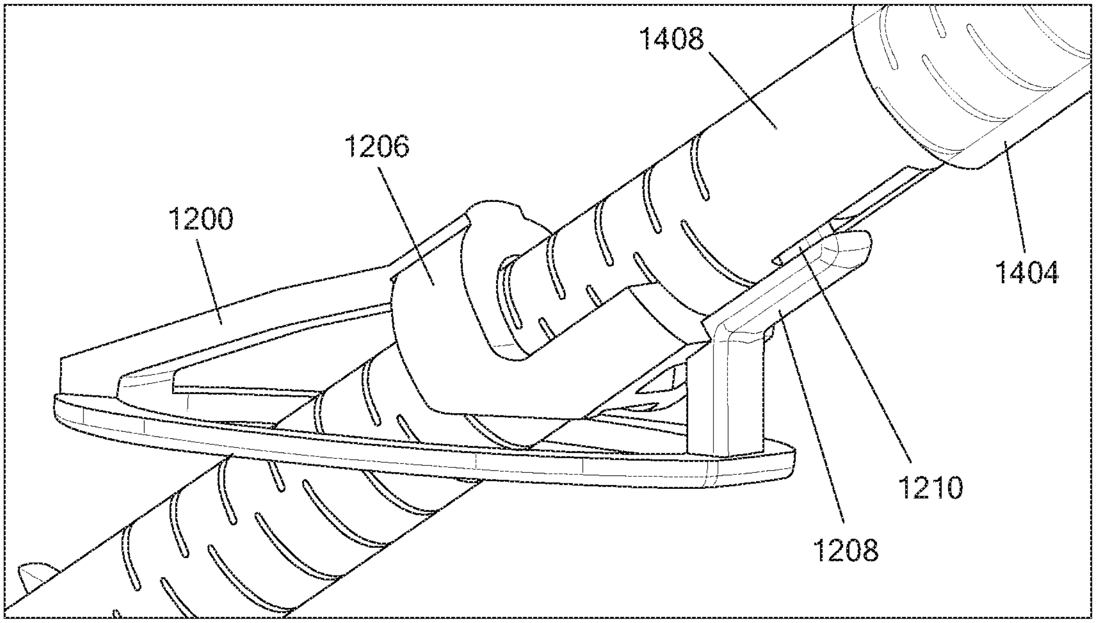
FIG. 104 is a perspective view of a vascular closure device and system with delivery shaft, according to aspects of the present embodiments.

FIG. 104 illustrates a perspective view of a vascular closure device 1000 and system with delivery shaft 1408, according to aspects of the present embodiments. Similar to the view in FIG. 103, the protrusion 1210 on the scaffold 1200 is engaged with a notch in the delivery shaft 1408. The delivery shaft 1408 is disposed through the interior and coaxially with the collar 1206 of the external fixation 1200.

Figure 105:
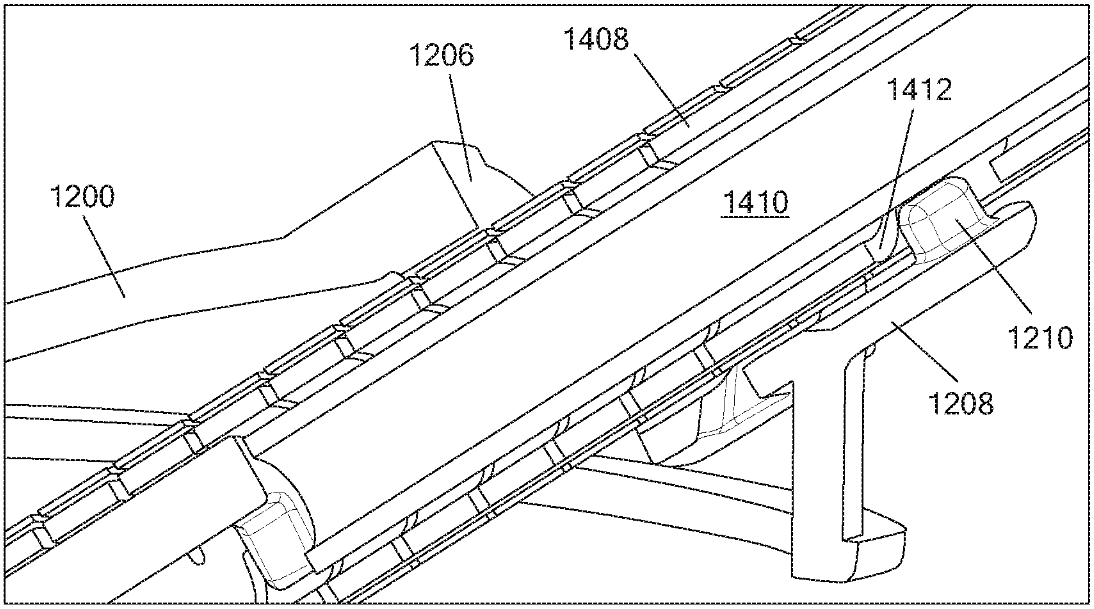
FIG. 105 is a cross-sectional view of a delivery shaft engaged with an external fixation, according to aspects of the present embodiments.

FIG. 105 illustrates a cross-sectional view of a delivery shaft 1408 engaged with an external fixation 1200, according to aspects of the present embodiments. The delivery shaft 1408 passes through the collar 1206 of the external fixation 1200. The push tube 1410 is disposed coaxially within the delivery shaft 1408, and presses against the neck 1060 of the scaffold 1050. An interior lip 1412 presses against the protrusion 1210 during the retraction steps to disengage the delivery system from the closure device 1000.

Figure 106:
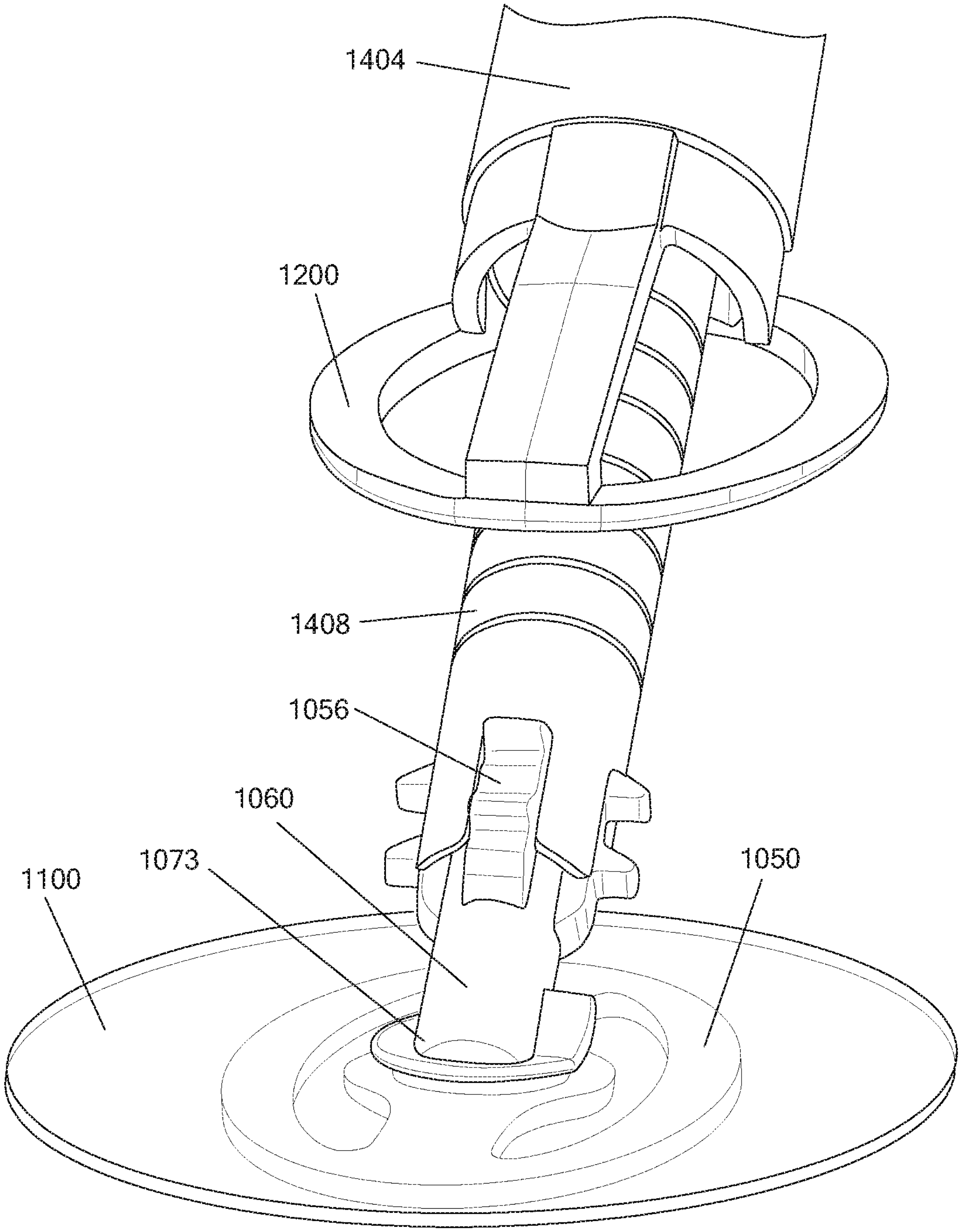
FIG. 106 is a front perspective view of a vascular closure device and system with delivery shaft, according to aspects of the present embodiments.

FIG. 106 illustrates a front perspective view of a vascular closure device 1000 and system with delivery shaft 1408 and fixation shaft 1404, according to aspects of the present embodiments. In this arrangement, the external fixation 1200 is not yet engaged with the scaffold 1050.

Figure 107:
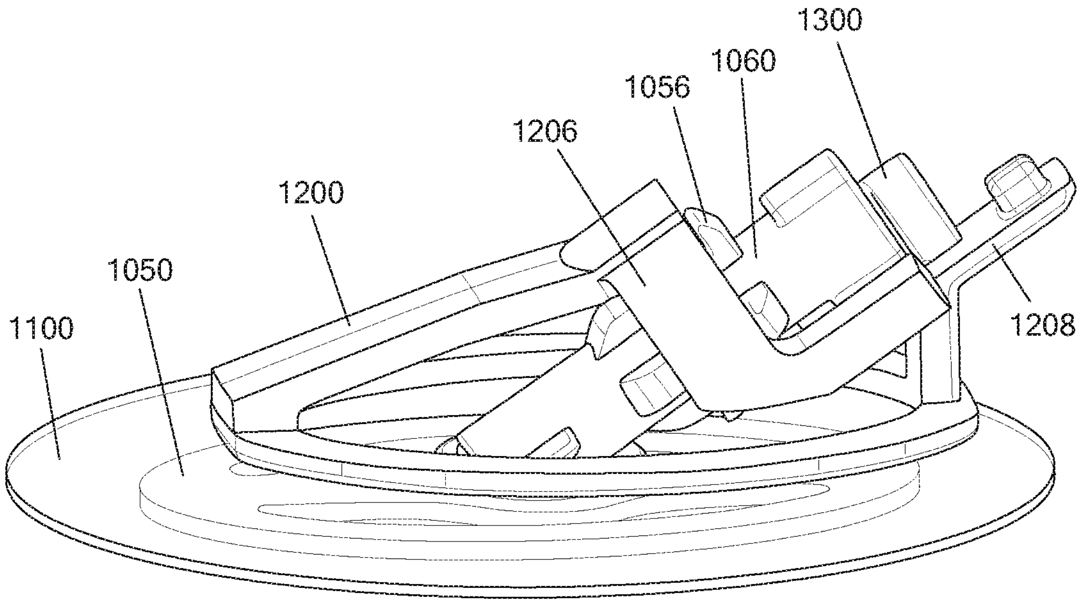
FIG. 107 is a perspective view of an assembled vascular closure device, according to aspects of the present embodiments.

FIG. 107 illustrates a perspective view of an assembled vascular closure device 1000, according to aspects of the present embodiments. In this assembled configuration, the external fixation 1200 is engaged with the scaffold 1050 by insertion of the scaffold neck 1060 through the collar 1206 of the external fixation 1200. The retaining tabs 1056 help hold the external fixation in position so that the wall of the vessel where the opening is being closed and the patch 1100 are clamped between the base ring of the external fixation 1200 and the base plate of the scaffold 1050. The closure pin 1300 is inserted into the opening in the neck 1060 of the scaffold, and helps to close the opening in the neck 1060 after the removal of the guidewire 1001.

Figure 108:
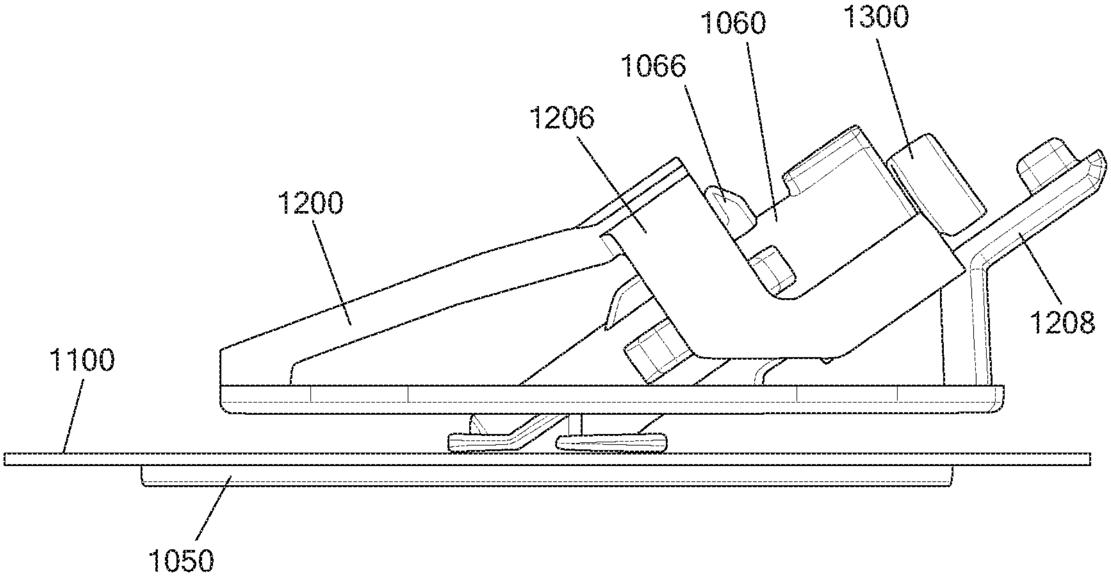
FIG. 108 is a side view of an assembled vascular closure device, according to aspects of the present embodiments.

FIG. 108 illustrates a side view of an assembled vascular closure device, with an external fixation 1200 in a higher position, according to aspects of the present embodiments. The first protrusion 1066 of the retaining tab 1056 is engaged with the collar 1206 of the external fixation 1200. This arrangement is also illustrated in a perspective view in FIG. 110.

Figure 109:
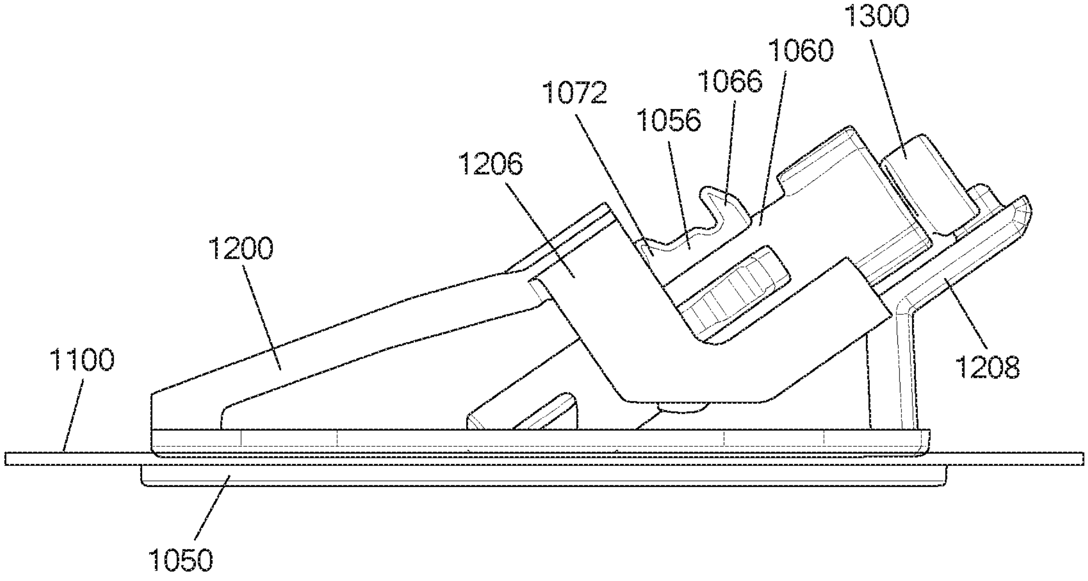
FIG. 109 is a side view of an assembled vascular closure device, according to aspects of the present embodiments.

FIG. 109 illustrates a side view of an assembled vascular closure device, with an external fixation 1200 in a lower position, according to aspects of the present embodiments. The second protrusion 1072 of the retaining tab 1056 is engaged with the collar 1206 of the external fixation 1200, so that the external fixation 1200 is closer to the patch 1100 and base plate of the scaffold 1050.

Figure 110:
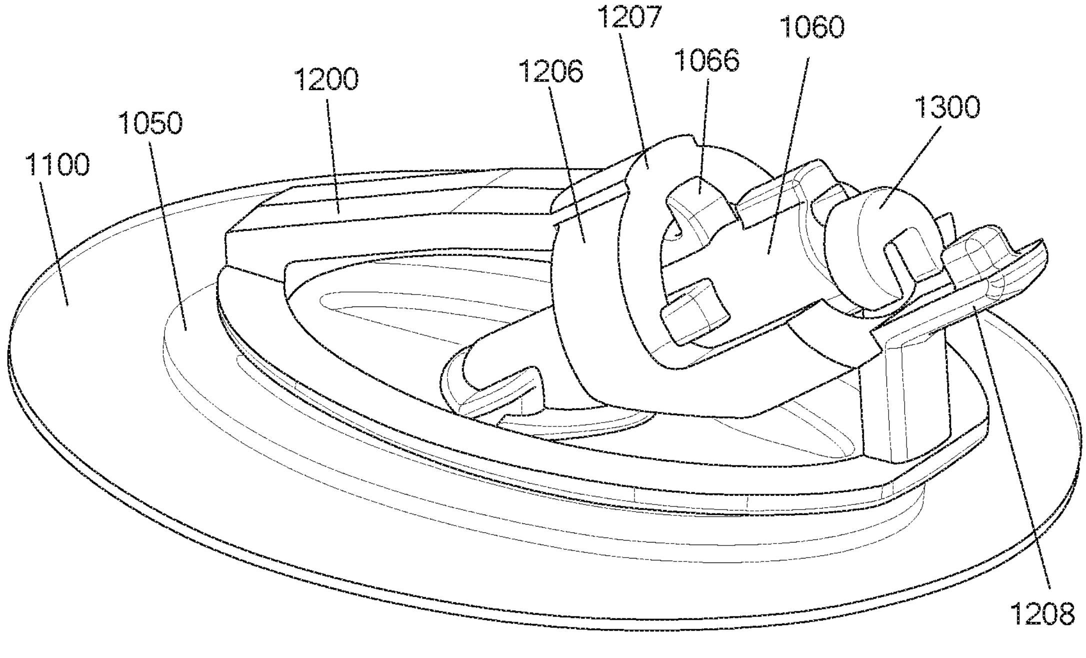
FIG. 110 is a posterior perspective view of an assembled vascular closure device, according to aspects of the present embodiments.

FIG. 110 illustrates a posterior perspective view of an assembled vascular closure device 1000, according to aspects of the present embodiments. The first protrusion 1066 of the retaining tab 1056 is engaged with the collar 1206 of the external fixation 1200, more specifically the protrusion 1066 is essentially hooked on the flat surface 1207. This arrangement is also illustrated in a side view in FIG. 108.

Deployment of Closure Device Using Delivery System with Handle

FIG. 111A through 111L illustrate sequential steps in deployment of a closure device 1000 in a body vessel, according to aspects of the present embodiments. These figures all illustrate the interior view of the lumen 1403 of a body vessel 1401 with an aperture 1405 that is to be closed by the closure device 1000. An introducer sheath 1518 is visible in FIG. 111A through FIG. 111K. The introducer is inserted into a surgical opening of the patient near the aperture 1405 in the body vessel that is to be closed by the closure device 1000.

Figure 111A:
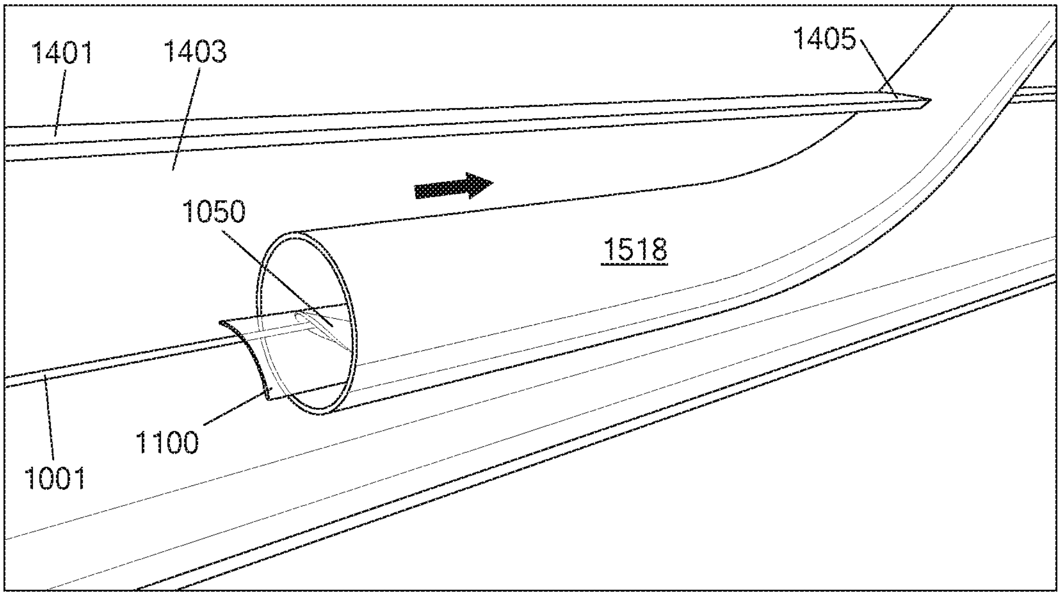
FIG. 111A through 111L are interior views in a body vessel or vessel interior showing sequential steps in deployment of a closure device, according to aspects of the present embodiments.

In FIG. 111A, a guidewire 1001 is disposed through an introducer sheath 1518 and the lumen 1403, and through the rolled interior of a patch 1100. The patch 1100 and scaffold 1050 are visible in their stowed positions within the introducer sheath 1518. During step 1606 of the delivery method 1600 (shown in FIG. 116), the introducer sheath 1518 is retracted pull away from the stowed patch 1100 and scaffold 1050.

Figure 111B:
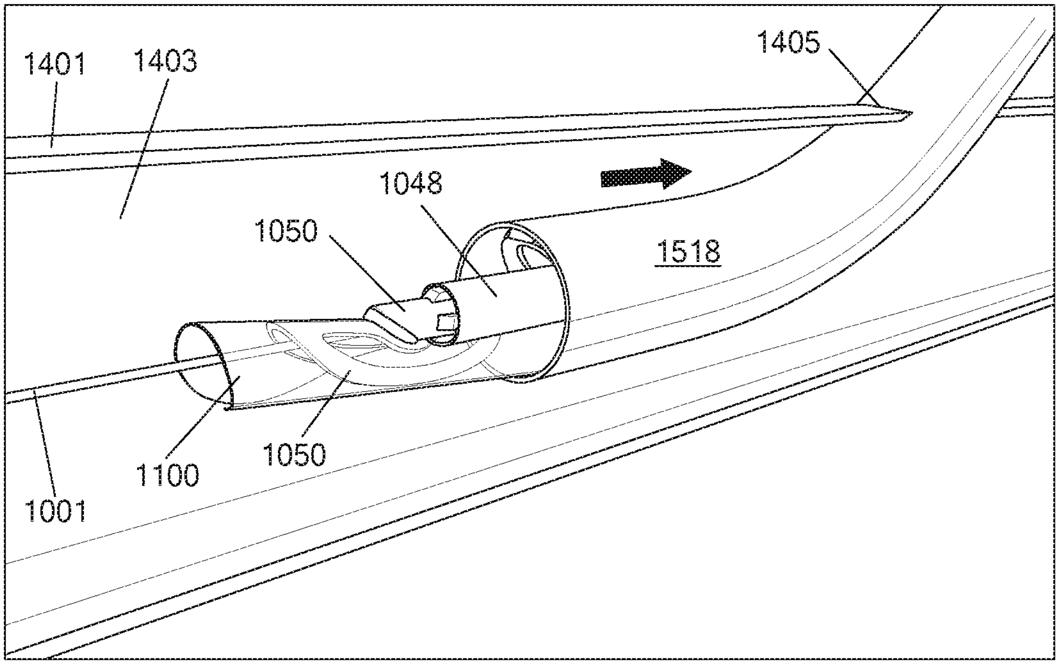

In FIG. 111B, the introducer sheath 1518 continues being retracted, and more of the patch 1100 and scaffold 1050 are visible outside of the introducer sheath 1518.

Figure 111C:
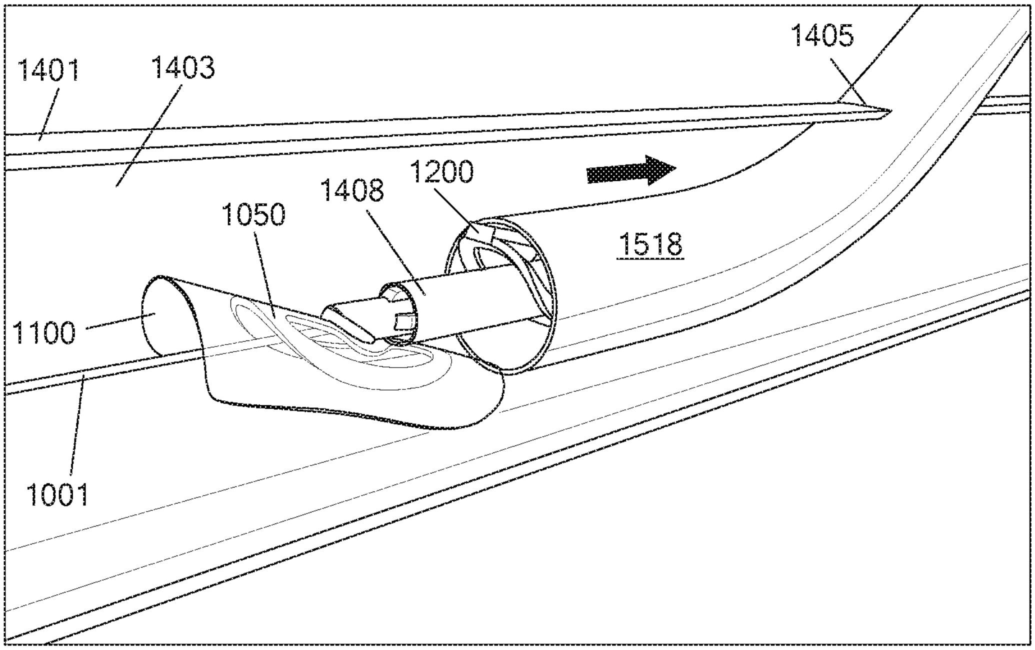

In FIG. 111C, the patch 1100 and scaffold 1050 are completely out of the introducer sheath 1518 and the external fixation 1200 is visible at the entrance of the introducer sheath 1518.

Figure 111D:
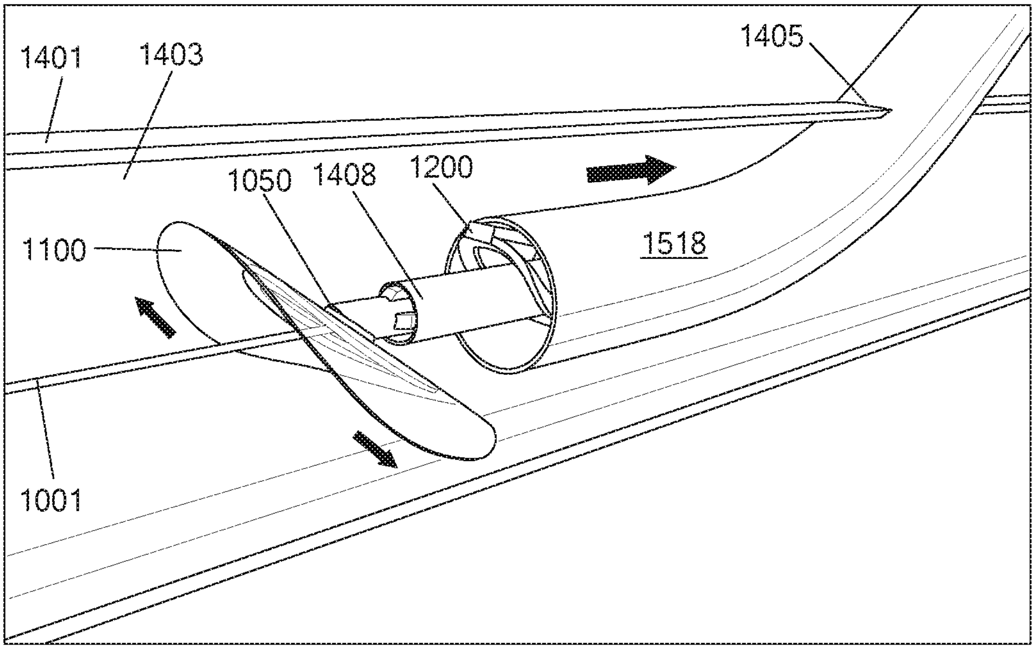

In FIG. 111D, the patch 1100 and scaffold 1050 are unrolled, and become generally flat.

Figure 111E:
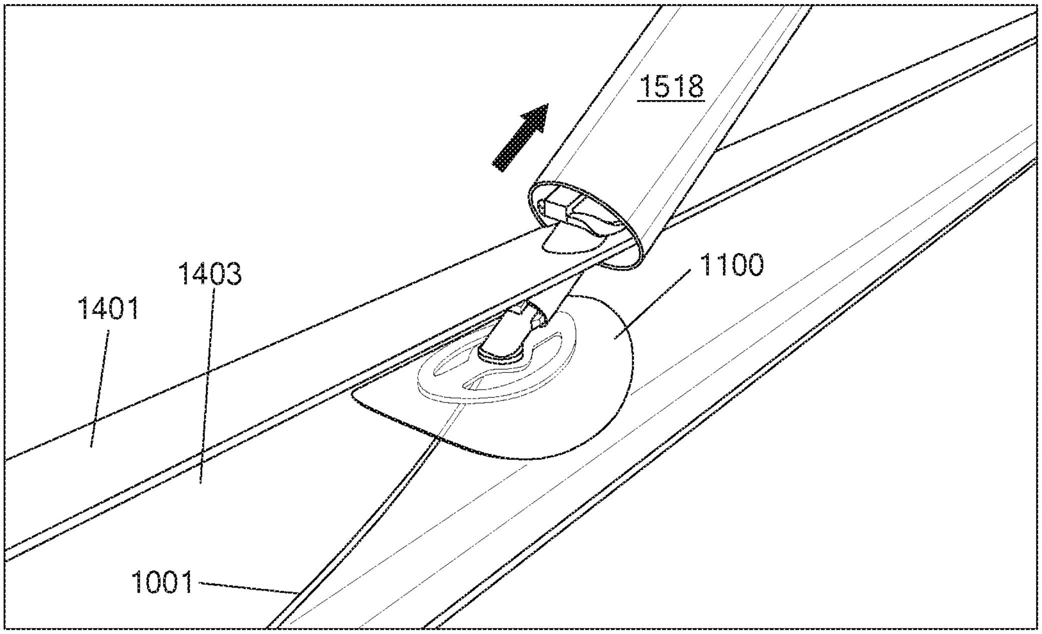
Figure 111F:
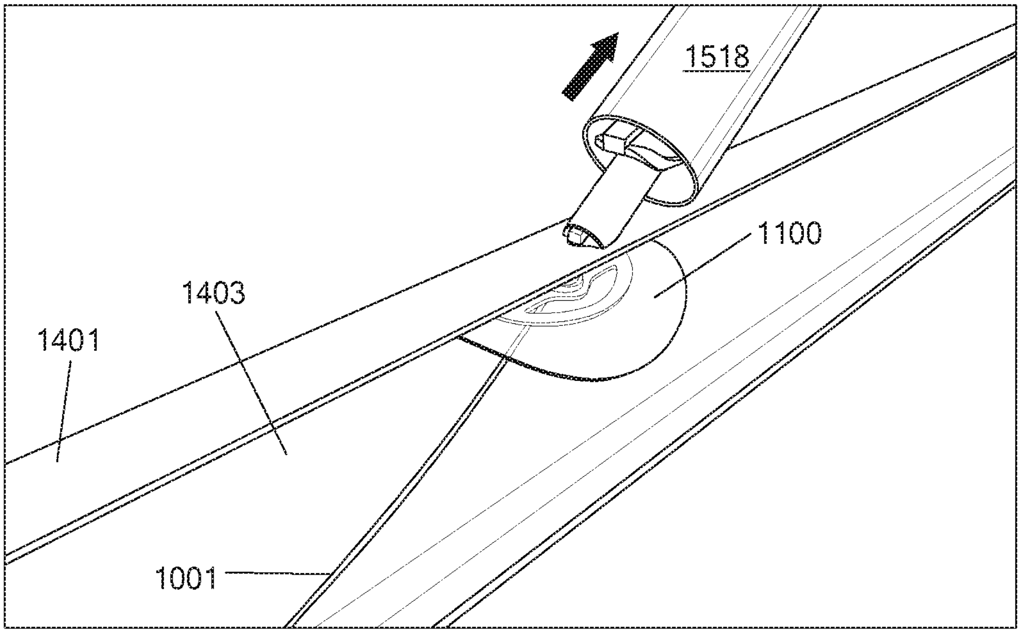

In FIGS. 111E and 111F, the delivery device is pulled outward so that the patch 1100 and scaffold 1050 move toward the wall 1401 of the vessel until the top surface of the patch 1100 is in contact with the interior of the wall 1401 (in FIG. 111F).

Figure 111G:
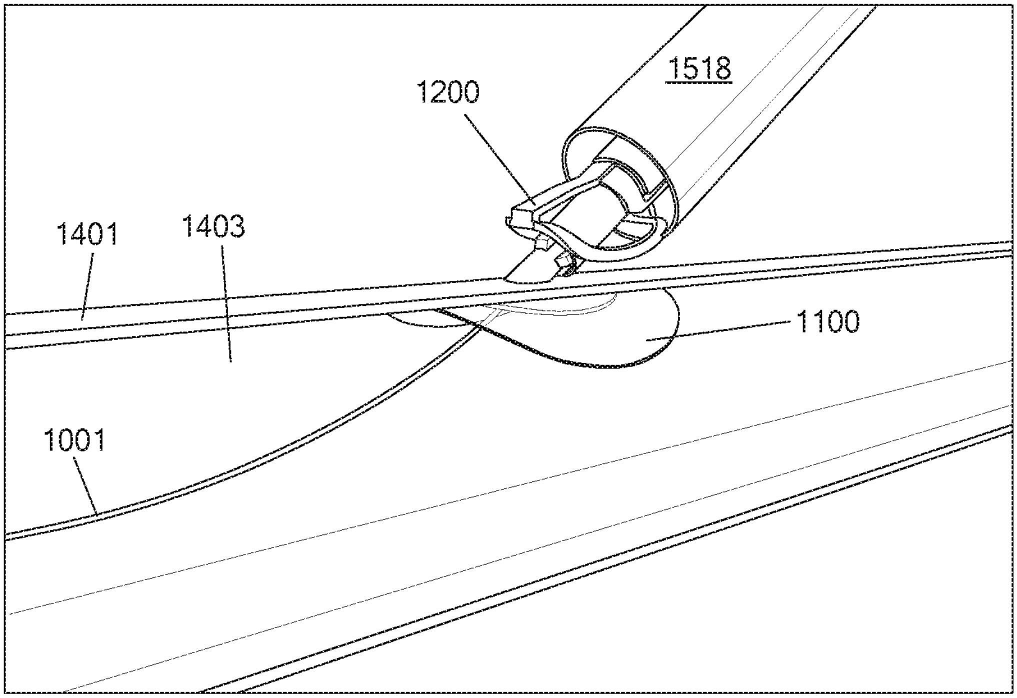

In FIG. 111G, while the patch 1100 and scaffold 1050 are in contact with the interior of the wall 1401, the external fixation 1200 is pushed toward the exterior of the vessel wall 1401 by the fixation shaft 1404.

Figure 111H:
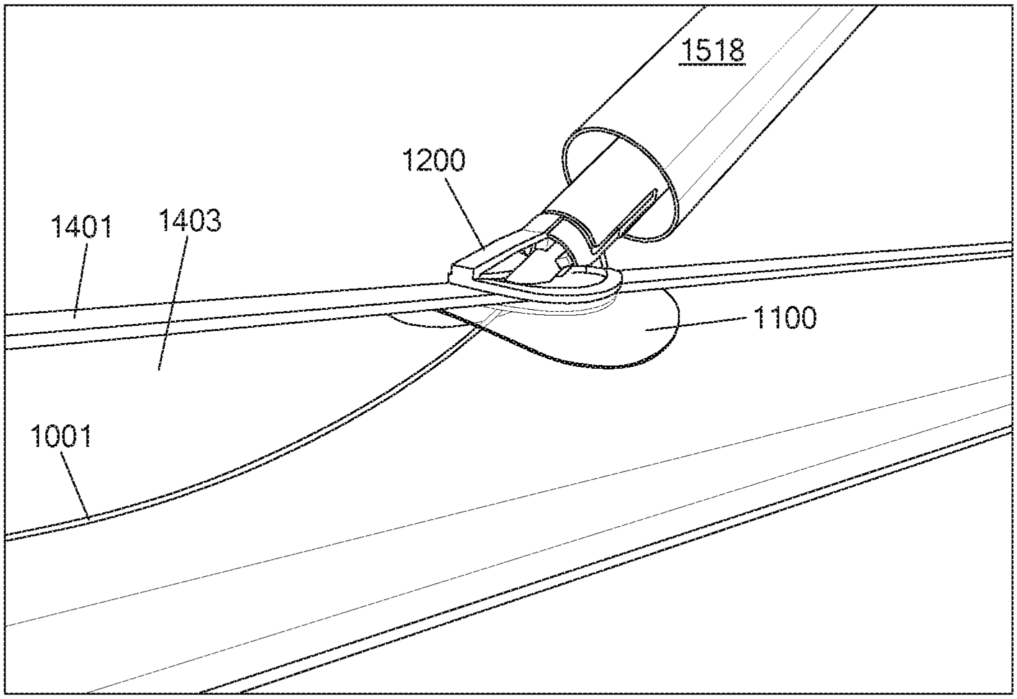

In FIG. 111H, the external fixation 1200 is in contact with the exterior of the vessel wall 1401. The external fixation 1200 engages with the scaffold 1050.

Figure 111I:
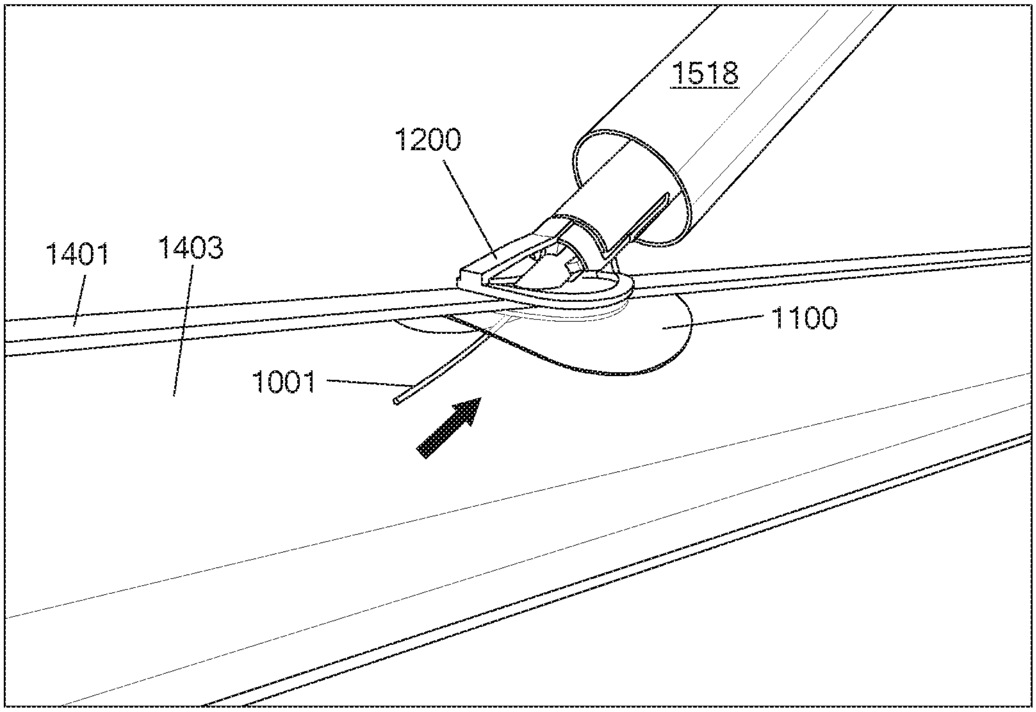
Figure 111J:
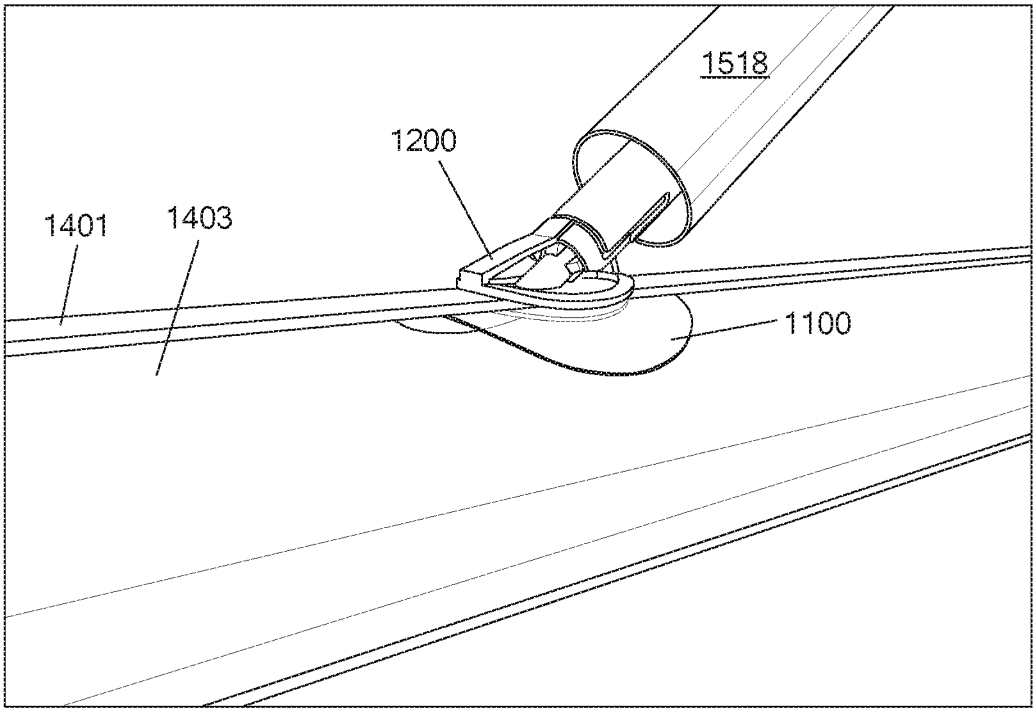

In FIG. 111I, the guidewire 1001 is being retracted. In FIG. 111J the guidewire is fully retracted and no longer visible in the lumen 1403 of the vessel.

Figure 111K:
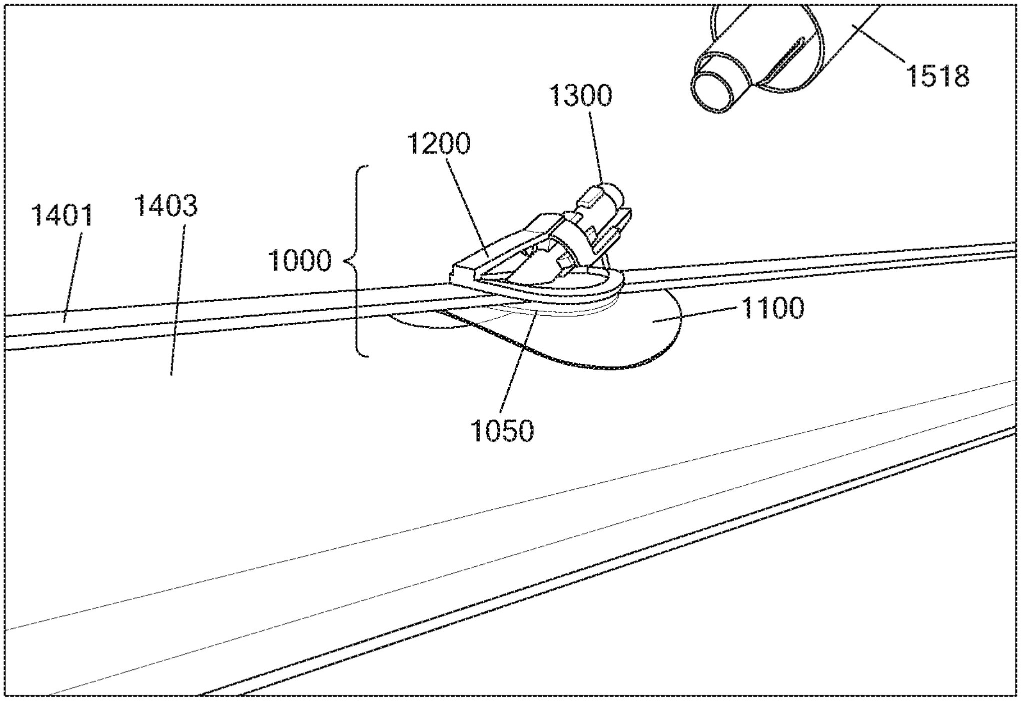

In FIG. 111K, the delivery system is disengaged from closure device 1000, and is moving away.

Figure 111L:
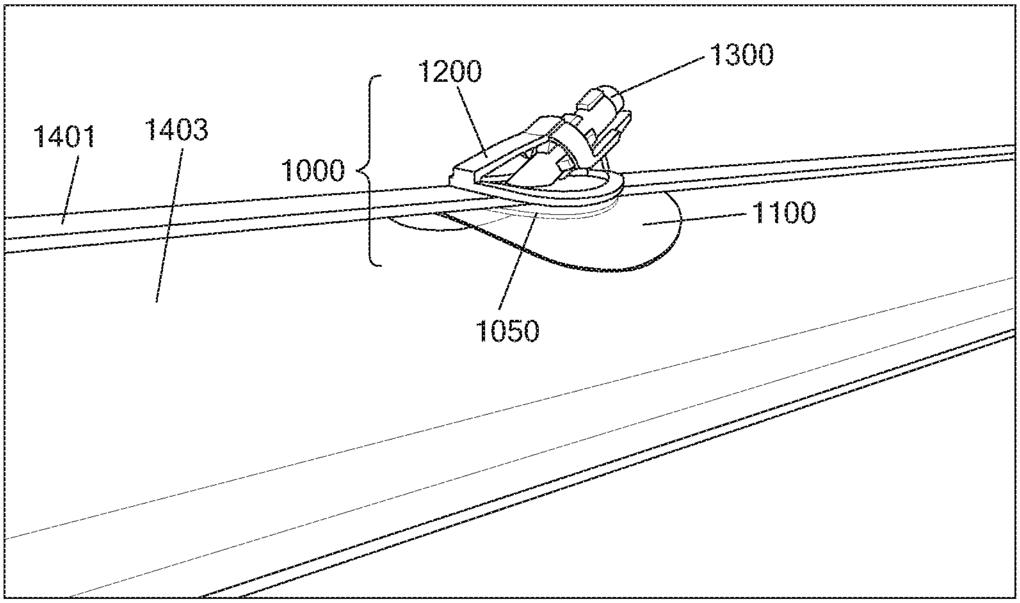

In FIG. 111L, the delivery system is fully removed from the body, and the closure device 1000 remains deployed at the vessel opening site. The patch 1100 is held at the aperture against the vessel wall 1401, sandwiched between the scaffold 1050 and external fixation 1200 which are engaged together, with the closure pin 1300 engaged to close the interior lumen 1064 of the scaffold neck 1060.

Figure 112A:
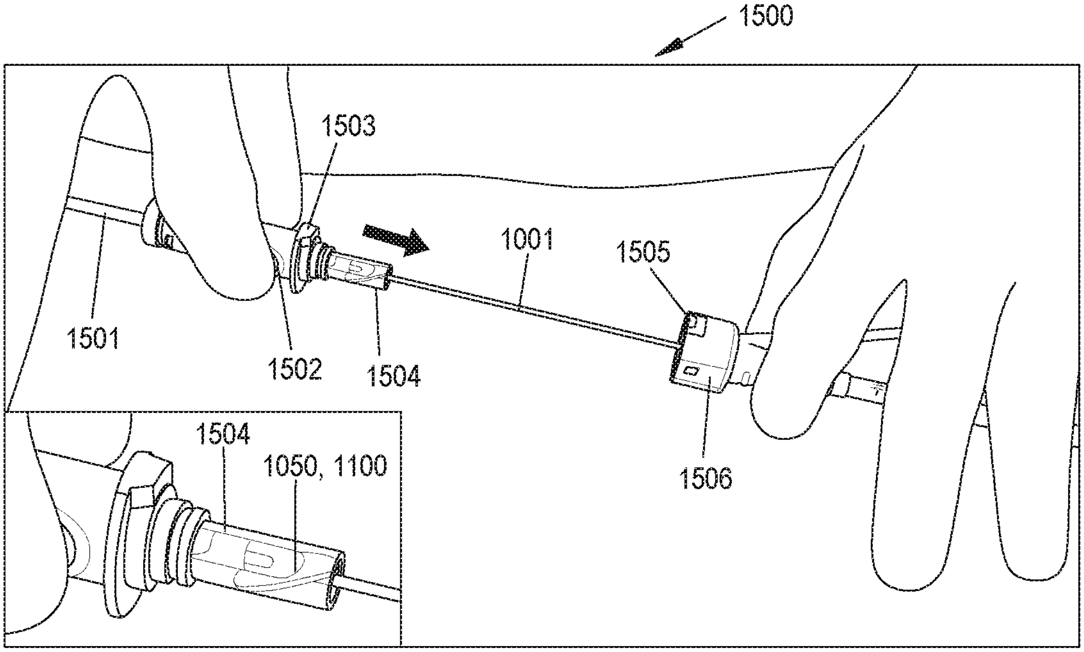
FIG. 112A through 112R are views of a delivery system handle showing sequential steps in deployment of a closure device, according to aspects of the present embodiments.
Figure 112B:
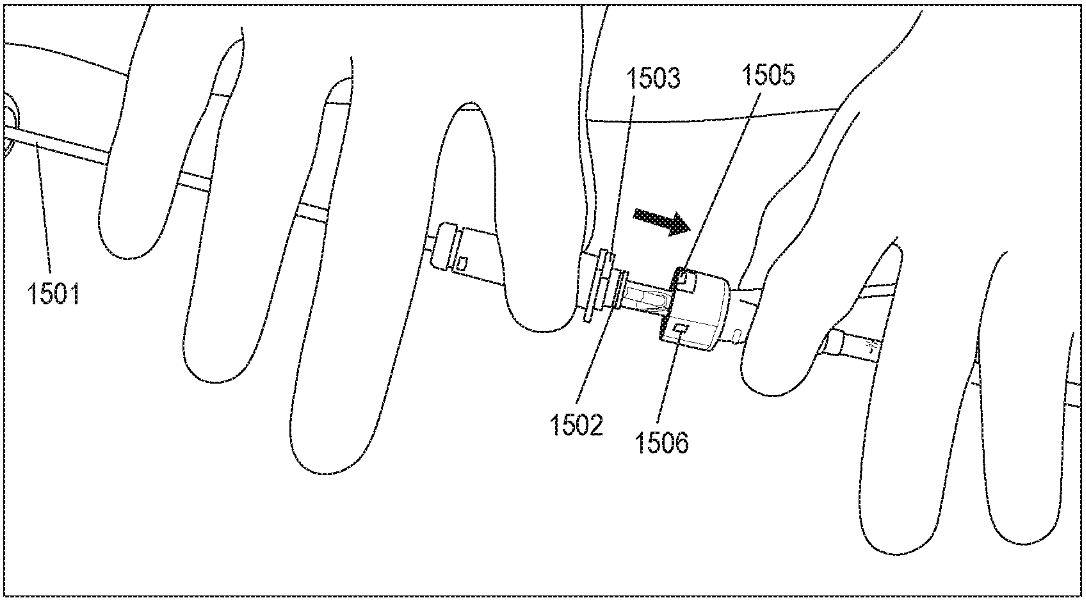
FIG. 112S is a perspective view of the exterior of a delivery system handle, according to aspects of the present embodiments.
FIGS. 112T and 112U are views of a delivery system handle near a handle front cap, according to aspects of the present embodiments.
Figure 112C:
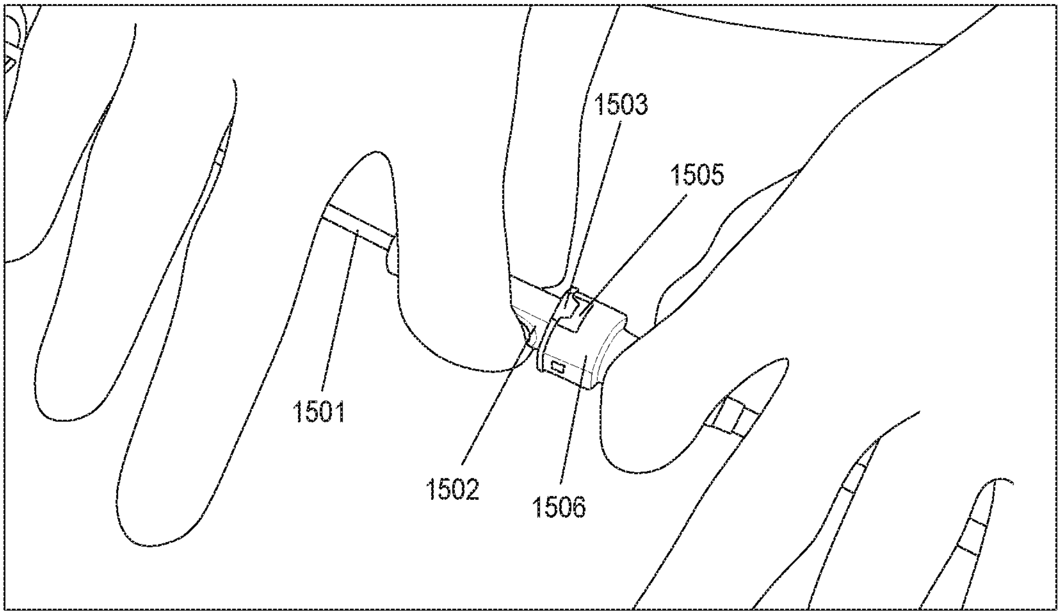
Figure 112D:
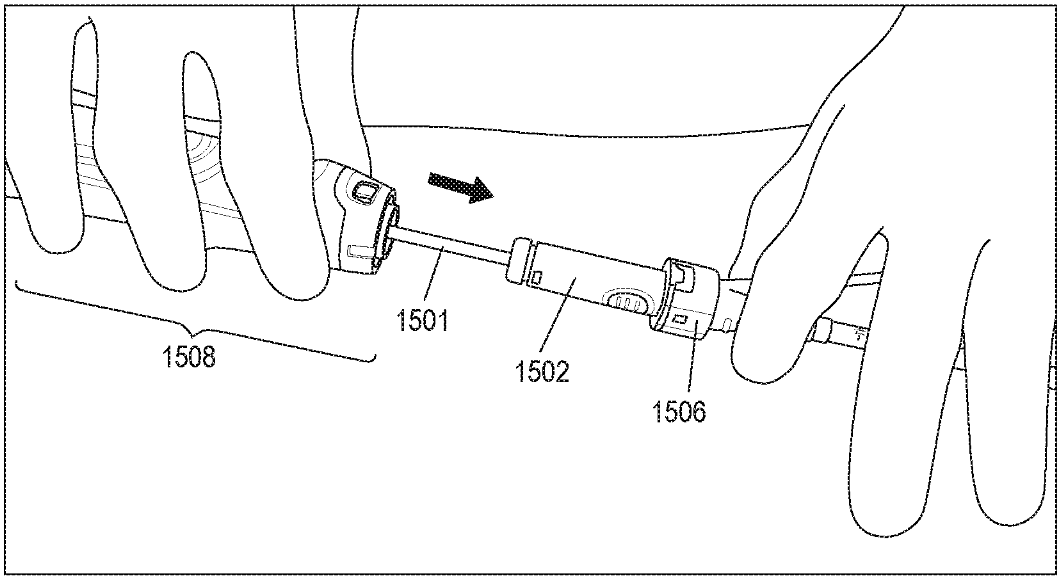
Figure 112E:
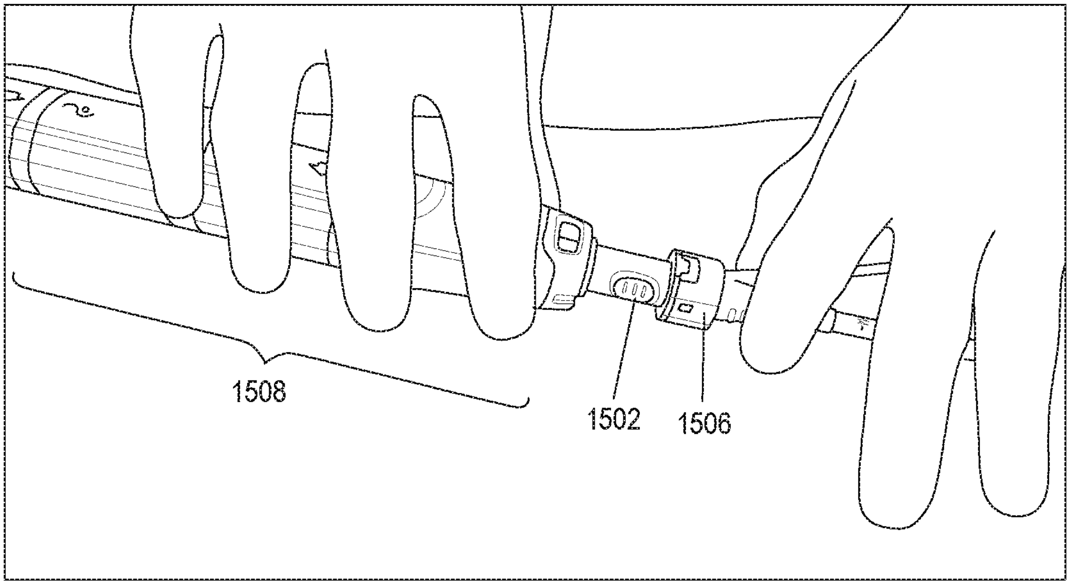
Figure 112F:
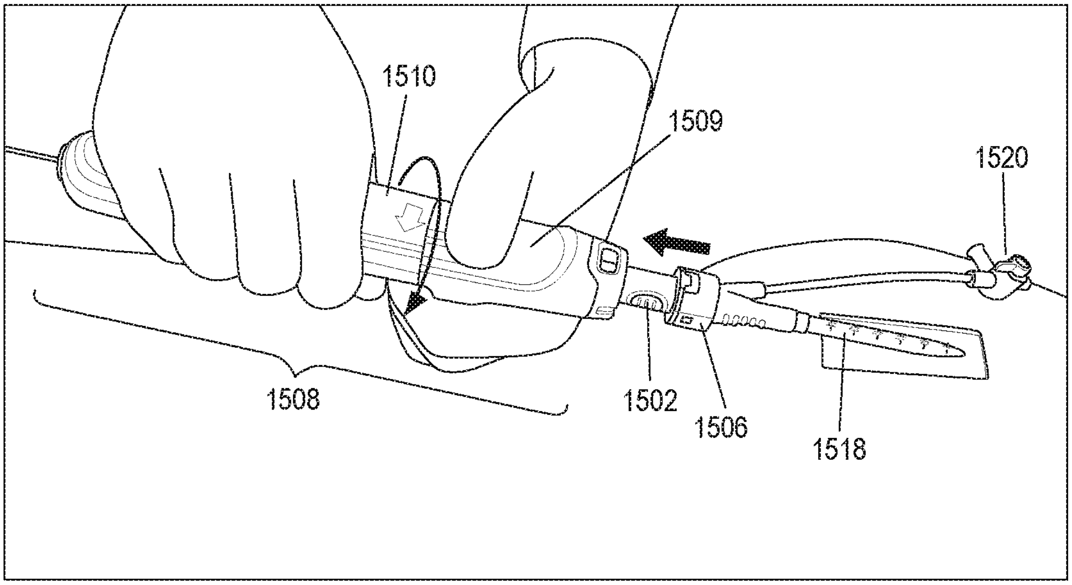
Figure 112G:
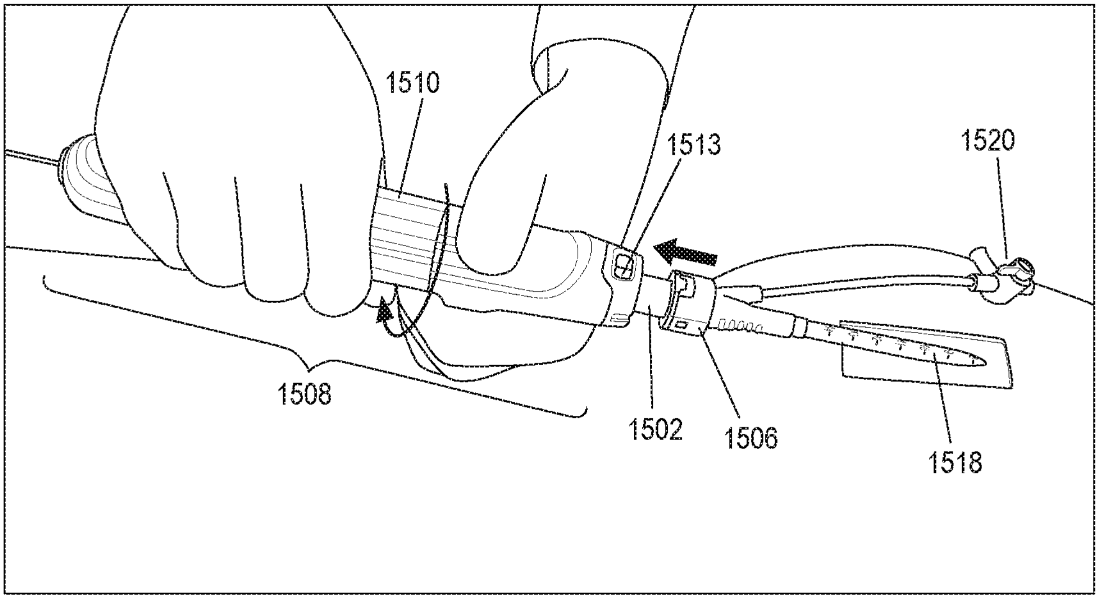
Figure 112H:
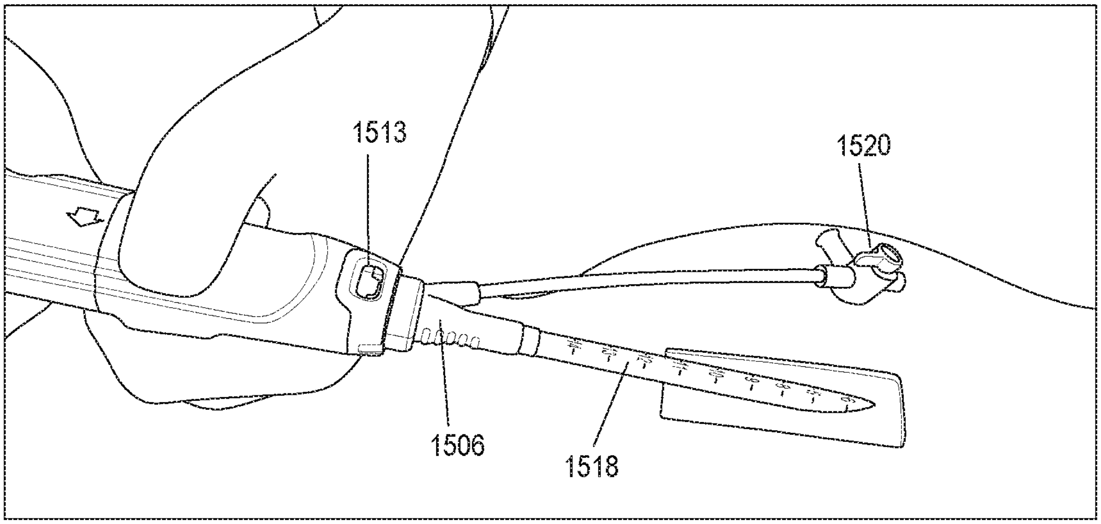
Figure 112I:
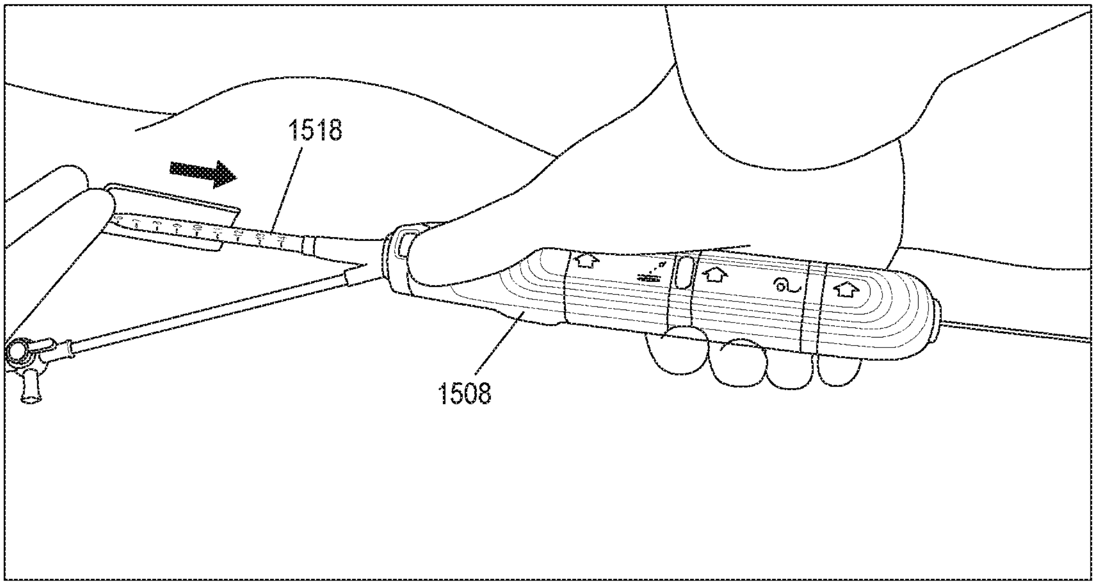
Figure 112J:
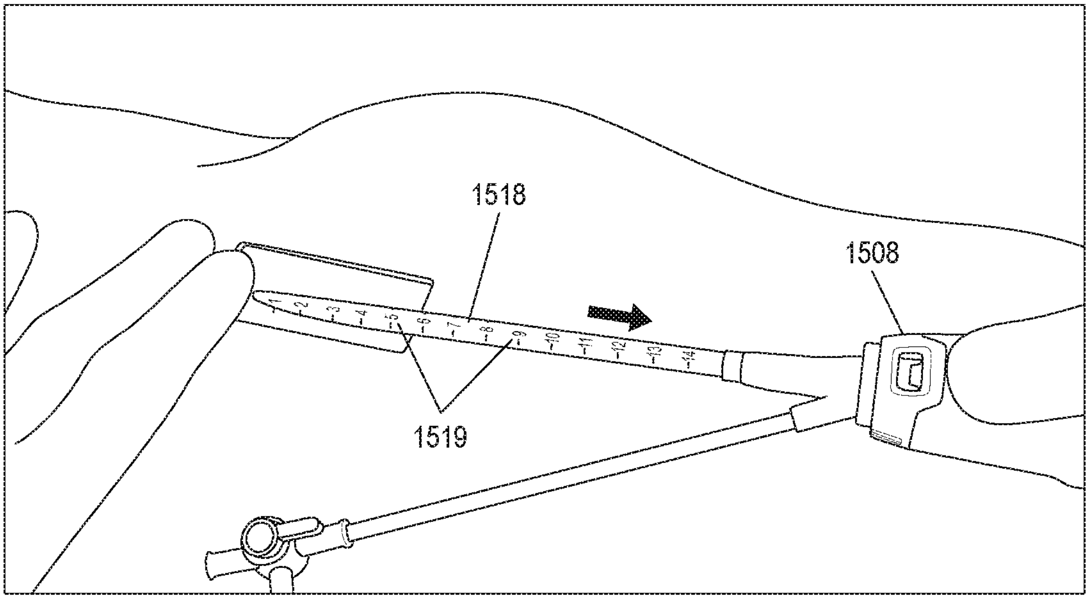
Figure 112K:
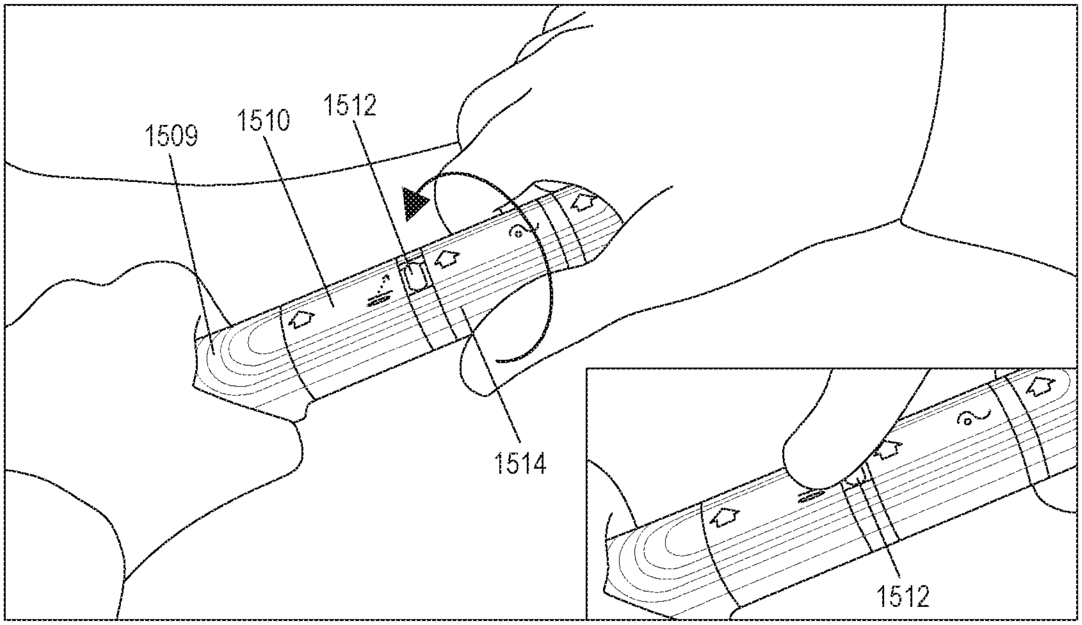
Figure 112L:
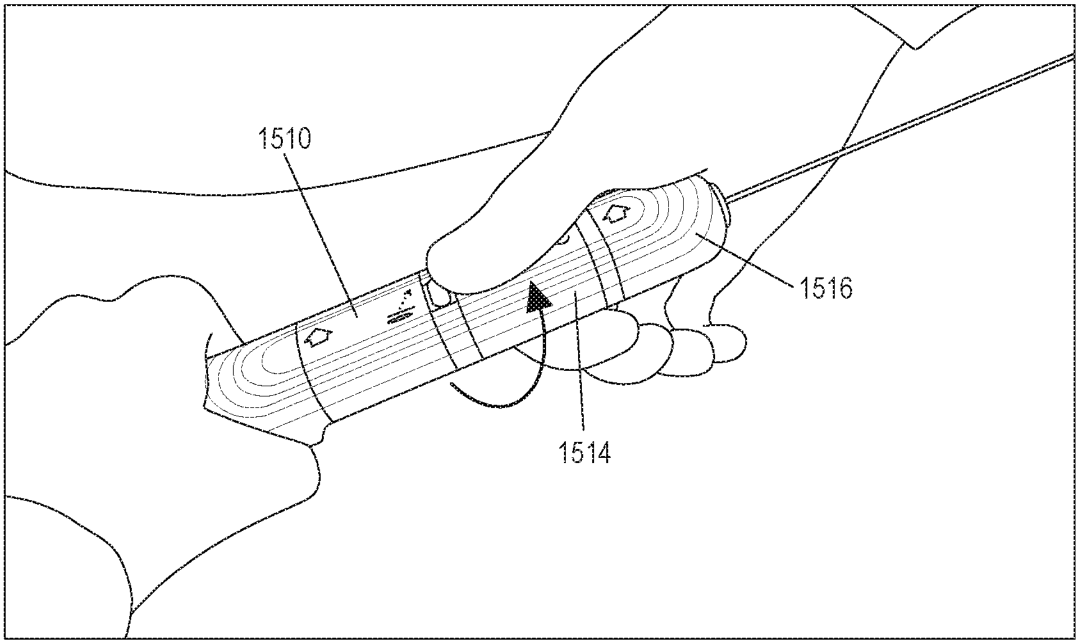
Figure 112M:
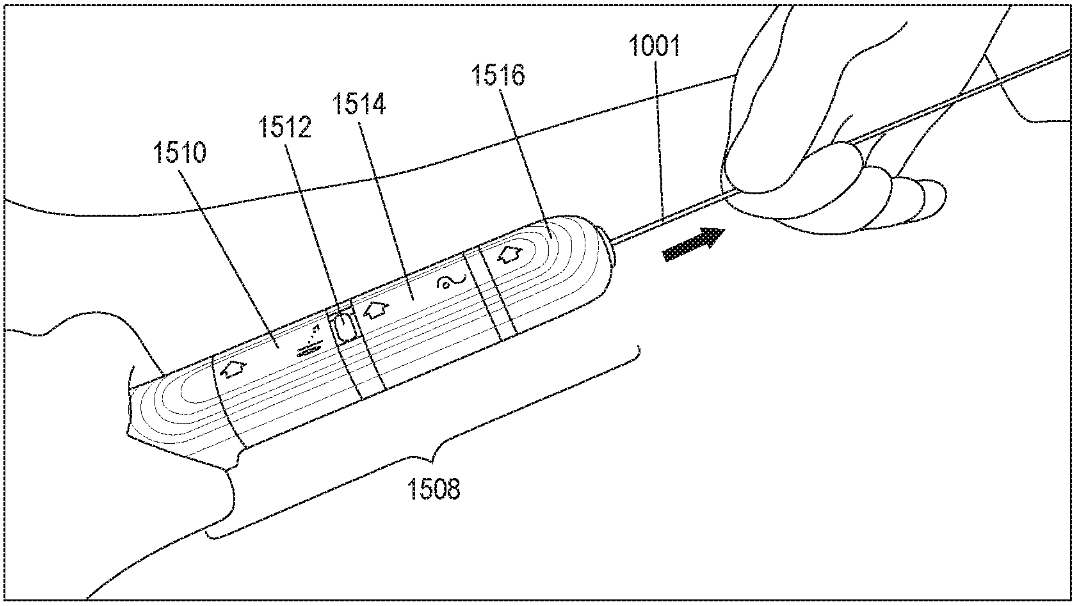
Figure 112N:
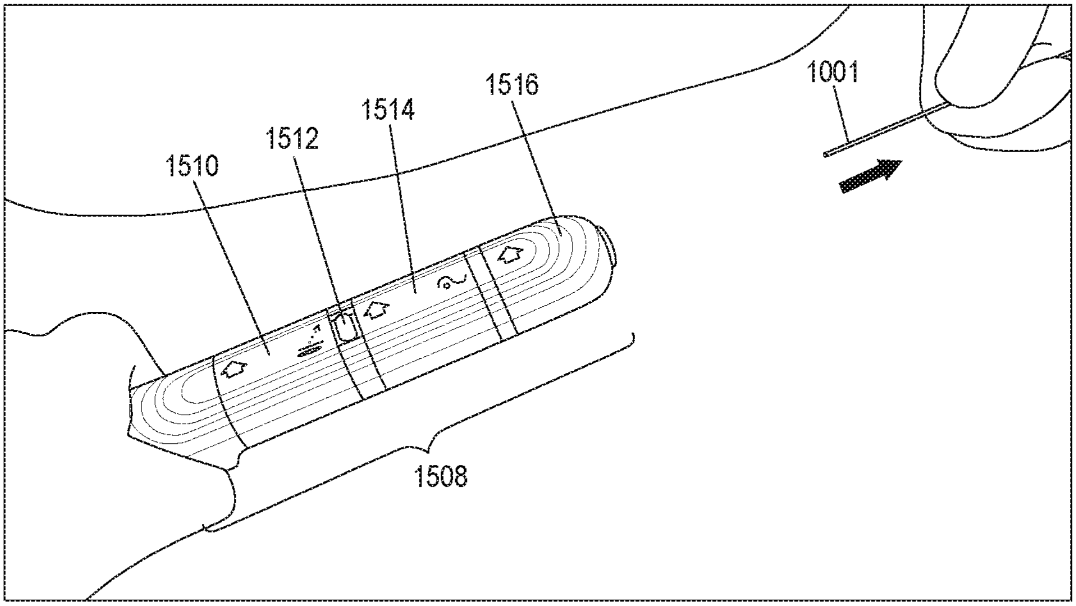
Figure 112O:
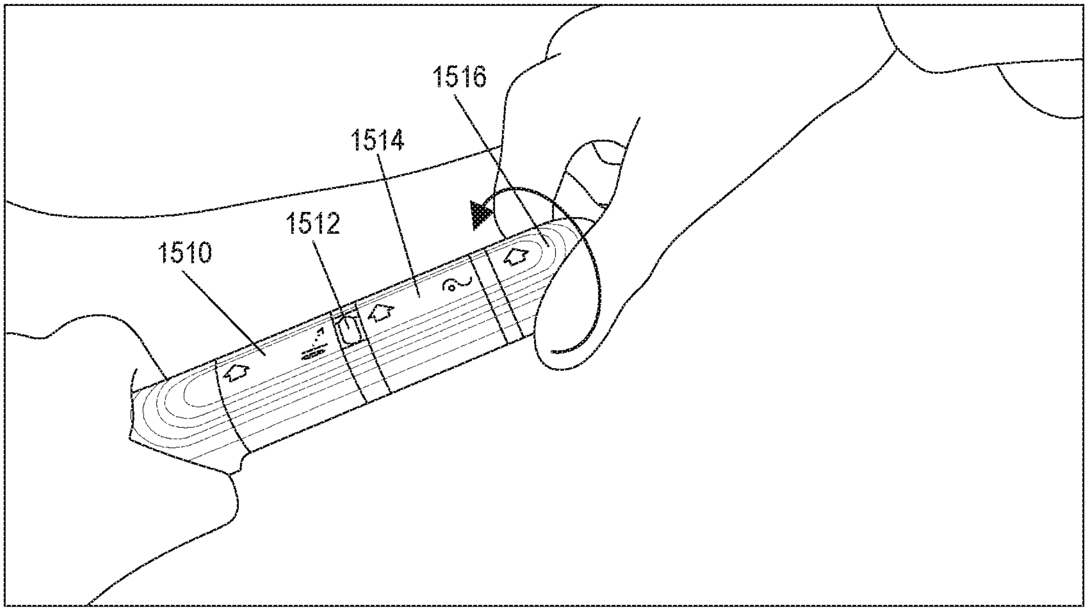
Figure 112P:
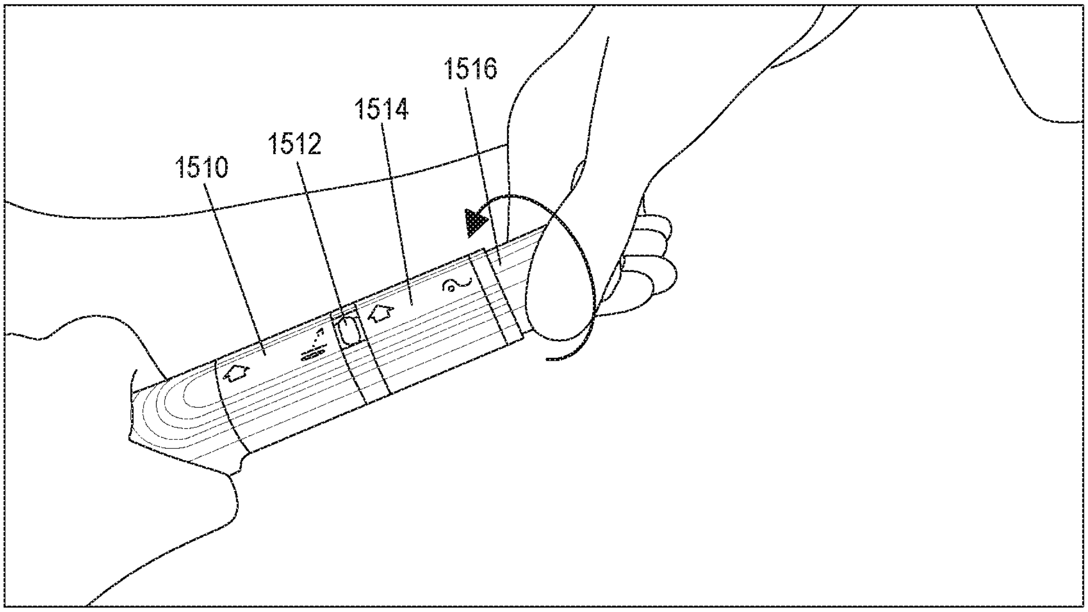
Figure 112Q:
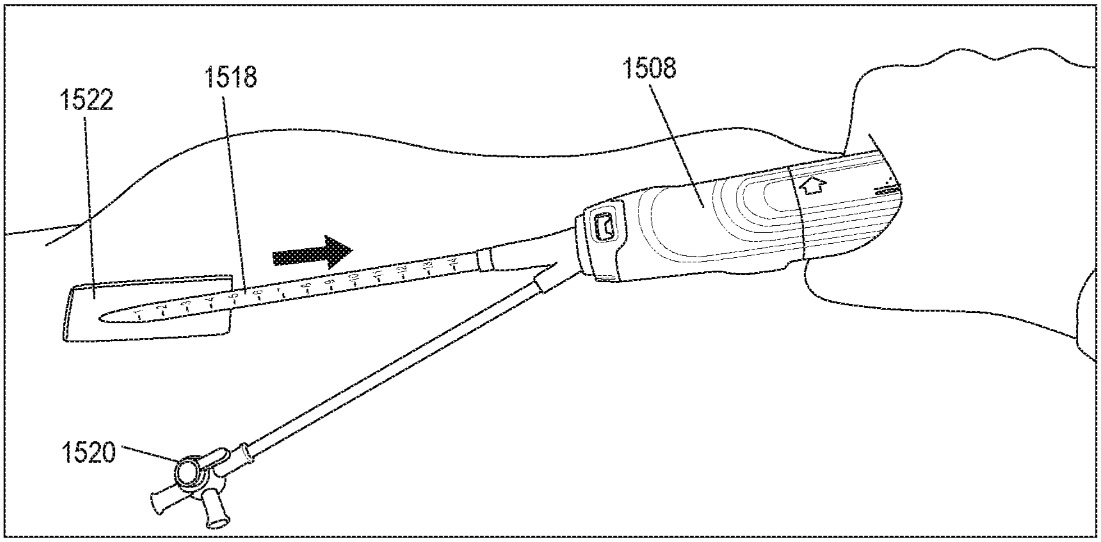
Figure 112R:
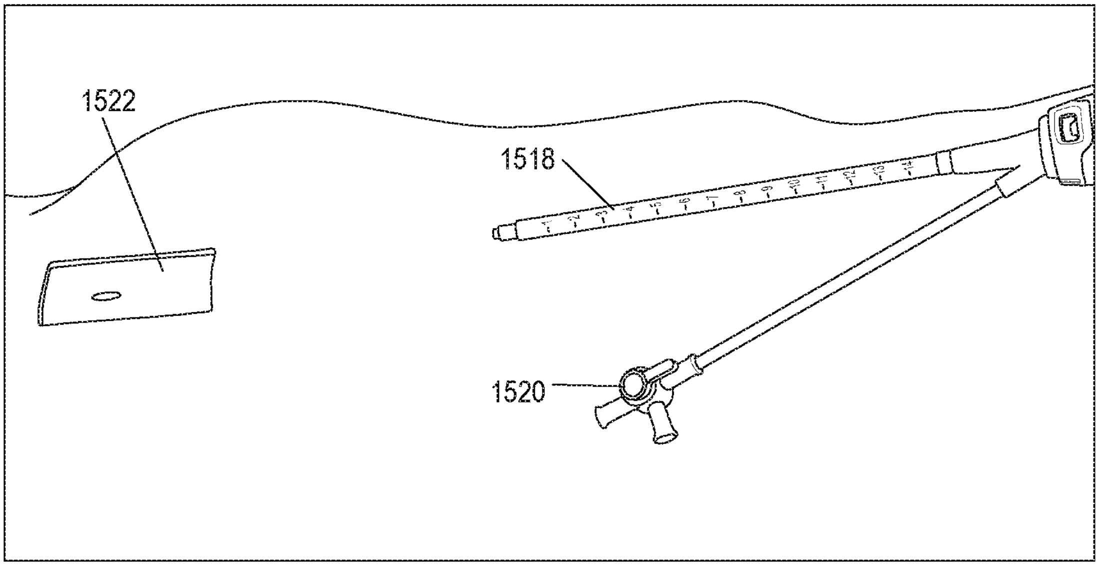

FIG. 112A through 112R illustrate views of a delivery system 1500, which includes a delivery system handle 1508, showing sequential steps in deployment of a closure device 1000, according to aspects of the present embodiments, including a scaffold 1050, a patch 1100, an external fixation 1200, and a closure pin 1300. The delivery system 1500 also includes a loading cannula 1502 and receiving funnel 1506 that is connected to an introducer sheath 1518.

Figure 112S:
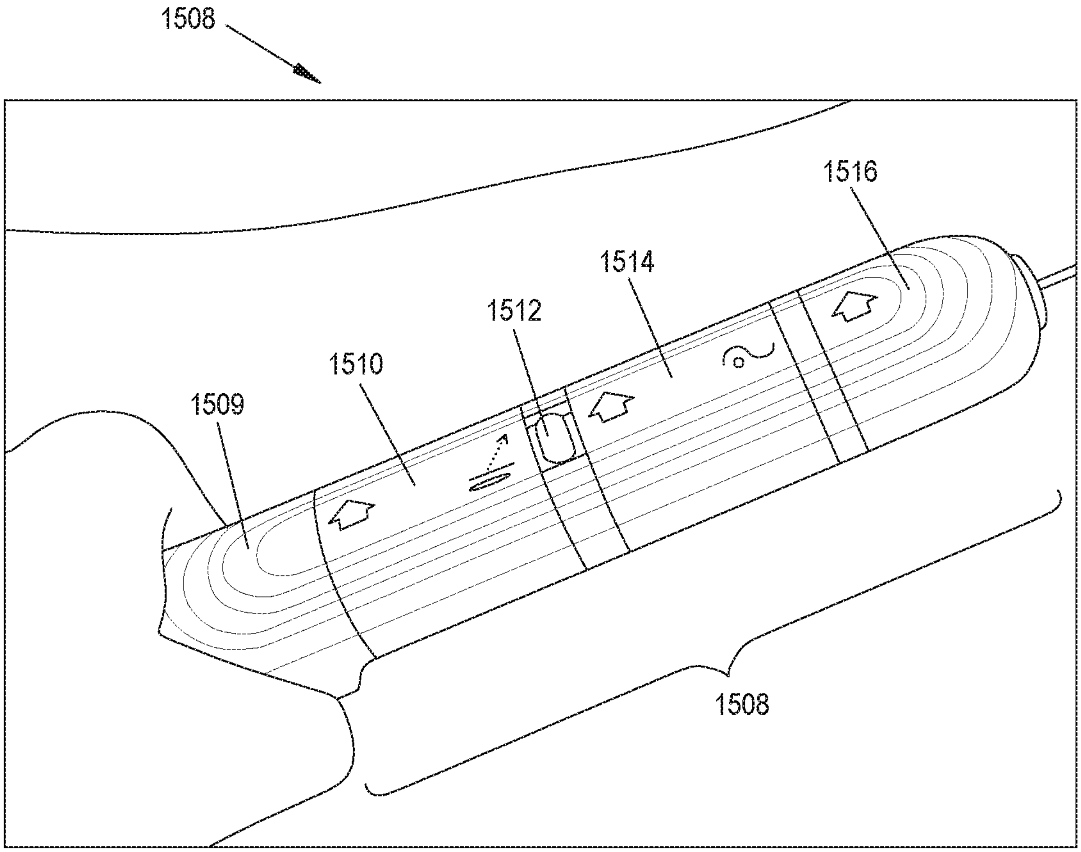
Figure 112T:
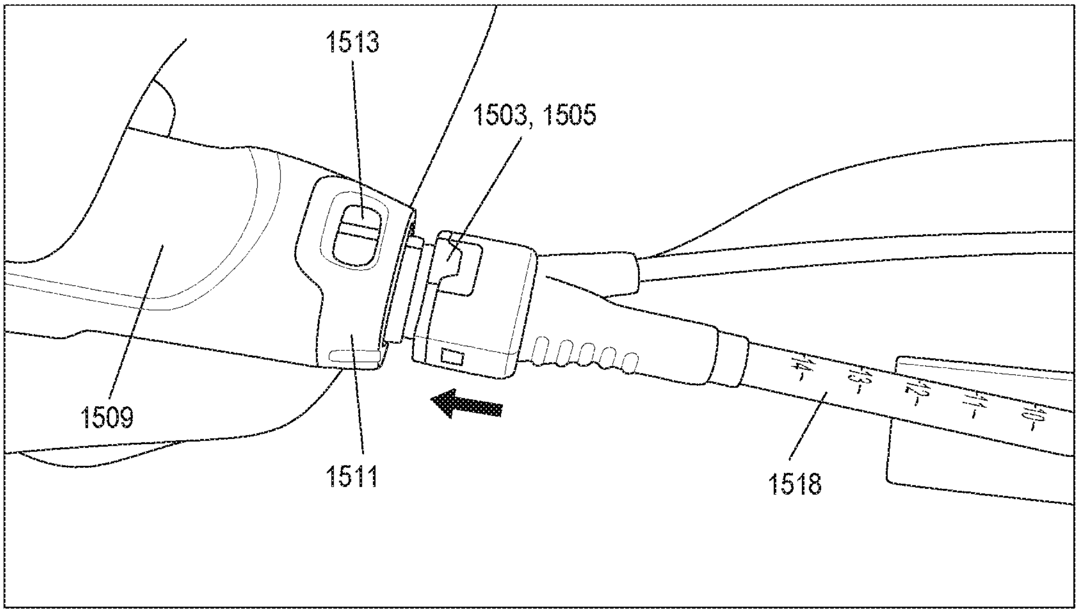
Figure 112U:
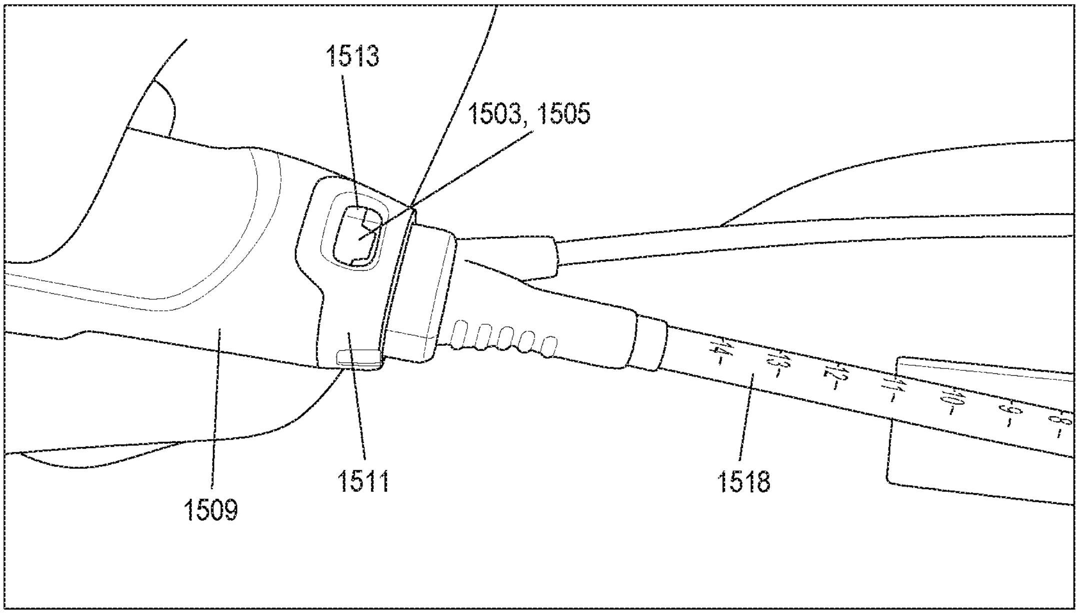

FIG. 112S illustrates a perspective view of the exterior of a delivery system handle 1508, according to aspects of the present embodiments. The handle 1508 may include a handle body 1509, a sheath cam 1510, a cam lock 1512 which may be in the form of a button, a fixation cam 1514, and a release cam 1516. Other features of the handle 1508 are illustrated in FIG. 112T and FIG. 112U, which include a front cap 1511 which includes a window 1513. The operation of the handle 1508 and window 1513 are described in further detail below.

In FIG. 112A, the introducer shaft 1518 is already inserted into a surgical opening in a subject near an aperture in a body vessel that is to be closed. The introducer shaft 1518 terminates in the receiving funnel 1506, which has a colored notch 1505 at its opening. The guidewire 1001 is inserted through the receiving funnel 1506 and the introducer shaft 1518. The loading cannula 1502 is loaded with the closure device 1000 parts (i.e., the scaffold 1050, the patch 1100, the external fixation 1200, and the closure pin 1300), and has a small colored tab 1503 at its distal edge. In the inset image, the cannula tube 1504 of the loading cannula 1502 contains the scaffold 1050 and patch 1100 visible in their stowed configurations. The external fixation 1200 and closure pin 1300 are not visible in this view. An operator or user or surgeon moves the loading cannula 1502 along the guidewire toward the receiving funnel 1506.

In FIG. 112B, the loading cannula 1502 is approaching the receiving funnel 1506.

In FIG. 112C, the loading cannula 1502 engages with the receiving funnel 1506, with the colored tab 1503 on the loading cannula 1502 inserting into the colored notch 1505 on the receiving funnel 1506. The engagement of the colored tab 1503 with the colored notch 1505 indicate to the user that the loading cannula 1502 and the receiving funnel 1506 are correctly connected together.

In FIG. 112D, a delivery system handle 1508 is inserted along a length of tube 1501, and the handle 1508 is pushed toward the loading cannula 1502 and receiving funnel 1506.

In FIG. 112E, the handle 1508 is fully inserted into position and engaged with the loading cannula 1502.

In FIG. 112F, a user rotates the sheath cam 1510 with one hand while holding the handle body 1509 with the other hand. This action causes the introducer sheath 1518 to retract proximally out of the surgical opening in the patient.

In FIG. 112G, as the user continues to rotate the sheath cam 1510, the introducer sheath 1518 continues to retract and the loading cannula 1502 moves into the handle 1508 as indicated by the arrow.

In FIG. 112H, the sheath is fully retracted, corresponding to a full 360° rotation of the sheath cam 1510. The window 1513 is an opening through which the user may see that the colored tab 1503 from the loading cannula 1502 and the colored notch 1505 from the receiving funnel 1506 (see also FIG. 112C) are visible within the window, which occurs when the sheath withdrawal step is complete. The front cap 1511, window 1513, and retraction of the colored tab 1503 and colored notch 1505 are also shown in FIG. 112T and FIG. 112U, which correspond to enlarged views of these steps in the deployment process.

In FIG. 112I, the user pulls on the handle 1508 toward the proximal direction to retract the delivery system. The portion of the sheath 1518 that is visible outside the body of the patient increases.

In FIG. 112J, the delivery system retraction is complete, corresponding to the configuration illustrated in FIG. 111F where the top surface of the patch 1100 and scaffold 1050 are in contact with the interior of the vessel wall 1401.

In FIG. 112K, in the inset image, the user presses the cam lock 1512 button. The cam lock 1512 prevents accidental rotation of the fixation cam 1514, and must be depressed by the user (i.e., by pressing the cam lock 1512 button), in order for the fixation cam 1514 to be rotated. In the main image of FIG. 112K, the user then rotates the fixation cam 1514 with one hand while grasping the handle body 1509 with the other hand. The rotation of the fixation cam 1514 pushes the external fixation 1200 toward the distal direction. This step corresponds to the scenario illustrated in FIG. 111G, as described above, where the external fixation 1200 is moving out of the sheath and toward the wall 1401 of the vessel.

In FIG. 112L, the user continues rotating the fixation cam 1514 until a full 360° is completed, at which point the external fixation 1200 is fully pushed out, corresponding to the scenario illustrated in FIG. 111H. The external fixation 1200 is at this point locked onto the neck 1060 of the scaffold 1050 on the retaining pads 1058 on the neck 1060.

In FIG. 112M, the user pulls the guidewire 1001 using one hand, moving the guidewire 1001 away from the handle 1508 and toward the distal direction, while grasping the handle 1508 with the other hand. In FIG. 112N, the guidewire 1001 is fully removed from the delivery system. The removal of the guidewire 1001 can also be seen in FIG. 111I, where the guidewire 1001 is in the process of being removed when viewed in the interior 1403 of the vessel. In FIG. 111J, the guidewire 1001 is no longer visible in the interior 1403 of the vessel.

In FIG. 112O, the user rotates the release cam 1516 with one hand while grasping the handle body 1509 with the other hand. In FIG. 112P, the user continues rotating the release cam 1516 until a full 180° turn is completed. This motion causes the closure pin 1300 to be pushed into location in the opening 1064 of the neck 1060 of the scaffold 1050 so that the opening 1064 is blocked after removal of the guidewire 1001. This motion also causes rotation of the bayonet hub 1542 (shown in FIG. 113) which results in releasing the closure device 1000 from the delivery system. This scenario also corresponds to the scenario illustrated in FIG. 111K, where the closure pin 1300 is pushed into the scaffold 1050 and the device 1000 is released from the shafts of the delivery system.

In FIG. 112Q, the user grasps the handle 1508 and pulls it away from the patient toward the proximal direction to remove the entire delivery system from the patient. The sheath 1518 is seen being pulled out of the aperture 1522. This scenario also corresponds to the scenario illustrated in FIG. 111K and FIG. 111L where the sheath 1518 is detached from the closure device 1000 and is moving away.

In FIG. 112R, the delivery system is completely removed from the body of the patient, and an aperture 1522 in the skin of the patient is visible.

Referring again to FIG. 112S, there may be several symbols and markings imprinted on the exterior surface of the handle 1508 to guide the user. On the sheath cam 1510, there is printed an arrow with a number 1 and the indication 360°. This indication instructs the user that the $1^{st}$ step is to rotate the sheath cam 1510 along the arrow direction, which is equivalent to a clockwise turn when viewing the handle from the proximal end toward the distal end, and that the rotation is for 360°. The sheath cam 1510 also has an indication with a number 2 and a dashed arrow and a symbolic representation of a heath and aperture. This indication instructs the user that the $2^{nd}$ step is to retract the delivery device which results in pulling out of the introducer sheath 1518.

Referring still to FIG. 112S, the cam lock 1512 button has an indication of a number 3, which instructs the user that the $3^{rd}$ step is to press the cam lock 1512 button. The fixation cam 1514 has an indication of an arrow with a number 4 and 360°. This indication instructs the user that the $4^{th}$ step is to rotate the fixation cam 1514 in the direction of the arrow, which is equivalent to a clockwise turn when viewing the handle from the proximal end toward the distal end, and that the rotation is for 360°. The fixation cam also has an indication of a number 5 along with a wavy line, instructing the user that the $5^{th}$ step is to remove the guidewire 1001. Finally, the release cam 1516 has an arrow indicated with a number 6 and a number 180°. This indication instructs the user that the $6^{th}$ step is to rotate the release cam 1516 in the direction of the arrow, which is equivalent to a clockwise turn when viewing the handle from the proximal end toward the distal end, and that the rotation is for 180°.

Figure 113:
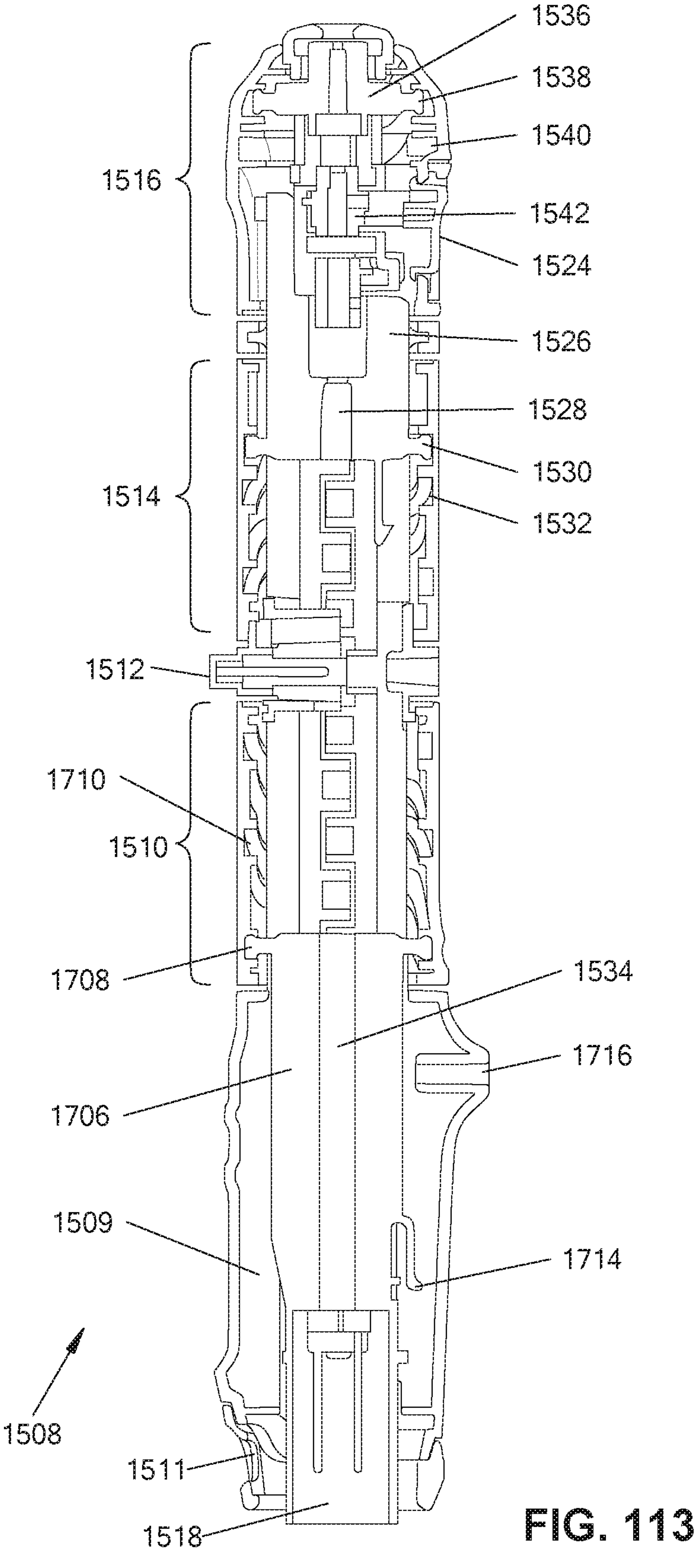
FIG. 113 is a cut-away side view of the interior of a delivery system handle, according to aspects of the present embodiments.

FIG. 113 illustrates a cut-away side view of the interior of a delivery system handle 1508, according to aspects of the present embodiments.

Figure 114:
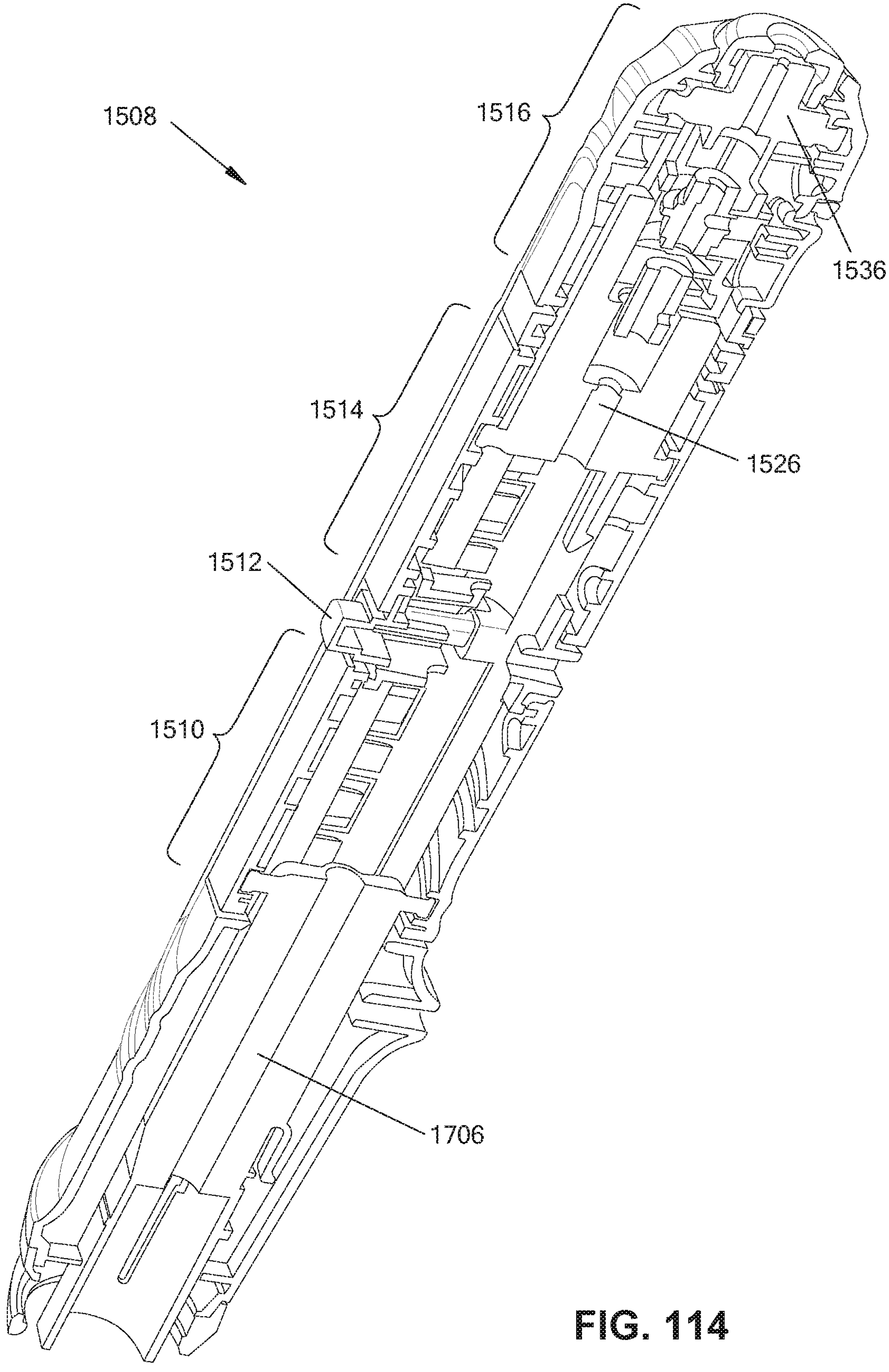
FIG. 114 is a cut-away perspective view of the interior of a delivery system handle, according to aspects of the present embodiments.

FIG. 114 illustrates a cut-away perspective view of the interior of a delivery system handle 1508, according to aspects of the present embodiments.

Figure 115:
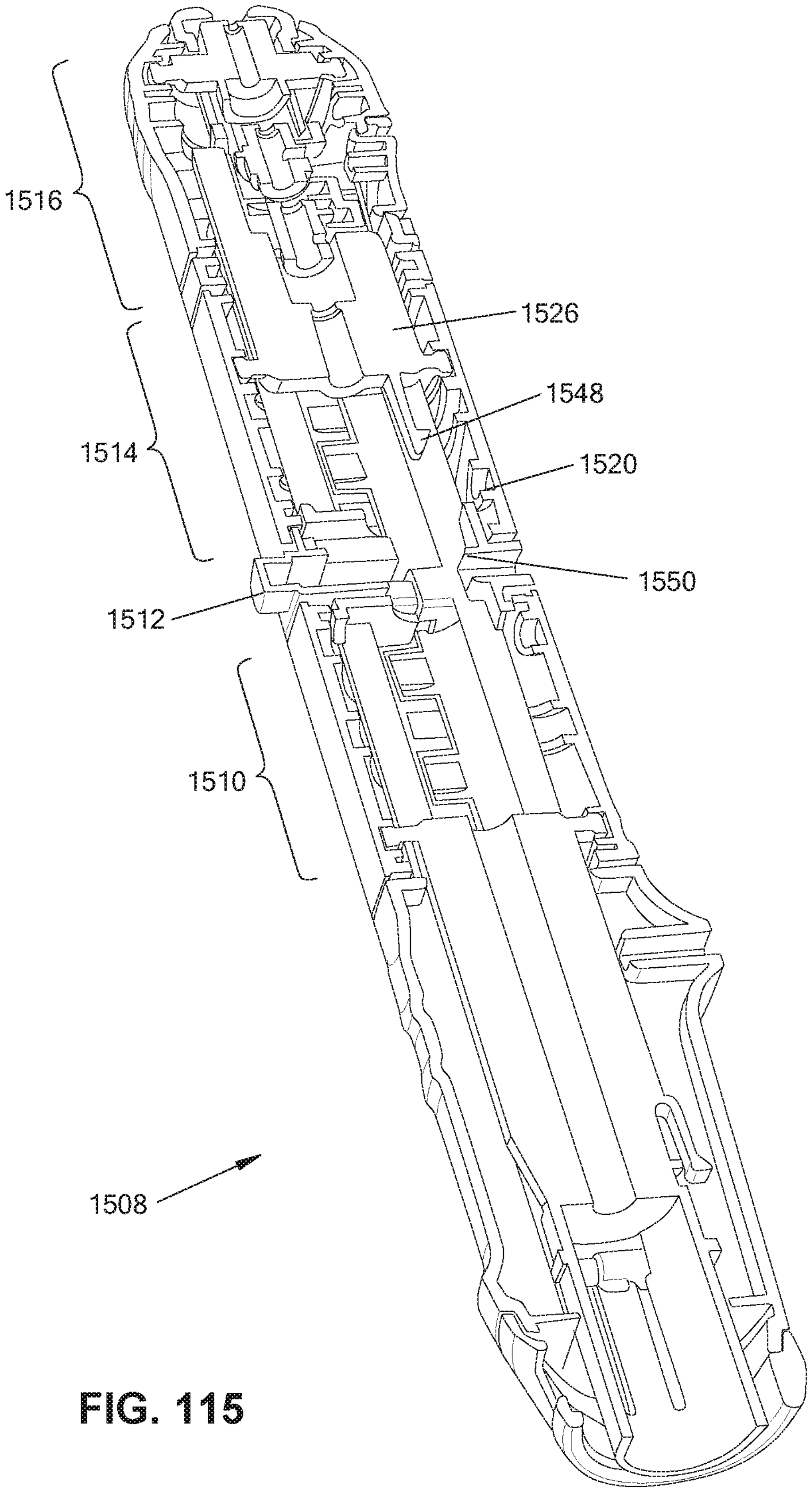

FIG. 115 illustrates another cut-away perspective view of the interior of a delivery system handle 1508, according to aspects of the present embodiments.

Figure 116:
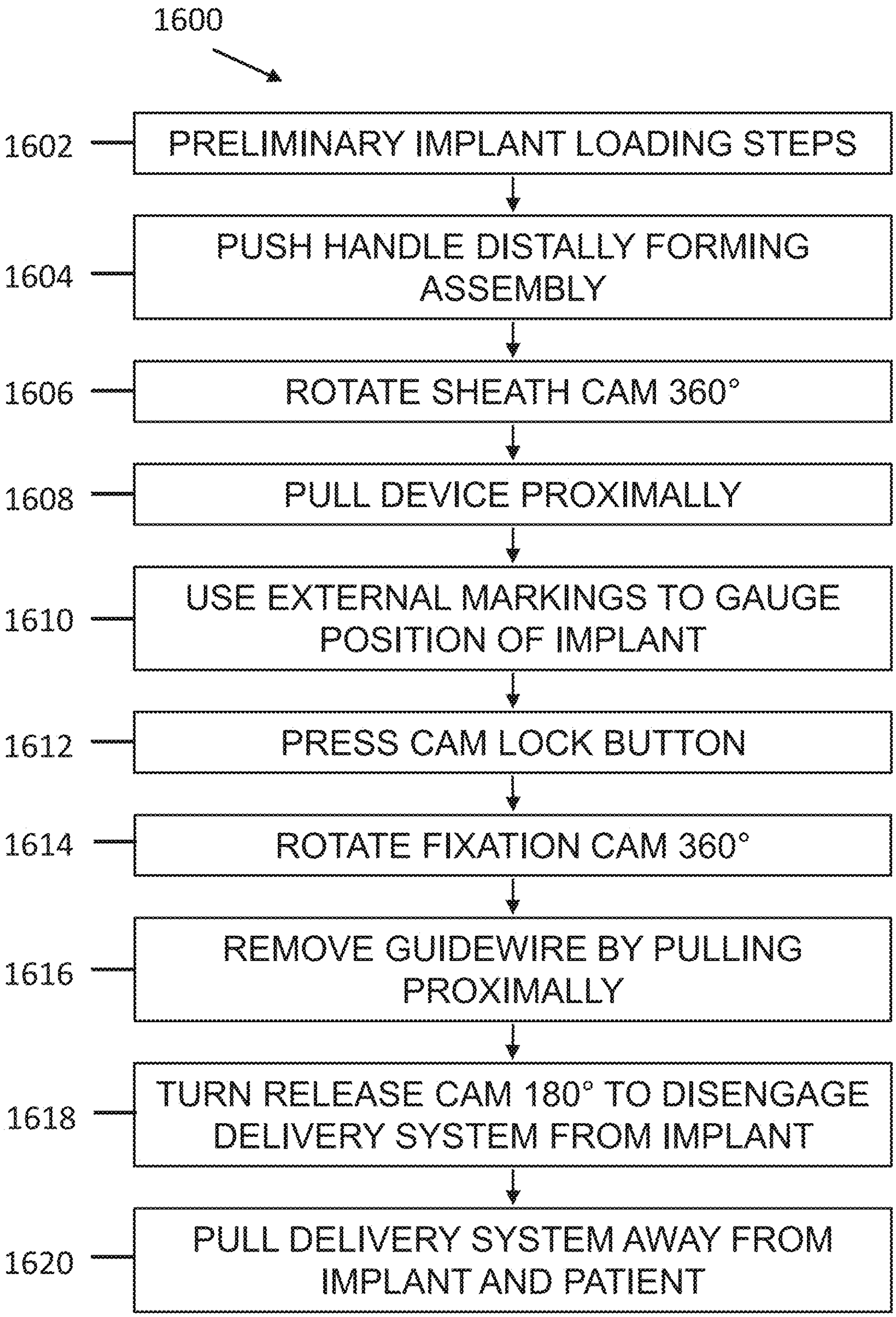

FIG. 116 illustrates a method 1600 of sealing an aperture, according to aspects of the present embodiments. At step 1602, the method 1600 may include preliminary implant loading steps. For example, preliminary implant loading steps may include one or more of the following steps: i) disposing the guidewire 1001 into and through the delivery system, the implant, the cannula assembly, and handle, ii) disposing the guidewire 1001 into the wound and/or vessel aperture, iii) disposing the delivery system subcutaneously and into the vessel through the aperture using the guidewire 1001 and using an introducer sheath 1518, and/or iv) loading the implant or closure device 1000 into the cannula assembly, as shown in FIGS. 112A-112C. The handle 1508 may include a handle body 1509 that includes two halves which include a handle body top and a handle body bottom configured to be snapped together, and further held together by a front cap 1511 at the distal end of the handle 1508. At step 1604, the method 1600 may include pushing the handle 1508 distally, forming the handle assembly. By pushing the handle distally, the cannula assembly is pushed distally through the delivery shaft 1408 and into the vessel. At step 1606, the method 1600 may include rotating a sheath cam 1510 (shown in FIG. 113) through an angle of 360 degrees. The sheath cam 1510 may include two semi-cylindrical halves (i.e., a sheath cam top and a sheath cam bottom that are configured to be snapped or held together to form a main chassis of the handle 1508). Step 1606 is illustrated in FIGS. 112F-112H. The direction of rotation of the sheath cam 1510 is clockwise when viewed from the proximal side looking distally. The rotation of the sheath cam 1510 causes retraction (i.e., movement toward the proximal direction) of the introducer sheath 1518, thereby allowing the patch 1100 and scaffold 1050 to expand within the vessel, as shown in FIGS. 111A-111D. The external fixation 1200, however, remains within the delivery shaft as shown in FIGS. 111B-111D.

Referring to FIGS. 111-116, the handle 1508 may include a sheath carriage 2706 coupled to (or monolithic with) the proximal end of the introducer shaft 1518. The sheath carriage 2706 may include a one or more external male threads 2708 which interface with internal female threads 2710 disposed within an interior circumference of the sheath cam 1510. As the sheath cam 1510 is rotated, the one or more external male threads 2708 interface with the internal threads 2710 of the sheath cam 1510, thereby causing the introducer shaft 1518 to retract proximally. Once the introducer shaft 1518 has fully retracted to a proximal-most location, a first prong 2714 interfaces with a first catch 2716, thereby preventing further rotation of the sheath cam 1510. At step 1608, the method 1600 may include pulling the entire device proximally such that the patch 1100 (with the help of the scaffold 1050) is secured against an inner wall of the vessel 1401, the inner wall surrounding and/or adjacent to the aperture in the vessel 1401. At step 1610, markings 1519 (shown in FIG. 112J) on the exterior of the introducer sheath 1518 may be used to gauge or assess how far the device should be pulled proximally in order to secure the patch 1100 against the inner wall of the vessel 1401. For example, when one of the numerical markings (for example, the line next to the "1" mark) on the introducer sheath 1518 line up with the edge of the skin (for example, at the aperture in the skin), then the device is correctly positioned in order for the patch to be secured against the inner wall of the vessel 1401, as shown in FIGS. 111E-111G (internal illustrations), as well as in FIGS. 112I and 112J (external views). Steps 1608 (pulling the device proximally) and 1610 (using the external markings to assess correct positioning of the patch) may therefore be performed simultaneously, in some embodiments. During steps 1608 and 1610, while the device is being pulled proximally, the external fixation 1200 is pulled back through the aperture of the vessel 1401 such that it is repositioned outside the vessel, as shown in FIGS. 111E-111G, which are in contrast to the position of FIGS. 111C and 111D, in which the external fixation 1200 is positioned within the vessel.

Referring still to FIGS. 112-116, at step 1612, the method may include pressing a release button (i.e., cam lock 1512) shown in FIG. 113. The cam lock 1512 (shown in FIGS. 113 and 112K) may be used to allow a fixation cam 1514 to be rotated. The fixation cam 1514 may be located proximally of the cam lock 1512 (which itself may be disposed proximally from the sheath cam 1510). Whereas the sheath cam 1510 may be used to retract the introducer shaft 1518 in a proximal direction, the fixation cam 1514 may be used to push the fixation cam 1404 distally via an internal rod, linkage, or coupling (not shown) disposed through a large bore 1534 disposed through the center of the sheath cam 1510 (and configured to translate distally therethrough). At step 1614, the method 1600 may include rotating the fixation cam 1514 through an angle of 360 degrees (i.e., in a clockwise direction when viewed from the proximal side looking distally) to push the fixation shaft 1404 (and external fixation 1200 coupled thereto) in a distal direction. The fixation cam 1514 is twistedly coupled to a fixation hub 1526 via one or more male threads 1530 on the fixation hub 1526 and internal female threads 1532 disposed within an interior circumference of the fixation cam. Twisting the fixation cam 1514 advances the external fixation 1200, which is coupled thereto by a second internal rod, linkage, or coupling (not shown) disposed within a medium bore 1528 at the center of the fixation hub 1526. By pushing the external fixation 1200 distally, fixation 1200 may slide along the neck 1060 of the scaffold 1050 in order to interface with corresponding features on the scaffold neck 1060 such that the implant is secured at the aperture (i.e., wound and/or puncture) location, as described herein, and as shown in FIG. 111H. When the implant is securely implanted in its final location, the patch 1100 and scaffold 1050 are pressed up against the inner wall of the vessel, the scaffold neck 1060 extends through the vessel aperture, and the external fixation 1200 presses against the external wall of the vessel 1401 and securely holds the closure device in place, as shown in FIG. 111H. As illustrated in FIG. 115, once the fixation hub 1526 has translated all the way forward (i.e., to a distal-most position) within the handle 1508, a second prong engages 1548 with a second catch 1550 (both shown in FIG. 115), thereby prohibiting further rotation of the fixation cam 1514.

Still referring to FIGS. 112-116, at step 1616, the method 1600 may include removing the guidewire 1001 from the vessel 1401, aperture, and device, by pulling the guidewire 1001 proximally from the proximal end of the handle 1508, as shown in FIGS. 111H-111J, as well as in FIGS. 112M and 112N. At step 1618, the method 1600 may include rotating the release cam 1516 through an angle of 180 degrees to disengage the delivery system from the implant. When the release cam 1516 is rotated 180 degrees clockwise, a push hub 1536 is distally advanced via a third set of male threads 1538 and female threads 1540, thereby pushing the pin 1300 into the interior lumen 1064 of the scaffold neck 1060, in order to minimize leakage through the scaffold neck 1060 once the guidewire 1001 is removed. In connection with the step 1618, a bayonet hub 1542 is rotated (i.e., via rotation of the release cam 1516), thereby causing the release of the implant from the distal tip of the delivery system. At step 1620, the method may include pulling the delivery system away from the implant and patient.

As shown in FIG. 114, each of the sheath carriage 2706, the fixation hub 1526, and the push hub 1536 translate axially (for example, proximally and/or distally) within the handle 1508 when the respective sheath cam 1510, fixation cam 1514, and release cam 1516 are rotated.

FIG. 115 shows another view of the interior of the delivery system handle 1508. The main components as above are also indicated.

Components of Delivery System

FIGS. 117-149 illustrate details of the delivery system assembly 1700, in many cases, the internal details of the delivery system assembly 1700, according to aspects of the present embodiments.

Figure 117:
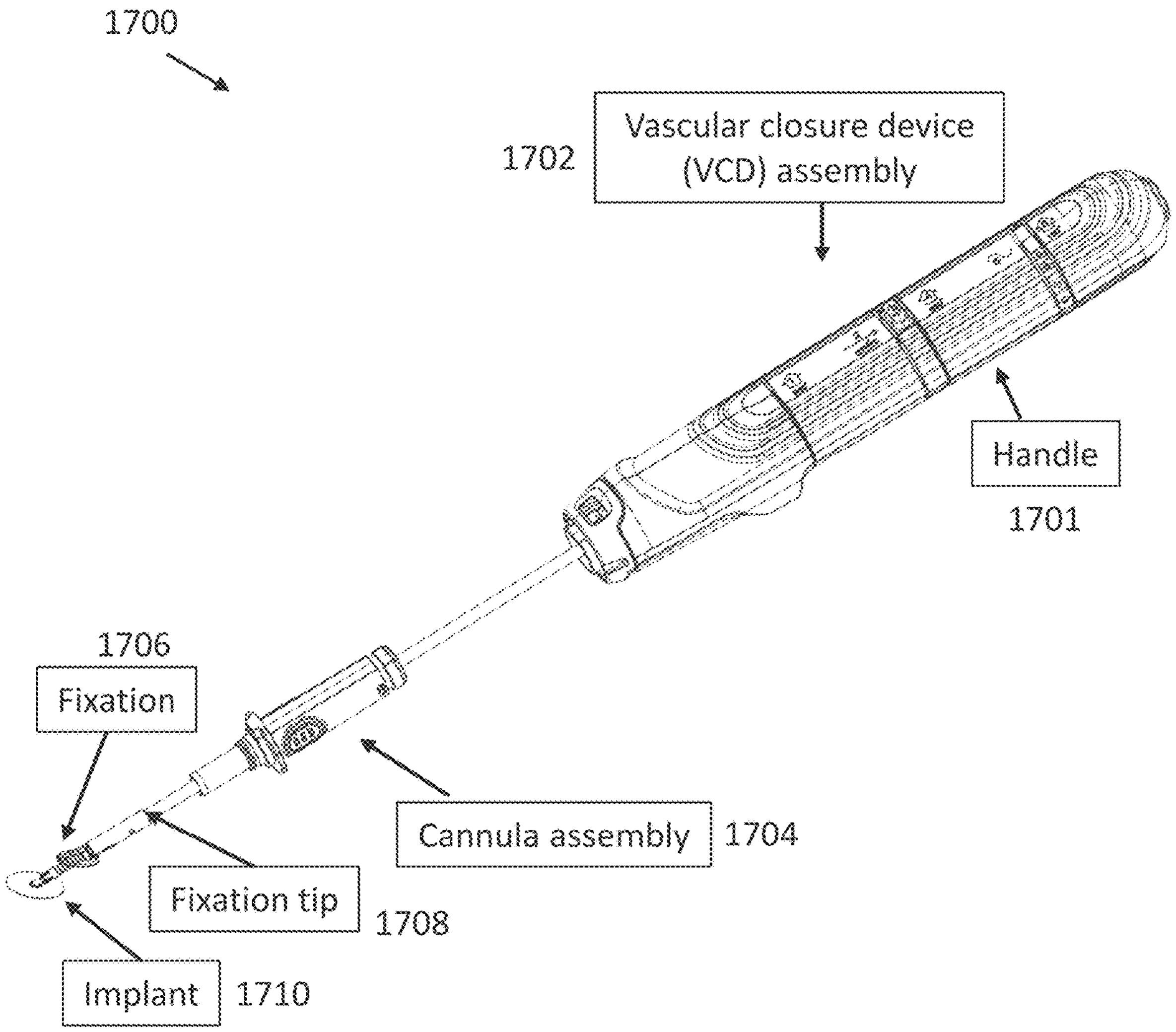

FIG. 117 is a perspective view of a delivery system assembly 1700, according to aspects of the present embodiments. The delivery system assembly 1700 includes a vascular closure device (VCD) assembly 1702 (which may also be called a handle 1702), a cannula assembly 1704, a fixation tip 1708, an external fixation 1706 releasably coupled to a fixation tip 1708, an implant 1702 (which may also be called a vascular closure device or a sealable implant or a closure device assembly) releasably coupled to a bayonet feature 1731 on a delivery shaft 1730 (shown in FIG. 142A) of the VCD assembly 1702. When the delivery system is used to deliver an implant into a patient to close a vessel aperture, the implant 1710 is considered at the distal end of the delivery device and the handle 1702 is at the proximal end of the delivery device. Throughout this description, the distal direction is toward the implant and patient, while the proximal direction is toward the handle and toward the user or operator.

Figure 118:
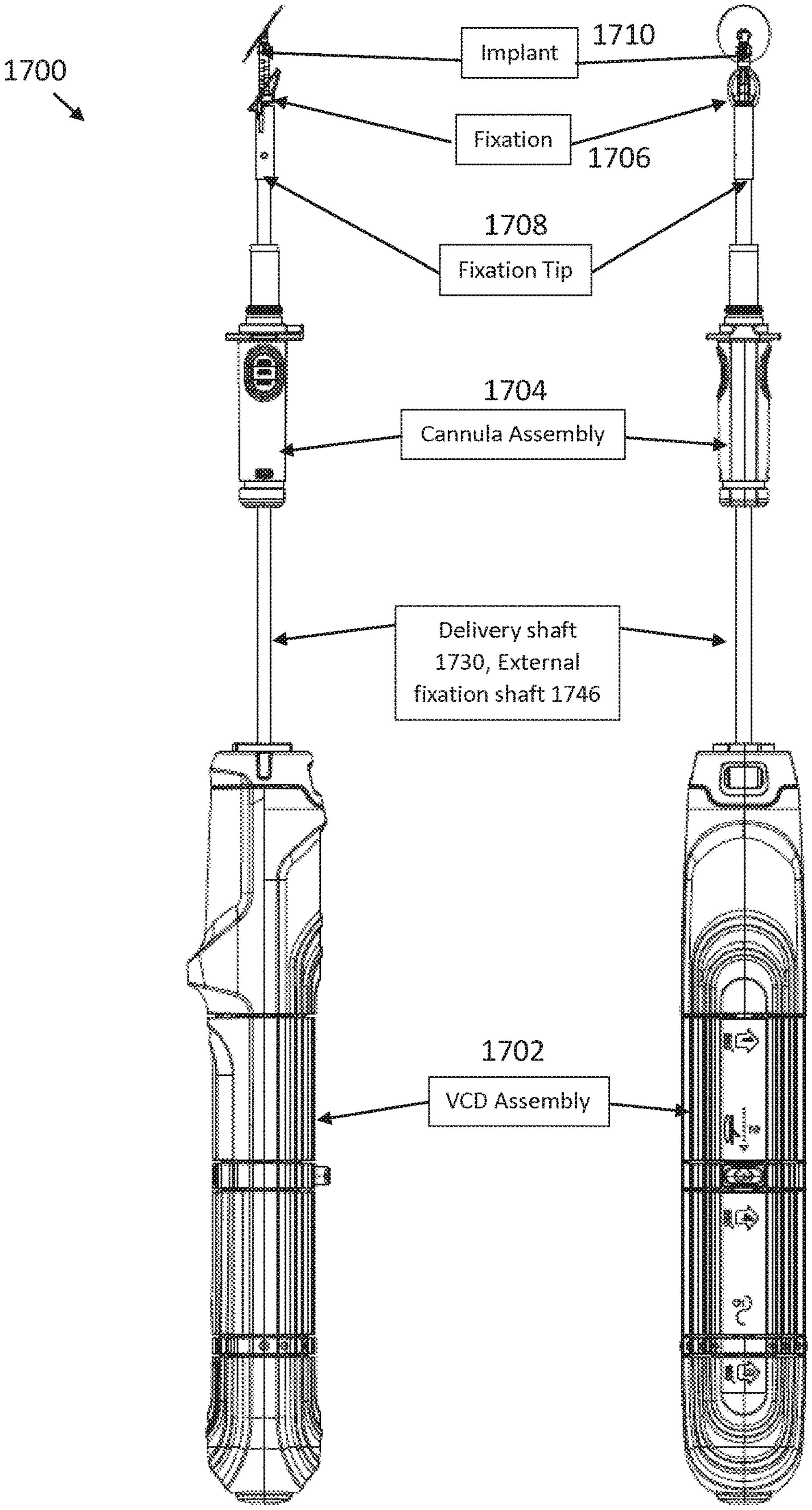

FIG. 118 is a side view (left) and a front view (right) of a delivery system assembly 1700, according to aspects of the present embodiments. In some embodiments, the VCD assembly 1702 includes a delivery shaft 1730 (also called a first shaft) disposed coaxially inside an external fixation shaft 1746 (also called a second shaft), which both pass through a cannula assembly 1704, with the external fixation shaft 1746 attached at its distal end to a fixation tip 1708. In some embodiments, the external fixation 1706 is releasably coupled to the fixation tip 1708. In some embodiments, the implant 1710 is releasably coupled to the delivery shaft 1730 of the VCD assembly.

Components of Handle

Figure 119:
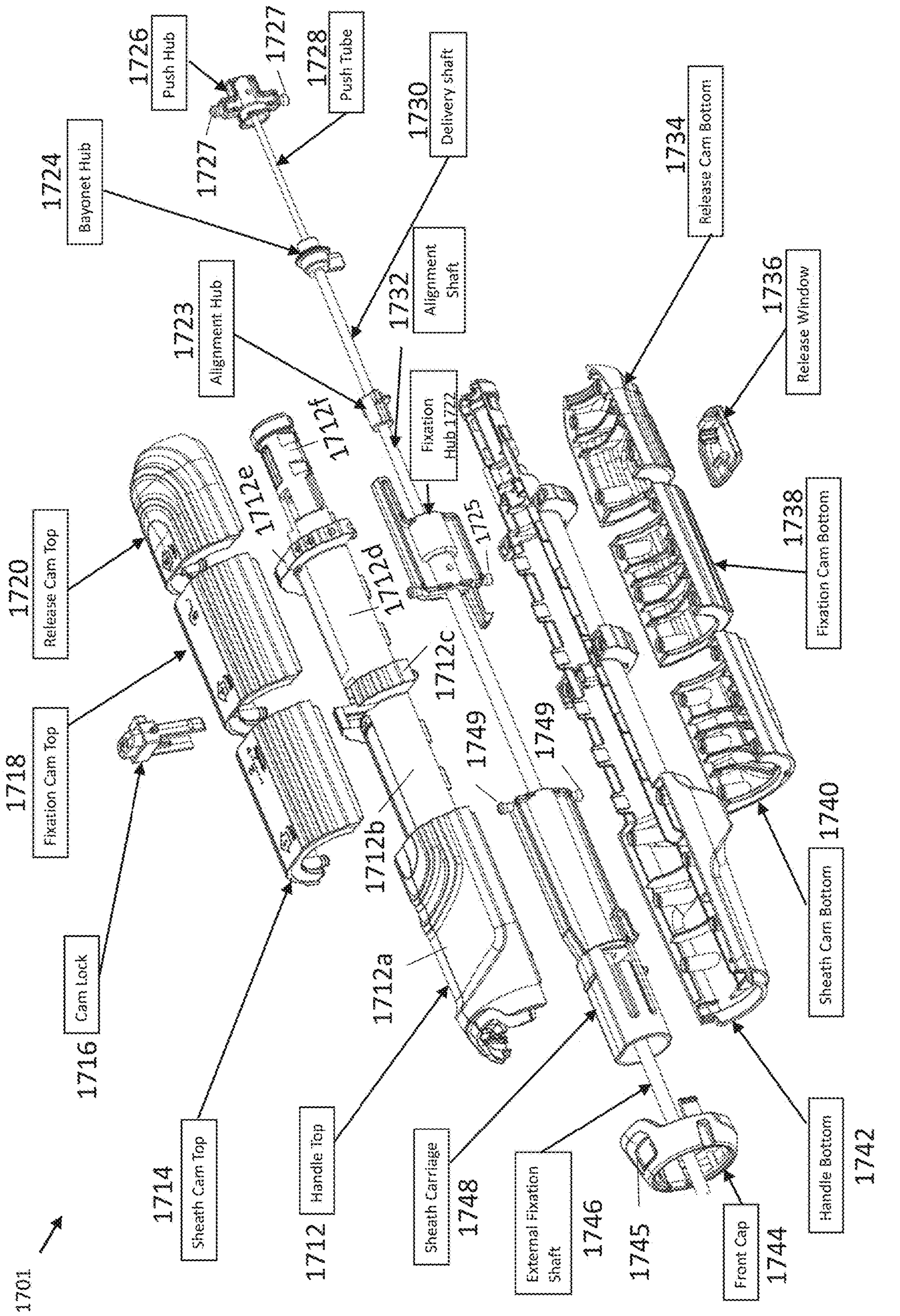

FIG. 119 is an image of exploded parts of a handle 1701 that is part of a vascular closure device (VCD) assembly 1702 that is part of a delivery system assembly 1700, according to aspects of the present embodiments. Beginning at the top left of FIG. 119, the VCD assembly 1702 includes across the top half of the handle from the distal end of the handle (i.e., the left side of image) to the proximal end of the handle (i.e., the right side of the image): a handle top 1712, a sheath cam top 1714, a cam lock 1716, a fixation cam top 1718, and a release cam top 1720. Across the bottom half of the handle from the distal end of the handle to the proximal end of the handle, the VCD assembly 1702 includes: a handle bottom 1742, a sheath cam bottom 1740, a fixation cam bottom 1738, a release window 1736, and a release cam bottom 1734. The sheath cam top 1714 and sheath cam bottom 1740 together form a sheath cam (also called a first cam); the fixation cam top 1718 and fixation cam bottom 1738 together form a fixation cam (also called a second cam); and the release cam top 1720 and release cam bottom 1734 together form a release cam (also called a third cam).

Referring still to FIG. 119, in some embodiments, when the handle 1701 is assembled, the handle bottom 1742 snaps into the handle top 1712 to form a substantially hollow cylinder with three raised portions and three depressed portions. From the distal end toward the proximal end, these portions are: a first raised portion 1712*a* with ridges to improve grip; a first depressed portion 1712*b* to accommodate a sheath cam 1714, 1740 to be assembled outside of and around the first depressed portion 1712*b*, and to include openings to allow a sheath carriage 1748 (also called a first hub) to pass through to reach the sheath cam pieces; a second raised portion 1712*c* to accommodate a cam lock 1716 and to separate the first depressed portion 1712*b* and second depressed portion 1712*d*; a second depressed portion 1712*d* to accommodate a fixation cam 1718, 1738 to be assembled outside of and around the second depressed portion, and to include openings to allow a fixation hub 1722 (also called a second hub) to pass through to reach the fixation cam pieces; a third raised portion 1712*e* separating the second depressed portion 1712*d* and third depressed portion 1712*f*; and a third depressed portion 1712*f* to accommodate a release cam 1720, 1734 to be assembled outside of and around the third depressed portion 1712*f*, and to include openings to allow a bayonet hub 1724 and push hub 1726 (also called a third hub) to protrude to reach the release cam pieces.

Referring still to FIG. 119, in some embodiments, the sheath cam bottom 1740 snaps into the sheath cam top 1714 over the combined handle top 1712 and handle bottom 1742 pieces to form the sheath cam, the fixation cam bottom 1738 snaps into the fixation cam top 1718 over the combined handle top and bottom pieces to form the fixation cam, and the release cam bottom 1734 snaps into the release cam top 1720 over the combined handle top and bottom pieces to form the release cam. A release cam window 1736 fits into an opening in the release cam bottom 1734. A front cap 1744 is at the distal end of the handle 1702 and fits over the joined handle top and bottom pieces. In some embodiments, the front cap 1744 is substantially shaped as a ring, and may include a window 1745 positioned at the top surface of the handle 1702. From the distal end to the proximal end of the handle 1702 passing through the interior of the handle 1702 in sequence are: an external fixation shaft 1746 coupled to a fixation hub 1722; a sheath carriage 1748; an alignment shaft 1732 connected to an alignment hub 1723; a delivery shaft 1730 connected to a bayonet hub 1724; and a push tube 1728 connected to a push hub 1726. In some embodiments, the following features are disposed coaxially, in order from the center radially outward: the push tube 1728 (also called a third shaft), the delivery shaft 1730 (also called a first shaft), the alignment shaft 1732 (also called a fourth shaft), and the external fixation shaft 1746 (also called a second shaft). In some embodiments, the alignment shaft 1732 may help align the external fixation 1706 and implant 1710 circumferentially.

Figure 120A:
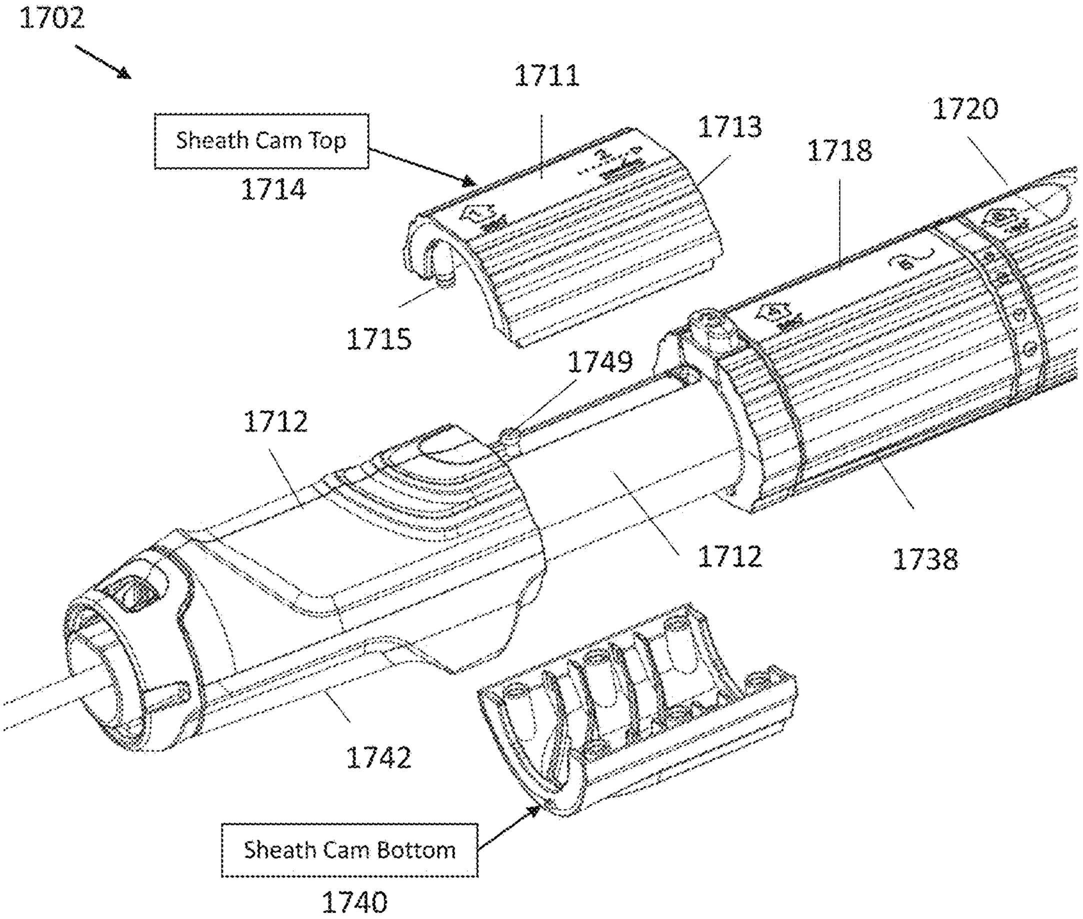
Figure 120B:
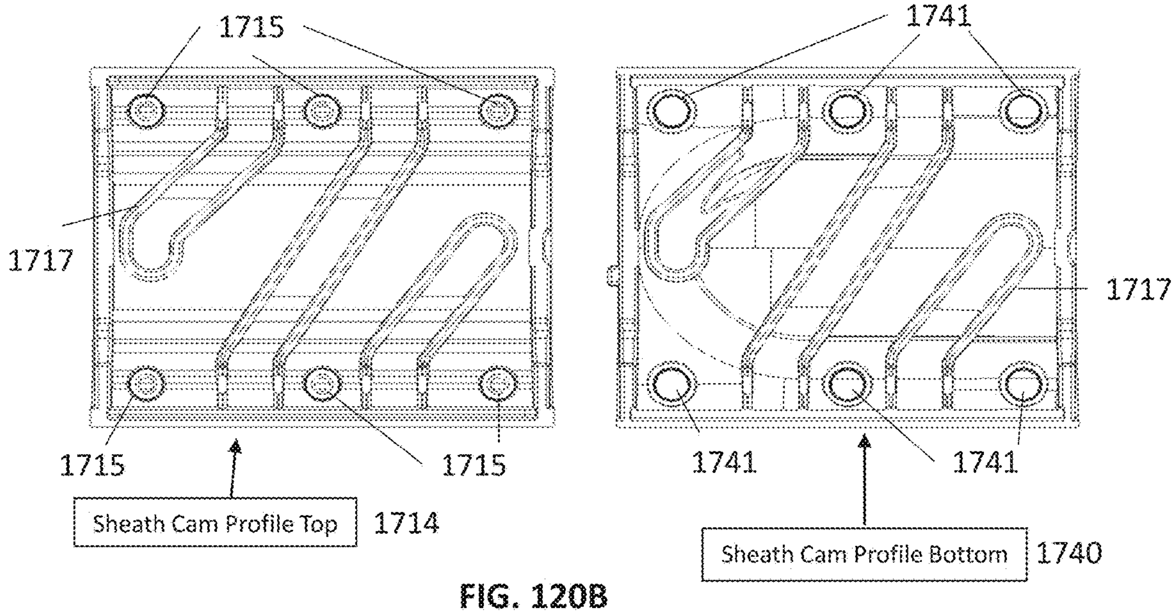

FIGS. 120A and 120B are images of parts of a VCD assembly 1702, in particular the sheath cam top 1714 and sheath cam bottom 1740, according to aspects of the present embodiments. The handle top 1712, handle bottom 1742, fixation cam top 1718, fixation cam bottom 1738, and release cam top 1720 are visible. In some embodiments, the sheath cam top 1714 and cam sheath bottom 1740 are substantially hollow half-cylinders, which form a complete cylinder when they are snapped together. The outer surfaces of the sheath cam top 1714 and sheath cam bottom 1740 include a series of parallel ridges 1713 parallel to the axial direction of the handle for improved grip. The sheath cam top 1714 includes six protruding pins 1715, with three pins along each straight edge of the inner concave surface of the sheath cam top 1714, which snap into six corresponding holes 1741 along the straight edges of the inner concave surface of the sheath cam bottom 1740. In some embodiments, the sheath cam top 1714 and sheath cam bottom 1740 each have a series of tracks 1717 positioned diagonally on the concave interior surfaces of the sheath cam top 1714 and sheath cam bottom 1740 such that the tracks 1717 come together in a helical formation, and engage with cam follower protrusions 1749 on the sheath carriage 1748 (also called a first hub). As a result of the helical formation of the tracks 1717, when the combined sheath cam top and bottom pieces are rotated about the central axis of the handle 1702, the sheath carriage 1748 is pulled axially toward the proximal end of the delivery device. In some embodiments, the sheath cam top 1714 may include a flat portion 1711 on the outer (concave) surface of the sheath cam top 1714, where indicators may be printed. Such indicators may include an arrow and a degree marking to instruct a user the direction to turn the sheath cam and how many degrees to turn (e.g., 360 degrees), followed by another marking to indicate pulling of the handle in the proximal direction. In some embodiments, turning the sheath cam effectively causes the implant 1710 to protrude from a sheath shaft 1793.

Figure 121A:
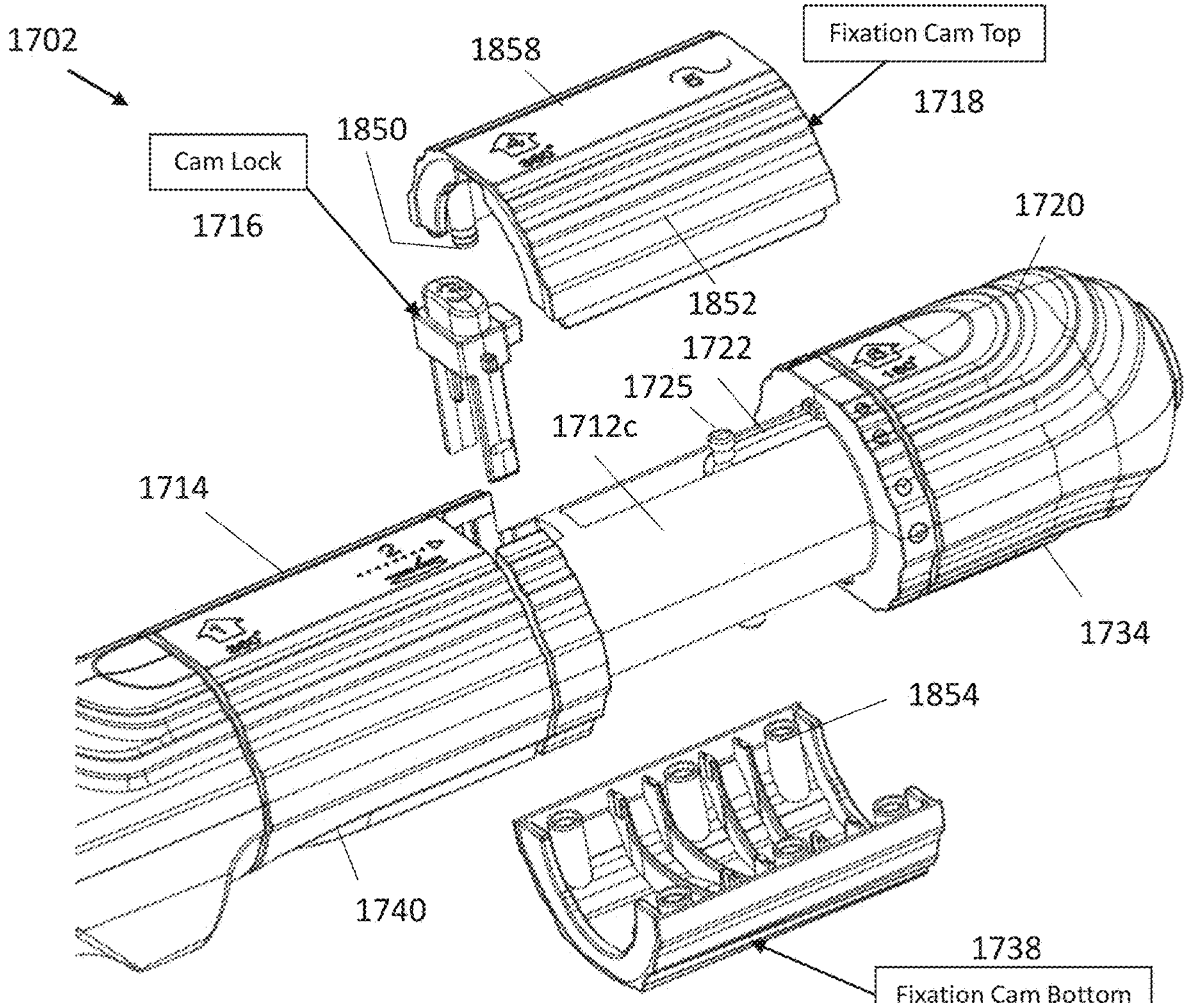
Figure 121B:
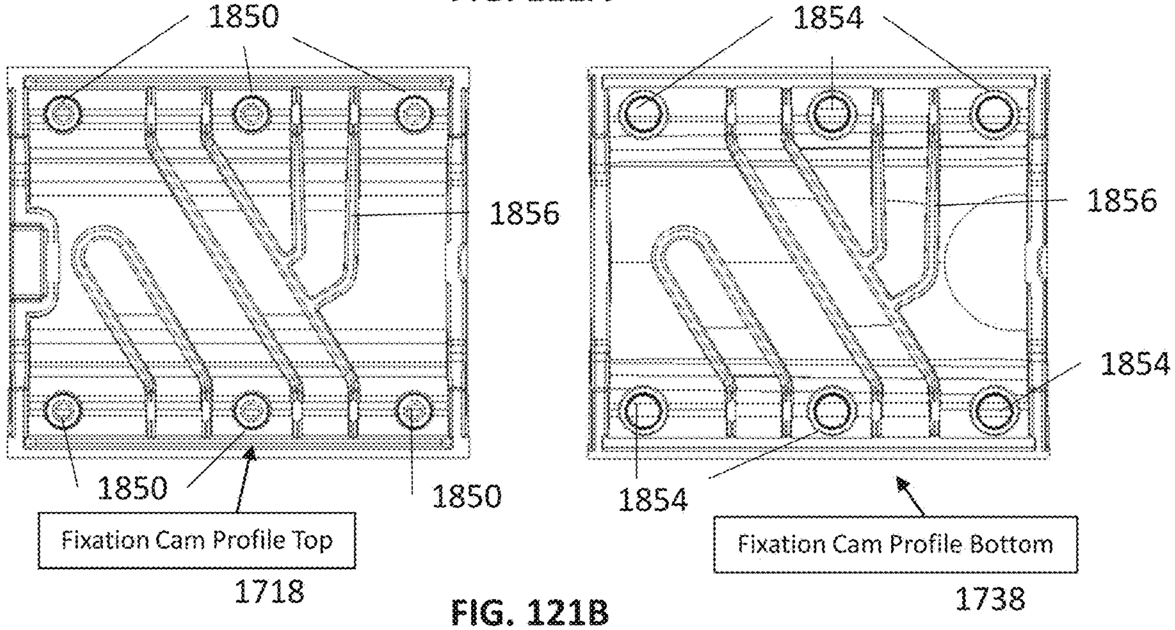

FIGS. 121A and 121B are parts of a VCD assembly, showing the fixation cam top 1718 and fixation cam bottom 1738 pieces, according to aspects of the present embodiments. The cam lock 1716, sheath cam top 1714, sheath cam bottom 1740, release cam top 1720, and release cam bottom 1734 are also visible in FIG. 121A. In some embodiments, the cam lock 1716 is shaped as a button that can be depressed. When the cam lock 1716 is in its initial protruding position, it prevents movement of the fixation cam 1718, 1738. When the cam lock 1716 is pressed into its depressed position, it allows movement of the fixation cam. The cam lock 1716 is needed to prevent premature rotation of the fixation cam 1718, 1738 so that the external fixation 1706 is kept away from the implant before it is in position in the vessel near the aperture to be closed. In some embodiments, the cam lock 1716 may include a nub that interfaces with a corresponding recess under the flat portion 1858 of the fixation cam top 1718. When the nub is interfacing (i.e., disposed within and surrounded by) the corresponding recess, rotation of the fixation cam top 1718 is not possible. By depressing the cam lock 1716 radially inwards, the nub moves radially inwards such that it no longer interfaces with the corresponding recess (i.e., the nub is no longer in contact with the corresponding recess), thereby allowing the fixation cam top 1718 to rotate.

Referring still to FIGS. 121A and 121B, in some embodiments, the fixation cam top 1718 and fixation cam bottom 1738 are substantially hollow half-cylinders, which form a complete cylinder when they are snapped together. In some embodiments, the outer surfaces of the fixation cam top 1718 and fixation cam bottom 1738 include a series of parallel ridges 1852 parallel to the axial direction of the handle for improved grip. The fixation cam top 1718 includes six protruding pins 1850, with three pins along each straight edge of the inner concave surface of the fixation cam top 1718, which snap into six corresponding holes 1854 along the straight edges of the inner concave surface of the fixation cam bottom 1738. In some embodiments, the fixation cam top 1718 and fixation cam bottom 1738 each have a series of tracks 1856 positioned diagonally on the concave interior surfaces of the fixation cam top 1718 and fixation cam bottom 1738 such that the tracks 1856 come together in a helical formation, and engage with cam follower protrusions 1725 on the fixation hub 1722. As a result of the helical formation of the tracks 1856, when the combined fixation hub top and bottom pieces are rotated about the central axis of the handle 1702, the fixation hub 1722 is pushed axially toward the distal end of the handle 1702 (i.e., away from the user/operator) such that the external fixation 1706 is pushed distally. In some embodiments, the fixation cam top 1718 may include a flat portion 1858 on the outer (concave) surface of the fixation cam top 1718, where indicators may be printed. Such indicators may include an arrow and a degree marking to instruct a user the direction to turn the fixation cam and how many degrees to turn (e.g., 360 degrees), followed by another marking to indicate pulling of a guidewire in the proximal direction. In some embodiments, a guidewire is inserted during a medical procedure into a patient (e.g., into a vessel through an opening in the vessel) and is left in place along with, optionally, a sheath assembly 1784 to guide the insertion and positioning of other surgical implements.

Figure 122A:
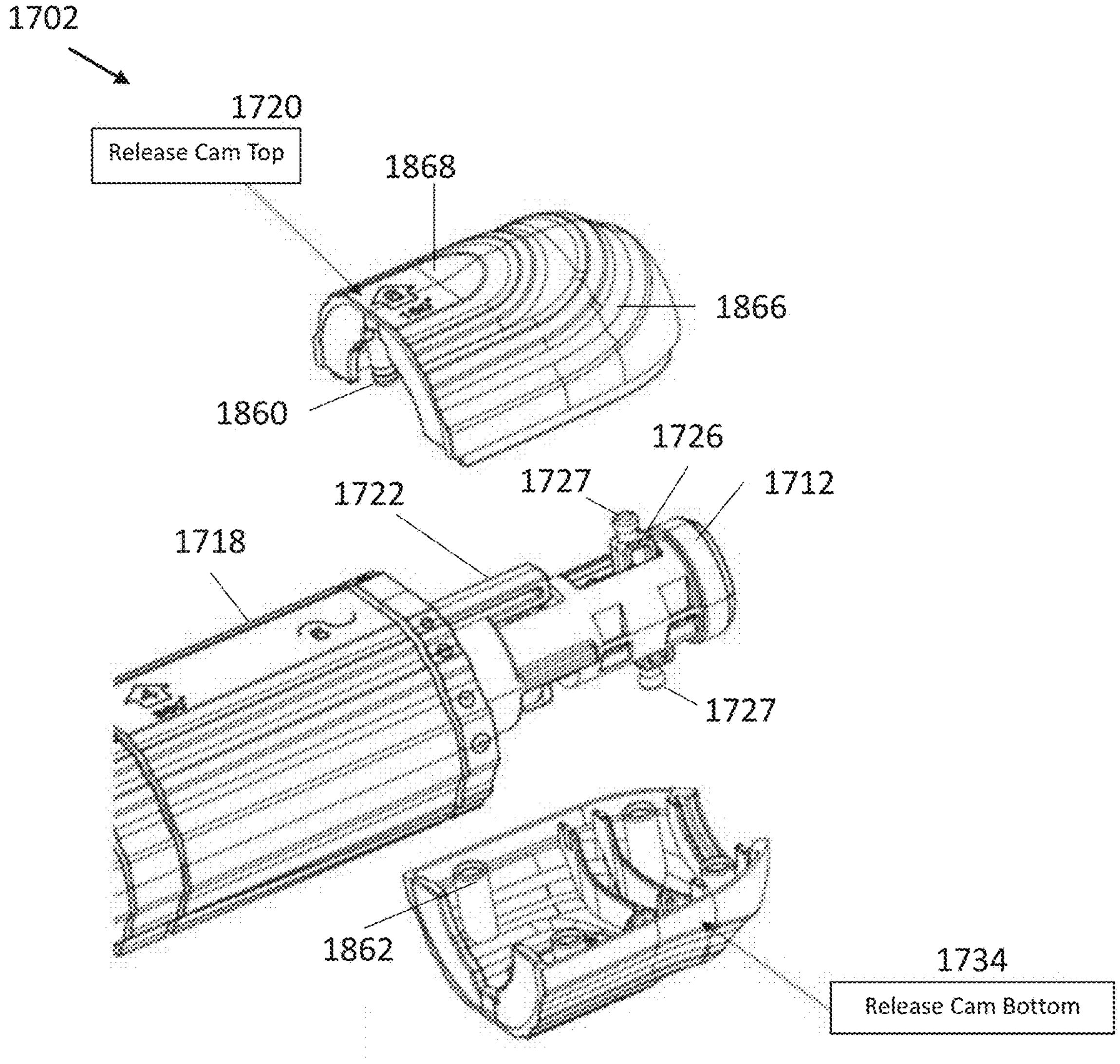
Figure 122B:
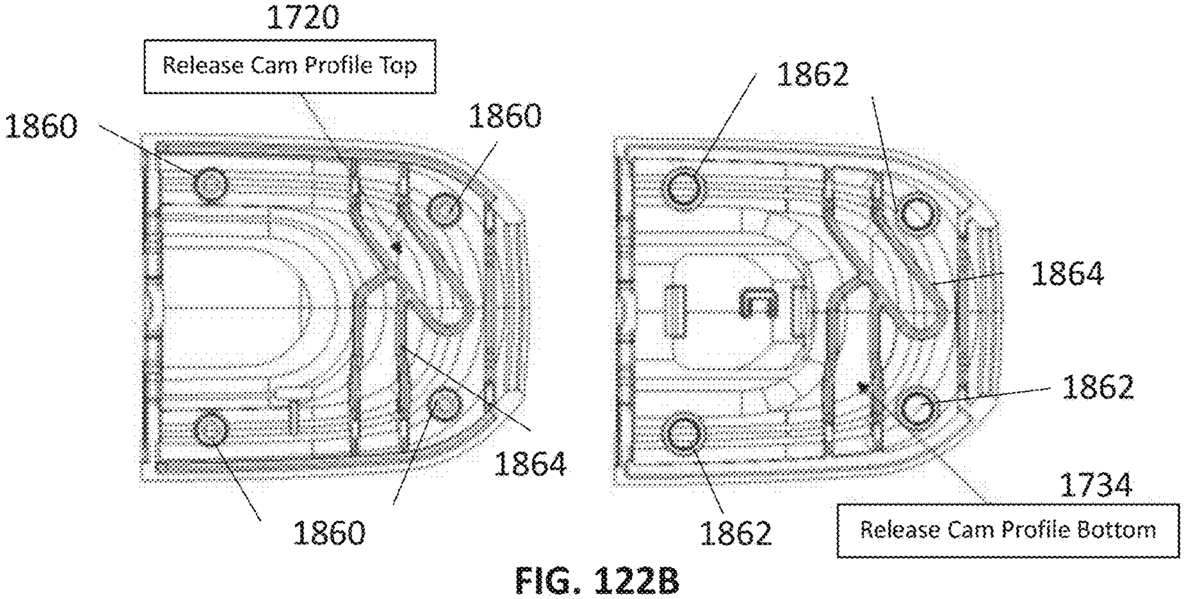

FIGS. 122A and 122B are images of parts of a VCD assembly (release cam top 1720, and release cam bottom 1734 pieces), according to aspects of the present embodiments. The handle top 1712, fixation hub 1722, fixation cam top 1718, and push hub 1726 are also visible in FIG. 122A. In some embodiments, the release cam top 1720 and release cam bottom 1734 are substantially half-cylinders (or semi-cylinders) with sloped ends at the proximal ends, which form a complete cylinder with a rounded, truncated conical proximal end. In some embodiments, the outer surfaces of the release cam top 1720 and release cam bottom 1734 include a series of curving ridges 1866 for improved grip. The release cam top 1720 includes four protruding pins 1860 (with one pin in each corner of the inner concave surface of the release cam top 1720) which snap into four corresponding holes 1862 in each corner of the inner concave surface of the release cam bottom 1734.

Referring still to FIGS. 122A and 122B, in some embodiments, the release cam top 1720 and release cam bottom 1734 each have a series of tracks 1864 positioned diagonally on the concave interior surfaces of the release cam top 1720 and release cam bottom 1734 such that the tracks 1864 come together in a helical formation, and engage with cam follower protrusions 1727 on the push hub 1726. As a result of the helical formation of the tracks 1864, when the combined release cam top 1720 and release cam bottom 1734 are rotated about the central axis of the handle 1702, the push hub 1726 moves in the proximal direction in the handle 1702, the bayonet hub assembly 1724 is rotated, and releases the scaffold 1792 from the bayonet feature 1731 of the delivery shaft 1730. The release cam top 1720 may include a flattened portion 1868 on which symbols may be printed (e.g., to indicate a direction of rotation and angle of rotation, e.g., 180 degrees).

Cannula Assembly, Loading Funnel, and Packaging Assembly

Figure 123A:
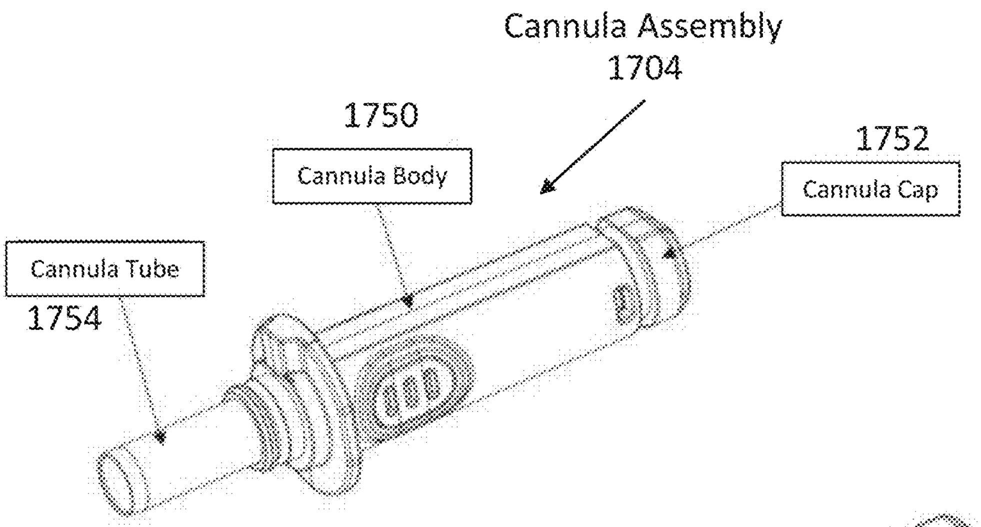
Figure 123B:
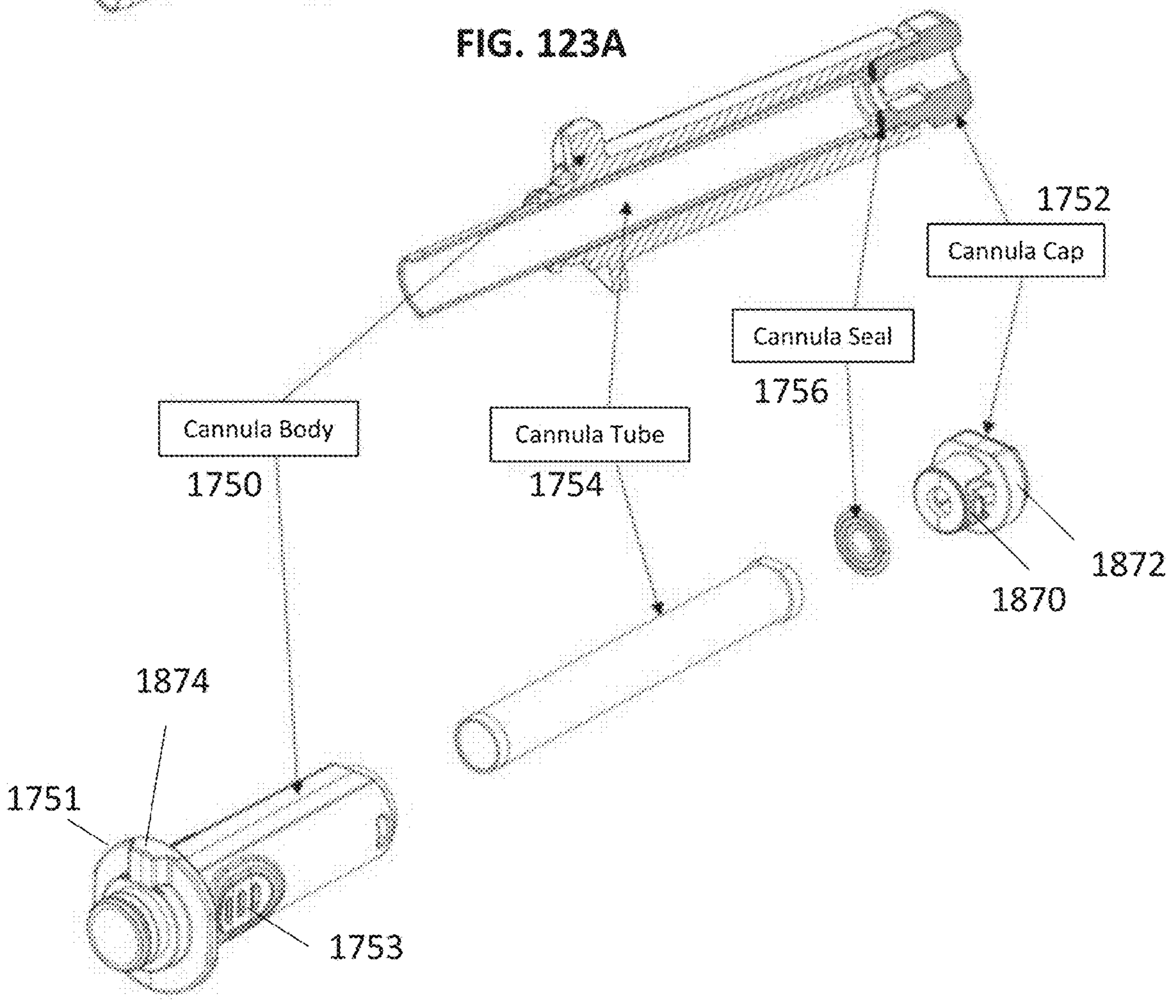

FIGS. 123A and 123B are images of a cannula assembly 1704 that is part of a delivery system assembly 1700, according to aspects of the present embodiments. In some embodiments, an implantable vascular closure device assembly 1710 may be stowed in a rolled configuration in the interior lumen of the cannula assembly 1704 prior to deployment of the closure device 1710, but is stored in an unrolled configuration within a funnel 1760 that is attached to a packaging tray 1772 and is moved into the cannula 1704 prior to deployment. In some embodiments, the cannula assembly 1704 may include a cannula body 1750, a cannula cap 1752, and a cannula tube 1754. In some embodiments, the cannula body 1750 is substantially cylindrical and includes a main (i.e., centerline) axis aligned with the main axis of the handle 1702 of the delivery system 1700. The cannula body 1750 includes a flange 1751 disposed near the distal end of the cannula body 1750, and two indentations 1753 disposed on opposite sides of the exterior of the cannula body 1750 that may be used as finger grips. The flange 1751 may have a protrusion 1874 shaped to fit into a notch 1786 on a sheath hub 1788 (shown in FIGS. 129A-129C).

Referring still to FIGS. 123A and 123B, in some embodiments, the cannula tube 1754 is substantially cylindrical and is disposed within the inner lumen of the cannula body 1750, with the outer diameter of the cannula tube 1754 slightly smaller than the inner diameter of the cannula body 1750, and includes a small flange at its proximal end. In some embodiments, the cannula tube 1754 is longer than the cannula body 1750 such that when the cannula tube 1754 is disposed in the lumen of the cannula body 1750, a portion of the cannula tube 1754 protrudes from the distal end of the cannula body 1750. In some embodiments, the cannula assembly 1704 also includes a cannula seal disposed within the inner lumen of the cannula body 1750 at the proximal end of the cannula body 1750 and sandwiched between the cannula tube 1754 and the cannula cap 1752. In some embodiments, the cannula cap 1752 includes a cylindrical body portion 1870 with an outer diameter that is slightly smaller than the inner diameter of the cannula body 1750, and the cannula cap 1752 further includes a cylindrical head portion 1872 with a diameter that is larger than the diameter of the cylindrical body portion 1870.

Figure 124A:
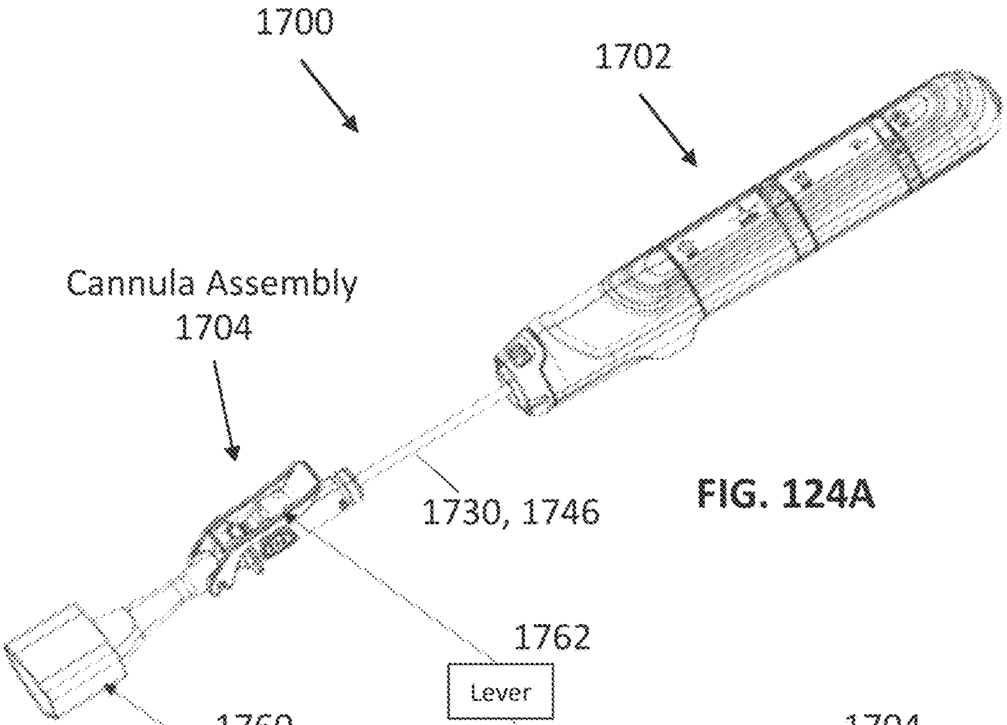
Figure 124B:
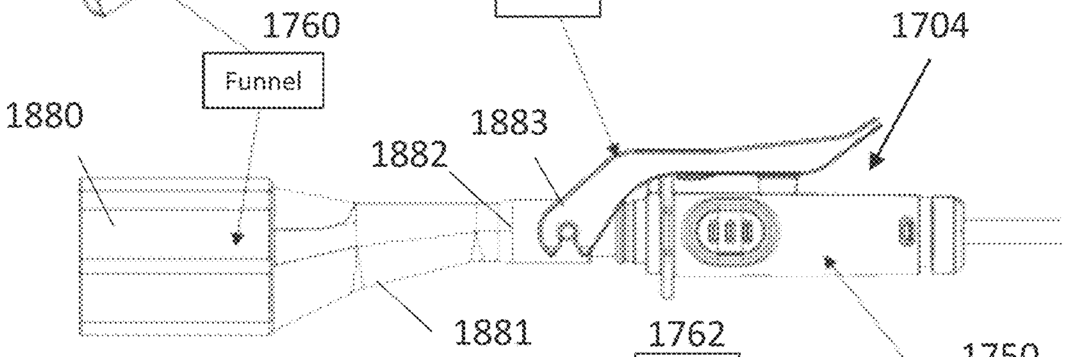
Figure 124C:
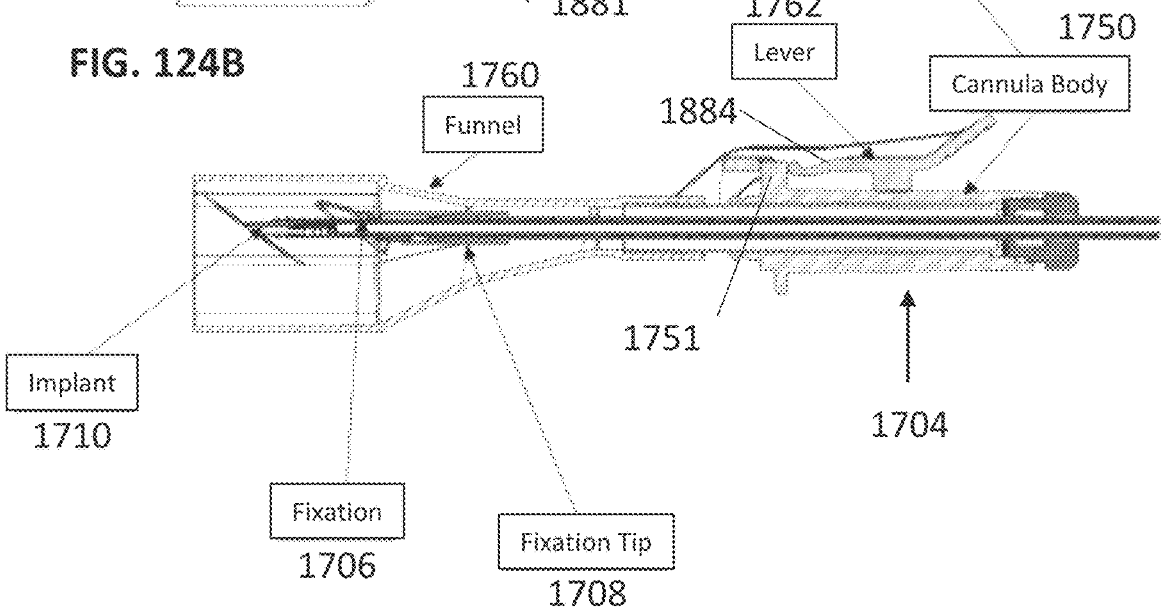

FIG. 124A is an image of a funnel 1760 (or loading funnel 1760), cannula assembly 1704 and VCD assembly 1702, according to aspects of the present embodiments. FIG. 124B is an image of a funnel 1760 and canula assembly 1704, including a lever 1762 and canula body 1750, according to aspects of the present embodiments. FIG. 124C is a cross-sectional view of a funnel 1760 and cannula assembly 1704, according to aspects of the present embodiments. The funnel 1760 contains the implant 1710 in an unrolled configuration before the implant 1710 is loaded for deployment, and is primarily used to store and protect the implant 1710 when the delivery device system 1700 is stored in a packaging tray and lid assembly 1770 for shipping and storage prior to use.

Referring still to FIG. 124A, the distal end of the delivery system handle 1702 is shown connected to a delivery shaft 1730 disposed coaxially inside an external fixation shaft 1746, which both pass through the distal end of the cannula assembly 1704, which is connected to a cylindrical spout portion 1882 at the proximal end of the funnel 1760. In some embodiments, the funnel 1760 includes a mouth portion 1880, a stem that includes a tapered conical portion 1881, and a cylindrical spout portion 1882. In some embodiments, the lever 1762 is attached to the spout portion 1882 of the funnel 1760 via a hinge 1883. In a storage configuration, the lever 1762 is bent down over the cannula body 1750 such that a tab 1884 on the lever 1762 is engaged with the proximal side of the cannula flange 1751 to prevent separation of the funnel 1760 and cannula 1704.

Referring still to FIGS. 124B and 124C, the lever 1762 of the funnel 1760 is shown in a storage configuration where it is bent over the cannula body 1750 such that a tab 1884 on the lever 1762 is engaged with the proximal side of the cannula flange 1751 to prevent separation of the funnel 1760 and cannula 1704. In the cross-sectional view of FIG. 124C, the implant 1710 and external fixation 1706 are visible within the lumen of the mouth portion 1880 of the funnel 1760.

FIG. 125A is an image of a delivery system assembly 1700 held in a packaging tray and lid assembly 1770 with packaging lid 1774 fixed, according to aspects of the present embodiments. In some embodiments, the packaging tray 1772 includes a rectangular exterior and a molded interior that matches the external shape of the delivery system assembly 1700, including the handle 1702, cannula assembly 1704, and loading funnel 1760. In some embodiments, the packaging tray 1772 may include one or more regions of the molded interior that are narrower in width to form pinch points that hold in the delivery system assembly. In some embodiments, the packaging lid 1774 includes multiple protrusions that are pressed into multiple corresponding depressions in the upper surface of the packaging tray 1772 so that the packaging lid 1774 is held fixed and prevents the delivery device system 1700 from being removed from the packaging tray 1772. In some embodiments, the packaging lid 1774 may include two separate lid pieces that each include multiple protrusions to be pressed into multiple depressions in the upper surface of the packaging tray 1772 to secure the packaging lid pieces.

FIG. 125B is an image of a delivery system assembly 1700 held in a packaging tray and lid assembly 1770 with packaging lid 1774 removed, according to aspects of the present embodiments. In some embodiments, the packaging lid 1774 may be removed from the packaging tray 1772 by pulling the packaging lid 1774 away from the packaging tray 1772 such that the multiple protrusions in the packaging lid 1774 are pulled out of the multiple corresponding depressions in the packaging tray 1772. In some embodiments, the delivery system 1700 does not readily detach from the packaging tray 1772 even when the packaging lid 1774 is removed because of the pinch points in the molded interior of the 1772 can retain the delivery system 1700.

FIG. 126A is an image of a delivery system assembly 1700 held in a packaging tray 1772 and with the VCD 1702 pulled in a proximal direction until the fixation tip 1708 meets the proximal end of the cannula tube 1754 and inner distal end of the cannula cap 1752, according to aspects of the present embodiments. FIG. 126B is a side view of a funnel 1760 and cannula assembly 1704, according to aspects of the present embodiments. FIG. 126C is a cross-sectional view of a funnel 1760 and cannula assembly 1704, where the VCD is pulled back until the fixation tip 1708 meets the proximal end of the cannula tube 1754 and inner distal end of the cannula cap 1752, according to aspects of the present embodiments. In this configuration, the cross-sectional view of FIG. 126C shows that the implant 1710 and external fixation 1706 have moved proximally out of the funnel 1760 and are loaded into the cannula tube 1754 inside the cannula assembly 1704. When the implant 1710 and external fixation 1706 are loaded into the cannula assembly 1704, they are ready for use (i.e., for implantation in a test subject).

FIG. 127A is an image of a delivery system assembly 1700 held in a packaging tray 1772 when lever 1762 is lifted, according to aspects of the present embodiments. FIG. 127B is an image of a delivery system assembly 1700 when the lever 1762 is lifted, and the implant 1710 is pulled back into the cannula 1704, according to aspects of the present embodiments. In some embodiments, the lever 1762 is lifted in order to detach the funnel 1760 from the cannula assembly 1704 (in particular, the portion of the cannula tube 1754 that protrudes from the cannula body 1750, which was inserted into the spout portion 1882 of the funnel 1760). In some embodiments, when the lever 1762 is lifted, the tab 1884 on the lever 1762 is disengaged from the flange 1751 of the cannula so that the cannula 1704 and funnel 1760 can be separated.

FIG. 128A is an image of a delivery system assembly 1700 being removed from the packaging tray 1772, according to aspects of the present embodiments. FIG. 128B is an image of the VCD assembly 1700 being pulled back from the funnel 1760 and lever 1762, according to aspects of the present embodiments. In some embodiments, once the lever 1762 is raised to release the cannula assembly 1704, the VCD assembly 1702 is freed to be completely pulled proximally out of the packaging tray 1772. As seen in FIG. 128A, the funnel 1760 remains in position in the packaging tray 1772 while the VCD assembly 1702 moves free of the packaging tray 1772 and funnel 1760. The implant 1710 and external fixation 1706 are loaded within the cannula 1704 and are ready for deployment to close a vascular opening. In some embodiments, the funnel 1760 remains in the packaging tray 1772.

Sheath Assembly and Handle for Deployment of Closure Device

FIG. 129A is a perspective view of the VCD assembly 1702 and cannula 1704 engaged with the sheath cap 1786 of the sheath assembly 1784, according to aspects of the present embodiments. FIG. 129B is a cross-sectional view of the cannula 1704 engaged with the sheath cap 1786 of the sheath assembly 1784, according to aspects of the present embodiments. FIG. 129C is an enlarged cross-sectional view of the cannula engaged with the sheath cap of the sheath assembly, according to aspects of the present embodiments. The cannula 1704 is engaged with the sheath cap 1786 of the sheath assembly 1784 by inserting the cannula tube 1754 into the sheath cap 1786, while aligning the protrusion 1874 on the flange 1751 of the cannula body 1750 with the notch 1881 of the sheath cap 1786 and the notch 1876 of the sheath hub 1788 so that the protrusion 1874 fits into the notches 1881, 1876. In some embodiments, in order to engage the cannula 1704 with the sheath cap 1786, the user or operator may need to push the cannula 1704 and sheath assembly 1784 together, and may need to push the cannula tube 1754 through the slit of the sheath seal 1790 held between the sheath hub 1788 and sheath cap 1786 (see FIGS. 146A and 146B).

Referring still to FIG. 129C, the implant 1710 and external fixation 1706 are visible inside the cannula tube 1754. The cannula tube 1754 is partially contained within the sheath hub 1788, and passes through the sheath cap 1786. The proximal end of the fixation tip 1708 abuts against the inner distal surface of the cannula cap 1752.

FIG. 130A is an image of a delivery system assembly 1700, where the VCD assembly 1702 is pushed forward until the cannula 1704 engages with the sheath carriage 1748 in the VCD assembly 1702, according to aspects of the present embodiments. FIG. 130B is an enlarged view of the sheath cap 1786 and cannula 1704 engaged with the sheath carriage 1748, according to aspects of the present embodiments. In some embodiments, pushing of the VCD assembly 1702 forward (i.e., distally) is with respect to the cannula 1704 and sheath assembly 1784, and is equivalent to pulling of the cannula 1704 and sheath assembly 1784 toward the VCD assembly 1702 (i.e., proximally). As the cannula 1704 approaches the VCD assembly 1702, the proximal end of the cannula 1704 enters the distal opening of the handle 1701 and front cap 1744, and the proximal end of the cannula 1704 then engages with the sheath carriage 1748 inside the handle 1701. In FIG. 130A, the cannula 1704 is partially visible outside the handle 1701, as the proximal end of the cannula 1704 is inside the handle. The view shown in FIG. 130B is inside the handle 1701, showing the cannula 1704 engaged with and inside of the sheath carriage 1748.

FIG. 131A is an image of a delivery system assembly 1700 with VCD assembly 1702 engaged with sheath assembly 1784 and with sheath cams 1714, 1740 on the VCD assembly 1702 rotated to push the implant 1710 towards the end of the sheath shaft 1793, according to aspects of the present embodiments. FIG. 131B is an image of a delivery system 1700 assembly with VCD assembly 1702 engaged with sheath assembly 1784 and with implant 1710 protruding from the end of the sheath shaft 1793 once the sheath cams 1714, 1740 are rotated 360 degrees, according to aspects of the present embodiments. As described earlier when referring to FIGS. 120A and 120B, the sheath cams 1714, 1740 have tracks 1717 arranged in a helical formation on the inner concave surfaces of the sheath cams 1714, 1740, which engage with cam follower protrusions 1749 on the sheath carriage 1748. Rotation of the sheath cams 1714, 1740 causes the sheath carriage 1748 to also rotate and be pulled proximally into the handle 1701, and thus also cause the implant 1710 to effectively be pushed out of the sheath shaft 1793. When the cannula 1704 is fully pulled into the handle 1701, along with the opening of the sheath hub 1788, the notches 1876, 1881 and protrusion 1874 are visible in the window 1745. In some embodiments, the notches 1876, 1881 and protrusion 1874 may be a different color so that they are readily visible in the window 1745 to visually indicate that the sheath 1784 has been fully retracted and that the implant 1710 is pushed out.

FIG. 132 is an enlarged view of the implant 1710 protruding from the end of the sheath 1792 after the sheath cams 1714, 1740 are rotated 360 degrees, according to aspects of the present embodiments. In this configuration, the implant 1710 (which includes the scaffold 1792 and patch 1794) are engaged together, while the external fixation 1706 is visible also protruding from the sheath 1792, but is some distance away from the rest of the implant 1710.

FIGS. 133A-133C show sequential views of the movements of the cannula body 1750 as it is engaged with the sheath carriage 1748 and moving into the handle 1701 upon rotation of the sheath cams 1714, 1740. FIG. 133A is a cross-sectional view of the cannula body 1750 engaged with the sheath carriage 1748, according to aspects of the present embodiments. FIG. 133B is a cross-sectional view of the cannula body 1750 engaged with the sheath carriage 1748, with the sheath carriage 1748 moving back in the handle 1701 when the sheath cams 1714, 1740 are rotated, according to aspects of the present embodiments. FIG. 133C is a cross-sectional view of the sheath carriage 1748 moving into the handle 1701 and snapping into the handle bottom 1742 once the sheath cams 1714, 1740 have been fully rotated, according to aspects of the present embodiments. The cross-sectional views in FIGS. 133A-133C correspond to the exterior perspective views of FIGS. 131A-131B. At the end of the rotation of the sheath cams 1714, 1740, the sheath carriage 1748 is pulled into the handle 1701, and pulls along with the cannula assembly 1704 and sheath assembly 1784, resulting in the implant 1710 protruding from the end of the sheath shaft 1793.

FIGS. 134A-134C show sequential cross-sectional views of the movement of the implant 1710 as the sheath cams 1714, 1740 are rotated. FIG. 134A is a cross-sectional view of the implant 1710 positioned near the tip of the sheath shaft 1793 but still fully contained within the sheath shaft 1793 while the cannula body 1750 is engaged with the sheath carriage 1748, according to aspects of the present embodiments. FIG. 134B is a cross-sectional view of the implant partially protruding from the tip of the sheath shaft 1793, according to aspects of the present embodiments. FIG. 134C is a cross-sectional view of the implant fully protruding from the tip of the sheath shaft 1793, according to aspects of the present embodiments. FIG. 134B corresponds to a condition when the sheath cams 1714, 1740 are partially rotated, and FIG. 134C corresponds to a condition when the sheath cams 1714, 1740 are fully rotated. The view of FIG. 134C corresponds to the views in FIGS. 133C, 131B, and 132.

FIG. 135A is an image of a handle 1701 of a VCD assembly 1702, with cam lock 1716 pressed to allow fixation cams 1718, 1738 to be rotated, according to aspects of the present embodiments. FIG. 135B is an image of a VCD assembly 1702 and sheath assembly 1784, with an implant 1710 protruding from the sheath 1792 and an external fixation 1706 advancing toward the implant 1710 after the fixation cams 1718, 1738 are rotated to push the external fixation towards the implant 1710, according to aspects of the present embodiments. In FIG. 135B, the fixation 1706 is partially protruding from the tip of the sheath shaft 1793.

FIGS. 136A, 136B, and 137A illustrate an embodiment of a vascular (artery or vein) implant delivery system which has fixation cams that are rotated to (i) retract the introducer sheath in order to expose the implant in the vessel, (ii) push the fixation component towards the implant and snap onto the scaffold, and (iii) deploy the guidewire hole blocking pin and release the implant.

FIG. 136A is an enlarged view of the external fixation 1706 moving toward the implant 1710 upon rotation of the fixation cams 1718, 1738, according to aspects of the present embodiments. The view in FIG. 136A corresponds to the view in FIG. 135B, when the external fixation 1706 has moved closer to the implant 1710 but has not yet fully reached the implant 1710, and when the fixation cams 1718, 1738 are partially rotated. FIG. 136B is an image of the VCD assembly 1702 engaged with the sheath assembly 1784, and with the external fixation 1706 snapped onto the scaffold 1792 protruding from the tip of the sheath shaft 1793 once the fixation cams are fully rotated 360 degrees, according to aspects of the present embodiments.

FIG. 137A is an enlarged view of the external fixation 1706 snapped onto the scaffold 1792 of the implant 1710, according to aspects of the present embodiments. The view in FIG. 137A corresponds to the view in FIG. 136B, when the fixation cams 1718, 1738 have been fully rotated and the external fixation 1706 is snapped onto the scaffold 1792. Further views of an external fixation engaging with a scaffold were described above in reference to FIGS. 107-110.

FIG. 137B is a cross-sectional view of a VCD assembly handle 1701 showing a cam lock 1716 preventing the fixation cams 1718, 1738 from rotating prematurely, and pressing the cam lock 1716 allows the fixation cams 1718, 1738 to rotate, according to aspects of the present embodiments. The manner in which the cam lock 1716 prevents rotation of the fixation cams 1718, 1738 is described in reference to FIGS. 121A and 121B.

FIG. 138A is a cross-sectional view of the VCD assembly handle 1701 and shows the fixation hub 1722 moving forward in the handle 1701 when the fixation cams 1718, 1738 are rotated, according to aspects of the present embodiments. In some embodiments, the fixation hub 1722 may include cam follower protrusions 1725 that engage with tracks 1856 in the fixation cams 1718, 1738, as described in reference to FIGS. 121A and 121B, so that when the fixation cams 1718, 1738 are rotated the fixation hub 1722 is pushed forward in the handle 1701. FIG. 138B is a cross-sectional view of the VCD assembly handle 1701 and shows the fixation hub 1722 snapping into the handle bottom 1742 once the fixation cams 1718, 1738 have been fully rotated 360 degrees, according to aspects of the present embodiments.

FIG. 138C is two cross-sectional views of the implant 1710 protruding from the sheath shaft 1793, the upper view showing the fixation 1706 and implant separated; after rotating the fixation cams 1718, 1738 causes the fixation 1706 to move forward, the fixation 1706 snaps onto the implant 1710 as shown in the lower view, according to aspects of the present embodiments. The upper view of FIG. 138C corresponds to the view of FIG. 136A where the fixation 1706 is moving towards the implant 1710, and the lower view of FIG. 138C corresponds to the view of FIG. 137A where the fixation 1706 is snapped onto the scaffold 1792.

FIG. 139A is an image of a VCD assembly 1702 with release cams 1720, 1734 partially rotated, which pushes the guidewire pin 1802 into the scaffold 1792 and simultaneously detaches the scaffold 1792 from the bayonet feature 1731 of the delivery shaft 1730, according to aspects of the present embodiments. During the deployment procedure, after the fixation 1706 is snapped onto the scaffold 1792 upon fully rotating the fixation cams 1718, 1738, the guidewire is removed by pulling the guidewire distally through the back of the handle 1701. The remaining hole in the scaffold 1792 where the guidewire was inserted must be sealed by insertion of the guidewire pin 1802.

FIG. 139B is an image of a VCD assembly with release cams 1720, 1734 rotated the full 180 degrees, which causes the scaffold 1792 to be unhooked from the bayonet feature 1731 of the delivery shaft 1730, so that the VCD assembly 1702 can be removed from the implant 1710, according to aspects of the present embodiments. The scaffold 1792 may include retaining pads 1058, 1059 that engage with the bayonet feature 1731 at the distal end of the delivery shaft 1730 that are then disengaged when the release cams 1720, 1734 are rotated. At this point, the implant 1710 includes the scaffold 1792 with scaffold neck disposed through the hole in the vessel, implant patch 1794 disposed over the scaffold base and pressed against the inner wall of the vessel, external fixation 1706 engaged with the scaffold 1792 on the exterior wall of the vessel, and guidewire pin 1802 pressed into the scaffold 1792 in the guidewire hole 1791.

FIG. 140A is a cross-sectional view of a VCD assembly handle 1701, showing the bayonet hub 1724, and release cams 1720, 1734, alignment hub 1723, push hub 1726, and release window 1736, according to aspects of the present embodiments. In some embodiments, the alignment hub 1723 may be engaged with the alignment shaft 1732.

FIG. 140B is a cross-sectional view of a VCD assembly handle 1701, showing the push hub 1726 moving forward in the handle 1701 and releasing the scaffold 1792 from the bayonet feature 1731 of the delivery shaft 1730 when the release cams 1720, 1734 are rotated, according to aspects of the present embodiments. In some embodiments, the push hub 1726 has cam follower protrusions 1727 that engage with the tracks 1864 in the release cams 1720, 1734, so that rotation of the release cams 1720, 1734 results in the push hub 1726 moving in a distal direction. The rotation of the release cams 1720, 1734 also rotates the bayonet hub assembly 1724, which rotates the delivery shaft 1730 to release the scaffold 1792 from the bayonet feature 1731 of the delivery shaft 1730. In some embodiments, the bayonet hub assembly 1724 and/or the alignment hub 1723 may be visible through the release window 1736 in the release cam bottom 1734, so that there is visual indication of the movements of the bayonet hub assembly 1724 and/or the alignment hub 1723 upon rotation of the release cams 1729, 1734.

FIG. 141A is a cross-sectional view of a VCD assembly handle 1701, showing the push hub 1726 has moved forward in the handle 1701, according to aspects of the present embodiments. This configuration corresponds to when the release cams 1720, 1734 have been rotated a full 180 degrees.

FIG. 141B is two cross-sectional views of the sheath shaft with fixation and implant pushed together and protruding from the sheath shaft end; in the upper view the guidewire pin 1802 is not yet inserted; in the lower view the guidewire pin 1802 is inserted into the scaffold 1792, blocking off the guidewire hole 1791, according to aspects of the present embodiments. In some embodiments, the guidewire hole 1791 in the scaffold 1792 is needed for the guidewire to pass through, so that the guidewire may guide the positioning of the implant 1710 at the opening in the vessel to be closed. The guidewire hole 1791, after the guidewire is removed, must be blocked off so that liquid from the vessel (e.g., blood) does not escape through the guidewire hole 1791.

FIG. 142A is two views of an implant 1710 and scaffold 1792 in relation to the delivery shaft 1730 and bayonet feature 1731; in the left view, the scaffold 1792 is hooked on the end of the bayonet feature 1731 of the delivery shaft 1730; in the right view, the scaffold 1791 is unhooked from the bayonet feature 1731 after the release cams 1720, 1734 are rotated, according to aspects of the present embodiments. Moving from the left view to the right view of FIG. 142A, the delivery shaft 1730 has been rotated when the release cams 1720, 1734 are rotated, so that a bayonet feature 1731 of the delivery shaft 1730 disengages from one or more retaining pads on the scaffold 1792.

FIG. 142B is two cut-away views of a VCD handle showing release cams 1720, 1734; upon rotation of the release cams 1720, 1734 the bayonet hub assembly 1724 rotates to release the scaffold, according to aspects of the present embodiments. In this view, a portion of the push hub 1726 is also visible where it protrudes from an opening in the handle top 1712, and is pushed in the distal direction upon rotation of the release cams 1720, 1734. A portion of the bayonet hub 1724 is visible through another opening in the handle top 1712.

FIG. 143A is an image of a delivery system assembly 1702 moving away from a released implant 1710, after the release cams 1720, 1734 are rotated so that the scaffold 1792 is unhooked from the bayonet feature 1731 of the delivery shaft 1730, according to aspects of the present embodiments. In this condition, the implant 1710 is completely disengaged from the delivery system 1702, and remains in the patient at the location of the hole to be closed in the vessel. The delivery system 1702 is withdrawn from the patient, and any additional steps needed to complete the surgical procedure may be taken (e.g., wound closure, skin treatment, etc.). FIG. 143B is an enlarged view of a fixation tip 1708 and sheath shaft tip 1793 moving away from an implant after the bayonet is unhooked from the scaffold of the implant, according to aspects of the present embodiments. FIG. 143B corresponds to an enlarged view of FIG. 143A.

Introducer Assembly

FIG. 144A is an image of an assembled introducer 1800, which includes a sheath assembly 1784 and a dilator assembly 1794, according to aspects of the present embodiments. FIG. 144B is a cross-sectional view of an assembled introducer 1800, which includes a sheath assembly 1784 and a dilator assembly 1794, according to aspects of the present embodiments. In both FIGS. 144A and 144B, the dilator assembly 1794 is inserted into the sheath assembly 1784 such that the dilator shaft 1798 is disposed coaxially inside the sheath shaft 1793, and the dilator hub 1796 is engaged with the sheath hub 1788 at the distal end of the introducer assembly 1800. In some embodiments, when the dilator assembly 1794 is inserted into the sheath assembly, a dilator shaft 1798 is inserted coaxially in the lumen of a sheath shaft 1793 such that a tapered distal portion 1886 of the dilator shaft 1798 protrudes from the distal opening of the sheath shaft 1793. In some embodiments, the introducer assembly 1800 may be used to expand an opening formed in a patient during a medical procedure (e.g., an opening in a vessel [e.g., a vein or an artery]). Different diameters of introducer assemblies may be used (e.g., different French values).

FIG. 145 is an image of a sheath assembly 1784, according to aspects of the present embodiments. In some embodiments, a sheath assembly 1784 may include a sheath hub 1788, a sheath shaft 1793, a flush tube 1780, and a three-way stopcock 1782. In some embodiments, the sheath shaft 1793 may have a series of distance markings (e.g., depth markings) on the exterior surface on the sheath shaft 1793 (e.g., centimeter, millimeter, inch, or other linearly spaced markings). The markings may be printed, inked, embossed, and/or engraved and may include a number and a line mark at each indication. In some embodiments, the sheath tube 1793 is substantially cylindrical and hollow, with a constant diameter throughout its length. The flush tube 1780 and stopcock 1782 may be used during a surgical procedure to flush certain fluids through the sheath assembly 1784. Further description of the components of the sheath assembly 1784 are in reference to FIGS. 146A, 146B, and 147. In some embodiments, the valve 1782 (i.e., three-way stopcock 1782) may be used to control the flow of various liquids (e.g., water, saline, other suitable fluids, etc.) through the flush tube 1780 and into the sheath assembly 1784.

FIG. 146A is an image of a sheath hub 1788 portion of a sheath assembly 1784, according to aspects of the present embodiments. In some embodiments, the sheath hub 1788 includes a mouth portion 1877 that is substantially cylindrical, connected to a body portion 1878 that includes a cylindrical main opening 1879 that is coaxial with the mouth portion 1877, and a cylindrical secondary opening 1879 disposed at an angle (e.g., about 20 degrees, about 30 degrees, about 45 degrees) from the central axis of the main opening 1879. The body portion 1878 of the sheath hub 1788 may include an external indication (e.g., printed, engraved, or embossed writing) of the sheath size (i.e., French value). In some embodiments, the sheath shaft 1793 is connected coaxially to the main opening 1879. In some embodiments, the flush tube 1780 is connected to the secondary opening 1880. In some embodiments, the diameter of the sheath shaft 1793 may be larger than the diameter of the flush tube 1780.

FIG. 146B is a cross-sectional view of a sheath hub 1788 portion of a sheath assembly, according to aspects of the present embodiments. In the cross-sectional view, a sheath cap 1786 is visible and is inserted into the opening of the mouth portion 1877 of the sheath hub 1788, and the sheath seal 1790 is visible inside the mouth portion 1877 below the sheath cap 1786. In some embodiments, the sheath seal 1790 is a round disk made of a flexible polymeric material (e.g., silicone, or others) with a raised lip, and a thin slit cut into the center of the disk. In some embodiments, the sheath seal 1790 may act as a hemostatic valve, stopping the flow of blood or other fluids when the sheath is inserted into a patient in a vessel, while being able to allow other objects to pass through when pushed through (e.g., dilator assembly, or fixation tip can be pushed through the slit of the sheath seal 1790).

FIG. 147 is an exploded view of the component parts of a sheath assembly 1784, according to aspects of the present embodiments. In some embodiments, the sheath cap 1786 is a round, cup-like shape with a notch 1881 that aligns with the notch 1876 in the sheath hub 1788 when the cap 1786 is inserted into the sheath hub 1788. In some embodiments, the flush tube 1780 is a hollow cylindrical tube with a constant diameter along its length. In some embodiments, the flush tube 1780 is shorter than the sheath shaft 1793. In some embodiments, the flush tube 1780 is made of a flexible polymeric material while the sheath shaft 1793 is made of a rigid polymeric material. In some embodiments, the 3-way stopcock 1782 includes three ports, where one of the ports is connected to the end of the flush tube 1780 that is not connected to the sheath hub 1788. In some embodiments, the 3-way stopcock 1782 includes a rotating valve or switch to control the flow of liquids through the stopcock 1782 (e.g., by controlling which of the other two ports is fluidly connected to the flush tube 1780 port, and/or by closing flow to the flush tube 1780 port).

FIG. 148A is an image of a dilator assembly 1794, according to aspects of the present embodiments. In some embodiments, the dilator assembly 1794 includes a dilator shaft 1798 and a dilator hub 1796. In some embodiments, the dilator shaft 1798 includes a hollow cylindrical body that is connected to the dilator hub 1796, and a tapered portion 1886 at the end of the dilator shaft 1798 not connected to the dilator hub 1796. In some embodiments, the outer diameter of the dilator shaft 1798 is matched with the inner diameter of the sheath shaft 1793 so that the dilator shaft 1798 may fit securely within the sheath shaft 1793. In some embodiments, the tapered portion 1886 of the dilator shaft 1798 narrows to an outer diameter that is approximately 25% (e.g., approximately 15%, approximately 20%, approximately 30%) of the outer diameter of the cylindrical portion of the dilator shaft 1798. In some embodiments, the tapering of the tapered portion 1886 of the dilator shaft 1798 occurs over a length that is approximately 10 times (e.g., approximately 5 times, 8 times, 12 times, in a range from about 5 times to about 12 times, etc.) the outer diameter of the cylindrical portion of the dilator shaft 1798, resulting in a gradual tapering to ease insertion of the dilator.

FIG. 148B is an image of a dilator hub 1796 portion of a dilator assembly, according to aspects of the present embodiments. The dilator hub 1796 includes a substantially cylindrical body portion 1795, which may have a dilator size (e.g., French value) printed on the exterior. In some embodiments, the dilator hub 1796 may include two spring clips 1797 on two sides of the dilator hub 1796, which may engage with indentations 1887 in the sides of the sheath hub 1788 when the dilator assembly 1794 is inserted into the sheath assembly 1784, in order to hold the sheath hub 1788 and dilator hub 1796 together. The dilator shaft 1798 may be inserted into the distal end of the dilator hub 1796 such that the dilator hub 1796 and dilator shaft 1798 are aligned coaxially.

FIG. 148C is a cross-sectional view of dilator hub 1796 portion of a dilator assembly 1794, according to aspects of the present embodiments. The dilator shaft 1798 is visible and is inserted through most of the interior length of the dilator hub 1796. A dilator insert 1799 is visible positioned coaxially within the dilator hub 1796, at the end of the dilator hub 1796 that does not have the dilator shaft 1798 In some embodiments, the dilator insert 1799 includes a central bore that narrows at a point near the middle of its length, where the narrowed point has an inner diameter to snugly fit a guidewire, so that the guidewire may be stably held in place but still be free to move through the dilator.

FIG. 149 is an exploded view of the component parts of a dilator assembly, according to aspects of the present embodiments. In some embodiments, the dilator shaft 1798 includes a hollow cylinder that is connected to the dilator hub 1796 at the proximal end of the dilator shaft 1798, and a gently tapered region at the distal end of the dilator shaft 1798. In some embodiments, the dilator insert 1799 has an outer diameter that closely matches the inner diameter of the dilator hub 1796 opening where the dilator insert 1799 may be inserted. In some embodiments, the dilator insert 1799 has an exterior appearance similar to two cones connected at their pointed ends.

Method of Preparing and Deploying Closure Device

The systems and devices described herein may be used to close an opening in a vessel in a subject, such as a vein or an artery. An opening in a vessel may occur as a result of injury or surgical procedure. For example, a surgical procedure may involve accessing a blood vessel using a needle (e.g., surgical needle, hypodermic needle), inserting a guidewire through the needle lumen, removing the needle while leaving the guidewire in place, inserting an introducer assembly (e.g., a dilator assembly inserted inside a sheath assembly) using the guidewire to position the introducer in the vessel (thus enlarging the opening by the dilator), and removing the dilator while leaving the sheath in place so that additional steps may be taken through the sheath. When the additional steps are completed, the opening in the vessel must be closed.

To close the opening, the present embodiments include using an implantable closure device 1710 which includes a support scaffold 1792, a flexible, bioabsorbable patch 1794 that covers the opening, and an external fixation 1706 which attaches to the scaffold 1792 to sandwich the patch 1794 between the scaffold 1792 and external fixation 1706. This closure device or implant 1710 may be deployed using a delivery device 1702 into the vessel.

FIG. 150 is a flow chart diagram of a method 1900 of loading an implant 1710 into a VCD assembly 1702, according to aspects of the present embodiments. The method 1900 may be used when applied to a delivery system 1700 provided in a packaging assembly 1770, where the implant 1710 is initially in the loading funnel 1760. The method 1900 may generally include the steps of: providing the implant and delivery device in the packaging tray (step 1902); removing a packaging lid from the packaging tray (step 1904); pulling a handle of the delivery device proximally within the packaging tray until the implant is inside a cannula of the delivery system (step 1906); lifting a lever on the loading funnel to detach the funnel from the cannula (step 1908); and pulling the handle further proximally, removing the delivery device (with implant loaded into the cannula), and removing the delivery device from the packaging tray.

FIG. 151 is a flow chart diagram of a method 1950 of sealing an aperture using a VCD assembly 1702 and implant 1710, according to aspects of the present embodiments. The method 1950 may generally include the steps of: providing a patient with a guidewire and a sheath assembly already disposed in an aperture of a vessel (the patient including the aperture in that vessel that is to be closed) (step 1952); providing a vascular closure device and delivery device (step 1954); loading an implant for vascular closure into a cannula of the delivery device, and removing the delivery device from a packaging tray in which the delivery device and implant were provided (step 1956, corresponding generally to method 1900); engaging the cannula of the delivery device with a sheath hub of the sheath assembly disposed in the patient (step 1958); pushing the delivery device distally until the implant reaches the end of the sheath shaft (step

1960); rotating a sheath cam on a handle of the delivery device by 360° to retract the cannula proximally and to push the implant distally out of the end of the sheath shaft (step 1962); pulling the delivery device assembly distally so that the implant reaches the inner wall of the vessel at the location of the aperture to be closed (step 1964); depressing a fixation cam lock on the handle of the delivery device to enable rotation of a fixation cam on the handle of the delivery device (step 1966); rotating the fixation cam on the handle of the delivery device by 360° to push an external fixation out of the cannula and onto a scaffold of the implant (step 1968); pulling the guidewire proximally out of the delivery device and away from patient (step 1970); rotating a release cam on the handle of the delivery device by 180° to push a guidewire closure pin into a guidewire lumen in the scaffold of the implant and to unhook the scaffold from a bayonet shaft of the delivery device (step 1972); and pulling the delivery device proximally away from the patient (step 1974).

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Although the present invention has been described with reference to particular examples and exemplary embodiments, it should be understood that the foregoing description is in no manner limiting. Moreover, the features described herein may be used in any combination.

What is claimed is:

1. A vascular closure system for sealing an aperture in a wall of a body vessel, comprising:

an implantable closure device;

a delivery device for delivery of the implantable closure device, the delivery device comprising:

a first shaft, a second shaft, and a third shaft, wherein each shaft is releasably coupled to a component of the implantable closure device for moving the implantable closure device into position at the aperture;

a handle, comprising: three cams disposed in linear arrangement with a first cam disposed adjacent to the distal end of the handle, a second cam disposed proximally from the first cam, and a third cam disposed proximally from the second cam, the three cams at least partially forming the outer structure of the handle; and a cannula assembly for holding the implantable closure device prior to positioning the implantable closure device at the aperture; and an introducer assembly comprising a sheath assembly, a dilator assembly disposed coaxially inside the sheath assembly, and a guidewire, wherein each of the three cams interacts with a corresponding first hub, second hub, and third hub disposed radially inward of each cam, each cam comprising a hollow cylinder, wherein at least one shaft of the first, second, and third shafts is disposed concentrically within at least one other shaft of the first, second, and third shafts, wherein each of the first cam, the second cam, and the third cam comprises a helical track on an inner surface of each hollow cylinder, and wherein each of the first hub, the second hub, and the third hub comprises two cam follower protrusions to interface with the helical tracks of each of the first cam, second cam, and third cam to convert rotational movement of the cams into linear movement of the hubs.

2. The vascular closure system of claim 1, wherein the implantable closure device comprises:

an external fixation configured to be disposed on the outside of the vessel wall;

a scaffold configured to be disposed on the inside of the vessel wall and interfacing with the external fixation, with at least a portion of the scaffold disposed through an aperture in the vessel wall; and a patch configured to be disposed on the inside of the vessel wall and sandwiched between the external fixation and the scaffold, the patch substantially covering the full area of the aperture, thereby sealing the aperture.

3. The vascular closure system of claim 2, wherein the dilator assembly comprises:

a dilator shaft comprising a hollow cylinder with a tapered distal end;

a dilator hub comprising a proximal mouth opening, two spring clips that can be releasably coupled with the sheath hub; and a dilator insert comprising a cylindrical body and a narrowed interior lumen.

4. The vascular closure system of claim 1, wherein each of the first cam, second cam, and third cam comprises a hollow cylinder comprising ridges parallel to the axis of the cylinder on the outer surface of the cylinder.

5. The vascular closure system of claim 4, wherein the rotational movement of the cams is converted into rotational movement of the hubs.

6. The vascular closure system of claim 1, wherein the handle comprises at least one cam lock for releasably stopping movement of at least one cam, wherein the cam lock comprises a depressible button.

7. The vascular closure system of claim 1, wherein the closure system further comprises a packaging tray and lid assembly containing the delivery device and implantable closure device, the packaging tray and lid assembly comprising:

a packaging tray for holding the delivery device and a packaging funnel; and a packaging lid releasably coupled to the packaging tray to retain the delivery device, wherein the packaging funnel contains the implantable closure device, wherein the packaging funnel is positioned at the distal end of the delivery device, and wherein each of (i) and (ii) as follows applies:

(i) the packaging tray comprises a rectangular exterior and an interior shaped to match the external shape of the delivery device and the packaging funnel, and (ii) the packaging lid comprises a plurality of protrusions that are releasably pressed into a plurality of indentations on the outer rim of the upper surface of the packaging tray.

8. The vascular closure system of claim 7, wherein (iii) as follows applies:

(iii) the packaging funnel comprises a mouth, a tapered stem, a spout, and a lever connected to the spout via a hinge for releasably coupling the packaging funnel to a portion of the delivery device.

9. The vascular closure system of claim 1, wherein the sheath assembly comprises:

a sheath shaft comprising a hollow cylinder and evenly spaced distance markings on the exterior surface of the hollow cylinder;

a sheath hub comprising a proximal mouth opening, a distal primary opening connected to the proximal end of the sheath shaft, and a flush tube opening disposed at an angle from the distal primary opening;

a flush tube connected to the flush tube opening;

a three-way stopcock valve connected to the distal end of the flush tube; and a sheath seal disposed within the proximal mouth opening of the sheath hub, the sheath seal comprising a flexible polymeric disc with a linear slit disposed in the center of the flexible polymeric disc.

10. The vascular closure system of claim 9, further comprising:

a first catch protruding radially inwardly from an inner surface of the distal end of the handle; and a first prong protruding outwardly from the sheath hub and positioned to interface with the first catch when the outermost shaft of the first, second and third shafts is fully retracted in a proximal-most position, the first catch and first prong preventing further rotation of both the first cam and sheath hub.

11. The vascular closure system of claim 1, wherein the cannula assembly comprises:

a cannula body comprising a hollow cylindrical body, a flange at the distal end of the cannula body, and a protrusion on the distal surface of the flange;

a cannula tube comprising a hollow cylinder disposed within the interior lumen of the cannula body; and a cannula cap disposed at the proximal end of the cannula body.

12. The vascular closure system of claim 1, further comprising:

a second catch protruding radially inwardly from an inner surface of the second cam; and a second prong protruding from the third hub and positioned to interface with the second catch, the second catch and the second prong preventing further rotation of the second cam when the third hub has translated all the way forward to a distal-most position.

13. A vascular closure system for sealing an aperture in a wall of a body vessel, the system comprising:

a vascular closure device assembly comprising a closure pin, a flexible patch, a scaffold comprising a scaffold base and scaffold neck, and an external fixation component, wherein the scaffold neck comprises multiple retaining tabs extending out of the scaffold neck; and a delivery device for delivery of the vascular closure device assembly, the delivery device comprising one or more rotatable fixation cams, wherein the one or more rotatable fixation cams are rotatable to perform (i), (ii), and (iii as follows:

(i) retract an introducer sheath;

(ii) push the external fixation component toward the scaffold and snap onto the scaffold; and (iii) deploy a guidewire hole blocking pin and release the vascular closure device.

14. The vascular closure system of claim 13, wherein the one or more rotatable fixation cams comprises one or more cams rotatable to push a guidewire pin into the scaffold and simultaneously detach the scaffold from a bayonet of a delivery shaft of the delivery device.

15. The vascular closure system of claim 13, wherein the external fixation component has a cage-like structure.

16. The vascular closure system of claim 13, wherein the delivery device for delivery of the vascular closure device assembly comprises:

one or more shafts each releasably coupled to a component of the vascular closure device assembly for moving the implantable vascular closure device assembly into position; and an introducer assembly comprising a sheath assembly, a dilator assembly disposed coaxially inside the sheath assembly, and a guidewire.

* * * * *